United States Patent
Kondo et al.

(10) Patent No.: US 10,995,084 B2
(45) Date of Patent: May 4, 2021

(54) PYRROLIDINE DERIVATIVE

(71) Applicant: KISSEI PHARMACEUTICAL CO., LTD., Matsumoto (JP)

(72) Inventors: Atsushi Kondo, Azumino (JP);
Naohide Morita, Azumino (JP);
Takehiro Ishikawa, Azumino (JP);
Masako Yoshida, Azumino (JP);
Akihiro Moriyama, Azumino (JP);
Isao Wanajo, Azumino (JP)

(73) Assignee: KISSEI PHARMACEUTICAL CO., LTD., Matsumoto (JP)

( * ) Notice: Subject to any disclaimer, the term of this patent is extended or adjusted under 35 U.S.C. 154(b) by 269 days.

(21) Appl. No.: 16/317,934

(22) PCT Filed: Jul. 20, 2017

(86) PCT No.: PCT/JP2017/026169
§ 371 (c)(1),
(2) Date: Jan. 15, 2019

(87) PCT Pub. No.: WO2018/016547
PCT Pub. Date: Jan. 25, 2018

(65) Prior Publication Data
US 2020/0299273 A1 Sep. 24, 2020

(30) Foreign Application Priority Data
Jul. 22, 2016 (JP) .............................. JP2016-144693

(51) Int. Cl.
*C07D 403/12* (2006.01)
*C07D 403/14* (2006.01)
*C07D 405/14* (2006.01)
*C07D 413/14* (2006.01)

(52) U.S. Cl.
CPC ......... *C07D 403/12* (2013.01); *C07D 403/14* (2013.01); *C07D 405/14* (2013.01); *C07D 413/14* (2013.01)

(58) Field of Classification Search
CPC .. C07D 401/14; C07D 403/12; C07D 403/14; C07D 405/14; A61K 31/501; A61K 31/506; A61P 9/00; A61P 25/06
See application file for complete search history.

(56) References Cited

U.S. PATENT DOCUMENTS

| | | | |
|---|---|---|---|
| 6,531,474 | B1 | 3/2003 | Wannamaker et al. |
| 2007/0287696 | A1 | 12/2007 | Burgey et al. |
| 2008/0027041 | A1 | 1/2008 | Hudkins et al. |
| 2010/0179166 | A1 | 7/2010 | Bell et al. |
| 2011/0098269 | A1 | 4/2011 | Becknell et al. |
| 2011/0105549 | A1 | 5/2011 | Wood et al. |
| 2013/0345192 | A1 | 12/2013 | Hopkins et al. |

FOREIGN PATENT DOCUMENTS

| | | |
|---|---|---|
| JP | 2007-519729 A | 7/2007 |
| JP | 2009-544709 A | 12/2009 |
| JP | 2010-529119 A | 8/2010 |
| WO | 99/47545 A2 | 9/1999 |
| WO | 2012/058645 A1 | 5/2012 |
| WO | 2015/161011 A1 | 10/2015 |

OTHER PUBLICATIONS

International Search Report dated Sep. 12, 2017 issued in counterpart International Application No. PCT/JP2017/026169 (2 pages, in English).
Luo et al., "Calcitonin gene-related peptide (CGRP) receptor antagonist: Novel aspartates and succinates", Bioorganic & Medicinal Chemistry Letters, vol. 22, 2012, pp. 2912-2916 (cited in the ISR; in English).
Edvinsson et al., "CGRP Receptor Antagonism and Migraine", Neurotherapeutics: The Journal of the American Society for Experimental NeuroTherapeutics, vol. 7, Apr. 2010, pp. 164-175 (cited in the Specification; in English).
Ho et al., "Randomized controlled trial of the CGRP receptor antagonist telcagepant for migraine prevention", Neurology, vol. 83, Sep. 9, 2014, pp. 958-966 (cited in the Specification; in English).
Dodick et al., "Safety and efficacy of LY2951742, a monoclonal antibody to calcitonin gene-related peptide, for the prevention of migraine: a phase 2, randomised, double-blind, placebo-controlled study", Lancet Neurol, vol. 13, Sep. 2014, pp. 885-892 (cited in the Specification; in English).
Erdmann et al., "Conformational stability of triazolyl functionalized collagen triple helices", Bioorganic & Medicinal Chemistry, vol. 21, 2013, pp. 3565-3568 (cited in the Specification; in English).

Primary Examiner — Deepak R Rao
(74) Attorney, Agent, or Firm — Westerman, Hattori, Daniels & Adrian, LLP

(57) ABSTRACT

The present invention aims to provide a novel compound which has CGRP receptor antagonist activity and which is useful for the treatment of various diseases mediated by CGRP receptors. That is, the present invention relates to the pyrrolidine derivatives represented by the following formula (I) or a pharmaceutically acceptable salt thereof. In the formulae, W is ring, X is a carbon atom or the like, $Y^1$ to $Y^4$ are carbon atoms or the like, and $R^1$ to $R^7$ is alkyl or the like. The compounds of the present invention or a pharmaceutically acceptable salt thereof have an excellent CGRP receptor antagonist activity, and thus are useful as agents for the treatment of various diseases mediated by CGRP receptors.

(I)

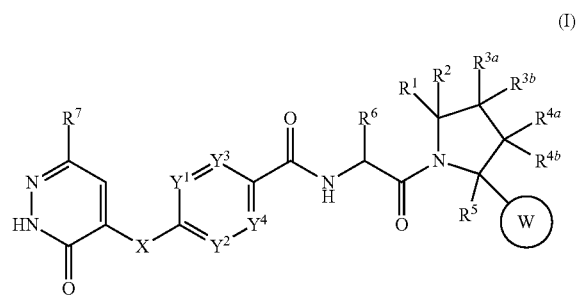

18 Claims, No Drawings

PYRROLIDINE DERIVATIVE

CROSS-REFERENCE TO RELATED APPLICATIONS

This application is a National Stage entry of International Application No. PCT/JP2017/026169 filed on Jul. 20, 2017, which claims priority from Japanese Patent Application No. 2016-144693 filed on Jul. 22, 2016, the entire disclosure of each of which is herein incorporated by reference.

TECHNICAL FIELD

The present invention relates to pyrrolidine derivatives useful as medicaments.

More particularly, the present invention relates to pyrrolidine derivatives or pharmaceutically acceptable salts thereof which have calcitonin gene-related peptide (CGRP) receptor antagonist activity and which are useful as agents for the treatment of various diseases mediated by CGRP receptors.

BACKGROUND ART

CGRP is a neuropeptide consisting of 37 amino acids and causes vasodilation and the like. As a receptor for CGRP, heterodimers (CGRP receptors) consisting of calcitonin receptor-like protein (CLR) and receptor activity-modifying protein 1 (RAMP 1) have been known. CGRP receptors exist on in the perivascular areas of spinal trigeminal nucleus subnucleus caudalis, trigeminal ganglion and brain stem. An increase in CGRP is said to cause allodynia (Non-patent literature 1).

In recent years, CGRP receptor antagonists, such as Olcegepant and Telcagepant, have been developed as agents for the treatment of acute migraine (Non-patent literature 2). A preventive effect in migraine (suppressing an onset of migraine) of CGRP receptor antagonists, such as Telcagepant and LY2951742, has also been reported (Non-patent literatures 3 and 4), and thus CGRP receptors have been attracting attention as a target for both agents for the treatment of acute migraine and preventive agents for migraine.

Some of the above CGRP receptor antagonists were, however, discontinued. Therefore, a novel CGRP receptor antagonist having efficacy and safety has been still desired.

Compounds comprising pyrrolidine ring are disclosed in patent literature 1 and Non-patent literature 5. Patent literatures 2 and 3 can be illustrated relating to CGRP receptor antagonists, and compounds comprising pyrrolidine ring are described in the patent literatures. In the meantime, heterocyclic compounds which are tyrosine kinase inhibitors are described in patent literature 4.

However, the pyrrolidine derivatives of the present invention are neither described nor suggested in the above literatures.

CITATION LIST

Patent Literature

Patent literature 1: U.S. Pat. No. 6,531,474
Patent literature 2: U.S. Published Application No. 2010/0179166
Patent literature 3: U.S. Published Application No. 2011/0105549
Patent literature 4: U.S. Published Application No. 2013/0345192

Non Patent Literature

Non-patent literature 1: Nagata, "Japanese Journal of Headache", 2012, Vol. 39, pp. 16-20
Non-patent literature 2: Edvinsson et al., "Neurotherapeutics", 2010, Vol. 7, No. 2, pp. 164-175
Non-patent literature 3: Ho et al., "Neurology", 2014, Vol. 83, pp. 958-966
Non-patent literature 4: Dodick et al., "Lancet Neurol", 2014, Vol. 13, pp. 885-892
Non-patent literature 5: Roman S. Erdmann et al., "Bioorganic & Medicinal Chemistry", 2013, Vol. 21, pp. 3565-3568

SUMMARY OF INVENTION

Problems to be Solved by the Invention

The present invention aims to provide a novel compound which has CGRP receptor antagonist activity and which is useful for the treatment of various diseases mediated by CGRP receptors.

Means for Solving the Problems

The present invention relates to a compound represented by the following formula (I) or a pharmaceutically acceptable salt thereof.

That is, the present invention relates to the following [1] to [15] and the like.

[1] A compound represented by the formula (I):

[Chem.1]

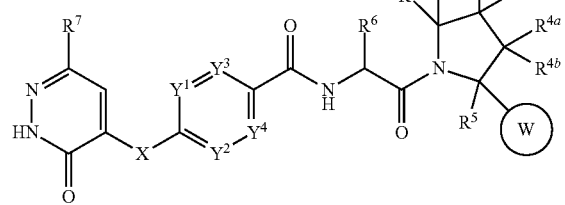

(I)

wherein
ring W is a group selected from the group consisting of following (a) to (d):
(a) $C_{3-6}$ cycloalkyl,
(b) phenyl which may have a substituent selected from substituent group A,
(c) 6-membered aromatic heterocycle which may have a substituent selected from substituent group A, and
(d) 5-membered aromatic heterocycle which may have a substituent selected from substituent group A,
X is a group selected from the group consisting of following (a) to (g):
(a) a carbon atom which may have a substituent selected from substituent group B,
(b) a nitrogen atom which may have a substituent selected from substituent group C,
(c) an oxygen atom, (d) —(C=O)—,
(e) a sulfur atom,
(f) —SO—, and
(g) —SO$_2$—;

$Y^1$, $Y^2$, $Y^3$ and $Y^4$ are each independently =CH—, =CR$^8$— or a nitrogen atom;

$R^8$ is a halogen atom, C$_{1-6}$ alkyl, halo-C$_{1-6}$ alkyl, hydroxy C$_{1-6}$ alkyl, C$_{1-6}$ alkoxy, halo-C$_{1-6}$ alkoxy, C$_{1-6}$ alkylsulfanyl, C$_{1-6}$ alkylsulfinyl, C$_{1-6}$ alkylsulfony, C$_{3-6}$ cycloalkyl, hydroxy, cyano, —NR$^a$R$^b$, —CONR$^a$R$^b$ or —CO$_2$R$^c$;

$R^a$ and $R^b$ are each independently a hydrogen atom, C$_{1-6}$ alkyl, halo-C$_{1-6}$ alkyl or hydroxy C$_{1-6}$ alkyl;

$R^c$ is a hydrogen atom or C$_{1-6}$ alkyl;

$R^1$ is a group selected from the group consisting of following (a) to (j):

[Chem. 2]

(a) 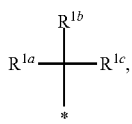

(b) 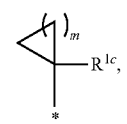

(c) 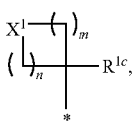

(d) 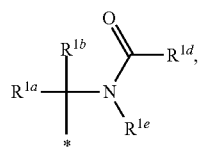

(e) 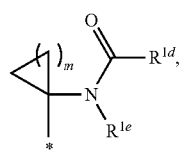

(f) 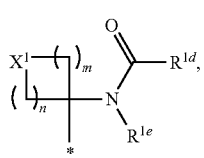

(g) 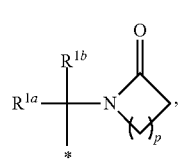

(h) 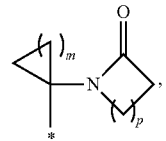

(i) 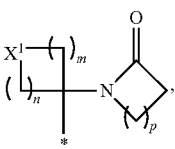

and (j) cyano;
wherein
bonds with * are bonding sites to pyrrolidine ring of the formula (I);

$X^1$ is a group selected from the group consisting of following (a) to (e):
(a) a nitrogen atom which may have a substituent selected from substituent group C,
(b) an oxygen atom,
(c) a sulfur atom,
(d) —SO—, and
(e) —SO$_2$—;

$R^{1a}$ and $R^{1b}$ are each independently a hydrogen atom, a halogen atom, C$_{1-6}$ alkyl, halo-C$_{1-6}$ alkyl, hydroxy C$_{1-6}$ alkyl, C$_{1-6}$ alkoxy or halo-C$_{1-6}$ alkoxy;

$R^{1c}$ is a group selected from the group consisting of following (a) to (r):
(a) C$_{1-6}$ alkyl which may have a substituent selected from substituent group D,
(b) phenyl which may have a substituent selected from substituent group E,
(c) 6-membered aromatic heterocycle which may have a substituent selected from substituent group E,
(d) 5-membered aromatic heterocycle which may have a substituent selected from substituent group E,
(e) a hydrogen atom,
(f) a halogen atom,
(g) C$_{1-6}$ alkoxy,
(h) halo-C$_{1-6}$ alkoxy,
(i) C$_{1-6}$ alkylsulfanyl,
(j) C$_{1-6}$ alkylsulfinyl,
(k) C$_{1-6}$ alkylsulfonyl,
(l) C$_{3-6}$ cycloalkyl,
(m) hydroxy,
(n) cyano,
(o) C$_{2-7}$ acyl,
(p) C$_{2-6}$ alkenyl,
(q) C$_{2-6}$ alkynyl, and
(r) —NR$^a$R$^b$;

$R^{1d}$ is C$_{1-6}$ alkyl, halo-C$_{1-6}$ alkyl, hydroxy C$_{1-6}$ alkyl, C$_{1-6}$ alkoxy, halo-C$_{1-6}$ alkoxy, C$_{3-6}$ cycloalkyl, —NR$^a$R$^b$ or phenyl which may have a substituent selected from substituent group E;

$R^{1e}$ is a hydrogen atom, C$_{1-6}$ alkyl or halo-C$_{1-6}$ alkyl;

m is an integer number 1 to 4;

n and p are each independently an integer number 1 to 3;

$R^2$, $R^{3a}$, $R^{3b}$, $R^{4a}$, $R^{4b}$ and $R^5$ are each independently a hydrogen atom, a halogen atom, C$_{1-6}$ alkyl, halo-C$_{1-6}$ alkyl, hydroxy C$_{1-6}$ alkyl, C$_{1-6}$ alkoxy, halo-C$_{1-6}$ alkoxy, C$_{3-6}$ cycloalkyl, hydroxy, cyano or —NR$^a$R$^b$;

$R^6$ is a hydrogen atom, $C_{1-6}$ alkyl, $C_{3-6}$ cycloalkyl, halo-$C_{1-6}$ alkyl or hydroxy $C_{1-6}$ alkyl;

$R^7$ is a hydrogen atom, $C_{1-6}$ alkyl, $C_{3-6}$ cycloalkyl or halo-$C_{1-6}$ alkyl;

substituent group A is a group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{1-6}$ alkylsulfanyl, $C_{1-6}$ alkylsulfinyl, $C_{1-6}$ alkylsulfonyl, $C_{3-6}$ cycloalkyl, hydroxy, cyano, —$NR^aR^b$, —$CONR^aR^b$ and —$CO_2R^c$;

substituent group B is a group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl and hydroxy;

substituent group C is a group consisting of $C_{1-6}$ alkyl, halo-$C_{1-6}$ alkyl and $C_{3-6}$ cycloalkyl;

substituent group D is a group consisting of a halogen atom, $C_{1-6}$ alkoxy, halo-$C_{1-6}$ alkoxy, $C_{1-6}$ alkylsulfanyl, $C_{1-6}$ alkylsulfinyl, $C_{1-6}$ alkylsulfonyl, $C_{3-6}$ cycloalkyl, hydroxy, cyano and —$NR^aR^b$; and substituent group E is a group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy and cyano; or a pharmaceutically acceptable salt thereof.

[2] The compound according to the above [1] or a pharmaceutically acceptable salt thereof, wherein $R^5$ is a hydrogen atom.

[3] The compound according to the above [1] or [2] or a pharmaceutically acceptable salt thereof, wherein $R^{3a}$, $R^{3b}$, $R^{4a}$ and $R^{4b}$ are hydrogen atoms.

[4] The compound according to any one of the above [1] to [3]:
wherein ring W is $C_{3-6}$ cycloalkyl or phenyl which may have a substituent selected from substituent group A; and substituent group A has the same meaning as described in the above [1];
or a pharmaceutically acceptable salt thereof.

[5] The compound according to any one of the above [1] to [4], wherein X is a group selected from the group consisting of following (a) to (c):
(a) a carbon atom which may have a substituent selected from substituent group B,
(b) a nitrogen atom which may have a substituent selected from substituent group C, and
(c) an oxygen atom;
and substituent group B and substituent group C have the same meaning as described in the above [1];
or a pharmaceutically acceptable salt thereof.

[6] The compound according to any one of the above [1] to [5] or a pharmaceutically acceptable salt thereof, wherein $R^2$ is a hydrogen atom.

[7] The compound according to any one of the above [1] to [6], wherein $R^1$ is a group selected from the group consisting of following (a) to (d) and (g):

[Chem.3]

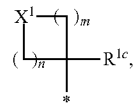
(a)

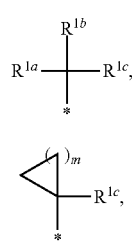
(b)

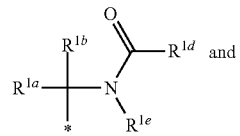
(c)

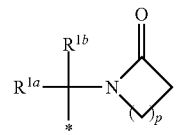
(d)

[Chem.4]

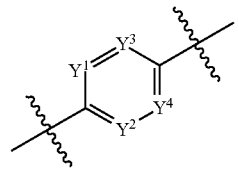
(g)

wherein
*, $X^1$, $R^{1a}$, $R^{1b}$, $R^{1c}$, $R^{1d}$, $R^{1e}$, m, n and p each have the same meaning as described in the above [1];
or a pharmaceutically acceptable salt thereof.

[8] The compound according to any one of the above [1] to [7]:

[Chem. 5]

wherein the group represented by the above formula is a group selected from the group consisting of following (a) to (f):

[Chem.6]

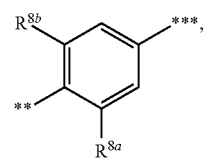
(a)

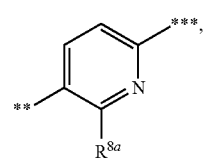
(b)

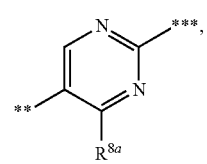
(c)

(d)

[chemical structure]
R8a (e)

[chemical structure]
R8a

[Chem.7]

(f)

[chemical structure]
R8a wherein
$R^{8a}$ is a hydrogen atom, a halogen atom, $C_{1-6}$ alkyl or halo-$C_{1-6}$ alkyl;
$R^{8b}$ is a hydrogen atom, a halogen atom, $C_{1-6}$ alkyl or $C_{1-6}$ alkoxy; and
bonds with  are bonding sites to X and bonds with * are bonding sites to the carbonyl of the formula (I);
or a pharmaceutically acceptable salt thereof.

[9] The compound according to any one of the above [1] to [8]:
wherein $X^1$ is an oxygen atom;
$R^{1a}$ and $R^{1b}$ are each independently a hydrogen atom, a halogen atom, $C_{1-6}$ alkyl or halo-$C_{1-6}$ alkyl;
$R^{1c}$ is a group selected from the group consisting of following (a) to (l):
(a) $C_{1-6}$ alkyl which may have a substituent selected from substituent group $D^1$,
(b) oxazolyl,
(c) a hydrogen atom,
(d) a halogen atom,
(e) $C_{1-6}$ alkoxy,
(f) $C_{1-6}$ alkylsulfanyl,
(g) $C_{1-6}$ alkylsulfonyl,
(h) hydroxy,
(i) cyano,
(j) $C_{2-7}$ acyl,
(k) $C_{2-6}$ alkenyl, and
(l) —$NR^{aa}R^{bb}$;
$R^{1d}$ is $C_{1-6}$ alkyl or phenyl;
$R^{1e}$ is a hydrogen atom or $C_{1-6}$ alkyl;
substituent group $D^1$ is a group consisting of a halogen atom and hydroxy; and
$R^{aa}$ and $R^{bb}$ are each independently a hydrogen atom or $C_{1-6}$ alkyl;
or a pharmaceutically acceptable salt thereof.

[10] The compound according to any one of the above [1] to [9] or a pharmaceutically acceptable salt thereof, wherein $R^6$ is a hydrogen atom, methyl, ethyl, isopropyl, hydroxymethyl or monofluoromethyl.

[11] The compound according to any one of the above [1] to [10] or a pharmaceutically acceptable salt thereof, wherein $R^7$ is a hydrogen atom or methyl.

[12] The compound according to the above [1] which is represented by the formula (IA):

[Chem.8]

(IA)

[chemical structure of formula IA]

wherein
$R^9$ and $R^{10}$ are each independently a hydrogen atom, a fluorine atom or a chlorine atom;
$X^a$ is —$CH_2$— or —O—;

[Chem.9]

[chemical structure]

the group represented by the above formula is a group selected from the group consisting of following (a) to (h):

[Chem. 10]

(a)

[phenyl structure]

(b)

[phenyl structure with F]

(c)

[phenyl structure with Cl]

(d)

[phenyl structure with F]

-continued (e) 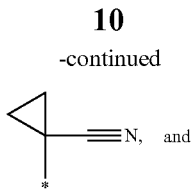

[Chem. 13]

(f) 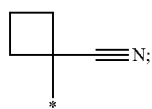

(g)

bonds with * are bonding sites to the pyrrolidine ring of the formula (IA); and
$R^{6a}$ is a hydrogen atom, methyl or ethyl;
or a pharmaceutically acceptable salt thereof.

[13] A compound represented by the following formula:

[Chem.14]

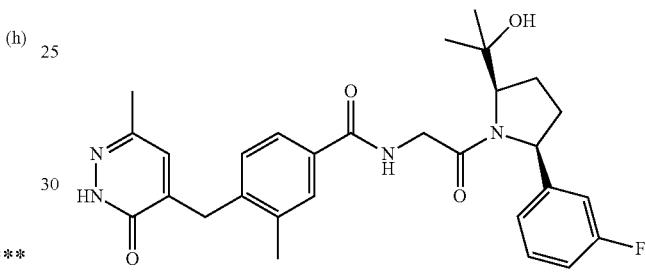

or a pharmaceutically acceptable salt thereof.

[14] A pharmaceutical composition comprising the compound according to any one of the above [1] to [13] or a pharmaceutically acceptable salt thereof, and pharmaceutical additive.

[15] The pharmaceutical composition according to the above [14] which is a pharmaceutical composition for use in the treatment of migraine.

In an embodiment, the present invention relates to a method for treating migraine, comprising administering a necessary amount of the pharmaceutical composition according to the above [14] to a patient.

In an embodiment, the present invention relates to a use of the compound according to any one of the above [1] to [13] or a pharmaceutically acceptable salt thereof for the manufacture of a pharmaceutical composition for use in the treatment of migraine.

Effect of the Invention

The compounds of the present invention have an excellent CGRP receptor antagonist activity, and thus the compounds of the present invention or pharmaceutically acceptable salts thereof are useful as agents for the treatment of various diseases mediated by CGRP receptors.

MODE FOR CARRYING OUT THE INVENTION

Hereinafter, embodiments of the present invention will be described in further detail.

In the present invention, each term has the following meaning unless otherwise specified.

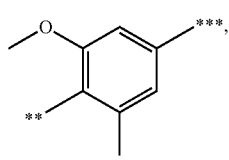

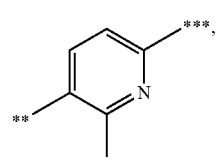

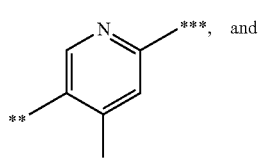

[Chem. 11]

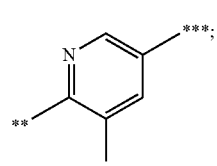

bonds with  are bonding sites to $X^a$, and bonds with * are bonding sites to the carbonyl of the formula (IA);

$R^{1f}$ is a group selected from the group consisting of following (a) to (g):

[Chem. 12]

(a) 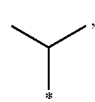

(b) 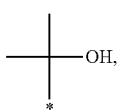

(c) 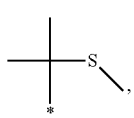

(d) 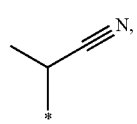

(e) 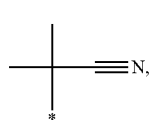

The term "halogen atom" means a fluorine atom, a chlorine atom, a bromine atom, or an iodine atom.

The term "$C_{1-6}$ alkyl" means a straight-chained or branched alkyl group having 1 to 6 carbon atoms. For example, methyl, ethyl, propyl, isopropyl, butyl, isobutyl, sec-butyl, tert-butyl and the like can be illustrated.

The term "$C_{2-6}$ alkenyl" means a straight-chained or branched alkenyl group having 2 to 6 carbon atoms. For example, vinyl, allyl, 1-propenyl, isopropenyl and the like can be illustrated.

The term "$C_{2-6}$ alkynyl" means a straight-chained or branched alkynyl group having 2 to 6 carbon atoms. For example, ethynyl 2-propynyl and the like can be illustrated.

The term "$C_{2-7}$ acyl" means a straight-chained or branched acyl group having 2 to 7 carbon atoms. For example, acetyl, propionyl, butyryl, isobutyryl, pivaloyl and the like can be illustrated.

The term "$C_{1-6}$ alkoxy" means a straight-chained or branched alkoxy group having 1 to 6 carbon atoms. For example, methoxy, ethoxy, propoxy, isopropoxy and the like can be illustrated.

The term "$C_{1-6}$ alkylsulfanyl" means a group represented by ($C_{1-6}$ alkyl)-S—. For example, methylsulfanyl, ethylsulfanyl, propylsulfanyl, butylsulfanyl, pentylsulfanyl, hexylsulfanyl and the like can be illustrated.

The term "$C_{1-6}$ alkylsulfinyl" means a group represented by ($C_{1-6}$ alkyl)-SO—. For example, methylsulfinyl, ethylsulfinyl, propylsulfinyl, butylsulfinyl, pentylsulfinyl, hexylsulfinyl and the like can be illustrated.

The term "$C_{1-6}$ alkylsulfonyl" means a group represented by ($C_{1-6}$ alkyl)-$SO_2$—. For example, methylsulfonyl, ethylsulfonyl, propylsulfonyl, butylsulfonyl, pentylsulfonyl, hexylsulfonyl and the like can be illustrated.

The term "hydroxy $C_{1-6}$ alkyl" means $C_{1-6}$ alkyl substituted by 1 to 3 hydroxy groups. For example, hydroxymethyl, 1-hydroxyethyl, 1-hydroxy-1, 1-dimethylmethyl, 2-hydroxyethyl, 2-hydroxy-2-methylpropyl, 3-hydroxypropyl and the like can be illustrated.

The term "halo-$C_{1-6}$ alkyl" means $C_{1-6}$ alkyl substituted by 1 to 3 of the same or different halogen atoms. For example, fluoromethyl, 2-fluoroethyl, difluoromethyl, trifluoromethyl, 2,2,2-trifluoroethyl, 3,3,3-trifluoropropyl, 4,4,4-trifluorobutyl and the like can be illustrated.

The term "halo-$C_{1-6}$ alkoxy" means $C_{1-6}$ alkoxy substituted by 1 to 3 of the same or different halogen atoms. For example, monofluoromethoxy, difluoromethoxy, trifluoromethoxy and the like can be illustrated.

The term "$C_{3-6}$ cycloalkyl" means a saturated alicyclic hydrocarbon group having 3 to 6 carbon atoms. For example, cyclopropyl, cyclobutyl, cyclopentyl, cyclohexyl and the like can be illustrated.

The term "5-membered aromatic heterocycle" means a 5-membered aromatic heterocyclic group having any 1 to 4 hetero atoms selected from an oxygen atom, a nitrogen atom and a sulfur atom in the ring. For example, furyl, pyrrolyl, thienyl, imidazolyl, pyrazolyl, 1,2,4-triazolyl, isothiazolyl, isoxazolyl, oxazolyl, thiazolyl, 1,3,4-oxadiazolyl, 1,2,4-oxadiazolyl and the like can be illustrated.

The term "6-membered aromatic heterocycle" means a 6-membered aromatic heterocyclic group having 1 to 4 nitrogen atoms in the ring. For example, pyridyl, pyrimidinyl, pyrazinyl, pyridazinyl and the like can be illustrated.

The term "phenyl which may have a substituent selected from substituent group A" means phenyl optionally substituted by 1 to 5 same or different groups selected from substituent group A. Unsubstituted phenyl or phenyl substituted by one or two of the above substituents is preferred.

The term "6-membered aromatic heterocycle which may have a substituent selected from substituent group A" means 6-membered aromatic heterocycle optionally substituted by 1 to 4 same or different groups selected from substituent group A. Unsubstituted 6-membered aromatic heterocycle or 6-membered aromatic heterocycle substituted by one or two of the above substituents is preferred.

The term "5-membered aromatic heterocycle which may have a substituent selected from substituent group A" means 5-membered aromatic heterocycle optionally substituted by 1 to 3 same or different groups selected from substituent group A. Unsubstituted 5-membered aromatic heterocycle or 5-membered aromatic heterocycle substituted by one or two of the above substituents is preferred.

The term "a carbon atom which may have a substituent selected from substituent group B" means a carbon atom optionally substituted by 1 or 2 same or different groups selected from substituent group B. —$CH_2$— or a carbon atom substituted by one of the above substituents is preferred.

The term "a nitrogen atom which may have a substituent selected from substituent group C" means a nitrogen atom optionally substituted one group selected from substituent group C. —NH— or a nitrogen atom substituted by one of the above substituents is preferred.

The term "$C_{1-6}$ alkyl which may have a substituent selected from substituent group D" means $C_{1-6}$ alkyl optionally substituted by 1 to 6 same or different groups selected from substituent group D. Unsubstituted $C_{1-6}$ alkyl or $C_{1-6}$ alkyl substituted by one or two of the above substituents is preferred.

The term "phenyl which may have a substituent selected from substituent group E" means phenyl optionally substituted by 1 to 5 same or different groups selected from substituent group E. Unsubstituted phenyl or phenyl substituted by one or two of the above substituents is preferred.

The term "6-membered aromatic heterocycle which may have a substituent selected from substituent group E" means 6-membered aromatic heterocycle optionally substituted by 1 to 4 same or different groups selected from substituent group E. Unsubstituted 6-membered aromatic heterocycle or 6-membered aromatic heterocycle substituted by one or two of the above substituents is preferred.

The term "5-membered aromatic heterocycle which may have a substituent selected from substituent group E" means 5-membered aromatic heterocycle optionally substituted by 1 to 3 same or different groups selected from substituent group E. Unsubstituted 5-membered aromatic heterocycle or 5-membered aromatic heterocycle substituted by one or two of the above substituents is preferred.

The term "$C_{1-6}$ alkyl which may have a substituent selected from substituent group $D^1$" means $C_{1-6}$ alkyl optionally substituted by 1 to 6 same or different groups selected from substituent group $D^1$. Unsubstituted $C_{1-6}$ alkyl or $C_{1-6}$ alkyl substituted by one or two of the above substituents is preferred.

The following abbreviations in the description and tables have the following meanings, respectively.

CAN: ceric ammonium nitrate
DIPEA: N,N-diisopropylethylamine
DMA: N,N-dimethylacetamide
DMAP: 4-dimethylaminopyridine
DMF: N,N-dimethylformamide
DMSO: dimethylsulfoxide
EDC-HCl: 1-(3-dimethylaminopropyl)-3-ethylcarbodiimide hydrochloride
HOBT: 1-hydroxybenzotriazole LAH: lithium aluminium hydride
LDA: lithium diisopropylamide
NMP: 1-methyl-2-pyrrolidone
TBME: tert-butyl methyl ether
TEMPO: 2,2,6,6-tetramethylpiperidine 1-oxyl free radical
THF: tetrahydrofuran

[Chem.15]

$$\text{(I)} \rightleftharpoons \text{(II)}$$

T3P (registered trademark): propylphosphonic acid anhydride (cyclic trimer)
DMP: dess-Martin periodinane
DME: 1,2-dimethoxyethane
CDI: 1,1'-carbonyldiimidazole
TBAF: tetrabutylammonium fluoride
NBS: N-bromosuccinimide
HMPA: hexamethylphosphoric triamide
amino-silica gel: aminopropylated silica gel
ODS column chromatography: octadecyl-silylated silica gel column chromatography
Ref. No.: Reference Example Number
Ex. No.: Example Number
Str.: chemical structure
Physical data: physical property
rac: racemic body (The "racemate" in the tables means racemic body with identified relative configuration.)
Ki: equilibrium dissociation constant
$IC_{50}$: concentration required for 50% inhibition
$^1$H-NMR: hydrogen nuclear magnetic resonance spectrum
DMSO-d6: dimethylsulfoxide-d6
$CDCl_3$: chloroform-dl
MS: mass spectrometry
HRMS: high-resolution mass spectrometry
ESI: electrospray ionization
ESI_APCI: multiionization using electrospray ionization-atmospheric pressure chemical ionization
calcd for: calculated value
Found: actual measured value
EDTA: ethylenediaminetetraacetic acid
HEPES: 2-[4-(2-hydroxyethyl)-1-piperazinyl]ethanesulfonic acid
MEM: minimum essential medium
DMEM: Dulbecco's modified Eagle medium In the case where the compounds represented by the formula (I) contain one or more asymmetric carbon atoms, stereoisomers in the R- or S-configuration at each of the asymmetric carbons and mixtures of any combinations thereof are included in the present invention. In such cases, racemic compounds, racemic mixtures, individual enantiomers and mixtures of diastereomers are also included in the scope of the present invention.

In the case where the compounds represented by the formula (I) have the cis-trans isomers, all the cis-trans isomers are included in the present invention.

In the case where tautomers of the compounds represented by the formula (I) exist, the present invention includes all the tautomers. For example, tautomers of the formula (I) represented by the following formula (II) can be illustrated.

In the present invention, stereochemical determination can also be determined according to well-known methods in the art.

A compound represented by the formula (I) can also be converted into pharmaceutically acceptable salts thereof according to a general method, if necessary. As such salts, an acid addition salt and a salt with a base can be illustrated.

As the acid addition salt, an acid addition salt with a mineral acid such as hydrochloric acid, hydrobromic acid, hydroiodic acid, sulfuric acid, nitric acid, phosphoric acid and the like, and an acid addition salt with an organic acid such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like can be illustrated.

As the salt with a base, a salt formed with an inorganic base such as lithium, sodium, potassium, calcium, magnesium and the like, and a salt formed with organic base such as N-methyl-D-glucamine, N,N'-dibenzylethylenediamine, triethylamine, piperidine, morpholine, pyrrolidine, arginine, lysine, choline and the like can be illustrated.

In the case where a compound represented by the formula (I) or a pharmaceutically acceptable salt thereof exists, for example, as crystal, the present invention includes all crystalline forms. For example, a pharmaceutically acceptable salt also includes a solvate thereof with a pharmaceutically acceptable solvent such as water, ethanol or the like, and a cocrystal thereof with an appropriate cocrystal former (co-former) and the like.

In an embodiment of the compounds represented by the formula (I) and (IA), for example, the compounds represented by the following formula (I-I) and (IA-I) are preferred.

[Chem. 16]

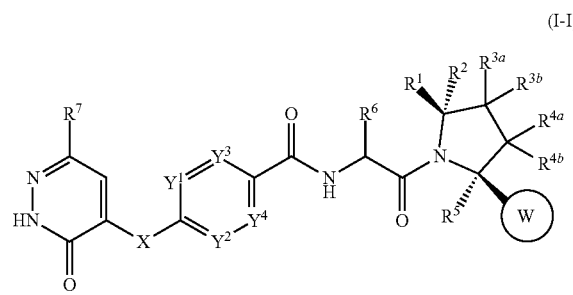
(I-I)

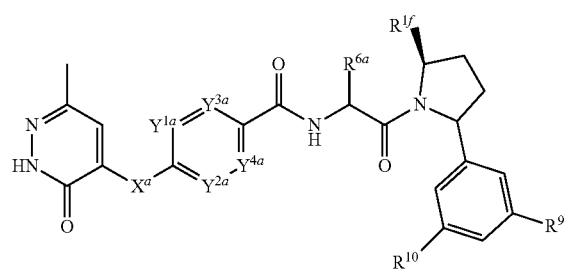
(IA-I)

The symbols in the formula have the same meanings as described in the above [1] or [12].

In an embodiment of the compounds represented by the formula (IA-I), for example, the compounds represented by the following formula (IA-I-I) or (IA-I-II) are preferred.

[Chem.17]

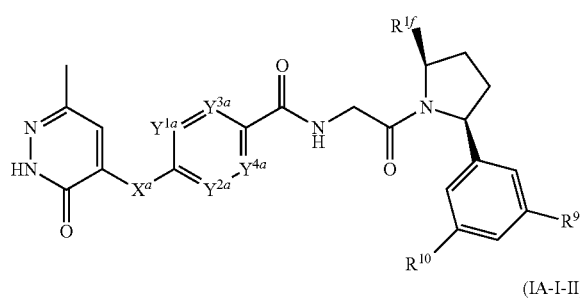
(IA-I-I)

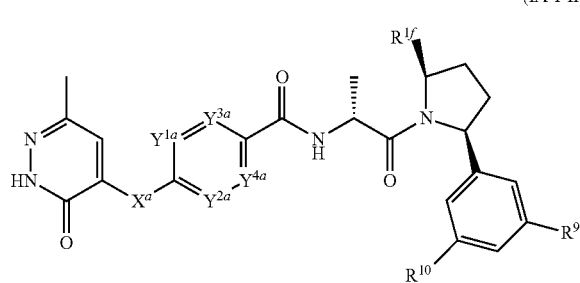
(IA-I-II)

The symbols in the formula have the same meanings as described in the above [12].

In an embodiment, the present invention relates to a compound selected from the group consisting of the following compounds or a pharmaceutically acceptable salt thereof.

[Chem. 18]

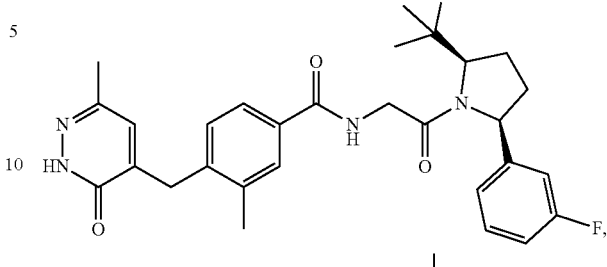

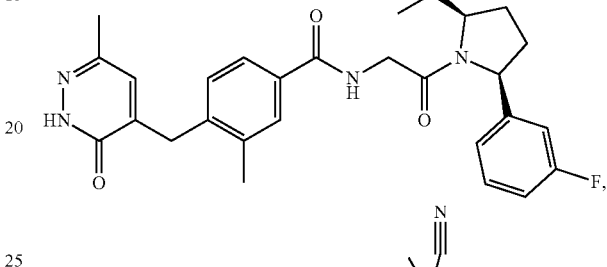

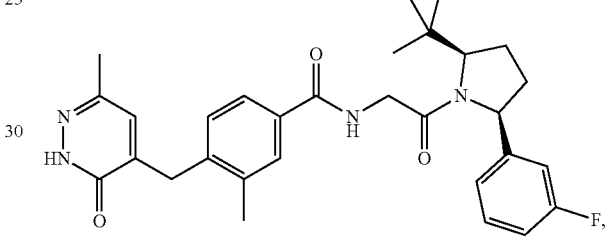

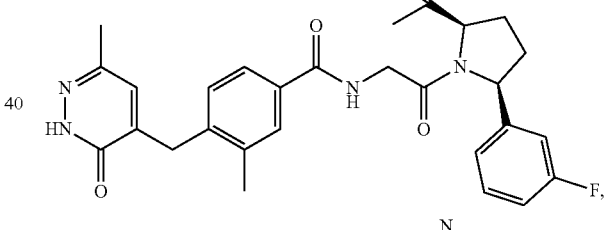

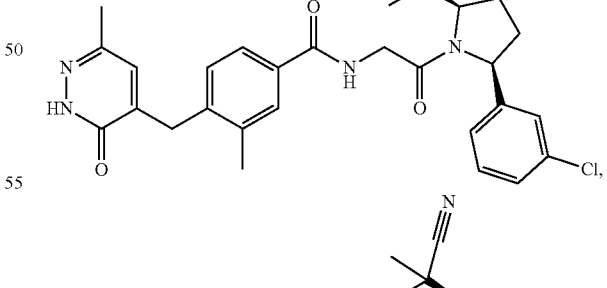

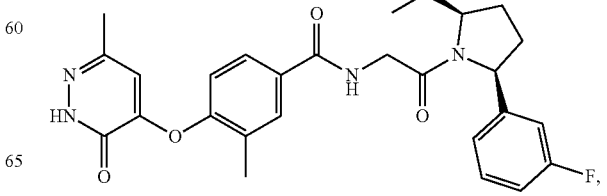

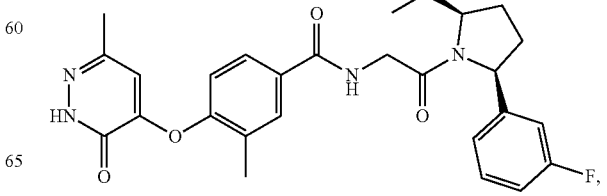

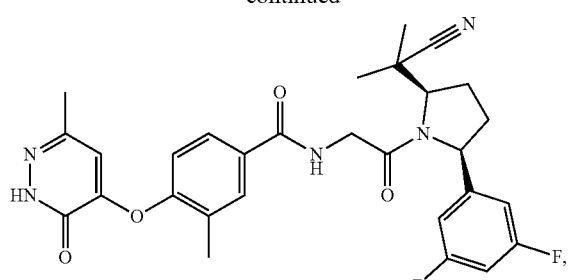
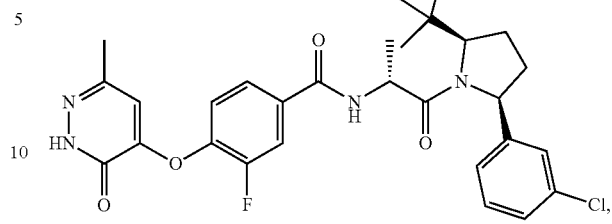
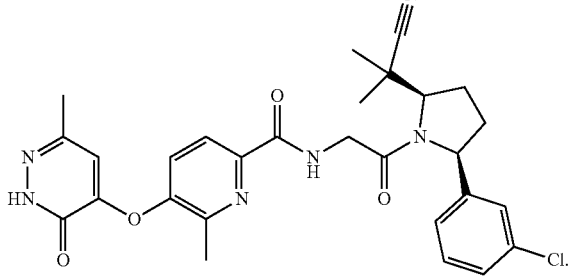
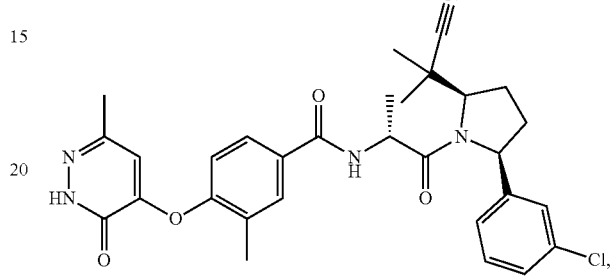
In an embodiment, the present invention relates to a compound selected from the group consisting of following compounds or a pharmaceutically acceptable salt thereof.
[Chem. 19]
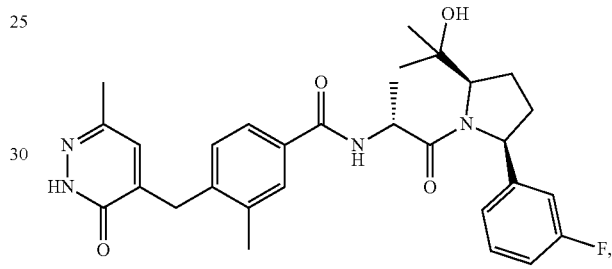
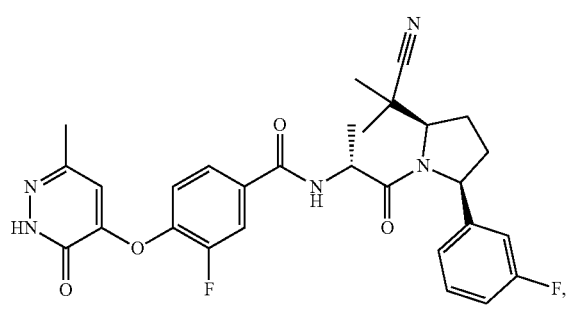 [SMILES: Cc1cc(Oc2ncc(C(=O)N[C@H](C)C(=O)N3[C@H](c4cccc(Cl)c4)CC[C@@H]3C(C)(C)C#N)cc2C)c(=O)[nH]n1]
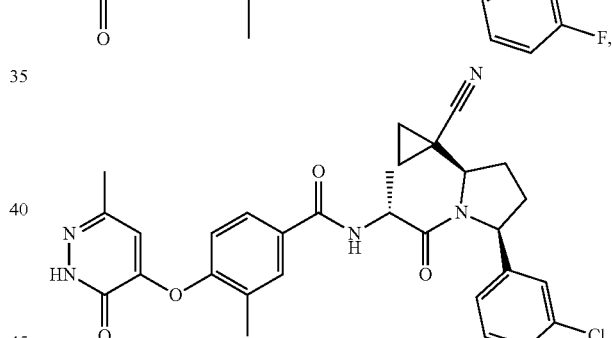
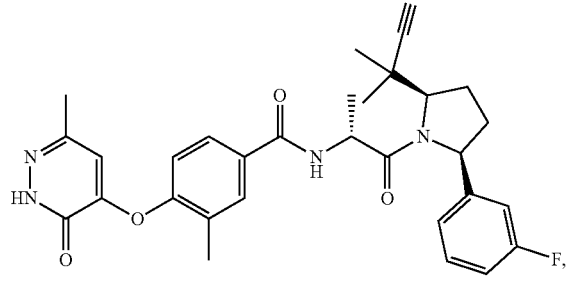
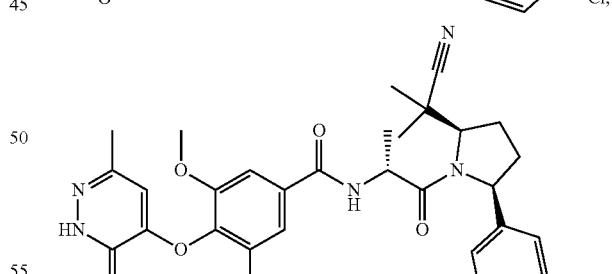
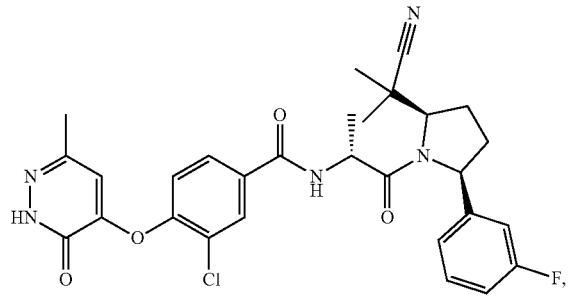
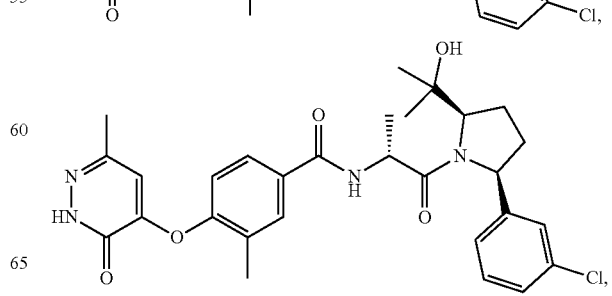

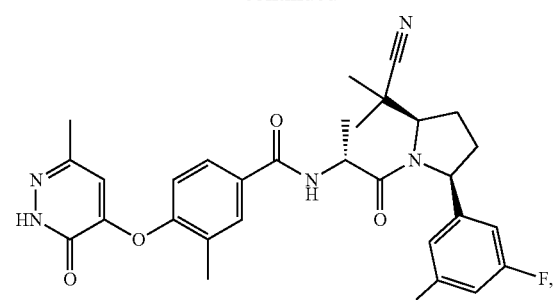
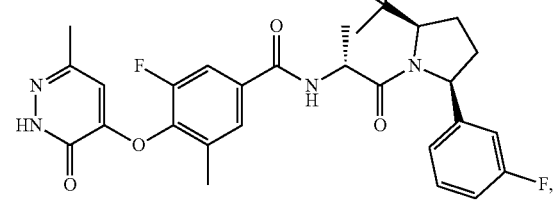
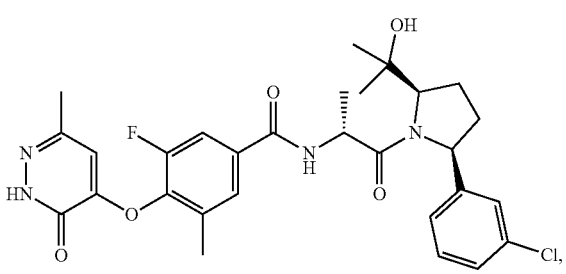
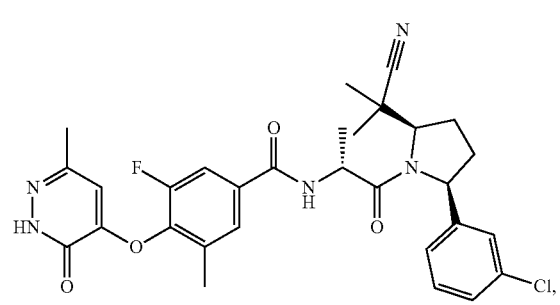
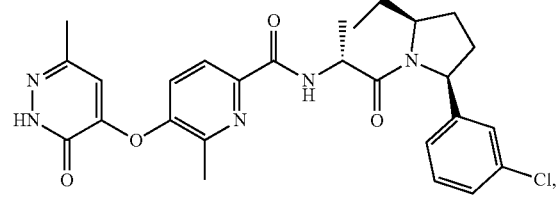
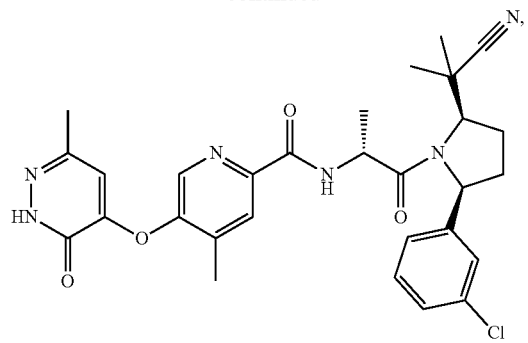
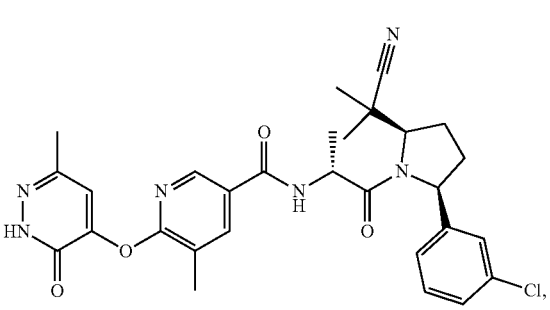
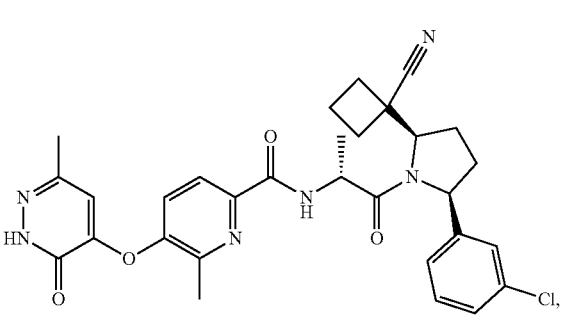
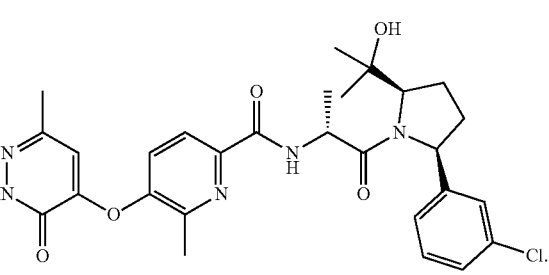
A compound represented by the formula (I) can be prepared, for example, by a method described in Schemes 1 to 9 or a similar method thereto, or a method described in literatures or a similar method thereto.
A compound represented by the formula (I) can be prepared, for example, by the method described in Process 1-1 or Process 1-2 in Scheme 1.

Scheme 1

[Chem. 20]

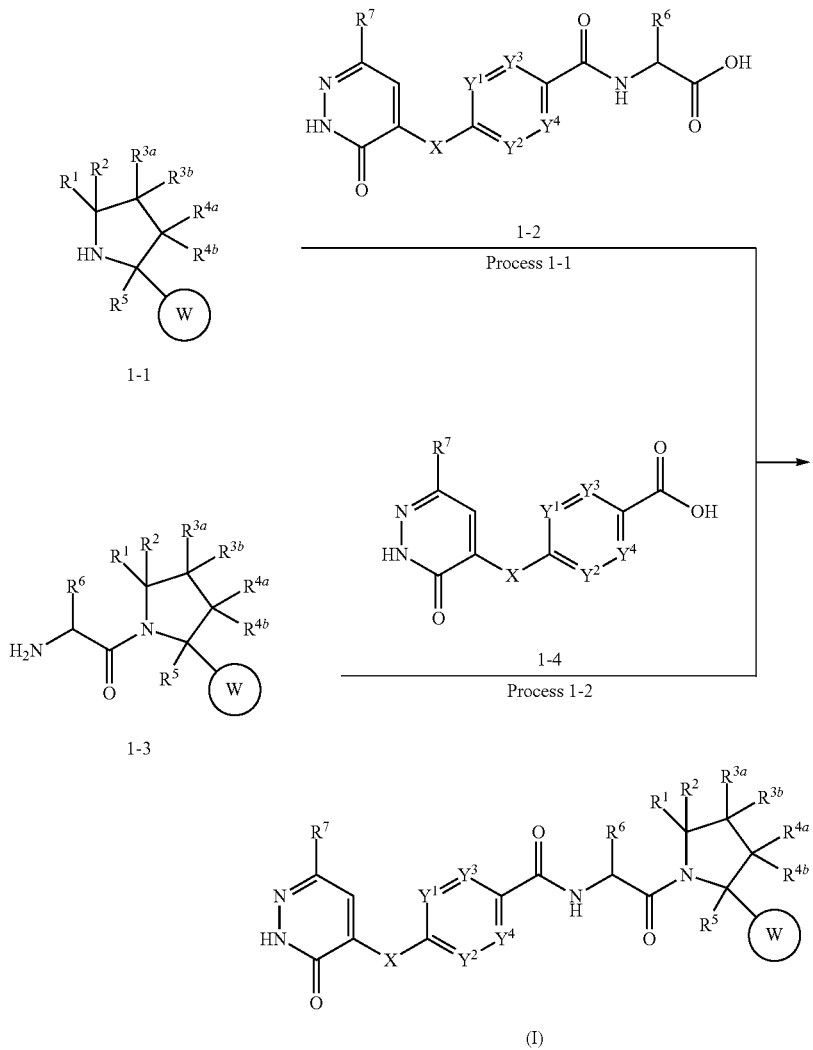

In the formulae, ring W, X, $Y^1$, $Y^2$, $Y^3$, $Y^4$, $R^1$, $R^2$, $R^{3a}$, $R^{3b}$, $R^{4a}$, $R^{4b}$, $R^5$, $R^6$ and $R^7$ have the same meanings as defined above.

Process 1-1

Compound (I) can also be prepared by reacting Compound (1-1) with Compound (1-2) in an inert solvent in the presence of a condensing reagent and a base. As the inert solvent, dichloromethane, 1,2-dichloroethane, DMF, THF, acetonitrile, a mixed solvent thereof and the like can be illustrated. As the condensing reagent, EDC-HCl, T3P and the like can be illustrated. As the base, triethylamine, DIPEA and the like can be illustrated. An additive such as HOBT and DMAP may be used, if necessary. The reaction temperature is usually at 0° C. to reflux temperature. The reaction time is usually from 30 minutes to 3 days, varying based on a used starting material, solvent, reaction temperature or the like. The reaction can also be conducted using a microwave reactor (Biotage).

Process 1-2

Compound (I) can also be prepared by reacting Compound (1-3) with Compound (1-4) by a method similar to the above Process 1-1.

Compound (1-3) can be prepared, for example, by the method described in Processes 2-1 to 2-4 in Scheme 2.

Scheme 2

[Chem. 21]

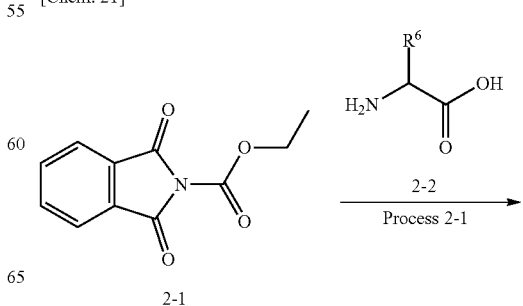

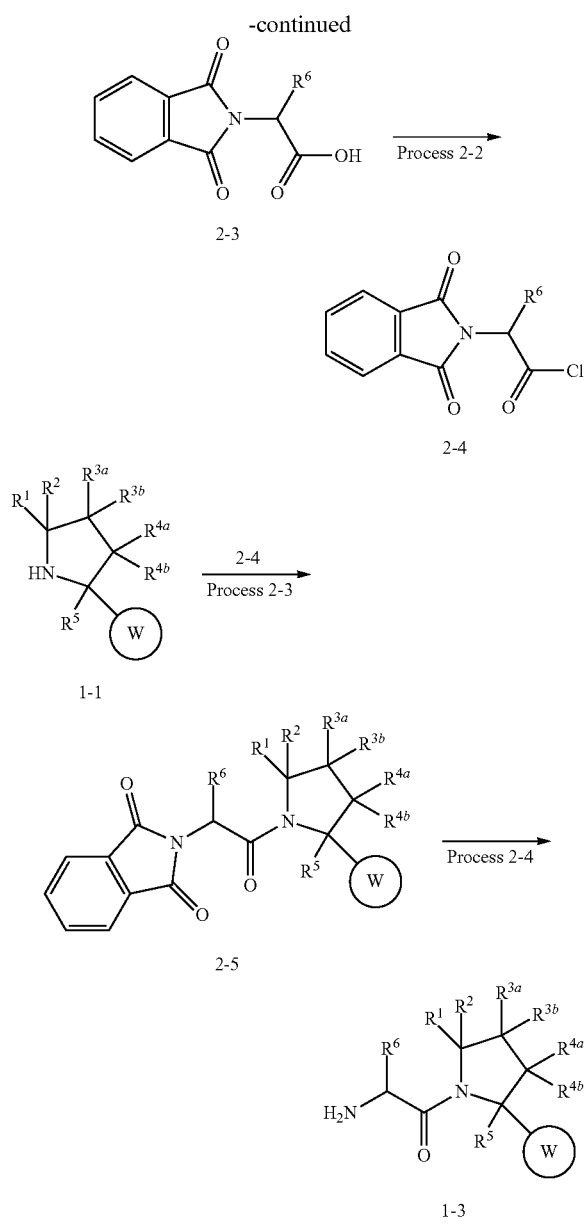

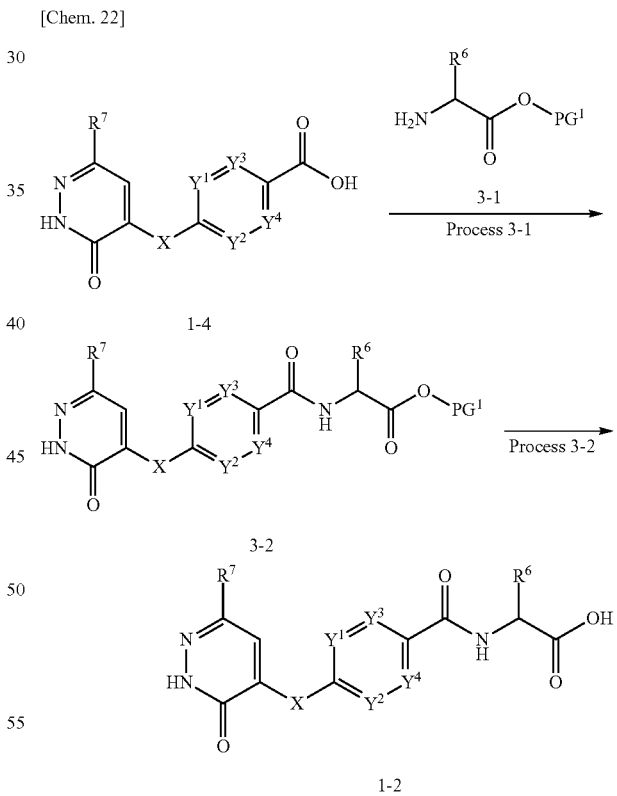

In the formulae, ring W, $R^1$, $R^2$, $R^{3a}$, $R^{3b}$, $R^{4a}$, $R^{4b}$, $R^5$ and $R^6$ have the same meanings as defined above.

Process 2-1

Compound (2-3) can also be prepared by reacting Compound (2-1) with Compound (2-2) in water in the presence of a base. As the base, triethylamine and the like can be illustrated. The reaction temperature is usually at 0° C. to reflux temperature. The reaction time is usually from 30 minutes to 3 days, varying based on a used starting material, solvent, reaction temperature or the like.

Compound (2-3) can also be prepared according to the method described in Japanese Patent No. 2514855.

Process 2-2

Compound (2-4) can also be prepared by reacting Compound (2-3) with oxalyl chloride or thionyl chloride in an inert solvent or in the absence of a solvent. As the inert solvent, dichloromethane, 1,2-dichloroethane and the like can be illustrated. An additive such as DMF may be used, if necessary. The reaction temperature is usually at 0° C. to reflux temperature. The reaction time is usually from 30 minutes to 1 day, varying based on a used starting material, solvent, reaction temperature or the like.

Process 2-3

Compound (2-5) can also be prepared by reacting Compound (1-1) with Compound (2-4) in an inert solvent in the presence of a base. As the inert solvent, dichloromethane, THF, a mixed solvent thereof and the like can be illustrated. As the base, triethylamine, DIPEA, 2,6-lutidine and the like can be illustrated. The reaction temperature is usually at −20° C. to reflux temperature. The reaction time is usually from 30 minutes to 3 days, varying based on a used starting material, solvent, reaction temperature or the like.

Process 2-4

Compound (1-3) can also be prepared by reacting Compound (2-5) with hydrazine monohydrate in an inert solvent. As the inert solvent, ethanol, THF, acetonitrile, a mixed solvent thereof and the like can be illustrated. The reaction temperature is usually at 0° C. to reflux temperature. The reaction time is usually from 30 minutes to 3 days, varying based on a used starting material, solvent, reaction temperature or the like.

Compound (1-2) can be prepared, for example, by the method described in Processes 3-1 and 3-2 in Scheme 3.

Scheme 3

[Chem. 22]

In the formulae, X, $Y^1$, $Y^2$, $Y^3$, $Y^4$, $R^6$ and $R^7$ have the same meanings as defined above. $PG^1$ is a protective group.

Process 3-1

Compound (3-2) can also be prepared by reacting Compound (1-4) with Compound (3-1) in an inert solvent in the presence of a condensing reagent and a base. As the inert solvent, dichloromethane, 1,2-dichloroethane, DMF, THF, acetonitrile, a mixed solvent thereof and the like can be illustrated. As the condensing reagent, EDC-HCl, T3P and the like can be illustrated. As the base, triethylamine, DIPEA and the like can be illustrated. An additive such as HOBT and DMAP may be used, if necessary. The reaction temperature is usually at 0° C. to reflux temperature. The reaction time is usually from 30 minutes to 3 days, varying based on a used starting material, solvent, reaction temperature or the like.

Process 3-2

Compound (1-2) can also be prepared by alkaline hydrolysis of Compound (3-2) in an inert solvent. As the inert solvent, water, methanol, ethanol, THF, acetonitrile, a mixed solvent thereof and the like can be illustrated. As the base, sodium hydroxide, potassium hydroxide, lithium hydroxide and the like can be illustrated. The reaction temperature is usually at 0° C. to reflux temperature. The reaction time is usually from 30 minutes to 3 days, varying based on a used starting material, solvent, reaction temperature or the like. Compound (1-2) can also be prepared by acid hydrolysis or hydrogenolysis instead of alkaline hydrolysis.

Compound (4-7) can be prepared, for example, by the method described in Processes 4-1 to 4-6 in Scheme 4.

Scheme 4

[Chem. 23]

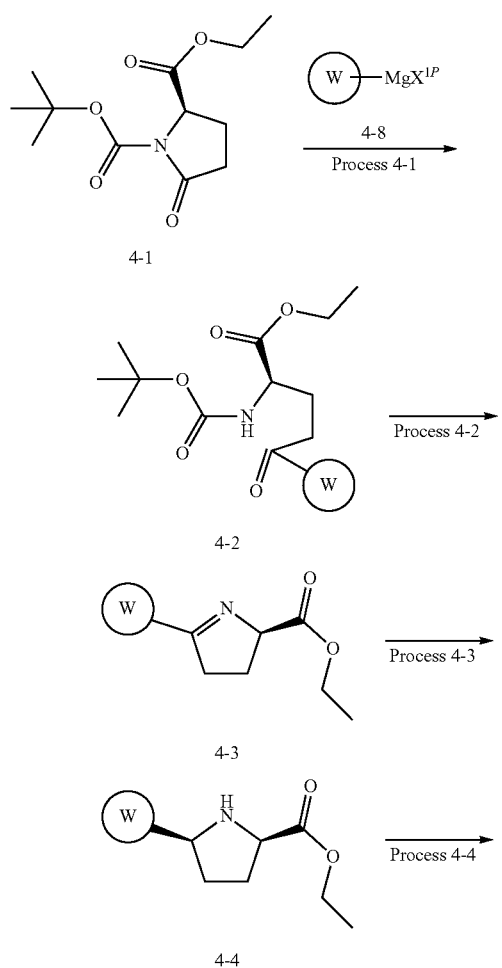

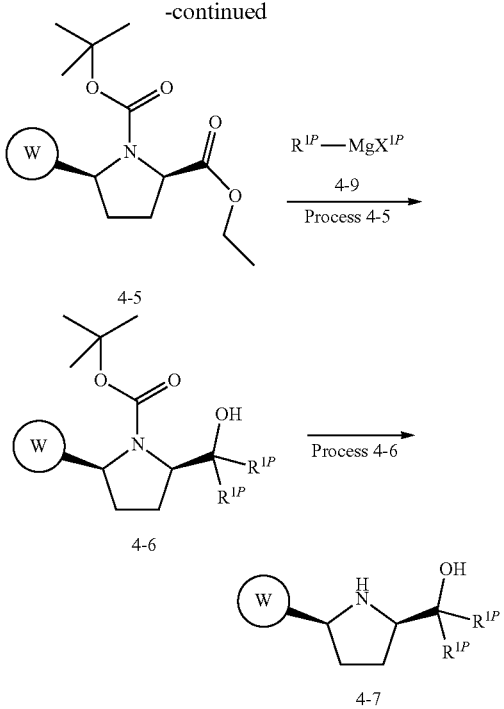

In the formulae, ring W has the same meaning as defined above. $X^{1P}$ is a chlorine atom, a bromine atom or an iodine atom. $R^{1P}$ is $C_{1-6}$ alkyl.

Process 4-1

Compound (4-2) can also be prepared by reacting Compound (4-1) with Grignard reagent (4-8) in an inert solvent. As the inert solvent, THF, diethyl ether, a mixed solvent thereof and the like can be illustrated. The reaction temperature is usually at −78° C. to at room temperature. The reaction time is usually from 30 minutes to 1 day, varying based on a used starting material, solvent, reaction temperature or the like.

Process 4-2

Compound (4-3) can also be prepared by ring-closure reaction of Compound (4-2) in an inert solvent in the presence of an acid. As the inert solvent, ethyl acetate, 1,4-dioxane, a mixed solvent thereof and the like can be illustrated. As the acid, hydrogen chloride and the like can be illustrated. The reaction temperature is usually at 0° C. to reflux temperature. The reaction time is usually from 30 minutes to 3 days, varying based on a used starting material, solvent, reaction temperature or the like.

Process 4-3

Compound (4-4) can also be prepared by catalytic reduction of Compound (4-3) under a hydrogen atmosphere in an inert solvent in the presence of a catalyst. As the inert solvent, methanol, ethanol, ethyl acetate, THF, a mixed solvent thereof and the like can be illustrated. As the catalyst, palladium on carbon powder, platinum on carbon powder and the like can be illustrated. The reaction temperature is usually at 0° C. to reflux temperature. The reaction time is usually from 30 minutes to 3 days, varying based on a used starting material, solvent, reaction temperature or the like.

Process 4-4

Compound (4-5) can also be prepared by reacting Compound (4-4) with di-tert-butyl dicarbonate in an inert solvent in the presence of a base. As the inert solvent, THF, diethyl ether, dichloromethane, a mixed solvent thereof and the like can be illustrated. As the base, triethylamine, DIPEA and the like can be illustrated. The reaction temperature is usually at 0° C. to reflux temperature. The reaction time is usually from 30 minutes to 3 days, varying based on a used starting material, solvent, reaction temperature or the like.

Process 4-5

Compound (4-6) can also be prepared by reacting Compound (4-5) with Grignard reagent (4-9) in an inert solvent. As the inert solvent, THF, diethyl ether, a mixed solvent thereof and the like can be illustrated. The reaction temperature is usually at −78° C. to at room temperature. The reaction time is usually from 30 minutes to 1 day, varying based on a used starting material, solvent, reaction temperature or the like.

Process 4-6

Compound (4-7) can also be prepared by reacting Compound (4-6) under an acidic condition in an inert solvent. As the inert solvent, ethyl acetate, 1,4-dioxane, dichloromethane, THF, a mixed solvent thereof and the like can be illustrated. As the acid, hydrogen chloride, trifluoroacetic acid and the like can be illustrated. The reaction temperature is usually at 0° C. to reflux temperature. The reaction time is usually from 30 minutes to 3 days, varying based on a used starting material, solvent, reaction temperature or the like.

Compound (5-5) can be prepared, for example, by the method described in Processes 5-1 to 5-5 in Scheme 5.

Scheme 5

[Chem. 24]

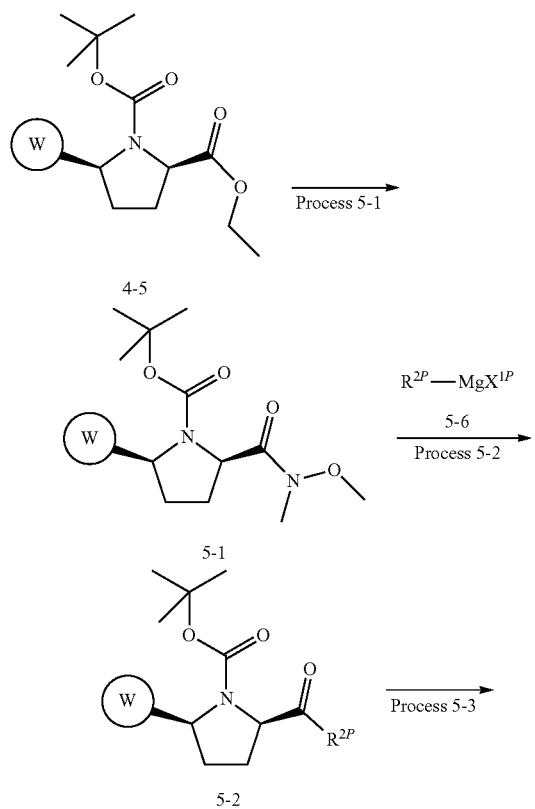

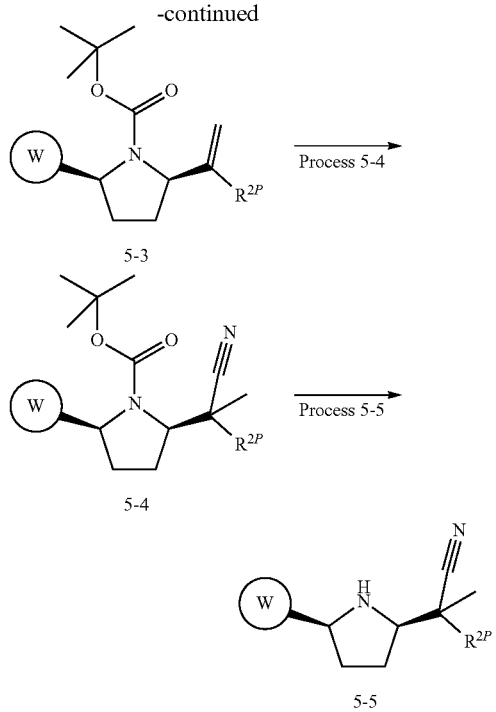

In the formulae, ring W and $X^{1P}$ have the same meanings as defined above. $R^{2P}$ is $C_{1-6}$ alkyl.

Process 5-1

Compound (5-1) can also be prepared by reacting Compound (4-5) with N,O-dimethylhydroxylamine hydrochloride in an inert solvent in the presence of a base. As the inert solvent, THF, diethyl ether, a mixed solvent thereof and the like can be illustrated. As the base, isopropylmagnesium chloride and the like can be illustrated. The reaction temperature is usually at −78° C. to at room temperature. The reaction time is usually from 30 minutes to 1 day, varying based on a used starting material, solvent, reaction temperature or the like.

Process 5-2

Compound (5-2) can also be prepared by reacting Compound (5-1) with Grignard reagent (5-6) in an inert solvent. As the inert solvent, THF, diethyl ether, a mixed solvent thereof and the like can be illustrated. The reaction temperature is usually at −20° C. to reflux temperature. The reaction time is usually from 30 minutes to 3 days, varying based on a used starting material, solvent, reaction temperature or the like.

Process 5-3

Compound (5-3) can also be prepared by Wittig reaction of Compound (5-2) with phosphorus ylide in an inert solvent. As the inert solvent, THF, diethyl ether, a mixed solvent thereof and the like can be illustrated. The reaction temperature is usually at −20° C. to reflux temperature. The reaction time is usually from 30 minutes to 3 days, varying based on a used starting material, solvent, reaction temperature or the like. Phosphorus ylide can also be prepared by reacting triphenylphosphonium salt with a base in an inert solvent. As the triphenylphosphonium salt, methyltriphenylphosphonium bromide and the like can be illustrated. As the inert solvent, THF, diethyl ether, a mixed solvent thereof and the like can be illustrated. As the base, potassium bis(trimethylsilyl)amide, butyllithium and the like can be illustrated. The reaction temperature is usually at −20° C. to reflux temperature. The reaction time is usually from 30 minutes to 1 day, varying based on a used starting material, solvent and reaction temperature or the like.

Process 5-4

Compound (5-4) can also be prepared by reacting Compound (5-3) with p-toluenesulfonyl cyanide in an inert solvent in the presence of a cobalt catalyst and phenylsilane. As the inert solvent, ethanol and the like can be illustrated. As the cobalt catalyst, 1,1,2,2-tetramethyl-1,2-ethane diamino-N,N'-bis(3,5-di-tert-butylsalicylidene)-cobalt (II) and the like can be illustrated. The reaction temperature is usually at 0° C. to reflux temperature. The reaction time is usually from 30 minutes to 3 days, varying based on a used starting material, solvent, reaction temperature or the like.

Process 5-5

Compound (5-5) can also be prepared by reacting Compound (5-4) under an acidic condition in an inert solvent. As the inert solvent, ethyl acetate, 1,4-dioxane, dichloromethane, THF, a mixed solvent thereof and the like can be illustrated. As the acid, hydrogen chloride, trifluoroacetic acid and the like can be illustrated. The reaction temperature is usually at 0° C. to reflux temperature. The reaction time is usually from 30 minutes to 3 days, varying based on a used starting material, solvent, reaction temperature or the like.

Compound (6-7) can be prepared, for example, by the method described in Processes 6-1 to 6-6 in Scheme 6.

[Chem. 25]

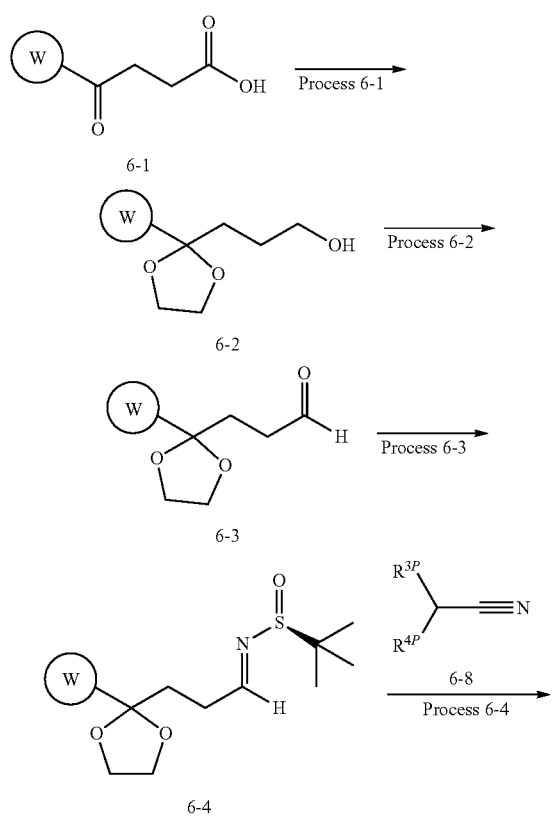

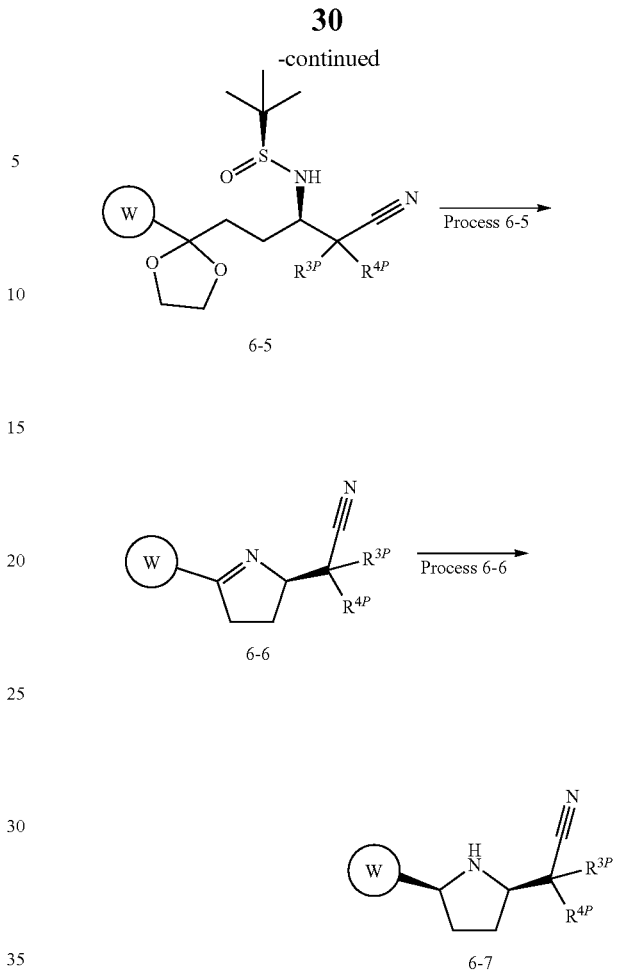

In the formulae, ring W has the same meaning as defined above. $R^{3P}$ and $R^{4P}$ are each independently a hydrogen atom or $C_{1-6}$ alkyl, and $R^{3P}$ and $R^{4P}$ may bind together to form a cyclic group with the neighboring a carbon atom.

Process 6-1

A carboxylic acid derivative can also be prepared by reacting Compound (6-1) with ethylene glycol in an inert solvent in the presence of an acidic catalyst. As the inert solvent, benzene, toluene and the like can be illustrated. As the acidic catalyst, p-toluenesulfonic acid and the like can be illustrated. The reaction temperature is usually at room temperature to reflux temperature. The reaction time is usually from 30 minutes to 3 days, varying based on a used starting material, solvent, reaction temperature or the like. Compound (6-2) can also be prepared by reduction reaction of the carboxylic acid derivative in an inert solvent in the presence of a reducing reagent. As the inert solvent, THF, 1,4-dioxane, diethyl ether, methanol, ethanol, a mixed solvent thereof and the like can be illustrated. As the reducing reagent, lithium aluminium hydride, lithium borohydride, sodium borohydride and the like can be illustrated. The reaction temperature is usually at −20° C. to reflux temperature. The reaction time is usually from 30 minutes to 3 days, varying based on a used starting material, solvent, reaction temperature or the like.

Process 6-2

Compound (6-3) can also be prepared by oxidation reaction of Compound (6-2) in an inert solvent in the presence of a nitroxylradical oxidation catalyst and a reoxidant. As the inert solvent, dichloromethane, an aqueous solution of sodium bicarbonate a mixed solvent thereof and the like can be illustrated. As the nitroxylradical oxidation catalyst, TEMPO, 2-azaadamantane-N-oxyl and the like can be illustrated. As the reoxidant, sodium hypochlorite pentahydrate, iodobenzene diacetate and the like can be illustrated. An additive such as tetrabutylammonium hydrogen sulfate and potassium bromide may be used, if necessary. The reaction temperature is usually at 0° C. to reflux temperature. The reaction time is usually from 30 minutes to 3 days, varying based on a used starting material, solvent, reaction temperature or the like.

Process 6-3

Compound (6-4) can also be prepared by reacting Compound (6-3) with (S)-(−)-2-methyl-2-propanesulfinamide in an inert solvent in the presence of titanium(IV) ethoxide or a dehydrating agent. As the inert solvent, THF, toluene, a mixed solvent thereof and the like can be illustrated. As the dehydrating agent, copper(II) sulfate, magnesium sulfate and the like can be illustrated. The reaction temperature is usually at 0° C. to reflux temperature. The reaction time is usually from 30 minutes to 7 days, varying based on a used starting material, solvent and reaction temperature or the like.

Process 6-4

Compound (6-5) can also be prepared by reacting Compound (6-4) with a compound which is obtained by deprotonation of Compound (6-8) in an inert solvent using a strong base. As the inert solvent, THF, diethyl ether, a mixed solvent thereof and the like can be illustrated. As the strong base, LDA, lithium bis(trimethylsilyl)amide and the like can be illustrated. An additive such as hexamethylphosphoric triamide may be used, if necessary. The reaction temperature is usually at −78° C. to at room temperature. The reaction time is usually from 30 minutes to 1 day, varying based on a used starting material, solvent, reaction temperature or the like.

Process 6-5

Compound (6-6) can also be prepared by ring-closure reaction of Compound (6-5) in an inert solvent in the presence of an acid. As the inert solvent, THF, ethyl acetate, 1,4-dioxane, methanol, water, a mixed solvent thereof and the like can be illustrated. As the acid, hydrogen chloride and the like can be illustrated. The reaction temperature is usually at 0° C. to reflux temperature. The reaction time is usually from 30 minutes to 3 days, varying based on a used starting material, solvent, reaction temperature or the like.

Process 6-6

Compound (6-7) can also be prepared by catalytic reduction of Compound (6-6) under a hydrogen atmosphere in an inert solvent in the presence of a catalyst. As the inert solvent, methanol, ethanol, ethyl acetate, THF, a mixed solvent thereof and the like can be illustrated. As the catalyst, palladium on carbon powder, platinum on carbon powder and the like can be illustrated. The reaction temperature is usually at 0° C. to reflux temperature. The reaction time is usually from 30 minutes to 3 days, varying based on a used starting material, solvent, reaction temperature or the like. Compound (6-7) can also be prepared by reduction reaction of Compound (6-6) in an inert solvent in the presence of a reducing reagent. As the inert solvent, THF, acetic acid, methanol, ethanol, a mixed solvent thereof and the like can be illustrated. As the reducing reagent, sodium triacetoxyborohydride, sodium borohydride and the like can be illustrated. The reaction temperature is usually at −20° C. to reflux temperature. The reaction time is usually from 30 minutes to 3 days, varying based on a used starting material, solvent, reaction temperature or the like.

Compound (7-3) can be prepared, for example, by the method described in Process 7-1 in Scheme 7.

Scheme 7

[Chem. 26]

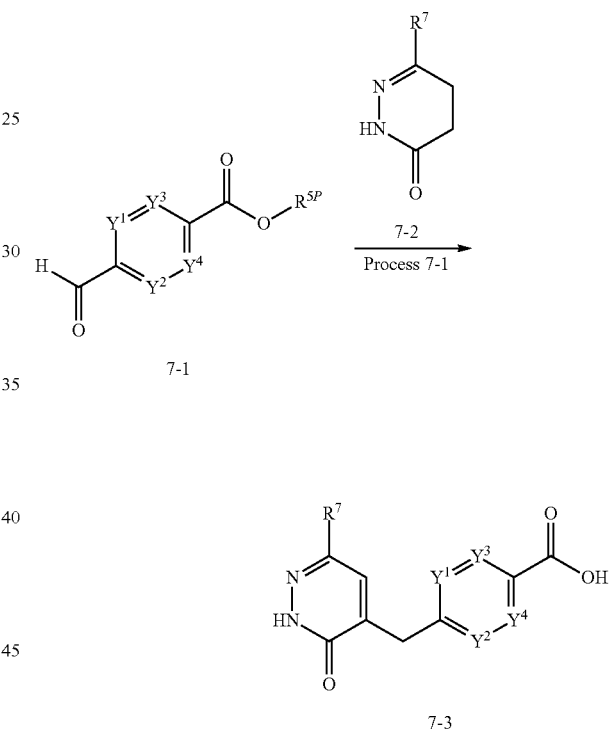

In the formulae, $Y^1$, $Y^2$, $Y^3$, $Y^4$ and $R^7$ have the same meanings as defined above. $R^{5P}$ is a hydrogen atom or $C_{1-6}$ alkyl.

Process 7-1

Compound (7-3) can also be prepared by reacting Compound (7-1) with Compound (7-2) in an inert solvent in the presence of a base. As the inert solvent, ethanol and the like can be illustrated. As the base, potassium hydroxide and the like can be illustrated. The reaction temperature is usually at 0° C. to reflux temperature. The reaction time is usually from 30 minutes to 3 days, varying based on a used starting material, solvent, reaction temperature or the like.

Compound (8-6) can be prepared, for example, by the method described in Processes 8-1 to 8-5 in Scheme 8.

Scheme 8

[Chem. 27]

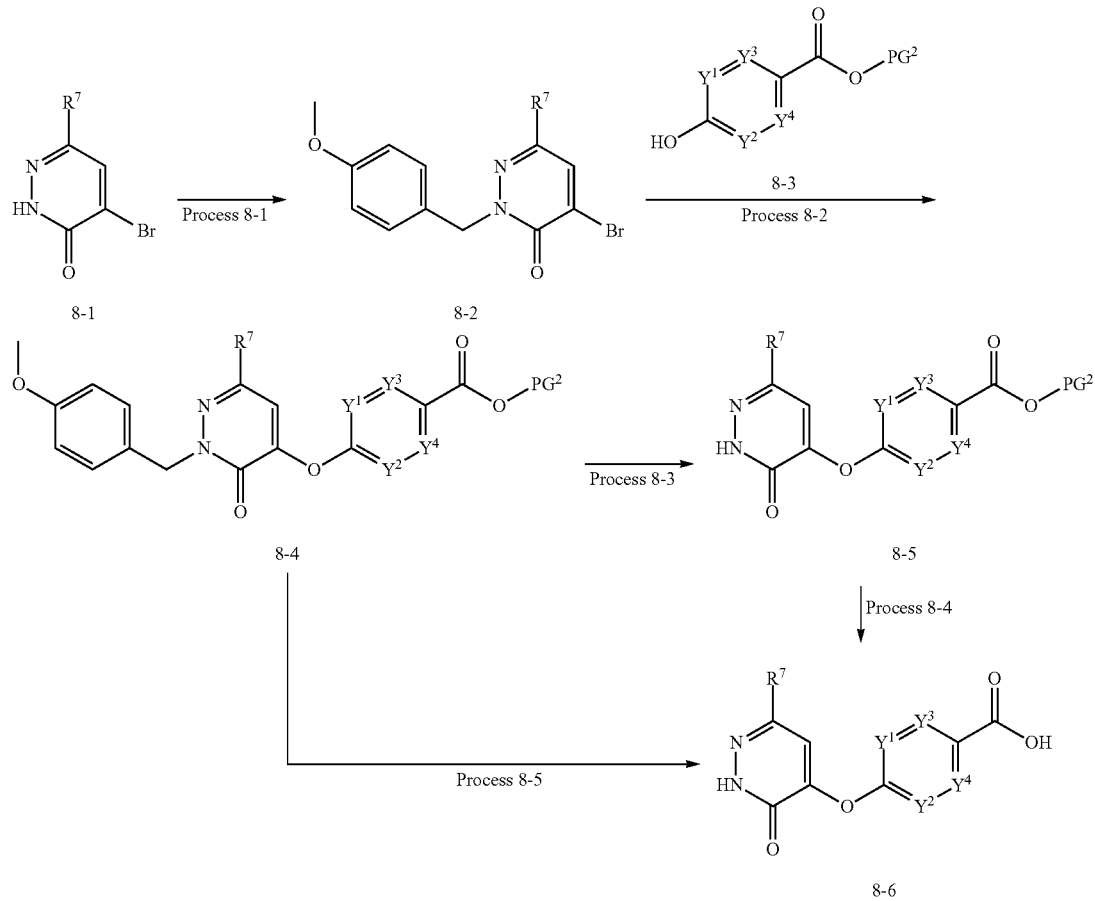

In the formulae, $Y^1$, $Y^2$, $Y^3$, $Y^4$ and $R^7$ have the same meanings as defined above. $PG^2$ is a protective group.

Process 8-1

Compound (8-2) can also be prepared by reacting Compound (8-1) with 4-methoxybenzyl chloride in an inert solvent in the presence of a base. As the inert solvent, DMF, DMA and the like can be illustrated. As the base, potassium carbonate and the like can be illustrated. The reaction temperature is usually at 0° C. to reflux temperature. The reaction time is usually from 30 minutes to 3 days, varying based on a used starting material, solvent, reaction temperature or the like.

Process 8-2

Compound (8-4) can also be prepared by reacting Compound (8-2) with Compound (8-3) in an inert solvent in the presence of a base. As the inert solvent, DMF, DMA and the like can be illustrated. As the base, potassium carbonate and the like can be illustrated. The reaction temperature is usually at 0° C. to reflux temperature. The reaction time is usually from 30 minutes to 3 days, varying based on a used starting material, solvent, reaction temperature or the like. The reaction can also be conducted using a microwave reactor (Biotage).

Process 8-3

Compound (8-5) can also be prepared by reacting Compound (8-4) with CAN in an inert solvent. As the inert solvent, acetonitrile, water, a mixed solvent thereof and the like can be illustrated. The reaction temperature is usually at 0° C. to reflux temperature. The reaction time is usually from 30 minutes to 3 days, varying based on a used starting material, solvent, reaction temperature or the like.

Process 8-4

Compound (8-6) can also be prepared by alkaline hydrolysis of Compound (8-5) in an inert solvent. As the inert solvent, water, methanol, ethanol, THF, acetonitrile, a mixed solvent thereof and the like can be illustrated. As the base, sodium hydroxide, potassium hydroxide, lithium hydroxide and the like can be illustrated. The reaction temperature is usually at 0° C. to reflux temperature. The reaction time is usually from 30 minutes to 3 days, varying based on a used starting material, solvent, reaction temperature or the like. Compound (8-6) can also be prepared by acid hydrolysis or hydrogenolysis instead of alkaline hydrolysis.

Process 8-5

Compound (8-6) can also be prepared by reacting Compound (8-4) under an acidic condition in an inert solvent. As the inert solvent, water, acetic acid, a mixed solvent thereof and the like can be illustrated. As the acid, hydrogen chloride and hydrogen bromide can be illustrated. The reaction temperature is usually at 0° C. to reflux temperature. The reaction time is usually from 30 minutes to 3 days, varying based on a used starting material, solvent, reaction temperature or the like.

Compound (8-4) and Compound (8-6) can also be prepared, for example, by the method described in Processes 9-1 to 9-5 in Scheme 9.

[Chem. 28]

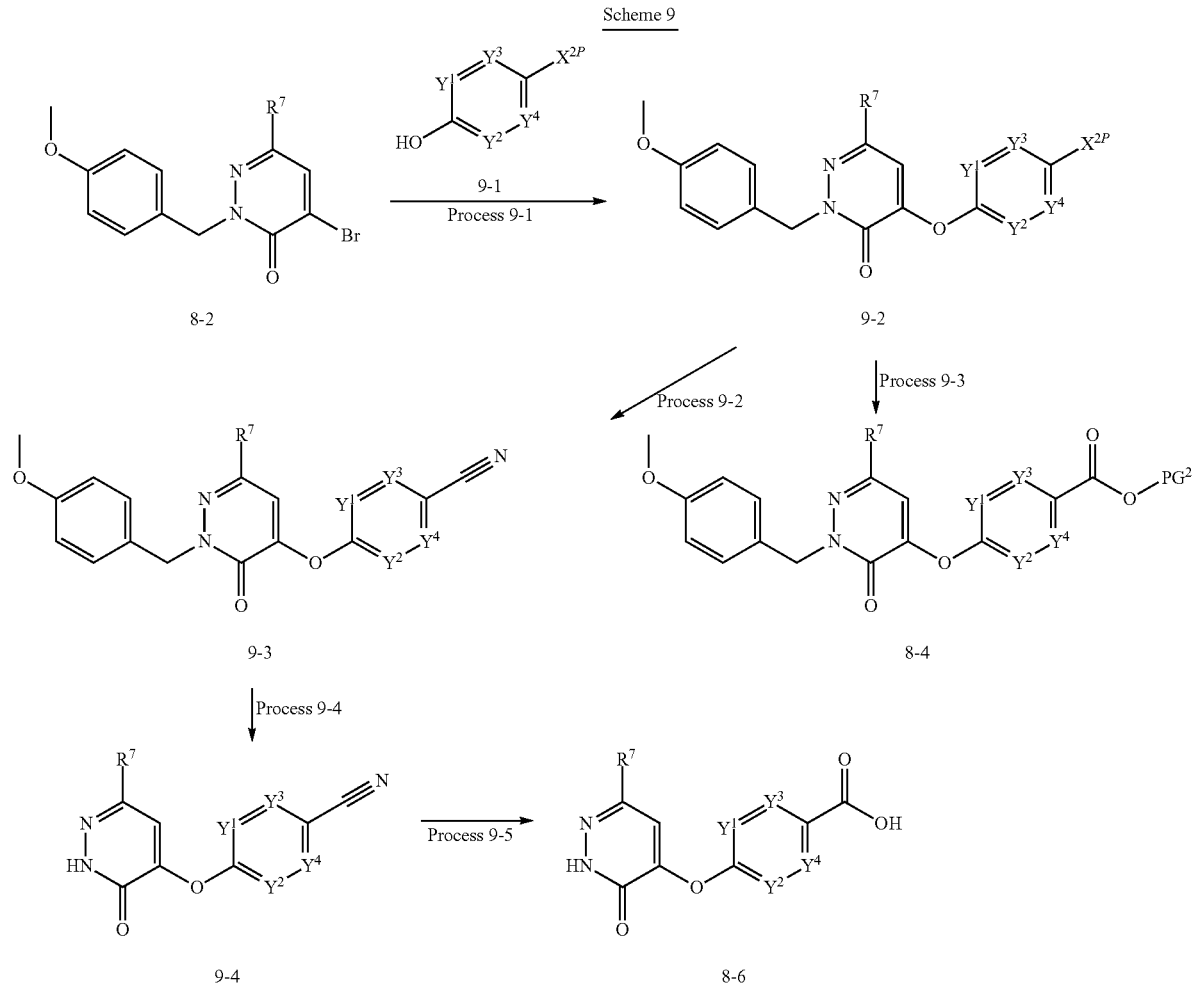

In the formulae, $Y^1$, $Y^2$, $Y^3$, $Y^4$, $R^7$ and $PG^2$ have the same meanings as defined above. $X^{2P}$ is a chlorine atom, a bromine atom, an iodine atom or a trifluoromethanesulfonyloxy group.

Process 9-1

Compound (9-2) can also be prepared by reacting Compound (8-2) with Compound (9-1) in an inert solvent in the presence of a base. As the inert solvent, DMF, DMA and the like can be illustrated. As the base, potassium carbonate and the like can be illustrated. The reaction temperature is usually at 0° C. to reflux temperature. The reaction time is usually from 30 minutes to 3 days, varying based on a used starting material, solvent, reaction temperature or the like. The reaction can also be conducted using a microwave reactor (Biotage).

Process 9-2

Compound (9-3) can also be prepared by conducting coupling reaction of Compound (9-2) with an inorganic cyanide in an inert solvent in the presence or absence of a palladium catalyst. As the inert solvent, DMF, DMA, NMP, THF, 1,4-dioxane, toluene, a mixed solvent thereof and the like can be illustrated. As the palladium catalyst, tetrakis(triphenylphosphine)palladium(0) and the like can be illustrated. As the inorganic cyanide, zinc cyanide, copper cyanide and the like can be illustrated. The reaction temperature is usually at 0° C. to reflux temperature. The reaction time is usually from 30 minutes to 3 days, varying based on a used starting material, solvent, reaction temperature or the like. The reaction can also be conducted using a microwave reactor (Biotage).

Process 9-3

Compound (8-4) can also be prepared by conducting coupling reaction of Compound (9-2) under a carbon monoxide atmosphere in an inert solvent in the presence of alcohol, a base and a palladium catalyst. As the inert solvent, DMF, DMA, NMP, THF, 1,4-dioxane, toluene, a mixed solvent thereof and the like can be illustrated. As the alcohol, methanol, ethanol and the like can be illustrated. As the base, triethylamine, DIPEA and the like can be illustrated. As the palladium catalyst, [1,1-bis(diphenylphosphino)ferrocene]dichloropalladium (II) and the like can be illustrated. An additive such as 1,1'-bis(diphenylphosphino)ferrocene and DMAP may be used, if necessary. The reaction temperature is usually at 0° C. to reflux temperature. The reaction time is usually from 30 minutes to 3 days, varying based on a used starting material, solvent, reaction temperature or the like.

Process 9-4

Compound (9-4) can also be prepared by reacting Compound (9-3) with CAN in an inert solvent. As the inert solvent, acetonitrile, water, a mixed solvent thereof and the like can be illustrated. The reaction temperature is usually at 0° C. to reflux temperature. The reaction time is usually from 30 minutes to 3 days, varying based on a used starting material, solvent, reaction temperature or the like.

Process 9-5

Compound (8-6) can also be prepared by acidic hydrolysis of Compound (9-4) in an inert solvent. As the inert solvent, water, methanol, ethanol, a mixed solvent thereof and the like can be illustrated. As the acid, hydrogen chloride and the like can be illustrated. The reaction temperature is usually at 0° C. to reflux temperature. The reaction time is usually from 30 minutes to 7 days, varying based on a used starting material, solvent, reaction temperature or the like. Compound (8-6) can also be prepared by alkaline hydrolysis instead of acidic hydrolysis.

The above-mentioned schemes are exemplary methods for preparing the compounds represented by the formula (I) or synthetic intermediates thereof. The above schemes can be changed or modified into schemes which a person ordinarily skilled in the art can easily understand.

In the above-mentioned schemes, when a protective group is necessary based on the kind of a functional group, operations of introduction and removal can also be conducted optionally in combination according to a general method. Examples regarding the types of protecting groups, protection and deprotection include the methods described in Theodora W. Greene & Peter G. M. Wuts Eds., "Greene's Protective Groups in Organic Synthesis," fourth edition, Wiley-Interscience, 2006.

When reaction is conducted using a microwave reactor in the above-mentioned schemes, the reaction can be conducted under the conditions of pressure range: 1 to 30 bar, power range: 1 to 400 W, reaction temperature: room temperature to 300° C., and reaction time: a minute to 1 day, varying based on a used starting material, solvent, model or the like.

The compounds represented by the formula (I) and synthetic intermediates thereof can also be isolated and purified, if required, according to isolation and purification techniques well known to a person ordinarily skilled in the art, such as solvent extraction, crystallization, recrystallization, chromatography, preparative high performance liquid chromatography or the like.

The compounds of the present invention have an excellent CGRP receptor antagonist activity, and thus can be used as agents for the prevention or treatment of various diseases mediated by CGRP receptors. The compounds of the present invention can be used, for example, as agents for the treatment of "primary headaches" including migraine, tension-type headache (TTH), trigeminal autonomic cephalalgias (TACs) and other primary headache disorders. The compounds of the present invention can also be used, for example, as agents for the treatment of "secondary headaches" (headache attributed to trauma or injury to the head and/or neck; headache attributed to cranial or cervical vascular disorder; headache attributed to non-vascular intracranial disorder; headache attributed to a substance or its withdrawal; headache attributed to infection; headache attributed to disorder of homoeostasis; headache or facial pain attributed to disorder of the cranium, neck, eyes, ears, nose, paranasal sinuses, teeth, mouth or other facial or cervical structure; and headache attributed to psychiatric disorder), "painful cranial neuropathies, other facial pain", "other headache disorders" and the like. The above headaches can also be classified by the international classification of headache disorders, 3rd edition, beta (ICHD-3 beta).

In an embodiment, the compounds of the present invention can also be used as agents for the treatment of acute migraine. When used as an agent for the treatment of acute migraine, the compounds of the present invention can be administered when headache occurs. When the effect is insufficient, the compounds of the present invention can be administered additionally In the present invention, the treatment of migraine includes the preventive treatment of migraine (suppressing the onset of migraine) in addition to the treatment of acute migraine. When used as an agent for the preventive treatment, the compounds of the present invention can be administered to a patient with migraine for suppressing the onset of migraine.

In an embodiment, the compounds of the present invention are also useful as agents for both the treatment of acute migraine and the preventive treatment of migraine in particular. The compounds of the present invention are also expected to be useful as agents for the treatment of cluster headache or headache attributed to overuse of a drug (medication-overuse headache, MOH).

In an embodiment, due to the excellent CGRP receptor antagonist activity, the compounds of the present invention can also be used as agents for the treatment of photophobia and light aversion (see JP-T-2014-515375, the term "JP-T" as used herein means a published Japanese translation of a PCT patent application); neuropathic pain and allodynia (see JP-T-2014-517699); bladder pain and interstitial cystitis (see JP-A-2011-046710); irritable bowel syndrome (IBS) (see JP-T-2014-517699); overactive bladder (see JP-T-2014-517699); diarrhea (see JP-T-2014-517845); or osteoarthritis (OA) (see JP-T-2013-532143).

The CGRP receptor antagonist activity of the compounds of the present invention can be determined according to well-known methods in the art. For example, assay of binding affinity for a CGRP receptor, functional assay of a CGRP receptor (cAMP activity assay), an evaluation of facial blood flow in marmoset and the like can be illustrated. A sustainability of medicinal effect (lasting antagonist activity) of the compounds of the present invention can also be determined according to well-known in vivo PD analysis methods in the art and the like.

The pharmaceutical composition of the present invention is used in various dosage forms depending on their usages. As such dosage forms, for example, powders, granules, fine granules, dry syrups, tablets, capsules, injections, liquids, ointments, suppositories and poultices can be illustrated, and the pharmaceutical composition is administered orally or parenterally.

The pharmaceutical composition of the present invention comprises a compound represented by the formula (I) or a pharmaceutically acceptable salt thereof as an active ingredient.

The pharmaceutical composition of the present invention can be prepared by using a compound represented by the formula (I) or a pharmaceutically acceptable salt thereof and at least one pharmaceutical additive. The pharmaceutical composition of the present invention can be prepared by appropriately admixing, diluting or dissolving using appropriate pharmaceutical additives such as excipients, disintegrants, binders, lubricants, diluents, buffers, tonicity agents, preservatives, wetting agents, emulsifying agents, dispersing agents, stabilizing agents, solubilizing agents and the like, according to a well-known formulation procedure depending upon the dosage form.

When the pharmaceutical composition of the present invention is used in the treatment, a dosage of a compound represented by the formula (I) or a pharmaceutically acceptable salt thereof as the active ingredient is appropriately decided depending on the age, sex, body weight, degree of disorders and treatment of each patient and the like. The dosage for an adult can be decided within the range of, for example, 0.1 to 1000 mg per day, 0.01 to 100 mg per day, 0.1 to 100 mg per day or 1 to 100 mg per day in the case of oral administration, and the daily dose can be divided into one, two, three or four times per day and administered. The dosage for an adult can be decided within the range of, for example, 0.1 to 1000 mg per day, 0.01 to 100 mg per day, 0.1 to 100 mg per day or 0.1 to 10 mg per day in the case of parenteral administration, and the daily dose can be divided into one, two, three or four times per day and administered.

In an embodiment, a compound represented by a formula (I) or the pharmaceutically acceptable salt thereof can also be used in combination with any other medicament other than CGRP receptor antagonists. As such other medicaments used in combination for the treatment of acute migraine, for example, acetaminophen, nonsteroidal anti-inflammatory drugs (NSAIDs), ergotamine formulation, triptans, anti-emetic agents, sedative/anesthetic agents, corticosteroids and the like can be illustrated. As such other medicaments used in combination for the preventive treatment of migraine, for example, antiepileptic agents, antidepressive agents, beta-blockers, calcium antagonists, angiotensin receptor antagonists (ARBs)/angiotensin-converting enzyme inhibitors (ACE) and the like can be illustrated.

When a compound represented by the formula (I) or a pharmaceutically acceptable salt thereof is used in combination with the other medicament, it can be administered as a formulation comprising these active ingredients or as formulations each of which is separately formulated from each active ingredient. When separately formulated, these formulations can be administered separately or concurrently. Furthermore, the dosage of the compound represented by the formula (I) or a pharmaceutically acceptable salt thereof can be appropriately reduced depending on the dosage of the other medicaments used in combination.

The compounds represented by the formula (I) may be each converted to a prodrug appropriately and be used. For example, a prodrug of a compound represented by the formula (I) can also be prepared by introducing an appropriate group forming a prodrug into any one or more groups selected from hydroxy or amino of the formula (I) using a corresponding reagent to produce a prodrug such as a halide compound in the usual way, and then suitably isolating and purifying in the usual way as occasion demands. As a group forming a prodrug, for example, a group described in "Development of medicine" 1990, Vol. 7, p. 163-198, published by Hirokawa Shoten can be illustrated.

EXAMPLES

The present invention is further illustrated in more detail by way of the following Examples. However, the present invention is not limited thereto.

Reference Example 1-1-A (2R)-2-{[(tert-butoxy)carbonyl]amino}-5-(3-fluorophenyl)-5-oxopentanoic acid ethyl To a solution of (R)-1-(tert-butoxycarbonyl)-5-oxopyrrolidine-2-carboxylic acid ethyl (12.86 g) in THF (260 mL) was added dropwise 3-fluorophenylmagnesium bromide (1.0 mol/L, THF) (100 mL) under an argon atmosphere at −40° C., and the mixture was stirred at the same temperature for 1 hour. To the reaction mixture were added a saturated aqueous solution of ammonium chloride and water. After stirring at room temperature for 2 hours, the mixture was extracted with ethyl acetate. The aqueous layer was extracted with ethyl acetate, and then the extract was combined with the above organic layer. The organic layer was dried over anhydrous magnesium sulfate, and concentrated under reduced pressure. The residue was purified by column chromatography on silica gel (eluent: n-hexane/ethyl acetate=90/10-60/40) to give the title compound (16.76 g).

Reference Example 1-1-B (2R,5S)-5-(3-fluorophenyl)pyrrolidine-2-carboxylic acid ethyl To a solution of Reference Example 1-1-A (16.76 g) in ethyl acetate (80 mL) was added hydrogen chloride in ethyl acetate (4 mol/L, 80 mL) at room temperature, and the mixture was stirred for 1.5 hours. The reaction mixture was concentrated under reduced pressure. The residue was diluted with ethyl acetate, and a saturated aqueous solution of sodium bicarbonate and water were added to the mixture. The organic layer was separated. The aqueous layer was extracted twice with ethyl acetate, and then the extract was combined with the above organic layer. The organic layer was washed with brine, dried over anhydrous magnesium sulfate, and concentrated under reduced pressure to give crude (2R)-5-(3-fluorophenyl)-3,4-dihydro-2H-pyrrole-2-carboxylic acid ethyl (11.47 g). To a solution of the obtained compound in ethanol (140 mL) was added platinum on carbon (5%, 1.10 g) under ice-cooling. The mixture was stirred under a hydrogen atmosphere at room temperature for 13 hours. The reaction mixture was filtered through Celite (registered trademark), and the filtrate was concentrated under reduced pressure. The residue was purified by column chromatography on silica gel (eluent: n-hexane/ethyl acetate=53/47-32/68) to give the title compound (8.86 g).

Reference Example 1-1-C (2R,5S)-1-(tert-butoxycarbonyl)-5-(3-fluorophenyl)pyrrolidine-2-carboxylic acid ethyl To a solution of Reference Example 1-1-B (8.86 g) and triethylamine (7.81 mL) in THF (110 mL) was added di-tert-butyl dicarbonate (8.97 g) in THF (10 mL), and the mixture was stirred at room temperature for 16 hours. The reaction mixture was concentrated under reduced pressure. The residue was purified by column chromatography on amino-silica gel (eluent: n-hexane/ethyl acetate=90/10-50/50) to give the title compound (12.63 g).

Reference Example 1-1-D

2-[(2R,5S)-5-(3-Fluorophenyl)pyrrolidin-2-yl]propan-2-ol hydrochloride

To a solution of Reference Example 1-1-C (2.0 g) in THF (40 mL) was added methylmagnesium bromide (3.0 mol/L, diethyl ether) (10 mL) under an argon atmosphere under ice-cooling, and the mixture was stirred at room temperature for 1 hour. To the reaction mixture were added a saturated aqueous solution of ammonium chloride and water. The mixture was extracted with ethyl acetate. The organic layer was dried over anhydrous sodium sulfate, and concentrated under reduced pressure to give crude (2S,5R)-2-(3-fluorophenyl)-5-(2-hydroxypropan-2-yl)pyrrolidin-1-carboxylic acid tert-butyl (2.33 g). To a solution of the obtained compound in ethyl acetate (10 mL) was added hydrogen chloride in ethyl acetate (4 mol/L, 20 mL), and the mixture was stirred at room temperature for 1 hour. The reaction mixture was concentrated under reduced pressure to give the crude title compound (1.66 g). MS (ESI_APCI, m/z): 224 (M+H)$^+$

Reference Example 1-2-A tert-Butyl (2S,5R)-2-(3-fluorophenyl)-5-[methoxy(methyl)carbamoyl]pyrrolidine-1-carboxylate To a suspension of Reference Example 1-1-C (600 mg) and N,O-dimethylhydroxylamine hydrochloride (347 mg) in THF (10 mL) was added isopropylmagnesium chloride (2.0 mol/L, THF) (3.56 mL) under an argon atmosphere at −15° C., and the mixture was stirred at the same temperature for 40 minutes. To the reaction mixture were added a saturated aqueous solution of ammonium chloride and water. The mixture was extracted with ethyl acetate. The organic layer was washed with brine, dried over anhydrous magnesium sulfate, and concentrated under reduced pressure to give the crude title compound (542 mg).

Reference Example 1-2-B tert-Butyl (2R,5 S)-2-acetyl-5-(3-fluorophenyl)pyrrolidine-1-carboxylate To a solution of Reference Example 1-2-A (542 mg) in THF (8 mL) was added methylmagnesium bromide (3.0 mol/L, diethyl ether) (1.02 mL) under an argon atmosphere under ice-cooling, and the mixture was stirred at room temperature for 1.5 hours. To the reaction mixture were added a saturated aqueous solution of ammonium chloride and water. The mixture was extracted with ethyl acetate. The organic layer was washed with brine, dried over anhydrous magnesium sulfate, and concentrated under reduced pressure to give the crude title compound (497 mg).

Reference Example 1-2-C tert-Butyl (2S,5R)-2-(3-fluorophenyl)-5-(prop-1-en-2-yl)pyrrolidine-1-carboxylate To a suspension of methyltriphenylphosphonium bromide (4.07 g) in THF (22 mL) was added dropwise a solution of potassium bis(trimethylsilyl)amide (1.0 mol/L, THF) (10.9 mL) at room temperature, and the mixture was stirred at room temperature for 1 hour. To the reaction mixture was added dropwise a solution of Reference Example 1-2-B (1.40 g) in THF (5 mL) under ice-cooling. The mixture was stirred under ice-cooling for 1 hour and stirred at room temperature for 2 hours. To the reaction mixture were added a saturated aqueous solution of ammonium chloride and water under ice-cooling. The mixture was extracted twice with ethyl acetate. The combined organic layer was washed with brine, dried over anhydrous magnesium sulfate, and concentrated under reduced pressure. The residue was purified by column chromatography on silica gel (eluent: n-hexane/ethyl acetate=100/0-85/15) to give the title compound (1.25 g).

Reference Example 1-2-D (2S,5R)-2-(3-Fluorophenyl)-5-(propan-2-yl)pyrrolidine To a solution of Reference Example 1-2-C (40.0 mg) in methanol (0.6 mL) and THF (0.6 mL) was added platinum on carbon (5%, 4.0 mg) under ice-cooling. The mixture was stirred under a hydrogen atmosphere at room temperature for 4 hours. The reaction mixture was filtered through Celite. The filtrate was concentrated under reduced pressure to give crude tert-butyl (2S,5R)-2-(3-fluorophenyl)-5-(propan-2-yl)pyrrolidine-1-carboxylate (40.4 mg). The mixture of the obtained compound and hydrogen chloride in 1,4-dioxane (4 mol/L, 0.8 mL) was stirred at room temperature for 1.5 hours. The reaction mixture was concentrated under reduced pressure. To the residue was added a saturated aqueous solution of sodium bicarbonate, and the mixture was extracted with dichloromethane. The organic layer was concentrated under reduced pressure to give the crude title compound (27.0 mg). MS (ESI_APCI, m/z): 208 (M+H)$^+$

Reference Example 1-3-A 1,1,2,2-Tetramethyl-1,2-ethanediamino-N,N'-bis(3,5-di-tert-butylsalicylidene)-cobalt (II)

A suspension of N,N'-bis(3,5-di-tert-butylsalicylidene)-1,1,2,2-tetramethylethylenediamine (500 mg) in ethanol (20 mL) was refluxed under an argon atmosphere for 10 minutes. To the mixture was added cobalt (II) acetate (161 mg), and then the mixture was refluxed for 2 hours. The mixture was allowed to cool to room temperature and then the precipitate was collected by filtration. The obtained solid was washed with ethanol, and dried under reduced pressure to give the title compound (303 mg). Reference literature: Gaspar, Boris; Carreira, Erick M., Angew. Chem. Int. Ed. 2007, 46, 4519-4522

Reference Example 1-3-B tert-Butyl (2R,5S)-2-(1-cyano-1-methylethyl)-5-(3-fluorophenyl)pyrrolidine-1-carboxylate To a solution of Reference Example 1-3-A (0.179 g) in ethanol (20 mL) were added a solution of Reference Example 1-2-C (3.0 g) in ethanol (80 mL) and p-toluenesulfonyl cyanide (5.34 g). To the mixture was added phenylsilane (1.57 mL) under an argon atmosphere. The reaction mixture was stirred at room temperature for 4 hours, and then to the reaction mixture were added a saturated aqueous solution of ammonium chloride and water under ice-cooling.

The mixture was stirred at room temperature for 40 minutes, and then the mixture was filtered through Celite. The filtrate was concentrated under reduced pressure. The residue was extracted twice with ethyl acetate. The combined organic layer was washed with brine, dried over anhydrous magnesium sulfate, and concentrated under reduced pressure. The residue was purified by column chromatography on silica gel (eluent: n-hexane/ethyl acetate=100/0-80/20) to give the title compound (2.20 g).

Reference Example 1-3-C

2-[(2R,5S)-5-(3-Fluorophenyl)pyrrolidin-2-yl]-2-methylpropanenitrile

To a solution of Reference Example 1-3-B (2.85 g) in dichloromethane (15 mL) was added trifluoroacetic acid (15 mL), and the mixture was stirred for 3 hours. The reaction mixture was concentrated under reduced pressure. The residue was diluted with dichloromethane and water. To the mixture was added potassium carbonate to basify the aqueous layer. The organic layer was separated. The aqueous layer was extracted with dichloromethane, and then the extract was combined with the above organic layer. The organic layer was dried over anhydrous sodium sulfate, and concentrated under reduced pressure. The residue was purified by column chromatography on silica gel (eluent: n-hexane/ethyl acetate=90/10-70/30) to give the title compound (1.54 g). MS (ESI_APCI, m/z): 233 (M+H)$^+$ Reference Example 1-4-A tert-Butyl (2S,5R)-2-(3-fluorophenyl)-5-[2-(methylsulfanyl)propan-2-yl]pyrrolidine-1-carboxylate To a solution of Reference Example 1-3-A (3.1 mg) in ethanol (0.5 mL) were added Reference Example 1-2-C (50 mg), 4-methylbenzene sulfonothioic acid S-methyl (105 mg) and phenylsilane (0.028 mL) under an argon atmosphere successively, and the mixture was stirred for 2 hours. To the reaction mixture was added brine, and the mixture was extracted with ethyl acetate. The organic layer was dried over anhydrous magnesium sulfate, and concentrated under reduced pressure. The residue was purified by column chromatography on silica gel (eluent: n-hexane/ethyl acetate=100/0-85/15) to give the title compound (46.2 mg).

Reference Example 1-4-B (2S,5R)-2-(3-Fluorophenyl)-5-[2-(methylsulfanyl)propan-2-yl]pyrrolidine The mixture of Reference Example 1-4-A (44.0 mg) and hydrogen chloride in 1,4-dioxane (4 mol/L, 0.5 mL) was stirred at room temperature for 1.5 hours. To the reaction mixture was added a saturated aqueous solution of sodium bicarbonate, and the mixture was extracted with dichloromethane. The organic layer was concentrated under reduced pressure. The residue was purified by column chromatography on silica gel (eluent: n-hexane/ethyl acetate=100/0-80/20) to give the title compound (14.6 mg). MS (ESI_APCI, m/z): 254 (M+H)$^+$ Reference Example 1-5-A Ethyl (2R)-2-{[(tert-butoxy)carbonyl]amino}-5-(3-chlorophenyl)-5-oxopentanoate To a solution of 1-chloro-3-iodobenzene (2.89 mL) in THF (60 mL) was added dropwise isopropylmagnesium chloride (2.0 mol/L, THF) (11.6 mL) under an argon atmosphere at −40° C., and the mixture was stirred at the same temperature for 15 minutes. To the reaction mixture was added dropwise a solution of ethyl (R)-1-(tert-Butoxycarbonyl)-5-oxopyrrolidine-2-carboxylate (3.0 g) in THF (20 mL) at −40° C., and the mixture was stirred at the same temperature for 1 hour. To the reaction mixture were added a saturated aqueous solution of ammonium chloride and water. The mixture was stirred at room temperature for 3 hours, and then extracted twice with ethyl acetate. The combined organic layer was dried over anhydrous magnesium sulfate, and concentrated under reduced pressure. The residue was purified by column chromatography on silica gel (eluent: n-hexane/ethyl acetate=90/10-60/40) to give the title compound (3.97 g).

Reference Example 1-5-B

Ethyl (2R,5S)-5-(3-chlorophenyl)pyrrolidine-2-carboxylate

The title compound was prepared in a similar manner to that described in Reference Example 1-1-B using Reference Example 1-5-A instead of Reference Example 1-1-A.

Reference Example 1-5-C

Ethyl (2R,5 S)-1-(tert-butoxycarbonyl)-5-(3-chlorophenyl)pyrrolidine-2-carboxylate The title compound was prepared in a similar manner to that described in Reference Example 1-1-C using Reference Example 1-5-B instead of Reference Example 1-1-B.

Reference Example 1-5-D

2-[(2R,5 S)-5-(3-Chlorophenyl)pyrrolidin-2-yl]propan-2-ol hydrochloride

To a solution of Reference Example 1-5-C (200 mg) in THF (3 mL) was added methylmagnesium bromide (3.0 mol/L, diethyl ether) (0.376 mL) under an argon atmosphere under ice-cooling. The mixture was stirred under ice-cooling for 30 minutes. To the reaction mixture was added a saturated aqueous solution of ammonium chloride, and the mixture was extracted with ethyl acetate. The organic layer was dried over anhydrous magnesium sulfate, and concentrated under reduced pressure to give crude tert-butyl (2S,5R)-2-(3-chlorophenyl)-5-(2-hydroxypropan-2-yl)pyrrolidine-1-carboxylate (220 mg). The mixture of the obtained compound (156 mg) and hydrogen chloride in 1,4-dioxane (4 mol/L, 1 mL) was stirred at room temperature for 1 hour. The reaction mixture was concentrated under reduced pressure to give the crude title compound (125 mg). MS (ESI_APCI, m/z): 240 (M+H)$^+$ Reference Example 1-6-A tert-Butyl (2S,5R)-2-(3-chlorophenyl)-5-[methoxy(methyl)carbamoyl]pyrrolidine-1-carboxylate The title compound was prepared in a similar manner to that described in Reference Example 1-2-A using Reference Example 1-5-C instead of Reference Example 1-1-C.

Reference Example 1-6-B tert-Butyl (2S,5R)-2-(3-chlorophenyl)-5-ethenylpyr-rolidine-1-carboxylate To a solution of Reference Example 1-6-A (300 mg) in THF (6 mL) was added LAH (37.0 mg) under an argon atmosphere under ice-cooling, and the mixture was stirred under ice-cooling for 1 hour. To the reaction mixture were added THF (6 mL) and sodium sulfate decahydrate (3.0 g) successively under ice-cooling. The mixture was stirred at room temperature for 1 hour, and then the mixture was filtered. The filtrate was concentrated under reduced pressure to give crude tert-butyl (2S,5R)-2-(3-chlorophenyl)-5-formylpyrrolidine-1-carboxylate (288 mg). To a suspension of methyltriphenylphosphonium bromide (639 mg) in THF (6.4 mL) was added n-butyllithium (1.63 mol/L, n-hexane) (1.0 mL) under ice-cooling. The mixture was stirred under ice-cooling for 15 minutes. To the mixture was added a solution of the obtained crude tert-butyl (2S,5R)-2-(3-chlorophenyl)-5-formylpyrrolidine-1-carboxylate in THF (1.6 mL). The mixture was stirred under ice-cooling for 10 minutes, and then stirred at room temperature for 40 minutes. To the reaction mixture was added water, and the mixture was extracted with dichloromethane. The organic layer was concentrated under reduced pressure. The residue was purified by column chromatography on silica gel (eluent: n-hexane/ethyl acetate=95/5-80/20) to give the title compound (99.1 mg).

Reference Example 1-6-C tert-Butyl (2S,5R)-2-(3-chlorophenyl)-5-(1-cyano-ethyl)pyrrolidine-1-carboxylate To a solution of Reference Example 1-6-B (99 mg) in ethanol (2 mL) were added p-toluenesulfonyl cyanide (185 mg), phenylsilane (0.051 mL) and Reference Example 1-3-A (5.9 mg) successively under an argon atmosphere, and the mixture was stirred at room temperature for 4 hours. The reaction mixture was concentrated under reduced pressure. The residue was purified by column chromatography on silica gel (eluent: n-hexane/ethyl acetate=95/5-65/35) to give a diastereomeric mixture of the title compound (89.7 mg).

Reference Example 1-6-D

2-[(2R,5S)-5-(3-Chlorophenyl)pyrrolidin-2-yl]pro-panenitrile

The mixture of Reference Example 1-6-C (89.7 mg) and hydrogen chloride in 1,4-dioxane (4 mol/L, 2 mL) was stirred at room temperature for 1 hour. The reaction mixture was concentrated under reduced pressure. To the residue were added a saturated aqueous solution of sodium bicarbonate and water. The mixture was extracted with dichloromethane. The organic layer was concentrated under reduced pressure to give a diastereomeric mixture of the crude title compound (55.6 mg). MS (ESI_APCI, m/z): 235 (M+H)$^+$

Reference Example 1-7-A tert-Butyl (2R,5 S)-2-acetyl-5-(3-chlorophenyl)pyr-rolidine-1-carboxylate The title compound was prepared in a similar manner to that described in Reference Example 1-2-B using Reference Example 1-6-A instead of Reference Example 1-2-A.

Reference Example 1-7-B tert-Butyl (2S,5R)-2-(3-chlorophenyl)-5-(prop-1-en-2-yl)pyrrolidine-1-carboxylate The title compound was prepared in a similar manner to that described in Reference Example 1-2-C using Reference Example 1-7-A instead of Reference Example 1-2-B.

Reference Example 1-7-C tert-Butyl (2S,5R)-2-(3-chlorophenyl)-5-(1-cyano-1-methylethyl)pyrrolidine-1-carboxylate To a solution of Reference Example 1-7-B (1.58 g) in ethanol (50 mL) were added Reference Example 1-3-A (0.089 g) and p-toluenesulfonyl cyanide (2.67 g). To the mixture was added phenylsilane (0.79 mL) under an argon atmosphere. The reaction mixture was stirred at room temperature for 2 hours, and then to the reaction mixture were added a saturated aqueous solution of ammonium chloride and water. The mixture was stirred at room temperature for 20 minutes, and then the mixture was filtered through Celite. The filtrate was concentrated under reduced pressure. The residue was extracted twice with ethyl acetate. The combined organic layer was washed with brine, dried over anhydrous magnesium sulfate, and concentrated under reduced pressure. The residue was purified by column chromatography on silica gel (eluent: n-hexane/ethyl acetate=100/0-80/20) to give the title compound (1.39 g).

Reference Example 1-7-D

2-[(2R,5S)-5-(3-Chlorophenyl)pyrrolidin-2-yl]-2-methylpropanenitrile

To a solution of Reference Example 1-7-C (1.39 g) in dichloromethane (8 mL) was added trifluoroacetic acid (8 mL), and the mixture was stirred for 1 hour. The reaction mixture was concentrated under reduced pressure. The residue was diluted with dichloromethane and water. To the mixture was added potassium carbonate to basify the aqueous layer. The organic layer was separated. The aqueous layer was extracted with dichloromethane, and then the extract was combined with the above organic layer. The organic layer was dried over anhydrous sodium sulfate, and concentrated under reduced pressure. The residue was purified by column chromatography on silica gel (eluent: n-hexane/ethyl acetate=90/10-70/30) to give the title compound (0.758 g). MS (ESI_APCI, m/z): 249 (M+H)$^+$

Reference Example 1-8-A

3-[2-(3-Chlorophenyl)-1,3-dioxolan-2-yl]propan-1-ol

A solution of 4-(3-chlorophenyl)-4-oxobutanoic acid (500 mg), ethylene glycol (1.30 mL) and p-toluenesulfonic acid monohydrate (44.7 mg) in toluene (10 mL) was refluxed for 80 minutes using Dean-Stark apparatus. The reaction mixture was allowed to cool to room temperature and then to the reaction mixture were added a saturated aqueous solution of ammonium chloride and water. The mixture was extracted twice with ethyl acetate. The combined organic layer was dried over anhydrous magnesium sulfate, and concentrated under reduced pressure. The residue was dissolved in THF (10 mL). To the mixture was added portionwise LAH (179 mg) under ice-cooling, and the mixture was stirred under ice-cooling for 20 minutes. The reaction mixture was diluted with THF (10 mL). To the mixture was added portionwise sodium sulfate decahydrate (1.0 g) under ice-cooling. The mixture was stirred at room temperature for 30 minutes, and then the mixture was filtered. The filtrate was concentrated under reduced pressure. To the residue was added water. The mixture was extracted twice with ethyl acetate. The combined organic layer was dried over anhydrous magnesium sulfate, and concentrated under reduced pressure to give the crude title compound (549 mg).

Reference Example 1-8-B (S)—N-{3-[2-(3-Chlorophenyl)-1,3-dioxolan-2-yl]propylidene}-2-methylpropane-2-sulfinamide To a solution of Reference Example 1-8-A (549 mg), TEMPO (7.1 mg) and tetrabutylammonium hydrogen sulfate (15.4 mg) in dichloromethane (5.5 mL) was added sodium hypochlorite pentahydrate (410 mg) under an argon atmosphere under ice-cooling, and the mixture was stirred under ice-cooling for 1 hour. To the reaction mixture were added an aqueous solution of sodium thiosulfate (1 mol/L), a saturated aqueous solution of sodium bicarbonate and water under ice-cooling. The mixture was stirred for several minutes, and then the mixture was extracted twice with dichloromethane. The combined organic layer was dried over anhydrous sodium sulfate, and concentrated under reduced pressure to give crude 3-[2-(3-chlorophenyl)-1,3-dioxolan-2-yl]propanal (580 mg). A solution of the obtained compound, (S)-(−)-2-methyl-2-propanesulfinamide (329 mg) and titanium(IV) ethoxide (0.725 mL) in THF (11 mL) was stirred under an argon atmosphere at room temperature for 3 hours. To the reaction mixture were added brine (1.1 mL) and ethyl acetate (11 mL). The mixture was stirred for 5 minutes, and then the mixture was filtered through Celite. The filtrate was concentrated under reduced pressure. The residue was purified by column chromatography on silica gel (eluent: n-hexane/ethyl acetate=80/20-50/50) to give the title compound (532 mg).

Reference Example 1-8-C (S)—N-[(1R)-3-[2-(3-Chlorophenyl)-1,3-dioxolan-2-yl]-1-(1-cyanocyclopropyl)propyl]-2-methylpropane-2-sulfinamide To a solution of lithium bis(trimethylsilyl)amide (1.0 mol/L, THF) (2.0 mL) in diethyl ether (6 mL) was added a solution of cyclopropanecarbonitrile (0.152 mL) in THF (1.2 mL) under an argon atmosphere under ice-cooling, and the mixture was stirred under ice-cooling for 10 minutes. To the reaction mixture was added a solution of Reference Example 1-8-B (200 mg) in THF (1.2 mL) under ice-cooling. The mixture was stirred under ice-cooling for 1 hour. To the reaction mixture were added a saturated aqueous solution of ammonium chloride, water and dichloromethane, and then the mixture was stirred. The organic layer was separated, and then concentrated under reduced pressure. The residue was purified by column chromatography on silica gel (eluent: n-hexane/ethyl acetate=60/40-0/100) to give the title compound (100 mg).

Reference Example 1-8-D

1-[(2R,5S)-5-(3-Chlorophenyl)pyrrolidin-2-yl]cyclopropane-1-carbonitrile

A solution of Reference Example 1-8-C (100 mg) in THF (1 mL) and concentrated hydrochloric acid (1 mL) was stirred at room temperature for 30 minutes. To the reaction mixture were added an aqueous solution of sodium hydroxide (5 mol/L, 2.5 mL) and dichloromethane under ice-cooling, and then the mixture was stirred. The organic layer was separated, and concentrated under reduced pressure to give crude 1-[(2R)-5-(3-chlorophenyl)-3,4-dihydro-2H-pyrrol-2-yl]cyclopropane-1-carbonitrile (53.7 mg). To a solution of the obtained compound in ethanol (2 mL) was added platinum on carbon (5%, 54.0 mg) under an argon atmosphere under ice-cooling. The mixture was stirred under a hydrogen atmosphere at room temperature for 4 hours. The reaction mixture was filtered through Celite, and the filtrate was concentrated under reduced pressure. The residue was purified by column chromatography on silica gel (eluent: n-hexane/ethyl acetate=90/10-60/40) to give the title compound (29.6 mg). MS (ESI_APCI, m/z): 247 (M+H)$^+$ Reference Example 1-9-A (S)—N-[(1R)-3-[2-(3-Chlorophenyl)-1,3-dioxolan-2-yl]-1-(1-cyanocyclobutyl)propyl]-2-methylpropane-2-sulfinamide The title compound was prepared in a similar manner to that described in Reference Example 1-8-C using cyclobutanecarbonitrile instead of cyclopropanecarbonitrile.

Reference Example 1-9-B

1-[(2R,5S)-5-(3-Chlorophenyl)pyrrolidin-2-yl]cyclobutane-1-carbonitrile

The title compound was prepared in a similar manner to that described in Reference Example 1-8-D using Reference Example 1-9-A instead of Reference Example 1-8-C. MS (ESI_APCI, m/z): 261 (M+H)$^+$ Reference Example 1-10-A Ethyl (2R)-5-(3,5-difluorophenyl)-3,4-dihydro-2H-pyrrole-2-carboxylate To a solution of 3,5-difluoroiodobenzene (1.12 g) in THF (8 mL) was added isopropylmagnesium chloride (2.0 mol/L, THF) (2.1 mL) under an argon atmosphere in ice salt bath, and the mixture was stirred in ice salt bath for 30 minutes. To the reaction mixture was added dropwise a solution of (R)-1-(tert-butoxycarbonyl)-5-oxopyrrolidine-2-carboxylic acid ethyl (0.546 g) in THF (13 mL) at −40° C., and the mixture was stirred at the same temperature for 1.5 hours. To the reaction mixture was added a saturated aqueous solution of ammonium chloride, and the mixture was extracted thrice with ethyl acetate. The combined organic layer was dried over anhydrous sodium sulfate, and concentrated under reduced pressure to give crude (2R)-2-{[(tert-butoxy)carbonyl]amino}-5-(3,5-difluorophenyl)-5-oxopentanoic acid ethyl (0.911 g). To a solution of the obtained compound in ethyl acetate (21 mL) was added hydrogen chloride in ethyl acetate (4 mol/L, 10.6 mL), and the mixture was stirred at room temperature for 3 hours. To the reaction mixture was added slowly a saturated aqueous solution of sodium bicarbonate, and the mixture was extracted thrice with ethyl acetate. The combined organic layer was dried over anhydrous sodium sulfate, and concentrated under reduced pressure. The residue was purified by column chromatography on amino-silica gel (eluent: n-hexane/ethyl acetate=95/5-70/30) to give the title compound (0.505 g).

Reference Example 1-10-B

Ethyl (2R,5 S)-5-(3,5-difluorophenyl)pyrrolidine-2-carboxylate

A mixture of Reference Example 1-10-A (505 mg), platinum on carbon (10%, wet) (50.0 mg) and ethanol (7 mL) was stirred under a hydrogen atmosphere at room temperature for 3 hours. The reaction mixture was filtered through Celite, and the filtrate was concentrated under reduced pressure. The residue was purified by column chromatography on silica gel (eluent: n-hexane/ethyl acetate=100/0-65/35) to give the title compound (390 mg).

Reference Example 1-10-C

Ethyl (2R,5 S)-1-(tert-butoxycarbonyl)-5-(3,5-difluorophenyl)pyrrolidine-2-carboxylate The title compound was prepared in a similar manner to that described in Reference Example 1-1-C using Reference Example 1-10-B instead of Reference Example 1-1-B.

Reference Example 1-10-D tert-Butyl (2S,5R)-2-(3,5-difluorophenyl)-5-[methoxy(methyl)carbamoyl]pyrrolidine-1-carboxylate The title compound was prepared in a similar manner to that described in Reference Example 1-2-A using Reference Example 1-10-C instead of Reference Example 1-1-C.

Reference Example 1-10-E tert-Butyl (2R,5 S)-2-acetyl-5-(3,5-difluorophenyl)pyrrolidine-1-carboxylate To a solution of Reference Example 1-10-D (531 mg) in THF (7 mL) was added methylmagnesium bromide (3.0 mol/L, diethyl ether) (1.43 mL) under an argon atmosphere under ice-cooling, and the mixture was stirred at room temperature for 30 minutes. To the reaction mixture was added a saturated aqueous solution of ammonium chloride, and the mixture was extracted thrice with ethyl acetate. The combined organic layer was dried over anhydrous sodium sulfate, and concentrated under reduced pressure. The residue was purified by column chromatography on silica gel (eluent: n-hexane/ethyl acetate=100/0-65/35) to give the title compound (444 mg).

Reference Example 1-10-F tert-Butyl (2S,5R)-2-(3,5-difluorophenyl)-5-(prop-1-en-2-yl)pyrrolidine-1-carboxylate The title compound was prepared in a similar manner to that described in Reference Example 1-2-C using Reference Example 1-10-E instead of Reference Example 1-2-B.

Reference Example 1-10-G tert-Butyl (2R,5S)-2-(1-cyano-1-methylethyl)-5-(3,5-difluorophenyl)pyrrolidine-1-carboxylate The title compound was prepared in a similar manner to that described in Reference Example 1-7-C using Reference Example 1-10-F instead of Reference Example 1-7-B.

Reference Example 1-10-H

2-[(2R,5S)-5-(3,5-Difluorophenyl)pyrrolidin-2-yl]-2-methylpropanenitrile

A mixture of Reference Example 1-10-G (278 mg), hydrogen chloride in ethyl acetate (4 mol/L, 4 mL) and ethyl acetate (4 mL) was stirred at room temperature for 5 hours. To the reaction mixture was added a saturated aqueous solution of sodium bicarbonate, and the mixture was extracted thrice with ethyl acetate. The combined organic layer was dried over anhydrous sodium sulfate, and concentrated under reduced pressure. The residue was purified by column chromatography on silica gel (eluent: n-hexane/ethyl acetate=100/0-70/30) to give the title compound (131 mg). MS (ESI_APCI, m/z): 251 (M+H)$^+$ Reference Example 2-1-A 3-Methyl-4-[(6-methyl-3-oxo-2,3-dihydropyridazin-4-yl)methyl]benzoic acid A mixture of 4,5-dihydro-6-methyl-3(2H)pyridazinone (8.35 g), methyl 4-formyl-3-methylbenzoate (13.27 g) and a solution of potassium hydroxide (12.54 g) in ethanol (446 mL) was stirred at 70° C. for 1 hour. The reaction mixture was acidified with hydrochloric acid (1 mol/L) under ice-cooling. The mixture was stirred under ice-cooling for 30 minutes, and then the precipitated solid was collected by filtration to give the title compound (6.98 g). MS (ESI_APCI, m/z): 259 (M+H)$^+$ Reference Example 2-2-A 4-Bromo-2-[(4-methoxyphenyl)methyl]-6-methyl-2,3-dihydropyridazin-3-one To a solution of 4-bromo-6-methyl-2H-pyridazine-3-one (31.12 g) in DMF (150 mL) were added potassium carbonate (34.13 g) and 4-methoxybenzyl chloride (24.66 mL), and the mixture was stirred at room temperature for 3 hours. To the reaction mixture was added water (310 mL) under ice-cooling. The mixture was stirred under ice-cooling for 1 hour, and the precipitated solid was collected by filtration. The obtained solid was washed with water, and dried under reduced pressure at 40° C. to give the title compound (44.95 g).

Reference Example 2-2-B

Methyl 3-fluoro-4-({2-[(4-methoxyphenyl)methyl]-6-methyl-3-oxo-2,3-dihydropyridazin-4-yl}oxy)benzoate A mixture of Reference Example 2-2-A (3.02 g), 3-fluoro-4-hydroxybenzoic acid methyl (6.65 g), potassium carbonate (8.10 g) and DMF (78 mL) was stirred under microwave irradiation at 150° C. for 30 minutes. To the reaction mixture was added water, and the mixture was extracted with ethyl acetate. The organic layer was washed with water, and then concentrated under reduced pressure. The residue was purified by column chromatography on silica gel (eluent: n-hexane/ethyl acetate=70/30-40/60) to give the title compound (2.25 g).

Reference Example 2-2-C

3-Fluoro-4-[(6-methyl-3-oxo-2,3-dihydropyridazin-4-yl)oxy]benzoic acid

A mixture of Reference Example 2-2-B (2.25 g), concentrated hydrochloric acid (18 mL) and acetic acid (15 mL) was stirred at 100° C. for 1 hour. To the reaction mixture were added dichloromethane and water. The mixture was stirred under ice-cooling for 1 hour, and the precipitated solid was collected by filtration. The obtained solid was washed with water, and dried under reduced pressure at 40° C. to give the title compound (0.942 g). MS (ESI_APCI, m/z): 265 (M+H)$^+$

Reference Example 2-3-A

Methyl 4-({2-[(4-methoxyphenyl)methyl]-6-methyl-3-oxo-2,3-dihydropyridazin-4-yl}oxy)-3-methylbenzoate A mixture of Reference Example 2-2-A (2.70 g), 4-hydroxy-3-methylbenzoic acid methyl (2.18 g), potassium carbonate (2.41 g) and DMF (70 mL) was stirred at 150° C. for 30 minutes. To the reaction mixture was added water, and the mixture was extracted with ethyl acetate. The organic layer was washed with water, and then concentrated under reduced pressure. The residue was purified by column chromatography on silica gel (eluent: n-hexane/ethyl acetate=70/30-40/60) to give the title compound (2.53 g).

Reference Example 2-3-B

3-Methyl-4-[(6-methyl-3-oxo-2,3-dihydropyridazin-4-yl)oxy]benzoic acid

A mixture of Reference Example 2-3-A (2.53 g), concentrated hydrochloric acid (22 mL) and acetic acid (18 mL) was stirred at 100° C. for 1 hour. The reaction mixture was allowed to cool to room temperature and then to the reaction mixture were added dichloromethane and water. The mixture was stirred under ice-cooling for 1 hour. The organic layer was separated, and then concentrated under reduced pressure. The residue was washed with diethyl ether to give the title compound (1.42 g). MS (ESI_APCI, m/z): 261 (M+H)$^+$

Reference Example 2-4-A

Ethyl 3-chloro-4-({2-[(4-methoxyphenyl)methyl]-6-methyl-3-oxo-2,3-dihydropyridazin-4-yl}oxy)benzoate A mixture of Reference Example 2-2-A (200 mg), 3-chloro-4-hydroxybenzoic acid ethyl (156 mg), potassium carbonate (215 mg) and DMF (4 mL) was stirred under microwave irradiation at 150° C. for 1 hour and at 160° C. for 1 hour. To the reaction mixture were added water and brine. The mixture was extracted with ethyl acetate. The organic layer was dried over anhydrous sodium sulfate, and concentrated under reduced pressure. The residue was purified by column chromatography on silica gel (eluent: n-hexane/ethyl acetate=90/10-50/50) to give the title compound (140 mg).

Reference Example 2-4-B

Ethyl 3-chloro-4-[(6-methyl-3-oxo-2,3-dihydropyridazin-4-yl)oxy]benzoate

To a solution of Reference Example 2-4-A (139 mg) in acetonitrile (8 mL) and water (1.6 mL) was added CAN (533 mg), and the mixture was stirred at room temperature for 3 hours. To the reaction mixture was added water, and the mixture was extracted with ethyl acetate. The organic layer was dried over anhydrous sodium sulfate, and concentrated under reduced pressure. The residue was purified by column chromatography on silica gel (eluent: n-hexane/ethyl acetate=70/30-20/80) to give the title compound (78.9 mg).

Reference Example 2-4-C

3-Chloro-4-[(6-methyl-3-oxo-2,3-dihydropyridazin-4-yl)oxy]benzoic acid

To a solution of Reference Example 2-4-B (78.9 mg) in THF (2 mL), methanol (1 mL) and water (0.115 mL) was added an aqueous solution of sodium hydroxide (2 mol/L, 0.385 mL), and the mixture was stirred at room temperature for 2 hours. To the reaction mixture was added hydrochloric acid (2 mol/L, 0.450 mL). The mixture was stirred at room temperature for 10 minutes, and then concentrated under reduced pressure. To the residue was added water (4 mL), and the suspension was filtered. The obtained solid was washed with water, and dried under reduced pressure at 60° C. to give the title compound (51.2 mg). MS (ESI_APCI, m/z): 281 (M+H)$^+$

Reference Example 2-5-A

4-[(6-Bromo-2-methylpyridin-3-yl)oxy]-2-[(4-methoxyphenyl)methyl]-6-methyl-2,3-dihydropyridazin-3-one A mixture of Reference Example 2-2-A (2.0 g), 6-bromo-2-methylpyridine-3-ol (1.28 g), potassium carbonate (1.79 g) and DMF (20 mL) was stirred at 150° C. for 1 hour. To the reaction mixture was added water, and the mixture was extracted twice with ethyl acetate. The combined organic layer was successively washed with water twice and brine, dried over anhydrous magnesium sulfate, and concentrated under reduced pressure. The residue was purified by column chromatography on amino-silica gel (eluent: n-hexane/ethyl acetate=70/30-40/60) to give the title compound (2.42 g).

Reference Example 2-5-B 5-({2-[(4-Methoxyphenyl)methyl]-6-methyl-3-oxo-2,3-dihydropyridazin-4-yl}oxy)-6-methylpyridine-2-carbonitrile A mixture of Reference Example 2-5-A (2.42 g), zinc cyanide (2.05 g), tetrakis(triphenylphosphine)palladium (0) (0.671 g) and DMF (30 mL) was stirred under an argon atmosphere at 120° C. for 1 hour. To the reaction mixture were added water and ethyl acetate. The mixture was filtered through Celite. To the filtrate was added water, and then the mixture was extracted with ethyl acetate. The organic layer was successively washed with water twice and brine, dried over anhydrous magnesium sulfate, and concentrated under reduced pressure. The residue was purified by column chromatography on silica gel (eluent: n-hexane/ethyl acetate=60/40-30/70) to give the title compound (1.83 g).

Reference Example 2-5-C

6-Methyl-5-[(6-methyl-3-oxo-2,3-dihydropyridazin-4-yl)oxy]pyridine-2-carbonitrile To a solution of Reference Example 2-5-B (1.83 g) in acetonitrile (25 mL) was added a solution of CAN (13.84 g) in water (25 mL), and the mixture was stirred at room temperature for 2 hours. To the reaction mixture was added water, and the mixture was extracted thrice with dichloromethane. The combined organic layer was washed with brine. To the aqueous layer was added an aqueous solution of sodium thiosulfate (1 mol/L), and the mixture was extracted with dichloromethane. The extract was washed with brine, and then combined with the above organic layer. The organic layer was dried over anhydrous sodium sulfate, and concentrated under reduced pressure. To the residue was added ethanol, and then the mixture was triturated. The obtained solid was collected by filtration, washed with ethanol, and dried under reduced pressure to give the title compound (0.743 g).

Reference Example 2-5-D

6-Methyl-5-[(6-methyl-3-oxo-2,3-dihydropyridazin-4-yl)oxy]pyridine-2-carboxylic acid A mixture of Reference Example 2-5-C (1.0 g) and concentrated hydrochloric acid (15 mL) was stirred at 100° C. for 3 hours. The mixture was allowed to cool to room temperature, and then an insoluble material was removed by filtration. The filtrate was concentrated under reduced pressure. To the residue were added water (25 mL) and an aqueous solution of sodium hydroxide (2 mol/L, 10 mL), and the mixture was stirred at room temperature for 1.5 hours. The precipitate was collected by filtration, washed with water, and dried under reduced pressure to give the title compound (618 mg). MS (ESI_APCI, m/z): 262 (M+H)$^+$ Reference Example 2-6-A 4-[(6-Bromo-4-methylpyridin-3-yl)oxy]-2-[(4-methoxyphenyl)methyl]-6-methyl-2,3-dihydropyridazin-3-one The title compound was prepared in a similar manner to that described in Reference Example 2-2-B using 6-bromo-4-methylpyridine-3-ol instead of 3-fluoro-4-hydroxybenzoic acid methyl.

Reference Example 2-6-B

Ethyl 5-({2-[(4-methoxyphenyl)methyl]-6-methyl-3-oxo-2,3-dihydropyridazin-4-yl}oxy)-4-methylpyridine-2-carboxylate A solution of Reference Example 2-6-A (1.24 g), [1,1'-bis(diphenylphosphino)ferrocene]dichloropalladium (II) dichloromethane complex (0.244 g), 1,1'-bis(diphenylphosphino)ferrocene (0.331 g), triethylamine (1.25 mL), DMAP (0.109 g) and ethanol (12.5 mL) in NMP (12.5 mL) was stirred at 110° C. under a carbon monoxide atmosphere overnight. To the reaction mixture were added [1,1-bis(diphenylphosphino)ferrocene]dichloropalladium (II) dichloromethane complex (0.244 g), 1,1'-bis(diphenylphosphino)ferrocene (0.331 g), triethylamine (1.25 mL) and DMAP (0.109 g), and the mixture was stirred at 110° C. under a carbon monoxide atmosphere for 4 hours. To the reaction mixture were added water and brine. The mixture was extracted with ethyl acetate. The organic layer was dried over anhydrous sodium sulfate, and concentrated under reduced pressure. The residue was purified by column chromatography on silica gel (eluent: n-hexane/ethyl acetate=50/50-10/90) to give the title compound (0.719 g).

Reference Example 2-6-C

Ethyl 4-methyl-5-[(6-methyl-3-oxo-2,3-dihydropyridazin-4-yl)oxy]pyridine-2-carboxylate To a solution of Reference Example 2-6-B (0.719 g) in acetonitrile (36 mL) and water (7.2 mL) was added CAN (2.89 g), and the mixture was stirred at room temperature overnight. To the reaction mixture were added water and a saturated aqueous solution of ammonium chloride. The mixture was extracted twice with ethyl acetate. The combined organic layer was dried over anhydrous sodium sulfate, and concentrated under reduced pressure. The residue was purified by column chromatography on silica gel (eluent: ethyl acetate/methanol=100/0-90/10) to give the title compound (0.433 g).

Reference Example 2-6-D

4-Methyl-5-[(6-methyl-3-oxo-2,3-dihydropyridazin-4-yl)oxy]pyridine-2-carboxylic acid To a suspension of Reference Example 2-6-C (433 mg) in water (4.3 mL) was added an aqueous solution of sodium hydroxide (2 mol/L, 2.25 mL), and the mixture was stirred at room temperature for 1 hour. To the reaction mixture was added hydrochloric acid (2 mol/L, 2.30 mL). The mixture was concentrated under reduced pressure. To the residue was added water (6 mL), and the suspension was filtered. The obtained solid was washed with water, and dried under reduced pressure to give the title compound (282 mg). MS (ESI_APCI, m/z): 262 (M+H)$^+$ Reference Example 2-7-A tert-Butyl 6-fluoro-5-methylpyridine-3-carboxylate To a solution of 2-fluoro-3-methylpyridine-5-carboxylic acid (400 mg) in toluene (6 mL) and tert-butyl alcohol (3 mL) was added N,N-dimethylformamide di-tert-butyl acetal (1.90 mL) under an argon atmosphere at 100° C., and the mixture was stirred at the same temperature for 3 hours. The reaction mixture was allowed to cool to room temperature, and then to the reaction mixture were added water and brine. The mixture was extracted with ethyl acetate. The organic layer was dried over anhydrous sodium sulfate, and concentrated under reduced pressure. The residue was purified by column chromatography on silica gel (eluent: n-hexane/ethyl acetate=90/10-70/30) to give the title compound (318 mg).

Reference Example 2-7-B 4-(Benzyloxy)-2-[(4-methoxyphenyl)methyl]-6-methyl-2,3-dihydropyridazin-3-one The title compound was prepared in a similar manner to that described in Reference Example 2-3-A using benzyl alcohol instead of 4-hydroxy-3-methylbenzoic acid methyl.

Reference Example 2-7-C

4-Hydroxy-2-[(4-methoxyphenyl)methyl]-6-methyl-2,3-dihydropyridazin-3-one

To a suspension of Reference Example 2-7-B (771 mg) in ethyl acetate (35 mL) was added 10% palladium on carbon (wet, 300 mg). The mixture was stirred under a hydrogen atmosphere at room temperature for 2 hours. The reaction mixture was filtered through Celite. The filtrate was concentrated under reduced pressure to give the crude title compound (538 mg).

Reference Example 2-7-D tert-Butyl 6-({2-[(4-methoxyphenyl)methyl]-6-methyl-3-oxo-2,3-dihydropyridazin-4-yl}oxy)-5-methylpyridine-3-carboxylate A mixture of Reference Example 2-7-A (145 mg), Reference Example 2-7-C (154 mg), potassium carbonate (139 mg) and DMF (3 mL) was stirred under microwave irradiation at 80° C. for 30 minutes, at 120° C. for 30 minutes and at 150° C. for 1 hour. To the reaction mixture were added water and brine. The mixture was extracted with ethyl acetate. The organic layer was dried over anhydrous sodium sulfate, and concentrated under reduced pressure. The residue was purified by column chromatography on silica gel (eluent: n-hexane/ethyl acetate=90/10-70/30) to give the title compound (172 mg).

Reference Example 2-7-E tert-Butyl 5-methyl-6-[(6-methyl-3-oxo-2,3-dihydropyridazin-4-yl)oxy]pyridine-3-carboxylate The title compound was prepared in a similar manner to that described in Reference Example 2-4-B using Reference Example 2-7-D instead of Reference Example 2-4-A.

Reference Example 2-7-F

5-Methyl-6-[(6-methyl-3-oxo-2,3-dihydropyridazin-4-yl)oxy]pyridine-3-carboxylic acid hydrochloride The mixture of Reference Example 2-7-E (96.6 mg) and hydrogen chloride in 1,4-dioxane (4 mol/L, 3 mL) was stirred at room temperature for 5.5 hours. The reaction mixture was concentrated under reduced pressure to give the crude title compound (87.9 mg). MS (ESI_APCI, m/z): 262 (M+H)$^+$ Reference Example 2-8-A 4-(4-Bromo-2-fluoro-6-methylphenoxy)-2-[(4-methoxyphenyl)methyl]-6-methyl-2,3-dihydropyridazin-3-one A mixture of Reference Example 2-2-A (754 mg), 4-bromo-2-fluoro-6-methylphenol (500 mg), potassium carbonate (675 mg) and DMA (9 mL) was stirred under microwave irradiation at 150° C. for 1 hour. To the reaction mixture was added water, and the mixture was extracted with ethyl acetate. The organic layer was dried over anhydrous sodium sulfate, and concentrated under reduced pressure. To the residue was added ethyl acetate (4 mL), and the suspension was filtered. The obtained solid was washed with ethyl acetate, and dried under reduced pressure to give the title compound (613 mg).

Reference Example 2-8-B

Ethyl 3-fluoro-4-({2-[(4-methoxyphenyl)methyl]-6-methyl-3-oxo-2,3-dihydropyridazin-4-yl}oxy)-5-methylbenzoate A solution of Reference Example 2-8-A (600 mg), [1,1-bis(diphenylphosphino)ferrocene]dichloropalladium (II) dichloromethane complex (113 mg), 1,1'-bis(diphenylphosphino)ferrocene (154 mg), triethylamine (0.585 mL), DMAP (50.5 mg) and ethanol (5 mL) in NMP (5 mL) was stirred under a carbon monoxide atmosphere at 110° C. for 4 hours. The mixture was allowed to cool to room temperature, and then stirred overnight. To the reaction mixture was added water, and the mixture was extracted with ethyl acetate. The organic layer was dried over anhydrous sodium sulfate, and concentrated under reduced pressure. The residue was purified by column chromatography on silica gel (eluent: n-hexane/ethyl acetate=75/25-50/50) to give the title compound (342 mg).

Reference Example 2-8-C

Ethyl 3-fluoro-5-methyl-4-[(6-methyl-3-oxo-2,3-dihydropyridazin-4-yl)oxy]benzoate To a solution of Reference Example 2-8-B (0.345 g) in acetonitrile (17 mL) and water (3.4 mL) was added CAN (1.33 g), and the mixture was stirred at room temperature for 5 hours. To the reaction mixture were added water and a saturated aqueous solution of ammonium chloride. The mixture was extracted with ethyl acetate. The organic layer was dried over anhydrous sodium sulfate, and concentrated under reduced pressure. To the residue was added THF (2 mL), and the suspension was filtered. The obtained solid was washed with THF, and dried under reduced pressure to give the title compound (0.115 g).

Reference Example 2-8-D

3-Fluoro-5-methyl-4-[(6-methyl-3-oxo-2,3-dihydropyridazin-4-yl)oxy]benzoic acid

To a solution of Reference Example 2-8-C (115 mg) in THF (2 mL), methanol (1 mL) and water (0.54 mL) was added an aqueous solution of sodium hydroxide (2 mol/L, 0.560 mL), and the mixture was stirred at room temperature for 1 hour. To the reaction mixture was added hydrochloric acid (2 mol/L, 0.650 mL). The mixture was stirred at room temperature for 10 minutes, and then concentrated under reduced pressure. To the residue was added water (2 mL), and the suspension was filtered. The obtained solid was washed with water, and dried under reduced pressure at 50° C. to give the title compound (96.8 mg). MS (ESI_APCI, m/z): 279 (M+H)$^+$

Reference Example 2-9-A

Methyl 3-formyl-4-hydroxy-5-methoxybenzoate

A mixture of 4-hydroxy-3-methoxybenzoic acid methyl (500 mg), hexamethylenetetramine (193 mg) and trifluoroacetic acid (5 mL) was refluxed for 8 hours. After cooling to room temperature, the reaction mixture was concentrated under reduced pressure. To the residue was added water, and the mixture was extracted with ethyl acetate. The organic layer was successively washed with water and brine, dried over anhydrous magnesium sulfate, and concentrated under reduced pressure. The residue was purified by column chromatography on silica gel (eluent: n-hexane/ethyl acetate=80/20-0/100) to give the title compound (179 mg).

Reference Example 2-9-B

Methyl 4-hydroxy-5-methoxy-3-methylbenzoate

To a solution of Reference Example 2-9-A (175 mg) and concentrated hydrochloric acid (1 drop) in methanol (10 mL) was added 10% palladium on carbon (wet, 90.0 mg) under ice-cooling. The mixture was stirred under a hydrogen atmosphere at room temperature for 1 hour. The reaction mixture was filtered through Celite. The filtrate was concentrated under reduced pressure. The residue was purified by column chromatography on silica gel (eluent: n-hexane/ethyl acetate=90/10-70/30) to give the title compound (135 mg).

Reference Example 2-9-C

Methyl 3-methoxy-4-({2-[(4-methoxyphenyl)methyl]-6-methyl-3-oxo-2,3-dihydropyridazin-4-yl}oxy)-5-methylbenzoate The title compound was prepared in a similar manner to that described in Reference Example 2-5-A using Reference Example 2-9-B instead of 6-bromo-2-methylpyridin-3-ol.

Reference Example 2-9-D

Methyl 5-methoxy-3-methyl-4-[(6-methyl-3-oxo-2,3-dihydropyridazin-4-yl)oxy]benzoate To a suspension of Reference Example 2-9-C (0.170 g) in acetonitrile (4 mL) was added a solution of CAN (1.10 g) in water (2 mL), and the mixture was stirred at room temperature for 3 hours. To the reaction mixture were added water and an aqueous solution of sodium thiosulfate (1 mol/L). The mixture was extracted twice with dichloromethane. The combined organic layer was washed with brine, dried over anhydrous sodium sulfate, and concentrated under reduced pressure. The residue was purified by column chromatography on amino-silica gel (eluent: ethyl acetate/methanol=100/0-85/15) to give the title compound (0.020 g).

Reference Example 2-9-E

3-Methoxy-5-methyl-4-[(6-methyl-3-oxo-2,3-dihydropyridazin-4-yl)oxy]benzoic acid To a solution of Reference Example 2-9-D (19.0 mg) in methanol (1 mL) was added an aqueous solution of sodium hydroxide (2 mol/L, 0.10 mL) at room temperature, and the mixture was stirred at 60° C. for 3 hours. The reaction mixture was concentrated under reduced pressure. To the residue were added water (2 mL) and hydrochloric acid (2 mol/L, 0.150 mL). The mixture was stirred for 10 minutes at room temperature, and then the precipitate was collected by filtration. The obtained solid was washed with water, and dried under reduced pressure to give the title compound (15.0 mg). MS (ESI_APCI, m/z): 291 (M+H)$^+$

Reference Example 3-1-A

2-{2-[(2S,5R)-2-(3-Fluorophenyl)-5-(2-hydroxypropan-2-yl)pyrrolidin-1-yl]-2-oxoethyl}-2,3-dihydro-1H-isoindole-1,3-dione To a solution of N-phthaloylglycine (1.18 g) in dichloromethane (22 mL) were successively added oxalyl chloride (0.670 mL) and DMF (0.050 mL) under an argon atmosphere under ice-cooling, and the mixture was stirred at room temperature for 40 minutes. The reaction mixture was concentrated under reduced pressure. To a suspension of the obtained compound and Reference Example 1-1-D (1.0 g) in THF (26 mL) was added DIPEA (2.0 mL) under ice-cooling, and the mixture was stirred at room temperature for 3 hours. To the reaction mixture were added a saturated aqueous solution of ammonium chloride and water. The mixture was extracted with ethyl acetate. The organic layer was dried over anhydrous sodium sulfate, and concentrated under reduced pressure. The residue was purified by column chromatography on silica gel (eluent: n-hexane/ethyl acetate=80/20-30/70) to give the title compound (1.51 g).

Reference Example 3-1-B

2-Amino-1-[(2S,5R)-2-(3-fluorophenyl)-5-(2-hydroxypropan-2-yl)pyrrolidin-1-yl]ethan-1-one To a solution of Reference Example 3-1-A (1.51 g) in ethanol (60 mL) was added hydrazine monohydrate (ca. 80%, 2.30 mL), and the mixture was stirred at room temperature overnight. The reaction mixture was filtered, and the filtrate was concentrated under reduced pressure. The residue was purified by column chromatography on amino-silica gel (eluent: ethyl acetate/methanol=92/8) to give the title compound (0.870 g). MS (ESI_APCI, m/z): 281 (M+H)$^+$

Reference Example 3-2-A

2-[(2R)-1-[(2S,5R)-2-(3-Fluorophenyl)-5-(2-hydroxypropan-2-yl)pyrrolidin-1-yl]-1-oxopropan-2-yl]-2,3-dihydro-1H-isoindole-1,3-dione A solution of (R)-2-phthalimidopropionic acid (50.0 mg) in thionyl chloride (2 mL) was refluxed for 2 hours. The reaction mixture was allowed to cool to room temperature, and then the reaction mixture was concentrated under reduced pressure. To the residue was added diethyl ether, and the mixture was concentrated under reduced pressure. To a suspension of the obtained compound and Reference Example 1-1-D (30.0 mg) in THF (2 mL) was added DIPEA (0.20 mL), and the mixture was stirred at room temperature for 2 days. To the reaction mixture were added a saturated aqueous solution of ammonium chloride, water and dichloromethane, and the mixture was stirred. The organic layer was separated, and then concentrated under reduced pressure. The residue was purified by column chromatography on silica gel (eluent: n-hexane/ethyl acetate=70/30-30/70) to give the title compound (42.0 mg).

Reference Example 3-2-B (2R)-2-Amino-1-[(2S,5R)-2-(3-fluorophenyl)-5-(2-hydroxypropan-2-yl)pyrrolidin-1-yl]propan-1-one To a solution of Reference Example 3-2-A (42.0 mg) in ethanol (4 mL) was added hydrazine monohydrate (ca. 80%, 0.124 mL), and the mixture was stirred at room temperature for 2 hours. The reaction mixture was concentrated under reduced pressure. The residue was purified by column chromatography on amino-silica gel (eluent: ethyl acetate/methanol=90/10) to give the title compound (25.6 mg). MS (ESI_APCI, m/z): 295 (M+H)$^+$

Reference Example 3-3-A

2-[(2R,5 S)-1-[(2R)-2-(1,3-Dioxo-2,3-dihydro-1H-isoindol-2-yl)propanoyl]-5-(3-fluorophenyl)pyrrolidin-2-yl]-2-methylpropanenitrile To a solution of (R)-2-phthalimidopropionic acid (283 mg) in dichloromethane (5 mL) were successively added oxalyl chloride (0.145 mL) and DMF (0.005 mL) under ice-cooling, and the mixture was stirred at room temperature for 1 hour. The reaction mixture was concentrated under reduced pressure. To a solution of Reference Example 1-3-C (150 mg) and DIPEA (0.338 mL) in THF (5 mL) was added a solution of the above obtained compound in dichloromethane (2.5 mL) under ice-cooling, and the mixture was stirred at room temperature for 1 hour. To the reaction mixture were added a saturated aqueous solution of sodium bicarbonate and water. The mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=70/30-40/60) to give the title compound (215 mg).

Reference Example 3-3-B

2-[(2R,5 S)-1-[(2R)-2-Aminopropanoyl]-5-(3-fluorophenyl)pyrrolidin-2-yl]-2-methylpropanenitrile To a solution of Reference Example 3-3-A (212 mg) in ethanol (10 mL) was added hydrazine monohydrate (ca. 80%, 0.306 mL), and the mixture was stirred at 50° C. for 4 hours. To the reaction mixture was added ethyl acetate. The mixture was stirred at room temperature for 5 minutes, and then the mixture was filtered. The filtrate was concentrated under reduced pressure. To the residue were added a saturated aqueous solution of sodium bicarbonate and water. The mixture was extracted with ethyl acetate. The organic layer was washed with brine, dried over anhydrous magnesium sulfate, and concentrated under reduced pressure to give the crude title compound (107 mg). MS (ESI_APCI, m/z): 304 (M+H)$^+$

Reference Example 3-4-A (S)—N-[(2R)-4-[2-(3-Chlorophenyl)-1,3-dioxolan-2-yl]-1-cyano-,1,1-dimethylbutan-2-yl]-2-methylpropane-2-sulfinamide A solution of 4-(3-chlorophenyl)-4-oxobutanoic acid (15.0 g), ethylene glycol (39.50 mL) and p-toluenesulfonic acid monohydrate (1.34 g) in toluene (150 mL) was refluxed using Dean-Stark apparatus for 80 minutes. The reaction mixture was allowed to cool to room temperature, and then to the reaction mixture was added water. The organic layer was separated. The aqueous layer was extracted with ethyl acetate, and then the extract was combined with the above organic layer. The organic layer was dried over anhydrous magnesium sulfate, and concentrated under reduced pressure. A suspension of LAH (5.36 g) in THF (255 mL) was cooled to −15° C. under an argon atmosphere. To the mixture was added dropwise a solution of the above obtained compound in THF (53 mL). The reaction mixture was stirred under ice-cooling for 30 minutes, and to the reaction mixture was added dropwise water (5.4 mL) under ice-cooling. To the mixture were added an aqueous solution of sodium hydroxide (5 mol/L, 5.4 mL), water (16.2 mL) and Celite successively. The mixture was stirred at room temperature for 30 minutes. The mixture was filtered, and then washed with ethyl acetate. To the filtrate were added water and brine, and the organic layer was separated. The aqueous layer was extracted with ethyl acetate, and then the extract was combined with the above organic layer. The organic layer was dried over anhydrous magnesium sulfate, and concentrated under reduced pressure. To a mixture of the obtained compound, TEMPO (0.220 g), potassium bromide (0.840 g), dichloromethane (68 mL) and a saturated aqueous solution of sodium bicarbonate (68 mL) was added dropwise a mixture of sodium hypochlorite pentahydrate (12.77 g), water (38.8 mL) and a saturated aqueous solution of sodium bicarbonate (8.6 mL) under an argon atmosphere under ice-cooling. The mixture was stirred under ice-cooling for 30 minutes. To the mixture was added a solution of sodium hypochlorite pentahydrate (2.32 g) in water (7 mL) under ice-cooling. The reaction mixture was stirred under ice-cooling for 30 minutes, and to the reaction mixture was added an aqueous solution of sodium thiosulfate (1 mol/L, 95 mL) under ice-cooling. The mixture was stirred at room temperature for 10 minutes, and then the mixture was extracted with dichloromethane. The aqueous layer was extracted twice with a mixed solvent of ethyl acetate and hexane (ethyl acetate/hexane=4/1), and then the extract was combined with the above organic layer. The organic layer was washed with brine, dried over anhydrous magnesium sulfate, and concentrated under reduced pressure to give crude 3-[2-(3-chlorophenyl)-1,3-dioxolan-2-yl]propanal (15.63 g). To a solution of the obtained compound (13.63 g) and (S)-(−)-2-methyl-2-propanesulfinamide (6.86 g) in toluene (136 mL) was added copper (II) sulfate (5.42 g), and the mixture was stirred at 60° C. for 3.5 hours. The reaction mixture was allowed to cool to room temperature. The reaction mixture was filtered, and then washed with ethyl acetate. The filtrate was concentrated under reduced pressure, and the residue was dissolved in THF. The mixture was concentrated under reduced pressure to give crude (S)—N-{3-[2-(3-chlorophenyl)-1,3-dioxolan-2-yl]propylidene}-2-methylpropane-2-sulfinamide (21.42 g). To a solution of LDA (1.13 mol/L, n-hexane/THF) (175 mL) in THF (195 mL) was added dropwise isobutyronitrile (17.80 mL) under an argon atmosphere under ice-cooling, and the mixture was stirred under ice-cooling for 10 minutes. The reaction mixture was cooled to −75° C., and then to the reaction mixture was added dropwise a solution of the above obtained (S)—N-{3-[2-(3-chlorophenyl)-1,3-dioxolan-2-yl]propylidene}-2-methylpropane-2-sulfinamide in THF (44 mL). The mixture was stirred at the same temperature for 1 hour. To the reaction mixture were added a saturated aqueous solution of ammonium chloride and water. The mixture was extracted twice with ethyl acetate. The combined organic layer was washed with brine, dried over anhydrous sodium sulfate, and concentrated under reduced pressure. The residue was dissolved in TBME (290 mL) at 40° C. To the mixture was added heptane (290 mL) at 40° C. The mixture was stirred at the same temperature for 10 minutes, stirred at room temperature for 1.5 hours, and stirred under ice-cooling for 1.5 hours. The precipitated solid was collected by filtration, washed with TBME/heptane, and dried under reduced pressure at 40° C. to give the title compound (13.95 g).

Reference Example 3-4-B

2-[(2R,5S)-5-(3-Chlorophenyl)-1-[(2R)-2-(1,3-dioxo-2,3-dihydro-1H-isoindol-2-yl)propanoyl]pyrrolidin-2-yl]-2-methylpropanenitrile To a suspension of Reference Example 3-4-A (15.94 g) in THF (32 mL) was added concentrated hydrochloric acid (32 mL) under an argon atmosphere under ice-cooling, and the mixture was stirred at room temperature for 50 minutes. The reaction mixture was cooled to −15° C., and to the reaction mixture was added an aqueous solution of sodium hydroxide (5 mol/L, 85 mL). The mixture was extracted with ethyl acetate. The aqueous layer was extracted with ethyl acetate, and then the extract was combined with the above organic layer. The organic layer was washed with brine, dried over anhydrous magnesium sulfate, and concentrated under reduced pressure to give crude 2-[(2R)-5-(3-chlorophenyl)-3,4-dihydro-2H-pyrrol-2-yl]-2-methylpropanenitrile (9.76 g). A solution of the obtained compound and acetic acid (22.60 mL) in THF (49 mL) was heated to 35° C. To the mixture was added portionwise sodium triacetoxyborohydride (12.58 g), and the mixture was stirred at 45° C. for 2 hours. The reaction mixture was diluted with ethyl acetate (115 mL), and to the mixture was added dropwise an aqueous solution of sodium hydroxide (5 mol/L, 120 mL) under ice-cooling. The organic layer was separated. The aqueous layer was extracted with ethyl acetate, and then the extract was combined with the above organic layer. The organic layer was washed with brine, dried over anhydrous magnesium sulfate, and concentrated under reduced pressure to give crude 2-[(2R,5S)-5-(3-chlorophenyl)pyrrolidin-2-yl]-2-methylpropane nitrile (10.44 g). To a solution of (R)-2-phthalimidopropionic acid (13.0 g) in dichloromethane (130 mL) were successively added oxalyl chloride (7.65 mL) and DMF (0.130 mL) under an argon atmosphere under ice-cooling, and the mixture was stirred at room temperature for 1.5 hours. The reaction mixture was concentrated under reduced pressure. To the residue was added toluene, and the mixture was concentrated under reduced pressure at 50° C. to give crude (2R)-2-(1,3-dioxo-2,3-dihydro-1H-isoindol-2-yl)propanoylchloride (15.91 g). A solution of the above obtained 2-[(2R,5S)-5-(3-chlorophenyl)pyrrolidin-2-yl]-2-methylpropane nitrile and 2,6-lutidine (9.20 mL) in dichloromethane (99 mL) under an argon atmosphere was cooled to −15° C. To the mixture was added dropwise a solution of the above obtained (2R)-2-(1,3-dioxo-2,3-dihydro-1H-isoindol-2-yl)propanoylchloride in dichloromethane (65 mL). The mixture was stirred under ice-cooling for 2 hours. To the reaction mixture were added hydrochloric acid (1 mol/L, 158 mL), dichloromethane, water and brine under ice-cooling. The organic layer was separated. The aqueous layer was extracted with dichloromethane, and then the extract was combined with the above organic layer. The organic layer was successively washed with a saturated aqueous solution of sodium bicarbonate and brine, dried over anhydrous magnesium sulfate, and concentrated under reduced pressure. To the residue was added ethanol (69 mL), and the mixture was stirred at 60° C. for 20 minutes. The mixture was allowed to cool to room temperature, and then stirred overnight. The suspension was filtered. The obtained solid was washed with ethanol, and dried under reduced pressure at 60° C. to give the title compound (14.38 g).

Reference Example 3-4-C

2-[(2R,5S)-1-[(2R)-2-Aminopropanoyl]-5-(3-chlorophenyl)pyrrolidin-2-yl]-2-methylpropanenitrile To a suspension of Reference Example 3-4-B (13.37 g) in ethanol (334 mL) was added hydrazine monohydrate (ca. 80%, 18.60 mL), and the mixture was stirred at 60° C. for 5 hours. The reaction mixture was allowed to cool to 30° C. The reaction mixture was filtered, and the filtrate was concentrated under reduced pressure. To the residue were added a saturated aqueous solution of sodium bicarbonate and water. The mixture was extracted with ethyl acetate. The aqueous layer was extracted with ethyl acetate, and then the extract was combined with the above organic layer. The organic layer was washed with brine, dried over anhydrous magnesium sulfate, and concentrated under reduced pressure to give the crude title compound (9.26 g). MS (ESI_APCI, m/z): 320 (M+H)$^+$ Reference Example 3-5-A 2-[(2R,5S)-1-[2-(1,3-Dioxo-2,3-dihydro-1H-isoindol-2-yl)acetyl]-5-(3-fluorophenyl)pyrrolidin-2-yl]-2-methylpropanenitrile The title compound was prepared in a similar manner to that described in Reference Example 3-3-A using N-phthaloylglycine instead of (R)-2-phthalimidopropionic acid.

Reference Example 3-5-B

2-[(2R,5S)-1-(2-Aminoacetyl)-5-(3-fluorophenyl)pyrrolidin-2-yl]-2-methylpropanenitrile The title compound was prepared in a similar manner to that described in Reference Example 3-3-B using Reference Example 3-5-A instead of Reference Example 3-3-A. MS (ESI_APCI, m/z): 290 (M+H)+

Reference Example 3-6-A (2R)-2-(1,3-Dioxo-2,3-dihydro-1H-isoindol-2-yl) butanoic acid To a suspension of N-ethoxycarbonylphthalimide (5.0 g) and (R)-(−)-2-aminobutyric acid (2.35 g) in water (10 mL) was slowly added triethylamine (3.18 mL) under ice-cooling, and the mixture was stirred at room temperature for 3.5 hours. To the reaction mixture was added concentrated hydrochloric acid (4.0 mL) under ice-cooling. To the mixture were added water and ethyl acetate, and the organic layer was separated. The organic layer was successively washed with water and brine, dried over anhydrous magnesium sulfate, and concentrated under reduced pressure. The residue was diluted with ethyl acetate, and to the mixture were added water and hydrochloric acid (2 mol/L, 10 mL). The organic layer was separated. The organic layer was successively washed with water thrice and brine, dried over anhydrous magnesium sulfate, and concentrated under reduced pressure. The residue was diluted with ethyl acetate, and to the mixture were added water and hydrochloric acid (2 mol/L, 10 mL). The organic layer was separated. The organic layer was successively washed with water 6 times and brine, dried over anhydrous magnesium sulfate, and concentrated under reduced pressure to give the crude title compound (4.14 g).

Reference Example 3-6-B

2-[(2R,5S)-1-[(2R)-2-(1,3-Dioxo-2,3-dihydro-1H-isoindol-2-yl)butanoyl]-5-(3-fluorophenyl)pyrrolidin-2-yl]-2-methylpropanenitrile The title compound was prepared in a similar manner to that described in Reference Example 3-3-A using Reference Example 3-6-A instead of (R)-2-phthalimidopropionic acid.

Reference Example 3-6-C

2-[(2R,5S)-1-[(2R)-2-Aminobutanoyl]-5-(3-fluorophenyl)pyrrolidin-2-yl]-2-methylpropanenitrile The title compound was prepared in a similar manner to that described in Reference Example 3-3-B using Reference Example 3-6-B instead of Reference Example 3-3-A. MS (ESI_APCI, m/z): 318 (M+H)+

Reference Example 3-7-A (2R)-2-Amino-1-[(2S,5R)-2-(3-chlorophenyl)-5-(2-hydroxypropan-2-yl)pyrrolidin-1-yl]propan-1-one To a mixture of (R)-2-phthalimidopropionic acid (219 mg), DMF (1 drop) and dichloromethane (7 mL) was added oxalyl chloride (0.172 mL) under ice-cooling. The reaction mixture was stirred under ice-cooling for 1 hour, and then concentrated under reduced pressure. A mixture of the obtained compound, Reference Example 1-5-D (141 mg), triethylamine (0.285 mL) and dichloromethane (3 mL) was stirred at room temperature overnight. To the reaction mixture was added water. The organic layer was separated, and then concentrated under reduced pressure. The residue was purified by column chromatography on silica gel (eluent: n-hexane/ethyl acetate=50/50-20/80) to give 2-[(2R)-1-[(2S,5R)-2-(3-chlorophenyl)-5-(2-hydroxypropan-2-yl)pyrrolidin-1-yl]-1-oxopropan-2-yl]-2,3-dihydro-1H-isoindole-1,3-dione. To a solution of the obtained compound in ethanol (5 mL) was added hydrazine monohydrate (ca. 80%, 0.230 mL), and the mixture was stirred at 40° C. for 2 hours. The reaction mixture was filtered, and the filtrate was concentrated under reduced pressure. To the residue was added an aqueous solution of sodium hydroxide (2 mol/L), and the mixture was extracted with dichloromethane. The organic layer was dried over anhydrous sodium sulfate, and concentrated under reduced pressure. The residue was purified by column chromatography on amino-silica gel (eluent: ethyl acetate/methanol=100/0-90/10) to give the title compound (199 mg). MS (ESI_APCI, m/z): 311 (M+H)+

Reference Example 3-8-A

2-[(2R,5S)-1-[(2R)-2-Aminopropanoyl]-5-(3-chlorophenyl)pyrrolidin-2-yl]propanenitrile To a solution of (R)-2-phthalimidopropionic acid (156 mg) in dichloromethane (4 mL) were successively added oxalyl chloride (0.082 mL) and DMF (0.010 mL) under an argon atmosphere under ice-cooling, and the mixture was stirred at room temperature for 2 hours. The reaction mixture was concentrated under reduced pressure. To a suspension of the obtained compound and the diastereomeric mixture of Reference Example 1-6-D (55.7 mg) in THF (2 mL) was added DIPEA (0.250 mL), and the mixture was stirred at room temperature for 3 hours. To the reaction mixture was added water, and the mixture was extracted with dichloromethane. The organic layer was dried over anhydrous sodium sulfate, and concentrated under reduced pressure to give crude 2-[(2R,5 S)-5-(3-chlorophenyl)-1-[(2R)-2-(1,3-dioxo-2,3-dihydro-1H-isoindol-2-yl)propanoyl]pyrrolidin-2-yl]propanenitrile. To a solution of the obtained compound in ethanol (6 mL) was added hydrazine monohydrate (ca. 80%, 0.190 mL), and the mixture was stirred at 35° C. for 3 hours. The reaction mixture was filtered, and the filtrate was concentrated under reduced pressure. The residue was purified by column chromatography on amino-silica gel (eluent: ethyl acetate/methanol=100/0-90/10) to give a diastereomeric mixture of the title compound (76.1 mg). MS (ESI_APCI, m/z): 306 (M+H)+

Reference Example 3-9-A

2-[(2R,5S)-5-(3-Chlorophenyl)-1-[2-(1,3-dioxo-2,3-dihydro-1H-isoindol-2-yl)acetyl]pyrrolidin-2-yl]-2-methylpropanenitrile The title compound was prepared in a similar manner to that described in Reference Example 3-3-A using N-phthaloylglycine and Reference Example 1-7-D instead of (R)-2-phthalimidopropionic acid and Reference Example 1-3-C.

Reference Example 3-9-B

2-[(2R,5S)-1-(2-Aminoacetyl)-5-(3-chlorophenyl) pyrrolidin-2-yl]-2-methylpropanenitrile The title compound was prepared in a similar manner to that described in Reference Example 3-3-B using Reference Example 3-9-A instead of Reference Example 3-3-A. MS (ESI_APCI, m/z): 306 (M+H)+

Reference Example 3-10-A

1-[(2R,5S)-1-[(2R)-2-Aminopropanoyl]-5-(3-chlorophenyl)pyrrolidin-2-yl]cyclopropane-1-carbonitrile To a solution of (R)-2-phthalimidopropionic acid (52.6 mg) in dichloromethane (2 mL) were successively added oxalyl chloride (0.028 mL) and DMF (0.005 mL) under an argon atmosphere under ice-cooling, and the mixture was stirred at room temperature for 2 hours. The reaction mixture was concentrated under reduced pressure. To a suspension of the obtained compound and Reference Example 1-8-D (29.7 mg) in THF (2 mL) was added DIPEA (0.084 mL), and the mixture was stirred at room temperature overnight. To the reaction mixture was added water, and the mixture was extracted with dichloromethane. The organic layer was dried over anhydrous sodium sulfate, and concentrated under reduced pressure to give crude 1-[(2R,5S)-5-(3-chlorophenyl)-1-[(2R)-2-(1,3-dioxo-2,3-dihydro-1H-isoindol-2-yl)propanoyl]pyrrolidin-2-yl]cyclopropane-1-carbonitrile. To a solution of the obtained compound in ethanol (3 mL) was added hydrazine monohydrate (ca. 80%, 0.100 mL), and the mixture was stirred at 40° C. for 2 hours. The reaction mixture was concentrated under reduced pressure. To the residue was added ethyl acetate, and the mixture was filtered. The filtrate was concentrated under reduced pressure. The residue was purified by column chromatography on amino-silica gel (eluent: ethyl acetate/methanol=100/0-90/10) to give the title compound (35.0 mg). MS (ESI_APCI, m/z): 318 (M+H)$^+$

Reference Example 3-11-A

1-[(2R,5S)-1-[(2R)-2-Aminopropanoyl]-5-(3-chlorophenyl)pyrrolidin-2-yl]cyclobutane-1-carbonitrile The title compound was prepared in a similar manner to that described in Reference Example 3-10-A using Reference Example 1-9-B instead of Reference Example 1-8-D. MS (ESI_APCI, m/z): 332 (M+H)$^+$

Reference Example 3-12-A

2-[(2R,5S)-5-(3,5-Difluorophenyl)-1-[2-(1,3-dioxo-2,3-dihydro-1H-isoindol-2-yl)acetyl]pyrrolidin-2-yl]-2-methylpropanenitrile To a suspension of N-phthaloylglycine (59.3 mg) and DMF (1 drop) in dichloromethane (1 mL) was added oxalyl chloride (0.037 mL) under ice-cooling, and the mixture was stirred under ice-cooling for 1 hour. The reaction mixture was concentrated under reduced pressure. A mixture of the obtained compound, Reference Example 1-10-H (40.2 mg), triethylamine (0.089 mL) and dichloromethane (1.6 mL) was stirred at room temperature for 1 hour. To the reaction mixture was added water, and the mixture was extracted thrice with dichloromethane. The combined organic layer was concentrated under reduced pressure. The residue was purified by column chromatography on silica gel (eluent: n-hexane/ethyl acetate=80/20-0/100) to give the title compound (72.9 mg).

Reference Example 3-12-B

2-[(2R,5)-1-(2-Aminoacetyl)-5-(3,5-difluorophenyl)pyrrolidin-2-yl]-2-methylpropanenitrile The title compound was prepared in a similar manner to that described in Reference Example 3-3-B using Reference Example 3-12-A instead of Reference Example 3-3-A. MS (ESI_APCI, m/z): 308 (M+H)$^+$

Reference Example 3-13-A

2-[(2R,5S)-5-(3,5-Difluorophenyl)-1-[(2R)-2-(1,3-dioxo-2,3-dihydro-1H-isoindol-2-yl)propanoyl]pyrrolidin-2-yl]-2-methylpropanenitrile The title compound was prepared in a similar manner to that described in Reference Example 3-3-A using Reference Example 1-10-H instead of Reference Example 1-3-C.

Reference Example 3-13-B

2-[(2R,5S)-1-[(2R)-2-Aminopropanoyl]-5-(3,5-difluorophenyl)pyrrolidin-2-yl]-2-methylpropanenitrile The title compound was prepared in a similar manner to that described in Reference Example 3-3-B using Reference Example 3-13-A instead of Reference Example 3-3-A. MS (ESI_APCI, m/z): 322 (M+H)$^+$

Reference Example 4-1-A

Ethyl 2-({3-methyl-4-[(6-methyl-3-oxo-2,3-dihydropyridazin-4-yl)methyl]phenyl}formamido)acetate To a mixture of Reference Example 2-1-A (9.35 g), glycine ethyl ester hydrochloride (7.58 g), HOBT (5.88 g), triethylamine (20.20 mL) and DMF (120 mL) was added EDC-HCl (10.42 g). The mixture was stirred at room temperature for 2 hours. To the reaction mixture was added water, and the mixture was extracted with ethyl acetate. The organic layer was washed with water, and then concentrated under reduced pressure. The residue was purified by column chromatography on silica gel (eluent: ethyl acetate/methanol=100/0-40/60) to give the title compound (5.96 g).

Reference Example 4-1-B 2-({3-Methyl-4-[(6-methyl-3-oxo-2,3-dihydropyridazin-4-yl)methyl]phenyl}formamido)acetic acid To a mixture of Reference Example 4-1-A (5.96 g), THF (30 mL) and methanol (30 mL) was added an aqueous solution of sodium hydroxide (2 mol/L, 4.75 mL). The reaction mixture was stirred at room temperature overnight, and then concentrated under reduced pressure. To the residue were added water and hydrochloric acid (2 mol/L, 4.75 mL). The precipitated solid was collected by filtration to give the title compound (5.15 g). MS (ESI_APCI, m/z): 314 (M−H)$^-$ Chemical structures of typical Reference Example are shown in the following tables.

TABLE 1

| Ref. No. | Str. |
|---|---|
| 1-1-D | 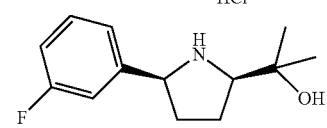 |

TABLE 1-continued

| Ref. No. | Str. |
|---|---|
| 1-2-D | (structure) |
| 1-3-C | (structure) |
| 1-4-B | (structure) |
| 1-5-D | (structure, HCl) |
| 1-6-D | (structure) |
| 1-7-D | (structure) |
| 1-8-D | (structure) |
| 1-9-B | (structure) |
| 1-10-H | (structure) |
| 2-1-A | (structure) |

TABLE 1-continued

| Ref. No. | Str. |
|---|---|
| 2-2-C | (structure) |
| 2-3-B | (structure) |
| 2-4-C | (structure) |
| 2-5-D | (structure) |
| 2-6-D | (structure) |

TABLE 2

| Ref. No. | Str. |
|---|---|
| 2-7-F | (structure, HCl) |
| 2-8-D | (structure) |

TABLE 2-continued

| Ref. No. | Str. |
|---|---|
| 2-9-E | |
| 3-1-B | |
| 3-2-B | |
| 3-3-B | |
| 3-4-C | |
| 3-5-B | |
| 3-6-C | |
| 3-7-A | |
| 3-8-A | |
| 3-9-B | |
| 3-10-A | |
| 3-11-A | |
| 3-12-B | |
| 3-13-B | |

TABLE 3

| Ref. No. | Str. |
|---|---|
| 4-1-B | ![structure: methyl-pyridazinone with benzamide-glycine] |

Example 1A-1

N-{2-[(2S,5R)-2-(3-Fluorophenyl)-5-(propan-2-yl)pyrrolidin-1-yl]-2-oxoethyl}-3-methyl-4-[(6-methyl-3-oxo-2,3-dihydropyridazin-4-yl)methyl]benzamide To a solution of Reference Example 1-2-D (26.0 mg), Reference Example 4-1-B (43.5 mg) and DIPEA (0.066 mL) in 1,2-dichloroethane (1.3 mL) was added T3P (50% in ethyl acetate, ca. 1.7 mol/L) (0.147 mL), and the mixture was stirred at 50° C. for 4.5 hours. To the reaction mixture was added water, and the mixture was extracted with dichloromethane. The organic layer was concentrated under reduced pressure. The residue was purified by column chromatography on amino-silica gel (eluent: ethyl acetate/methanol=100/0-90/10) to give the title compound (36.2 mg). HRMS (ESI) calcd for $C_{29}H_{34}FN_4O_3(M+H)^+$: 505.2609, Found: 505.2614

Example 1A-2

N-{2-[(2R,5S)-2-(1-Cyano-1-methylethyl)-5-(3-fluorophenyl)pyrrolidin-1-yl]-2-oxoethyl}-3-methyl-4-[(6-methyl-3-oxo-2,3-dihydropyridazin-4-yl)methyl]benzamide A solution of Reference Example 1-3-C (67.0 mg), Reference Example 4-1-B (100 mg), T3P (50% in ethyl acetate, ca. 1.7 mol/L) (0.339 mL) and DIPEA (0.151 mL) in 1,2-dichloroethane (3 mL) was stirred at 110° C. under microwave irradiation for 1 hour and at 130° C. for 4 hours. To the reaction mixture was added water, and the mixture was extracted with dichloromethane. The organic layer was concentrated under reduced pressure. The residue was purified by column chromatography on amino-silica gel (eluent: ethyl acetate/methanol=100/0-90/10), and then purified by column chromatography on silica gel (eluent: ethyl acetate/methanol=100/0-90/10) to give the title compound (46.0 mg).
HRMS (ESI) calcd for $C_{30}H_{33}FN_5O_3(M+H)^+$: 530.2562, Found: 530.2562.

Example 1A-3

N-{2-[(2S,5R)-2-(3-Fluorophenyl)-5-[2-(methylsulfanyl)propan-2-yl]pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 1A-2 using Reference Example 1-4-B instead of Reference Example 1-3-C. HRMS (ESI) calcd for $C_{30}H_{36}FN_4O_3S$ $(M+H)^+$: 551.2487, Found: 551.2480.

Example 1A-4

N-{2-[(2S,5R)-2-(3-Chlorophenyl)-5-(1-cyano-1-methylethyl)pyrrolidin-1-yl]-2-oxoethyl}-3-methyl-4-[(6-methyl-3-oxo-2,3-dihydropyridazin-4-yl)methyl]benzamide A solution of Reference Example 1-7-D (50.0 mg), Reference Example 4-1-B (88.8 mg), T3P (50% in ethyl acetate, ca. 1.7 mol/L) (0.24 mL) and DIPEA (0.105 mL) in 1,2-dichloroethane (1 mL) was stirred at 130° C. under microwave irradiation for 4 hours. To the reaction mixture were added a saturated aqueous solution of ammonium chloride and water. The mixture was extracted with dichloromethane. The organic layer was dried over anhydrous sodium sulfate, and concentrated under reduced pressure. The residue was purified by column chromatography on amino-silica gel (eluent: ethyl acetate/methanol=100/0-94/6) to give the title compound (44.8 mg). HRMS (ESI) calcd for $C_{30}H_{33}ClN_5O_3$ $(M+H)^+$: 546.2266, Found: 546.2267.

Example 2A-1

N-{2-[(2S,5R)-2-(3-Fluorophenyl)-5-(2-hydroxypropan-2-yl)pyrrolidin-1-yl]-2-oxoethyl}-3-methyl-4-[(6-methyl-3-oxo-2,3-dihydropyridazin-4-yl)methyl]benzamide A solution of Reference Example 3-1-B (20.0 mg), Reference Example 2-1-A (22.1 mg), EDC-HCl (27.4 mg), HOBT (19.3 mg) and triethylamine (0.050 mL) in acetonitrile (2 mL) was stirred at room temperature overnight. To the reaction mixture were added a saturated aqueous solution of ammonium chloride, water and dichloromethane, and the mixture was stirred. The organic layer was separated, and then concentrated under reduced pressure. The residue was purified by column chromatography on silica gel (eluent: ethyl acetate/methanol=100/0-94/6) to give the title compound (28.0 mg). HRMS (ESI) calcd for $C_{29}H_{34}FN_4O_4$ $(M+H)^+$: 521.2559, Found: 521.2560.

Example 2A-2

N-{2-[(2R,5S)-2-(1-Cyano-1-methylethyl)-5-(3-fluorophenyl)pyrrolidin-1-yl]-2-oxoethyl}-3-methyl-4-[(6-methyl-3-oxo-2,3-dihydropyridazin-4-yl)oxy]benzamide To a suspension of Reference Example 3-5-B (30.0 mg), Reference Example 2-3-B (28.5 mg), HOBT (18.1 mg) and triethylamine (0.029 mL) in DMF (1 mL) was added EDC-HCl (29.8 mg), and the mixture was stirred at room temperature for 13 hours. To the reaction mixture were added water and a saturated aqueous solution of sodium bicarbonate. The mixture was extracted with ethyl acetate. The organic layer was successively washed with water twice and brine, dried over anhydrous magnesium sulfate, and concentrated under reduced pressure. The residue was purified by column chromatography on amino-silica gel (eluent: ethyl acetate/methanol=100/0-85/15) to give the title compound (40.0 mg).
HRMS (ESI) calcd for $C_{29}H_{31}FN_5O_4(M+H)^+$: 532.2355, Found: 532.2344.

Example 2A-3

N-{2-[(2S,5R)-2-(3-Chlorophenyl)-5-(1-cyano-1l-methylethyl)pyrrolidin-1-yl]-2-oxoethyl}-6-methyl-5-[(6-methyl-3-oxo-2,3-dihydropyridazin-4-yl)oxy]pyridine-2-carboxamide The title compound was prepared in a similar manner to that described in Example 2A-2 using Reference Example 3-9-B and Reference Example 2-5-D instead of Reference Example 3-5-B and Reference Example 2-3-B.

HRMS (ESI) calcd for $C_{28}H_{30}ClN_6O_4(M+H)^+$: 549.2012, Found: 549.2006.

Example 2A-4

N-{2-[(2R,5S)-2-(1-Cyano-1-methylethyl)-5-(3,5-difluorophenyl)pyrrolidin-1-yl]-2-oxoethyl}-3-methyl-4-[(6-methyl-3-oxo-2,3-dihydropyridazin-4-yl)oxy]benzamide A mixture of Reference Example 3-12-B (49.4 mg), Reference Example 2-3-B (45.9 mg), EDC-HCl (46.1 mg), HOBT (26 mg), triethylamine (0.034 mL) and DMF (1 mL) was stirred at 50° C. for 3 hours. The reaction mixture was allowed to cool to near room temperature, and then to the reaction mixture was added water. The mixture was extracted with ethyl acetate. The organic layer was washed with water thrice, dried over anhydrous sodium sulfate, and concentrated under reduced pressure. The residue was purified by column chromatography on silica gel (eluent: ethyl acetate/methanol=100/0-85/15) to give the title compound (69.0 mg).

HRMS (ESI) calcd for $C_{29}H_{30}F_2N_5O_4(M+H)^+$: 550.2260, Found: 550.2259.

Example 2B-1

N-[(2R)-1-[(2S,5R)-2-(3-Chlorophenyl)-5-(1-cyano-1-methylethyl)pyrrolidin-1-yl]-1-oxopropan-2-yl]-3-methyl-4-[(6-methyl-3-oxo-2,3-dihydropyridazin-4-yl)oxy]benzamide To a suspension of Reference Example 3-4-C (212 mg), Reference Example 2-3-B (225 mg), HOBT (134 mg) and triethylamine (0.183 mL) in DMF (4 mL) was added EDC-HCl (191 mg), and the mixture was stirred at room temperature for 5 hours. To the reaction mixture were added water and a saturated aqueous solution of sodium bicarbonate. The mixture was extracted with ethyl acetate. The organic layer was successively washed with water thrice and brine, dried over anhydrous magnesium sulfate, and concentrated under reduced pressure. The residue was purified by column chromatography on silica gel (eluent: ethyl acetate/methanol=100/0-90/10), and then purified by column chromatography on amino-silica gel (eluent: ethyl acetate/methanol=100/0-90/10) to give the title compound (307 mg).

HRMS (ESI) calcd for $C_{30}H_{33}ClN_5O_4(M+H)^+$: 562.2216, Found: 562.2218.

Example 2B-2

N-[(2R)-1-[(2S,5R)-2-(3-Chlorophenyl)-5-(1-cyano-1-methylethyl)pyrrolidin-1-yl]-1-oxopropan-2-yl]-6-methyl-5-[(6-methyl-3-oxo-2,3-dihydropyridazin-4-yl)oxy]pyridine-2-carboxamide To a suspension of Reference Example 3-4-C (160 mg), Reference Example 2-5-D (157 mg), HOBT (102 mg) and triethylamine (0.138 mL) in DMF (2.5 mL) was added EDC-HCl (144 mg), and the mixture was stirred at room temperature for 4 hours. To the reaction mixture were added water and a saturated aqueous solution of sodium bicarbonate. The mixture was extracted with ethyl acetate. The organic layer was successively washed with water twice and brine, dried over anhydrous magnesium sulfate, and concentrated under reduced pressure. The residue was purified by column chromatography on amino-silica gel (eluent: ethyl acetate/methanol=100/0-85/15) to give the title compound (220 mg).

HRMS (ESI) calcd for $C_{29}H_{32}ClN_6O_4(M+H)^+$: 563.2168, Found: 563.2166.

Example 2B-3

N-[(2R)-1-[(2S,5R)-2-(3-Fluorophenyl)-5-(2-hydroxypropan-2-yl)pyrrolidin-1-yl]-1-oxopropan-2-yl]-3-methyl-4-[(6-methyl-3-oxo-2,3-dihydropyridazin-4-yl)methyl]benzamide A mixture of Reference Example 2-1-A (39.5 mg), Reference Example 3-2-B (25.0 mg), EDC-HCl (32.5 mg), HOBT (22.9 mg), triethylamine (0.059 mL) and DMF (1 mL) was stirred at room temperature overnight. To the reaction mixture were added a saturated aqueous solution of ammonium chloride, water and dichloromethane, and the mixture was stirred. The organic layer was separated, and then concentrated under reduced pressure. The residue was purified by ODS column chromatography (eluent: water/acetonitrile=70/30-20/80) to give the title compound (18.6 mg).

HRMS (ESI) calcd for $C_{30}H_{36}FN_4O_4(M+H)^+$: 535.2715, Found: 535.2690.

Example 2B-4

N-[(2R)-1-[(2R,5S)-2-(1-Cyano-1-methylethyl)-5-(3-fluorophenyl)pyrrolidin-1-yl]-1-oxopropan-2-yl]-3-fluoro-4-[(6-methyl-3-oxo-2,3-dihydropyridazin-4-yl)oxy]benzamide To a suspension of Reference Example 3-3-B (30.0 mg), Reference Example 2-2-C (27.6 mg), HOBT (17.3 mg) and triethylamine (0.027 mL) in DMF (1 mL) was added EDC-HCl (28.4 mg), and the mixture was stirred at room temperature for 2 hours. To the reaction mixture were added water and a saturated aqueous solution of sodium bicarbonate. The mixture was extracted with ethyl acetate. The organic layer was successively washed with water and brine, dried over anhydrous magnesium sulfate, and concentrated under reduced pressure. The residue was purified by column chromatography on amino-silica gel (eluent: ethyl acetate/methanol=100/0-85/15) to give the title compound (39.0 mg).

HRMS (ESI) calcd for $C_{29}H_{30}F_2N_5O_4(M+H)^+$: 550.2260, Found: 550.2257.

Example 2B-5

N-[(2R)-1-[(2R,5S)-2-(1-Cyano-1-methylethyl)-5-(3-fluorophenyl)pyrrolidin-1-yl]-1-oxopropan-2-yl]-3-methyl-4-[(6-methyl-3-oxo-2,3-dihydropyridazin-4-yl)oxy]benzamide To a suspension of Reference Example 3-3-B (11.6 mg), Reference Example 2-3-B (10.0 mg), HOBT (6.70 mg) and triethylamine (0.011 mL) in DMF (0.6 mL) was added EDC-HCl (11.0 mg), and the mixture was stirred at room temperature for 4 hours. To the reaction mixture were added water and a saturated aqueous solution of sodium bicarbonate. The mixture was extracted with ethyl acetate. The organic layer was successively washed with water and brine, dried over anhydrous magnesium sulfate, and concentrated under reduced pressure. The residue was purified by column chromatography on amino-silica gel (eluent: ethyl acetate/methanol=100/0-85/15) to give the title compound (15.9 mg).

HRMS (ESI) calcd for $C_{30}H_{33}FN_5O_4(M+H)^+$: 546.2511, Found: 546.2507.

Example 2B-6

3-Chloro-N-[(2R)-1-[(2R,5 S)-2-(1-cyano-1-methylethyl)-5-(3-fluorophenyl)pyrrolidin-1-yl]-1-oxopropan-2-yl]-4-[(6-methyl-3-oxo-2,3-dihydropyridazin-4-yl)oxy]benzamide To a suspension of Reference Example 3-3-B (10.8 mg), Reference Example 2-4-C (10.0 mg), HOBT (6.20 mg) and triethylamine (0.010 mL) in DMF (0.6 mL) was added EDC-HCl (10.2 mg), and the mixture was stirred at room temperature for 4 hours. To the reaction mixture were added water and a saturated aqueous solution of sodium bicarbonate. The mixture was extracted with ethyl acetate. The organic layer was successively washed with water and brine, dried over anhydrous magnesium sulfate, and concentrated under reduced pressure. The residue was purified by column chromatography on amino-silica gel (eluent: ethyl acetate/methanol=100/0-85/15) to give the title compound (15.8 mg).

HRMS (ESI) calcd for $C_{29}H_{30}ClFN_5O_4(M+H)^+$: 566.1965, Found: 566.1965.

Example 2B-7

N-[(2R)-1-[(2S,5R)-2-(3-Chlorophenyl)-5-(1-cyano-1-methylethyl)pyrrolidin-1-yl]-1-oxopropan-2-yl]-3-fluoro-4-[(6-methyl-3-oxo-2,3-dihydropyridazin-4-yl)oxy]benzamide To a suspension of Reference Example 3-4-C (47.0 mg), Reference Example 2-2-C (40.9 mg), HOBT (25.6 mg) and triethylamine (0.041 mL) in DMF (1.5 mL) was added EDC-HCl (42.4 mg), and the mixture was stirred at room temperature for 13 hours. To the reaction mixture were added water and a saturated aqueous solution of sodium bicarbonate. The mixture was extracted with ethyl acetate. The organic layer was successively washed with water and brine, dried over anhydrous magnesium sulfate, and concentrated under reduced pressure. The residue was purified by column chromatography on amino-silica gel (eluent: ethyl acetate/methanol=100/0-85/15) to give the title compound (59.6 mg).

HRMS (ESI) calcd for $C_{29}H_{30}ClFN_5O_4(M+H)^+$: 566.1965, Found: 566.1946.

Example 2B-8

N-[(2R)-1-[(2S,5R)-2-(3-Chlorophenyl)-5-(1-cyano-1-methylethyl)pyrrolidin-1-yl]-1-oxopropan-2-yl]-4-methyl-5-[(6-methyl-3-oxo-2,3-dihydropyridazin-4-yl)oxy]pyridine-2-carboxamide A solution of Reference Example 2-6-D (19.9 mg), Reference Example 3-4-C (22.2 mg), EDC-HCl (26.7 mg), HOBT (18.8 mg) and triethylamine (0.078 mL) in DMF (2 mL) was stirred at room temperature for 7 hours. To the reaction mixture was added water, and the mixture was extracted with ethyl acetate. The organic layer was washed with water, dried over anhydrous sodium sulfate, and concentrated under reduced pressure. The residue was purified by ODS column chromatography (eluent: water/acetonitrile=70/30-20/80) to give the title compound (20 mg).

HRMS (ESI) calcd for $C_{29}H_{32}ClN_6O_4(M+H)^+$: 563.2168, Found: 563.2170.

Example 2B-9

N-[(2R)-1-[(2S,5R)-2-(3-Chlorophenyl)-5-(2-hydroxypropan-2-yl)pyrrolidin-1-yl]-1-oxopropan-2-yl]-3-methyl-4-[(6-methyl-3-oxo-2,3-dihydropyridazin-4-yl)oxy]benzamide A solution of Reference Example 2-3-B (50.2 mg), Reference Example 3-7-A (50.0 mg), EDC-HCl (61.3 mg), HOBT (43.6 mg) and triethylamine (0.135 mL) in DMF (2 mL) was stirred at room temperature for 2 hours. To the reaction mixture was added water, and the mixture was extracted with ethyl acetate. The organic layer was washed with water, dried over anhydrous sodium sulfate, and concentrated under reduced pressure. The residue was purified by ODS column chromatography (eluent: water/acetonitrile=70/30-20/80) to give the title compound (49.9 mg).

HRMS (ESI) calcd for $C_{29}H_{34}ClN_4O_5(M+H)^+$: 553.2212, Found: 553.2204.

Example 2B-10

Isomer A and Isomer B of N-[(2R)-1-[(2S,5R)-2-(3-Chlorophenyl)-5-(1-cyanoethyl)pyrrolidin-1-yl]-1-oxopropan-2-yl]-3-methyl-4-[(6-methyl-3-oxo-2,3-dihydropyridazin-4-yl)oxy]benzamide A solution of Reference Example 2-3-B (77.7 mg), Reference Example 3-8-A (76.1 mg), EDC-HCl (94.8 mg), HOBT (67.4 mg) and triethylamine (0.21 mL) in DMF (2 mL) was stirred at room temperature for 2 hours. To the reaction mixture was added water, and the mixture was extracted with ethyl acetate. The organic layer was washed with water, dried over anhydrous sodium sulfate, and concentrated under reduced pressure. The residue was purified by ODS column chromatography (eluent: water/acetonitrile=70/30-20/80) to give isomer A (9.4 mg) which was formerly eluted and isomer B (44.8 mg) which was latterly eluted of the title compound, respectively.

Isomer A HRMS (ESI) calcd for $C_{29}H_{31}ClN_5O_4(M+H)^+$: 548.2059, Found: 548.2048.

Isomer B HRMS (ESI) calcd for $C_{29}H_{31}ClN_5O_4(M+H)^+$: 548.2059, Found: 548.2054.

Example 2B-11

N-[(2R)-1-[(2S,5R)-2-(3-Chlorophenyl)-5-(1-cyano-1-methylethyl)pyrrolidin-1-yl]-1-oxopropan-2-yl]-5-methyl-6-[(6-methyl-3-oxo-2,3-dihydropyridazin-4-yl)oxy]pyridine-3-carboxamide A solution of Reference Example 2-7-F (27.9 mg), Reference Example 3-4-C (30.0 mg), EDC-HCl (35.7 mg), HOBT (25.4 mg) and triethylamine (0.079 mL) in DMF (2 mL) was stirred at room temperature for 2 hours. To the reaction mixture was added water, and the mixture was extracted with ethyl acetate. The organic layer was washed with water, dried over anhydrous sodium sulfate, and concentrated under reduced pressure. The residue was purified by ODS column chromatography (eluent: water/acetonitrile=70/30-20/80) to give the title compound (18.9 mg).

HRMS (ESI) calcd for $C_{29}H_{32}ClN_6O_4(M+H)^+$: 563.2168, Found: 563.2182.

Example 2B-12

N-[(2R)-1-[(2S,5R)-2-(3-Chlorophenyl)-5-(1-cyanocyclopropyl)pyrrolidin-1-yl]-1-oxopropan-2-yl]-3-methyl-4-[(6-methyl-3-oxo-2,3-dihydropyridazin-4-yl)oxy]benzamide A solution of Reference Example 2-3-B (43.0 mg), Reference Example 3-10-A (35.0 mg), EDC-HCl (41.9 mg), HOBT (29.8 mg) and triethylamine (0.092 mL) in DMF (1 mL) was stirred at room temperature for 2 hours. To the reaction mixture was added water, and the mixture was extracted with ethyl acetate. The organic layer was washed with water, dried over anhydrous sodium sulfate, and concentrated under reduced pressure. The residue was purified by ODS column chromatography (eluent: water/acetonitrile=70/30-20/80) to give the title compound (32.9 mg).

HRMS (ESI) calcd for $C_{30}H_{31}ClN_5O_4(M+H)^+$: 560.2059, Found: 560.2061.

Example 2B-13

N-[(2R)-1-[(2S,5R)-2-(3-Chlorophenyl)-5-(1-cyanocyclobutyl)pyrrolidin-1-yl]-1-oxopropan-2-yl]-6-methyl-5-[(6-methyl-3-oxo-2,3-dihydropyridazin-4-yl)oxy]pyridine-2-carboxamide A solution of Reference Example 2-5-D (28.3 mg), Reference Example 3-11-A (30.0 mg), EDC-HCl (26.0 mg), HOBT (18.3 mg) and triethylamine (0.063 mL) in DMF (1 mL) was stirred at room temperature overnight. To the reaction mixture was added water, and the mixture was extracted with ethyl acetate. The organic layer was washed with water, dried over anhydrous sodium sulfate, and concentrated under reduced pressure. The residue was purified by ODS column chromatography (eluent: water/acetonitrile=70/30-20/80) to give the title compound (29.9 mg).

HRMS (ESI) calcd for $C_{30}H_{32}ClN_6O_4(M+H)^+$: 575.2168, Found: 575.2160.

Example 2B-14

N-[(2R)-1-[(2S,5R)-2-(3-Chlorophenyl)-5-(2-hydroxypropan-2-yl)pyrrolidin-1-yl]-1-oxopropan-2-yl]-3-fluoro-5-methyl-4-[(6-methyl-3-oxo-2,3-dihydropyridazin-4-yl)oxy]benzamide A solution of Reference Example 2-8-D (17.9 mg), Reference Example 3-7-A (20.0 mg), EDC-HCl (24.5 mg), HOBT (17.4 mg) and triethylamine (0.072 mL) in DMF (1 mL) was stirred at room temperature for 2 hours. To the reaction mixture was added water, and the mixture was extracted with ethyl acetate. The organic layer was washed with water, dried over anhydrous sodium sulfate, and concentrated under reduced pressure. The residue was purified by ODS column chromatography (eluent: water/acetonitrile=70/30-20/80) to give the title compound (20.7 mg).

HRMS (ESI) calcd for $C_{29}H_{33}ClFN_4O_5(M+H)^+$: 571.2118, Found: 571.2115.

Example 2B-15

N-[(2R)-1-[(2S,5R)-2-(3-Chlorophenyl)-5-(2-hydroxypropan-2-yl)pyrrolidin-1-yl]-1-oxopropan-2-yl]-6-methyl-5-[(6-methyl-3-oxo-2,3-dihydropyridazin-4-yl)oxy]pyridine-2-carboxamide A solution of Reference Example 2-5-D (16.8 mg), Reference Example 3-7-A (20.0 mg), EDC-HCl (24.5 mg), HOBT (17.4 mg) and triethylamine (0.072 mL) in DMF (1 mL) was stirred at room temperature for 2 hours. To the reaction mixture was added water, and the mixture was extracted with ethyl acetate. The organic layer was washed with water, dried over anhydrous sodium sulfate, and concentrated under reduced pressure. The residue was purified by ODS column chromatography (eluent: water/acetonitrile=70/30-20/80) to give the title compound (17.7 mg).

HRMS (ESI) calcd for $C_{28}H_{33}ClN_5O_5(M+H)^+$: 554.2165, Found: 554.2164.

Example 2B-16

N-[(2R)-1-[(2R,5S)-2-(1-Cyano-1-methylethyl)-5-(3,5-difluorophenyl)pyrrolidin-1-yl]-1-oxopropan-2-yl]-3-methyl-4-[(6-methyl-3-oxo-2,3-dihydropyridazin-4-yl)oxy]benzamide A mixture of Reference Example 3-13-B (20.4 mg), Reference Example 2-3-B (18.2 mg), EDC-HCl (15.8 mg), HOBT (11.1 mg), triethylamine (0.013 mL) and DMF (1 mL) was stirred at 50° C. for 2 hours. The reaction mixture was allowed to cool to room temperature, and then to the reaction mixture was added water. The mixture was extracted with ethyl acetate. The organic layer was washed with water thrice, dried over anhydrous sodium sulfate, and concentrated under reduced pressure. The residue was purified by column chromatography on amino-silica gel (eluent: ethyl acetate/methanol=100/0-80/20), and then purified by ODS column chromatography (eluent: water/acetonitrile=90/10-10/90) to give the title compound (17.0 mg).

HRMS (ESI) calcd for $C_{30}H_{32}F_2N_5O_4(M+H)^+$: 564.2417, Found: 564.2429.

Example 2B-17

N-[(2R)-1-[(2R,5S)-2-(1-Cyano-1-methylethyl)-5-(3-fluorophenyl)pyrrolidin-1-yl]-1-oxopropan-2-yl]-3-fluoro-5-methyl-4-[(6-methyl-3-oxo-2,3-dihydropyridazin-4-yl)oxy]benzamide A solution of Reference Example 2-8-D (25.0 mg), Reference Example 3-3-B (30.0 mg), EDC-HCl (20.7 mg), HOBT (24.0 mg) and triethylamine (0.05 mL) in DMF (2 mL) was stirred at room temperature for 5 hours. To the reaction mixture was added water, and the mixture was extracted with ethyl acetate. The organic layer was washed with water, dried over anhydrous sodium sulfate, and concentrated under reduced pressure. The residue was purified by ODS column chromatography (eluent: water/acetonitrile=70/30-20/80) to give the title compound (27.4 mg).

HRMS (ESI) calcd for $C_{30}H_{32}F_2N_5O_4(M+H)^+$: 564.2417, Found: 564.2409.

Example 2B-18

N-[(2R)-1-[(2S,5R)-2-(3-Chlorophenyl)-5-(1-cyano-1-methylethyl)pyrrolidin-1-yl]-1-oxopropan-2-yl]-3-methoxy-5-methyl-4-[(6-methyl-3-oxo-2,3-dihydropyridazin-4-yl)oxy]benzamide To a suspension of Reference Example 3-4-C (14.4 mg), Reference Example 2-9-E (13.7 mg), HOBT (9.0 mg) and triethylamine (0.012 mL) in DMF (0.6 mL) was added EDC-HCl (12.9 mg), and the mixture was stirred at room temperature for 5 hours. To the reaction mixture were added water and a saturated aqueous solution of sodium bicarbonate. The mixture was extracted with ethyl acetate. The organic layer was successively washed with water twice and brine, dried over anhydrous magnesium sulfate, and concentrated under reduced pressure. The residue was purified by column chromatography on amino-silica gel (eluent: ethyl acetate/methanol=100/0-90/10) to give the title compound (22.1 mg).

HRMS (ESI) calcd for $C_{31}H_{35}ClN_5O_5$ $(M+H)^+$: 592.2321, Found: 592.2314.

Example 2B-19

N-[(2R)-1-[(2S,5R)-2-(3-Chlorophenyl)-5-(1-cyano-1-methylethyl)pyrrolidin-1-yl]-1-oxopropan-2-yl]-3-fluoro-5-methyl-4-[(6-methyl-3-oxo-2,3-dihydropyridazin-4-yl)oxy]benzamide To a solution of Reference Example 3-4-C (26.5 mg), Reference Example 2-8-D (15.4 mg), HOBT (10.5 mg) and triethylamine (0.031 mL) in DMF (1 mL) was added EDC-HCl (14.8 mg), and the mixture was stirred at room temperature for 4 hours. To the reaction mixture was added water, and the mixture was extracted thrice with dichloromethane. The combined organic layer was dried over anhydrous sodium sulfate, and concentrated under reduced pressure. The residue was purified by ODS column chromatography (eluent: water/acetonitrile=70/30-20/80) to give the title compound (21.3 mg).

HRMS (ESI) calcd for $C_{30}H_{32}ClFN_5O_4(M+H)^+$: 580.2121, Found: 580.2117.

Example 2C-1

N-[(2R)-1-[(2R,5S)-2-(1-Cyano-1-methylethyl)-5-(3-fluorophenyl)pyrrolidin-1-yl]-1-oxobutan-2-yl]-3-fluoro-4-[(6-methyl-3-oxo-2,3-dihydropyridazin-4-yl)oxy]benzamide To a suspension of Reference Example 3-6-C (30.0 mg), Reference Example 2-2-C (26.3 mg), HOBT (16.5 mg) and triethylamine (0.026 mL) in DMF (1 mL) was added EDC-HCl (27.3 mg), and the mixture was stirred at room temperature for 4 hours. To the reaction mixture were added water and a saturated aqueous solution of sodium bicarbonate. The mixture was extracted with ethyl acetate. The organic layer was successively washed with water thrice and brine, dried over anhydrous magnesium sulfate, and concentrated under reduced pressure. The residue was purified by column chromatography on amino-silica gel (eluent: ethyl acetate/methanol=100/0-90/10) to give the title compound (38.3 mg).

HRMS (ESI) calcd for $C_{30}H_{32}F_2N_5O_4(M+H)^+$: 564.2417, Found: 564.2430.

Example 2C-2

N-[(2R)-1-[(2R,5S)-2-(1-Cyano-1-methylethyl)-5-(3-fluorophenyl)pyrrolidin-1-yl]-1-oxobutan-2-yl]-3-methyl-4-[(6-methyl-3-oxo-2,3-dihydropyridazin-4-yl)oxy]benzamide The title compound was prepared in a similar manner to that described in Example 2C-1 using Reference Example 2-3-B instead of Reference Example 2-2-C.

HRMS (ESI) calcd for $C_{31}H_{35}FN_5O_4(M+H)^+$: 560.2668, Found: 560.2671.

The following tables show chemical structure, physical property and Ki (see, Test Example 1) of Example.

TABLE 4

| Ex. No. | Str. | Physical data | Ki (nM) |
|---|---|---|---|
| 1A-1 | | $^1$H-NMR δ ppm (DMSO-d6): 0.75-1.30 (6H, m), 1.60-2.30 (10H, m), 3.78 (2H, s), 4.85-5.25 (1H, m), 6.60-6.70 (1H, m), 6.85-7.85 (7H, m), 8.30-8.65 (1H, m), 12.75 (1H, s) | 0.18 |

TABLE 4-continued

| Ex. No. | Str. | Physical data | Ki (nM) |
|---|---|---|---|
| 1A-2 | | ¹H-NMR δ ppm (DMSO-d6): 1.30-1.65 (6H, m), 1.95-2.35 (9H, m), 3.78 (2H, s), 3.95-4.40 (2H, m), 5.10-5.30 (1H, m), 6.66 (1H, s), 6.90-7.80 (7H, m), 8.40-8.60 (1H, m), 12.75 (1H, s) | 0.06 |
| 1A-3 | | ¹H-NMR δ ppm (DMSO-d6): 1.10 (3H, s), 1.39 (3H, s), 1.75-2.30 (12H, m), 3.78 (2H, s), 5.10-5.40 (1H, m), 6.60 (1H, s), 6.85-7.85 (7H, m), 8.40-8.60 (1H, m), 12.75 (1H, brs) | |
| 1A-4 | | ¹H-NMR δ ppm (DMSO-d6): 1.30-1.60 (6H, m), 1.90-2.35 (9H, m), 3.78 (2H, s), 3.97-4.50 (2H, m), 5.00-5.30 (1H, m), 5.57 (1H, s), 7.10-7.80 (7H, m), 8.40-8.57 (1H, m), 12.74 (1H, brs) | 0.03 |
| 2A-1 | | ¹H-NMR δ ppm (DMSO-d6): 0.90-1.37 (6H, m), 1.71-2.41 (10H, m), 3.78 (2H, s), 4.03-4.45 (2H, m), 4.67-5.20 (2H, m), 6.63-6.71 (1H, m), 6.87-7.85 (7H, m), 8.33-8.61 (1H, m), 12.74 (1H, brs) | 0.49 |
| 2A-2 | | ¹H-NMR δ ppm (DMSO-d6): 1.30-1.65 (6H, m), 2.00-2.35 (9H, m), 4.00-4.37 (2H, m), 5.05-5.35 (1H, m), 6.40 (1H, s), 6.90-8.00 (7H, m), 8.50-8.66 (1H, m), 12.94 (1H, brs) | 0.10 |

TABLE 5

| Ex. No. | Str. | Physical data | Ki (nM) |
|---|---|---|---|
| 2A-3 | | ¹H-NMR δ ppm (DMSO-d6): 1.28-1.63 (6H, m), 2.00-2.30 (6H, m), 2.45 (3H, s), 3.43-3.62 (1H, m), 4.05-4.50 (2H, m), 5.05-5.30 (1H, m), 6.79 (1H, s), 7.10-7.65 (5H, m), 7.85 (1H, d, J = 8.5 Hz), 8.55-8.75 (1H, m), 13.03 (1H, brs) | 0.10 |
| 2A-4 | | ¹H-NMR δ ppm (CDCl₃): 2.11-2.28 (8H, m), 2.50-2.64 (2H, m), 3.50-3.67 (1H, m), 4.28-4.48 (2H, m), 4.91-5.05 (1H, m), 6.03 (1H, s), 6.70-7.12 (5H, m), 7.62-7.78 (2H, m), 10.09 (1H, brs) | 0.05 |
| 2B-1 | | ¹H-NMR δ ppm (DMSO-d6): 0.97 (3H, d, J = 6.9 Hz), 1.43 (6H, s), 1.96-2.31 (9H, m), 4.17-4.42 (2H, m), 5.55-5.69 (1H, m), 6.40 (1H, s), 7.10 (1H, d, J = 8.5 Hz), 7.32-7.60 (4H, m), 7.74-7.82 (1H, m), 7.87-7.94 (1H, m), 8.69 (1H, d, J = 5.5 Hz), 12.95 (1H, brs) | 0.05 |
| 2B-2 | | ¹H-NMR δ ppm (DMSO-d6): 0.92-1.62 (9H, m), 2.00-2.31 (6H, m), 2.44 (3H, s), 4.22-4.54 (2H, m), 5.02-5.54 (1H, m), 6.73-6.82 (1H, m), 7.10-7.72 (5H, m), 7.84-8.00 (1H, m), 8.42-8.58 (1H, m), 13.04 (1H, brs) | 0.09 |
| 2B-3 | | ¹H-NMR δ ppm (DMSO-d6): 0.72-1.36 (9H, m), 1.68-1.84 (1H, m), 1.91-2.40 (9H, m), 3.78 (2H, s), 4.18 (1H, d, J = 8.8 Hz), 4.33-4.49 (1H, m), 4.72-4.84 (1H, m), 5.36-5.60 (1H, m), 6.62-6.69 (1H, m), 7.02-7..53 (4H, m), 7.57-7.83 (3H, m), 8.43-8.62 (1H, m), 12.75 (1H, brs) | 0.19 |

TABLE 5-continued

| Ex. No. | Str. | Physical data | Ki (nM) |
|---|---|---|---|
| 2B-4 | | $^1$H-NMR δ ppm (DMSO-d6): 0.96 (3H, d, J = 6.9 Hz), 1.43 (6H, s), 1.95-2.32 (6H, m), 4.23-4.40 (2H, m), 5.52-5.66 (1H, m), 6.79 (1H, s), 6.93-7.60 (5H, m), 7.74-8.02 (2H, m), 8.81 (1H, d, J = 5.7 Hz), 13.04 (1H, brs) | 0.11 |

TABLE 6

| Ex. No. | Str. | Physical data | Ki (nM) |
|---|---|---|---|
| 2B-5 | | $^1$H-NMR δ ppm (DMSO-d6): 0.96 (3H, d, J = 6.8 Hz), 1.43 (6H, s), 1.92-2.35 (9H, m), 4.21-4.42 (2H, m), 5.56-5.68 (1H, m), 6.40 (1H, s), 7.05-7.57 (5H, m), 7.73-8.00 (2H, m), 8.68 (1H, d, J = 5.7 Hz), 12.95 (1H, brs) | 0.08 |
| 2B-6 | | $^1$H-NMR δ ppm (DMSO-d6): 0.96 (3H, d, J = 6.8 Hz), 1.43 (6H, s), 1.95-2.36 (6H, m), 4.22-4.40 (2H, m), 5.52-5.64 (1H, m), 6.75 (1H, s), 7.10-7.56 (5H, m), 7.85-7.92 (1H, m), 8.15 (1H, d, J = 20 Hz), 8.85 (1H, d, J = 5.5 Hz), 13.05 (1H, brs) | 0.09 |
| 2B-7 | | $^1$H-NMR δ ppm (DMSO-d6): 0.97 (3H, d, J = 6.8 Hz), 1.43 (6H, s), 1.94-2.35 (6H, m), 4.20-4.41 (2H, m), 5.52-5.64 (1H, m), 6.79 (1H, s), 7.25-7.62 (5H, m), 7.74-8.04 (2H, m), 8.82 (1H, d, J = 5.6 Hz), 13.04 (1H, brs) | 0.08 |

TABLE 6-continued

| Ex. No. | Str. | Physical data | Ki (nM) |
|---|---|---|---|
| 2B-8 | | ¹H-NMR δ ppm (DMSO-d6): 0.85-1.62 (9H, m), 1.92-2.36 (9H, m), 4.20-4.50 (2H, m), 5.00-5.58 (1H, m), 6.62 (1H, s), 7.05-7.65 (4H, m), 8.02-8.14 (1H, m), 8.31-8.42 (1H, m), 8.55 (1H, d, J = 6.7 Hz), 13.00 (1H, brs) | 0.07 |
| 2B-9 | | ¹H-NMR δ ppm (DMSO-d6): 0.75-1.38 (9H, m), 1.65-1.87 (1H, m), 1.92-2.40 (9H, m), 4.18 (1H, d, J = 8.7 Hz), 4.32-4.47 (1H, m), 4.72-4.84 (1H, m), 5.33-5.47 (1H, m), 6.39 (1H, s), 7.06-7.64 (4H, m), 7.75-8.00 (3H, m), 8.53-8.66 (1H, m), 12.95 (1H, brs) | 0.04 |
| 2B-10 isomer A | | ¹H-NMR δ ppm (DMSO-d6): 0.87-1.41 (6H, m), 1.70-2.26 (9H, m), 3.18-3.28 (1H, m), 4.16-4.50 (2H, m), 5.45-5.60 (1H, m), 6.36-6.43 (1H, m), 7.05-7.98 (7H, m), 8.70 (1H, d, J = 5.8 Hz), 12.95 (1H, brs) | 0.12 |

TABLE 7

| Ex. No. | Str. | Physical data | Ki (nM) |
|---|---|---|---|
| 2B-10 isomerB | | ¹H-NMR δ ppm (DMSO-d6): 0.89-1.57 (6H, m), 1.68-2.30 (9H, m), 3.62-4.30 (3H, m), 5.53-5.70 (1H, m), 6.32-6.46 (1H, m), 7.00-8.06 (7H, m), 8.65-8.80 (1H, m), 12.95 (1H, brs) | 0.10 |

TABLE 7-continued
| Ex. No. | Str. | Physical data | Ki (nM) |
|---|---|---|---|
| 2B-11 | 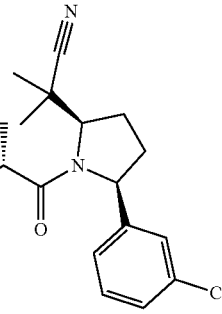 | ¹H-NMR δ ppm (DMSO-d6): 0.95 (3H, d, J = 6.6 Hz) 1.43 (6H, s), 1.95-2.36 (9H, m), 4.16-4.42 (2H, m), 5.48-5.65 (1H, m), 7.31 (1H, s) 7.35-7.58 (4H, m) 8.12-8.43 (2H, m) 8.78 (1H, d, J = 5.7 Hz) 13.00 (1H, brs) | 0.13 |
| 2B-12 | 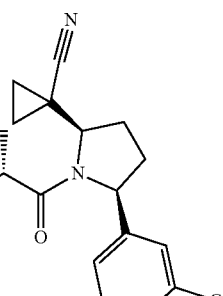 | ¹H-NMR δ ppm (DMSO-d6): 0.99 (3H, d, J = 6.9 Hz), 1.07-1.62 (4H, m), 1.85-2.26 (9H, m), 3.56-3.68 (1H, m), 4.13-4.36 (1H m), 5.53-5.66 (1H, m), 6.40 (1H, s), 7.04-8.02 (7H, m), 8.60-8.74 (1H, m), 12.95 (1H, brs) | 0.05 |
| 2B-13 | 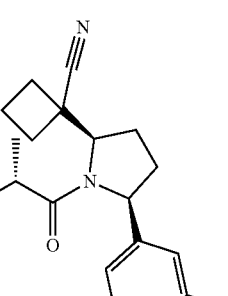 | ¹H-NMR δ ppm (DMSO-d6): 0.98 (3H, d, J = 6.8 Hz), 1.65-2.23 (9H, m), 2.60-2.72 (1H, m), 4.33-4.57 (2H, m), 5.43-5.53 (1H, m), 6.79 (1H, s), 7.07-8.02 (6H, m), 8.40-8.61 (1H, m), 13.04 (1H, brs) | 0.09 |
| 2B-14 | 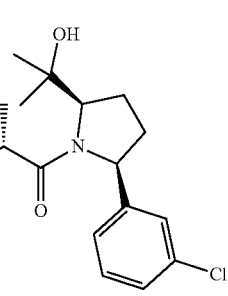 | ¹H-NMR δ ppm (DMSO-d6): 0.75-1.39 (9H, m), 1.66-1.85 (1H, m), 1.92-2.40 (9H, m), 4 18 (1H, d, J = 8.5 Hz), 4.34-4 46 (1H, m), 4.68-4.81 (1H, m), 5.30-5.45 (1H, m), 6.34-6.42 (1H, m), 7.13-7.90 (6H, m), 8.60-8.80 (1H, m), 12.99 (1H, brs) | 0.08 |
| 2B-15 | 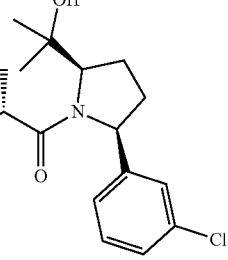 | ¹H-NMR δ ppm (DMSO-d6): 0.69-1.40 (9H, m), 1.69-1.87 (1H, m), 1.93-2.46 (9H, m), 3.97-4.27 (1H, m), 4.53-5.38 (3H, m), 6.70-6.80 (1H, m), 7.15-8.00 (6H, m), 8.37-8.58 (1H, m), 13.02 (1H, brs) | 0.09 |

TABLE 8

| Ex. No. | Str. | Physical data | Ki (nM) |
|---|---|---|---|
| 2B-16 | | ¹H-NMR δ ppm (CDCl₃): 1.09 (3H, d, J = 6.7 Hz), 2.11-2.28 (8H, m), 2.46-2.60 (2H, m), 4.37-4.47 (1H, m), 4.58-4.70 (1H, m), 5.44-5.58 (1H, m), 6.02 (1H, s), 6.50-6.58 (1H, m), 6.72-6.85 (1H, m), 7.03-7.18 (3H, m), 7.61-7.79 (2H, m), 10.13 (1H, brs) | 0.09 |
| 2B-17 | | ¹H-NMR δ ppm (DMSO-d6): 0.97 (3H, d, J-6.8 Hz), 1.43 (6H, s), 1.92-2.37 (9H, m), 4.22-4.40 (2H, m), 5.53-5.66 (1H, m), 6.33-6.42 (1H, m), 7.08-7.61 (4H, m), 7.70-7.94 (2H, m), 8.79 (1H, d, J = 5.7 Hz), 13.00 (1H, brs) | 0.11 |
| 2B-18 | | ¹H-NMR δ ppm (DMSO-d6): 0.99 (3H, d, J = 6.9 Hz), 1.43 (6H, s), 1.95-2.35 (9H, m), 3.79 (3H, s), 4.22-4.42 (2H, m), 5.56-5.68 (1H, m), 6.03 (1H, s), 7.33-7.65 (6H, m), 8.72-8.80 (1H, m), 12.88 (1H, brs) | 0.07 |
| 2B-19 | | ¹H-NMR δ ppm (DMSO-d6): 0 98 (3H, d, J = 7.0 Hz), 1 43 (6H, s), 1 93-2.35 (9H, m), 4.20-4.40 (2H, m), 5.52-5.64 (1H, m), 6.38 (1H, s), 7.35-7 90 (6H, m), 8 81 (1H, d, J = 5.4 Hz), 13.00 (1H, brs) | 0.07 |
| 2C-1 | | ¹H-NMR δ ppm (DMSO-d6): 0.38 (3H, t, J = 7.2 Hz), 1.15-1.65 (8H, m), 1.95-2.35 (6H, m), 4.16-4.38 (2H, m), 5.44-5.54 (1H, m), 6.78 (1H, s), 7.13-7.24 (1H, m), 7.27-7.59 (4H, m), 7.70-8.00 (2H, m), 8.74 (1H, d, J = 6.7 Hz), 13.03 (1H, brs) | 0.13 |

TABLE 8-continued

| Ex. No. | Str. | Physical data | Ki (nM) |
|---|---|---|---|
| 2C-2 | | $^1$H-NMR δ ppm (DMSO-d6): 0.38 (3H, t, J = 7.4 Hz), 1.15-1.72 (8H, m), 1.92-2.37 (9H, m), 4.16-4.37 (2H, m), 5.47-5.58 (1H, m), 6.40 (1H, s), 7.07-7.58 (5H, m), 7.74-8.00 (2H, m), 8.61 (1H, d, J = 6.7 Hz), 12.95 (1H, brs) | 0.11 |

Reference Example 5-1-A (2R,5S)-1-(tert-Butoxycarbonyl)-5-phenyl pyrrolidine-2-carboxylic acid methyl To a suspension of (2R,5S)-1-[(tert-butoxy)carbonyl]-5-phenylpyrrolidine-2-carboxylic acid (1.50 g) and potassium carbonate (1.42 g) in DMF (30 mL) was added iodomethane (0.480 mL), and the mixture was stirred at room temperature overnight. To the reaction mixture were added water, hexane and diethyl ether. The organic layer was separated. The organic layer was dried over anhydrous sodium sulfate, and concentrated under reduced pressure. The residue was purified by column chromatography on silica gel (eluent: n-hexane/ethyl acetate=100/0-60/40) to give the title compound (1.63 g).

Reference Example 5-1-B (2S,5S)-1-(tert-Butoxycarbonyl)-2-(hydroxymethyl)-5-phenyl pyrrolidine-2-carboxylic acid methyl To a solution of Reference Example 5-1-A (1.63 g) in THF (28 mL) was added lithium bis(trimethylsilyl)amide (1.0 mol/L, THF) (5.90 mL) under an argon atmosphere at −78° C., and the mixture was stirred at −40° C. for 40 minutes. To the mixture was added ethyl formate (0.865 mL) at −78° C. The reaction mixture was stirred at −78° C. for 2 hours, and then to the reaction mixture were added a saturated aqueous solution of ammonium chloride, water and ethyl acetate. The organic layer was separated. The organic layer was dried over anhydrous sodium sulfate, and concentrated under reduced pressure to give crude (2S,5S)-1-(tert-butoxycarbonyl)-2-formyl-5-phenylpyrrolidine-2-carboxylic acid methyl. To a solution of the obtained compound in methanol (30 mL) was added sodium borohydride (0.242 g). The reaction mixture was stirred at room temperature for 20 minutes, and then concentrated under reduced pressure. To the residue were added ethyl acetate, a saturated aqueous solution of ammonium chloride and water. The organic layer was separated. The organic layer was dried over anhydrous sodium sulfate, and concentrated under reduced pressure. The residue was purified by column chromatography on silica gel (eluent: n-hexane/ethyl acetate=90/10-60/40) to give the title compound (0.710 g).

Reference Example 5-1-C (2S,5S)-1-(tert-Butoxycarbonyl)-2-(methoxymethyl)-5-phenyl pyrrolidine-2-carboxylic acid methyl To a solution of Reference Example 5-1-B (200 mg) and iodomethane (0.0450 mL) in DMF (3 mL) was added sodium hydride (ca. 60%, 29.0 mg) under an argon atmosphere under ice-cooling. The mixture was allowed to warm to room temperature slowly, and then stirred overnight. To the reaction mixture were added ethyl acetate and water. The organic layer was separated. The organic layer was dried over anhydrous sodium sulfate, and concentrated under reduced pressure. The residue was purified by column chromatography on silica gel (eluent: n-hexane/ethyl acetate=100/0-70/30) to give the title compound (229 mg).

Reference Example 5-1-D tert-Butyl (2R,5S)-2-(hydroxymethyl)-2-(methoxymethyl)-5-phenylpyrrolidine-1-carboxylate To a solution of Reference Example 5-1-C (229 mg) in THF (4 mL) was added LAH (54.7 mg) under an argon atmosphere under ice-cooling, and the mixture was stirred at the same temperature for 1.5 hours. To the reaction mixture were added THF (4 mL) and sodium sulfate decahydrate (500 mg) successively under ice-cooling. The mixture was stirred at room temperature for 1 hour, and then the mixture was filtered. The filtrate was concentrated under reduced pressure to give the title compound (168 mg).

Reference Example 5-1-E tert-Butyl (2S,5 S)-2-formyl-2-(methoxymethyl)-5-phenylpyrrolidine-1-carboxylate To a solution of Reference Example 5-1-D (168 mg) in dichloromethane (4 mL) was added DMP (311 mg), and the mixture was stirred at room temperature for 1.5 hours. To the reaction mixture were added a saturated aqueous solution of sodium thiosulfate (2 mL) and a saturated aqueous solution of sodium bicarbonate (2 mL). The mixture was stirred at room temperature for 1 hour, and then to the mixture were added ethyl acetate and brine. The organic layer was separated. The organic layer was dried over anhydrous sodium sulfate, and concentrated under reduced pressure. The residue was purified by column chromatography on silica gel (eluent: n-hexane/ethyl acetate=100/0-80/20) to give the title compound (163 mg).

Reference Example 5-1-F tert-Butyl (2R,5 S)-2-ethenyl-2-(methoxymethyl)-5-phenylpyrrolidine-1-carboxylate To a suspension of methyltriphenylphosphonium bromide (223 mg) in THF (2 mL) was added n-butyllithium (2.65 mol/L, n-hexane) (0.240 mL) under ice-cooling. The mixture was stirred under ice-cooling for 15 minutes, and then to the mixture was added a solution of Reference Example 5-1-E (100 mg) in THF (1 mL). The mixture was stirred under ice-cooling for 10 minutes, and then stirred at room temperature for 50 minutes. To the reaction mixture were added ethyl acetate and water. The organic layer was separated. The organic layer was dried over anhydrous sodium sulfate, and concentrated under reduced pressure. The residue was purified by column chromatography on silica gel (eluent: n-hexane/ethyl acetate=100/0-80/20) to give the title compound (99.8 mg).

Reference Example 5-1-G (2R,5S)-2-Ethenyl-2-(methoxymethyl)-5-phenylpyrrolidine hydrochloride A mixture of Reference Example 5-1-F (99.8 mg) and hydrogen chloride in ethyl acetate (4 mol/L, 2.0 mL) was stirred at room temperature for 1 hour. The reaction mixture was concentrated under reduced pressure to give the title compound (80.8 mg). $^1$H-NMR δ ppm (DMSO-d6): 2.05-2.45 (4H, m), 3.38 (3H, s), 3.60 (2H, s), 4.70-4.84 (1H, m), 5.38-5.52 (2H, m), 6.11 (1H, dd, J=11.0, 17.5 Hz), 7.37-7.54 (5H, m), 8.70-9.00 (1H, br), 9.69-9.95 (1H, br)

Reference Example 5-2-A

Ethyl (2R,5 S)-5-(3-fluorophenyl)-1-(prop-2-en-1-yl)pyrrolidine-2-carboxylate

A mixture of Reference Example 1-1-B (111 mg), allyl bromide (0.079 mL), potassium carbonate (161 mg) and acetonitrile (1 mL) was stirred at 50° C. for 2 hours. The reaction mixture was allowed to cool to room temperature, and then to the reaction mixture were added ethyl acetate and water. The organic layer was separated, and then concentrated under reduced pressure. The residue was purified by column chromatography on silica gel (eluent: n-hexane/ethyl acetate=100/0-60/40) to give the title compound (131 mg).

Reference Example 5-2-B (2R,5 S)-5-(3-Fluorophenyl)-N-methoxy-N-methyl-1-(prop-2-en-1-yl)pyrrolidine-2-carboxamide The title compound was prepared in a similar manner to that described in Reference Example 1-2-A using Reference Example 5-2-A instead of Reference Example 1-1-C.

Reference Example 5-2-C

1-[(2R,5 S)-5-(3-Fluorophenyl)-1-(prop-2-en-1-yl)pyrrolidin-2-yl]ethan-1-one

The title compound was prepared in a similar manner to that described in Reference Example 1-10-E using Reference Example 5-2-B instead of Reference Example 1-10-D.

Reference Example 5-2-D (S)—N-[(1 S)-1-[(2R,5 S)-5-(3-Fluorophenyl)-1-(prop-2-en-1-yl)pyrrolidin-2-yl]ethyl]-2-methylpropane-2-sulfinamide A mixture of Reference Example 5-2-C (80.0 mg), (S)-(−)-2-methyl-2-propanesulfinamide (39.2 mg), titanium (IV) ethoxide (0.135 mL) and THF (2 mL) was stirred at 130° C. under microwave irradiation for 1 hour. To the mixture was added sodium borohydride (12.3 mg). The reaction mixture was stirred at room temperature for 1 hour, and then to the reaction mixture were successively added acetone (1 mL), methanol (1 mL) and brine (1 mL). The mixture was filtered through Celite. The filtrate was dried over anhydrous magnesium sulfate, and concentrated under reduced pressure. The residue was purified by column chromatography on silica gel (eluent: n-hexane/ethyl acetate=70/30-0/100) to give the title compound (65.8 mg).

Reference Example 5-2-E (S)—N-[(1 S)-1-[(2R,5S)-5-(3-Fluorophenyl)pyrrolidin-2-yl]ethyl]-2-methylpropane-2-sulfinamide A mixture of Reference Example 5-2-D (65.0 mg), tetrakis(triphenylphosphine)palladium (0) (10.6 mg), 1,3-dimethylbarbituric acid (86.4 mg) and 1,2-dichloroethane (5 mL) was stirred at 60° C. for 2 hours. The reaction mixture was concentrated under reduced pressure to give the crude title compound (125 mg). MS (ESI_APCI, m/z): 313 (M+H)$^+$ Reference Example 5-3-A (2S,5S)-1-(tert-Butoxycarbonyl)-5-(3-fluorophenyl)-2-(hydroxymethyl)pyrrolidine-2-carboxylic acid ethyl The title compound was prepared in a similar manner to that described in Reference Example 5-1-B using Reference Example 1-1-C instead of Reference Example 5-1-A.

Reference Example 5-3-B (2S,5S)-2-[(Benzyloxy)methyl]-1-(tert-butoxycarbonyl)-5-(3-fluorophenyl)pyrrolidine-2-carboxylic acid ethyl A solution of Reference Example 5-3-A (270 mg), benzyl bromide (0.120 mL) and tetrabutylammonium iodide (380 mg) in DMF (6 mL) was stirred under an argon atmosphere at room temperature for 5 minutes. To the mixture was added sodium hydride (ca. 60%, 45.0 mg) under ice-cooling. The mixture was allowed to warm to room temperature slowly, and then stirred overnight. To the reaction mixture were added ethyl acetate and water. The organic layer was separated. The organic layer was dried over anhydrous sodium sulfate, and concentrated under reduced pressure. The residue was purified by column chromatography on silica gel (eluent: n-hexane/ethyl acetate=100/0-80/20) to give the title compound (267 mg).

Reference Example 5-3-C tert-Butyl (2R,5S)-2-[(benzyloxy)methyl]-5-(3-fluorophenyl)-2-(hydroxymethyl)pyrrolidine-1-carboxylate The title compound was prepared in a similar manner to that described in Reference Example 5-1-D using Reference Example 5-3-B instead of Reference Example 5-1-C.

Reference Example 5-3-D tert-Butyl (2S,5S)-2-[(benzyloxy)methyl]-5-(3-fluorophenyl)-2-formylpyrrolidine-1-carboxylate The title compound was prepared in a similar manner to that described in Reference Example 5-1-E using Reference Example 5-3-C instead of Reference Example 5-1-D.

Reference Example 5-3-E tert-Butyl (2R,5S)-2-[(benzyloxy)methyl]-2-ethenyl-5-(3-fluorophenyl)pyrrolidine-1-carboxylate The title compound was prepared in a similar manner to that described in Reference Example 5-1-F using Reference Example 5-3-D instead of Reference Example 5-1-E.

Reference Example 5-3-F (2R,5 S)-2-[(Benzyloxy)methyl]-2-ethenyl-5-(3-fluorophenyl)pyrrolidine hydrochloride The title compound was prepared in a similar manner to that described in Reference Example 5-1-G using Reference Example 5-3-E instead of Reference Example 5-1-F. $^1$H-NMR δ ppm (DMSO-d6): 2.10-2.35 (3H, m), 3.68-3.78 (2H, m), 4.63 (2H, s), 4.76-4.90 (1H, m), 5.38-5.52 (2H, m), 6.15 (1H, dd, J=11.0, 17.7 Hz), 7.20-7.55 (9H, m), 8.86-9.10 (1H, br), 9.92-10.16 (1H, br)

Reference Example 5-4-A (S)—N-[(1S)-1-[(2R,5S)-5-(3-Fluorophenyl)-1-(prop-2-en-1-yl)pyrrolidin-2-yl]ethyl]-N,2-dimethylpropane-2-sulfinamide To a mixture of Reference Example 5-2-D (287 mg) and DMF (4 mL) was added sodium hydride (ca. 60%, 39.0 mg) under ice-cooling. The mixture was stirred at room temperature for 30 minutes, and then to the mixture was added iodomethane (0.0761 mL). The reaction mixture was stirred at room temperature for 30 minutes, and then to the reaction mixture were added water and diethyl ether. The organic layer was separated. The organic layer was washed with brine, dried over anhydrous magnesium sulfate, and concentrated under reduced pressure to give the title compound (60.5 mg).

Reference Example 5-4-B

[(1 S)-1-[(2R,5 S)-5-(3-Fluorophenyl)-1-(prop-2-en-1-yl)pyrrolidin-2-yl]ethyl](methyl)amine To a mixture of Reference Example 5-4-A (298 mg) and methanol (3 mL) was added hydrogen chloride in 1,4-dioxane (4 mol/L, 0.5 mL). The reaction mixture was stirred at room temperature for 1 hour, and then concentrated under reduced pressure. To the residue were added ethyl acetate and a saturated aqueous solution of sodium bicarbonate. The organic layer was separated, and concentrated under reduced pressure to give the title compound (187 mg).

Reference Example 5-4-C tert-Butyl N-[(1 S)-1-[(2R,5 S)-5-(3-fluorophenyl)-1-(prop-2-en-1-yl)pyrrolidin-2-yl]ethyl]-N-methylcarbamate A mixture of Reference Example 5-4-B (50.0 mg), di-tert-butyl dicarbonate (62.4 mg) and THF (10 mL) was stirred at 50° C. for 1 hour. The reaction mixture was concentrated under reduced pressure. The residue was purified by column chromatography on amino-silica gel (eluent: n-hexane/ethyl acetate=100/0-30/70) to give the title compound (55.0 mg).

Reference Example 5-4-D tert-Butyl N-[(1 S)-1-[(2R,5 S)-5-(3-fluorophenyl)pyrrolidin-2-yl]ethyl]-N-methylcarbamate The title compound was prepared in a similar manner to that described in Reference Example 5-2-E using Reference Example 5-4-C instead of Reference Example 5-2-D. MS (ESI_APCI, m/z): 323 (M+H)$^+$

Reference Example 5-5-A tert-Butyl N-[(1 S)-1-[methoxy(methyl)carbamoyl]-2-methylpropyl]carbamate A mixture of N-(tert-butoxycarbonyl)-L-valine (300 mg), N,O-dimethylhydroxylamine hydrochloride (208 mg), T3P (50% in ethyl acetate, ca. 1.7 mol/L) (1.62 mL), DIPEA (0.960 mL) and 1,2-dichloroethane (7 mL) was stirred at room temperature for 1 hour. To the reaction mixture were added water and dichloromethane. The organic layer was separated, and then concentrated under reduced pressure. The residue was purified by column chromatography on silica gel (eluent: n-hexane/ethyl acetate=90/10-50/50) to give the title compound (403 mg).

Reference Example 5-5-B tert-Butyl N-[(3 S)-6-(3-fluorophenyl)-2-methyl-4-oxohex-5-yn-3-yl]carbamate To a mixture of 1-ethynyl-3-fluorobenzene (663 mg) and THF (2 mL) was added n-butyllithium (2.65 mol/L, n-hexane) (1.98 mL) at −78° C. The mixture was stirred at −78° C. for 30 minutes, and then to the mixture was added a solution of Reference Example 5-5-A (359 mg) in THF (3 mL). The reaction mixture was stirred at −78° C. for 1 hour, and stirred at −20° C. for 1 hour. To the reaction mixture was added an aqueous solution of ammonium chloride. The organic layer was separated, and then concentrated under reduced pressure. The residue was purified by column chromatography on silica gel (eluent: n-hexane/ethyl acetate=100/0-0/100) to give the title compound (72.0 mg).

Reference Example 5-5-C tert-Butyl 5-(3-fluorophenyl)-3-oxo-2-(propan-2-yl)-2,3-dihydro-1H-pyrrole-1-carboxylate A mixture of Reference Example 5-5-B (70.0 mg), gold (I) chloride (5.1 mg) and THF (1.5 mL) was stirred under an argon atmosphere at room temperature for 1 hour. The reaction mixture was concentrated under reduced pressure. The residue was purified by column chromatography on silica gel (eluent: n-hexane/ethyl acetate=100/0-0/100) to give the title compound (66.6 mg).

Reference Example 5-5-D rac-tert-Butyl (2S,5 S)-5-(3-fluorophenyl)-2-isopropyl-3-oxopyrrolidine-1-carboxylate To a solution of Reference Example 5-5-C (280 mg) in methanol (5 mL) was added 10% palladium on carbon (wet, 112 mg) under ice-cooling. The mixture was stirred under a hydrogen atmosphere at room temperature for 3 hours. The reaction mixture was filtered through Celite, and the filtrate was concentrated under reduced pressure. The residue was purified by column chromatography on silica gel (eluent: n-hexane/ethyl acetate=100/0-80/20) to give the title compound (192 mg).

Reference Example 5-5-E rac-tert-Butyl (2S,3S,5S)-5-(3-fluorophenyl)-3-hydroxy-2-(propan-2-yl)pyrrolidine-1-carboxylate To a solution of Reference Example 5-5-D (152 mg) in ethanol (5 mL) was added sodium borohydride (35.8 mg) under ice-cooling, and the mixture was stirred at room temperature for 50 minutes. To the reaction mixture was added a saturated aqueous solution of ammonium chloride slowly, and then to the reaction mixture was added water. The mixture was extracted twice with ethyl acetate. The combined organic layer was washed with brine, dried over anhydrous magnesium sulfate, and concentrated under reduced pressure to give the title compound (157 mg).

Reference Example 5-5-F rac-tert-Butyl (2S,3S,5S)-3-(benzyloxy)-5-(3-fluorophenyl)-2-(propan-2-yl)pyrrolidine-1-carboxylate To a mixture of Reference Example 5-5-E (33.0 mg) and DMF (2 mL) was added sodium hydride (ca. 60%, 5.0 mg) under ice-cooling. The mixture was stirred at room temperature for 30 minutes, and then to the mixture was added benzyl bromide (0.016 mL). The mixture was stirred at room temperature overnight, and then to the mixture were added sodium hydride (ca. 60%, 5.0 mg) and benzyl bromide (0.0160 mL). The mixture was stirred at 50° C. for 1 hour. The reaction mixture was allowed to cool to room temperature, and then to the reaction mixture were added water and diethyl ether. The organic layer was separated. The organic layer was washed with water, dried over anhydrous magnesium sulfate, and concentrated under reduced pressure. The residue was purified by column chromatography on silica gel (eluent: n-hexane/ethyl acetate=100/0-0/100) to give the title compound (29.0 mg).

Reference Example 5-5-G rac-(2S,3S,5S)-3-(Benzyloxy)-5-(3-fluorophenyl)-2-(propan-2-yl)pyrrolidine hydrochloride To a mixture of Reference Example 5-5-F (29.0 mg) and dichloromethane (2 mL) was added hydrogen chloride in 1,4-dioxane (4 mol/L, 0.5 mL). The mixture was stirred at room temperature for 1 hour and stirred at 40° C. for 30 minutes. The reaction mixture was concentrated under reduced pressure to give the crude title compound (31.0 mg). MS (ESI_APCI, m/z): 314 (M+H)$^+$

Reference Example 5-6-A tert-Butyl (2S,5S)-2-ethyl-5-(3-fluorophenyl)-2-(hydroxymethyl)pyrrolidine-1-carboxylate To a solution of Reference Example 5-3-E (254 mg) in ethanol (5 mL) was added 10% palladium on carbon (wet, 132 mg). The mixture was stirred under a hydrogen atmosphere at room temperature for 1 hour. The reaction mixture was filtered through Celite, and the filtrate was concentrated under reduced pressure. The residue was purified by column chromatography on silica gel (eluent: n-hexane/ethyl acetate=85/15-50/50) to give the title compound (195 mg).

Reference Example 5-6-B tert-Butyl (2S,5 S)-2-ethyl-5-(3-fluorophenyl)-2-formylpyrrolidine-1-carboxylate The title compound was prepared in a similar manner to that described in Reference Example 5-1-E using Reference Example 5-6-A instead of Reference Example 5-1-D.

Reference Example 5-6-C

Isomer A and Isomer B of tert-butyl (2S,5S)-2-ethyl-5-(3-fluorophenyl)-2-(1-hydroxyethyl)pyrrolidine-1-carboxylate To a solution of Reference Example 5-6-B (60.0 mg) in THF (2 mL) was added methylmagnesium bromide (3.0 mol/L, diethyl ether) (0.200 mL) under an argon atmosphere under ice-cooling, and the mixture was stirred at the same temperature for 1 hour. To the reaction mixture were added a saturated aqueous solution of ammonium chloride, water and ethyl acetate. The organic layer was separated. The organic layer was dried over anhydrous sodium sulfate, and concentrated under reduced pressure. The residue was purified by column chromatography on silica gel (eluent: n-hexane/ethyl acetate=90/10-60/40) to give isomer A (16.0 mg) which was formerly eluted and isomer B (43.4 mg) which was latterly eluted of the title compound, respectively.

Reference Example 5-6-D

1-[(2S,5 S)-2-Ethyl-5-(3-fluorophenyl)pyrrolidin-2-yl]ethan-1-ol hydrochloride

A mixture of isomer B of Reference Example 5-6-C (43.4 mg) and hydrogen chloride in ethyl acetate (4 mol/L, 2 mL) was stirred at room temperature for 1.5 hours. The reaction mixture was concentrated under reduced pressure to give the crude title compound (40.4 mg).

Reference Example 5-7-A tert-Butyl (2R,5 S)-2-carbamoyl-5-phenylpyrrolidine-1-carboxylate To a suspension of (2R,5S)-1-[(tert-butoxy)carbonyl]-5-phenylpyrrolidine-2-carboxylic acid (274 mg), ammonium chloride (201 mg), EDC-HCl (360 mg) and HOBT (140 mg) in DMF (3 mL) was added DIPEA (1.35 mL), and the mixture was stirred at room temperature overnight. To the reaction mixture were added a saturated aqueous solution of ammonium chloride, water and ethyl acetate. The organic layer was separated. The organic layer was dried over anhydrous sodium sulfate, and concentrated under reduced pressure. The residue was purified by column chromatography on silica gel (eluent: n-hexane/ethyl acetate=75/25-30/70) to give the title compound (254 mg).

Reference Example 5-7-B (2R,5 S)-5-Phenylpyrrolidine-2-carboxamide hydrochloride A mixture of Reference Example 5-7-A (40.0 mg) and hydrogen chloride in ethyl acetate (4 mol/L, 2 mL) was stirred at room temperature for 1 hour. The reaction mixture was concentrated under reduced pressure to give the title compound (30.0 mg). $^1$H-NMR δ ppm (DMSO-d6): 1.98-2.24 (2H, m), 2.29-2.43 (2H, m), 4.27-4.39 (1H, m), 4.59-4.71 (1H, m), 5.76 (2H, s), 7.37-7.58 (5H, m), 7.76 (1H, brs), 8.06 (1H, brs)

Reference Example 5-8-A (2R)-1-(tert-Butoxycarbonyl)-4-[(dimethyl amino) methylidene]-5-oxopyrrolidine-2-carboxylic acid ethyl A solution of (R)-1-(tert-butoxycarbonyl)-5-oxopyrrolidine-2-carboxylic acid ethyl (2.00 g) and tert-butoxybis (dimethylamino)methane (2.16 g) in DME (20 mL) was refluxed for 14 hours. The reaction mixture was allowed to cool to room temperature, and then the reaction mixture was concentrated under reduced pressure. To the residue was added n-hexane (20 mL), and then the precipitated solid was collected by filtration. The obtained solid was washed with n-hexane, and dried under reduced pressure to give the title compound (2.30 g).

Reference Example 5-8-B (2R,4R)-1-(tert-Butoxycarbonyl)-4-methyl-5-oxopyrrolidine-2-carboxylic acid ethyl To a solution of Reference Example 5-8-A (2.30 g) in 2-propanol (25 mL) and ethyl acetate (5.0 mL) was added 10% palladium on carbon (wet, 0.929 g) under ice-cooling. The mixture was stirred under a hydrogen atmosphere at room temperature for 3 days. The reaction mixture was filtered through Celite, and the filtrate was concentrated under reduced pressure. The residue was purified by column chromatography on silica gel (eluent: n-hexane/ethyl acetate=80/20-40/60) to give the title compound (1.81 g).

Reference Example 5-8-C

Ethyl (2R,4S)-4-methyl-5-phenyl-3,4-dihydro-2H-pyrrole-2-carboxylate and ethyl (2R,4R)-4-methyl-5-phenyl-3,4-dihydro-2H-pyrrole-2-carboxylate To a solution of Reference Example 5-8-B (1.81 g) in THF (30 mL) was added dropwise phenylmagnesium bromide (1.0 mol/L, THF) (13.3 mL) under an argon atmosphere at −40° C., and the mixture was stirred at the same temperature for 2 hours. To the reaction mixture were added a saturated aqueous solution of ammonium chloride and water, and the mixture was extracted with ethyl acetate. The organic layer was dried over anhydrous magnesium sulfate, and concentrated under reduced pressure. The residue was purified by column chromatography on silica gel (eluent: n-hexane/ethyl acetate=94/6-73/27) to give (2R)-2-{[(tert-butoxy)carbonyl]amino}-4-methyl-5-oxo-5-phenylpentanoic acid ethyl (1.69 g). To a solution of the obtained compound in ethyl acetate (15 mL) was added hydrogen chloride in ethyl acetate (4 mol/L, 15 mL), and the mixture was stirred at room temperature for 14 hours. The reaction mixture was concentrated under reduced pressure. The residue was diluted with ethyl acetate, and a saturated aqueous solution of sodium bicarbonate and water were added to the mixture. The organic layer was separated. The aqueous layer was extracted with ethyl acetate, and then the extract was combined with the above organic layer. The organic layer was washed with brine, dried over anhydrous magnesium sulfate, and concentrated under reduced pressure. The residue was purified by column chromatography on silica gel (eluent: n-hexane/ethyl acetate=95/5-75/25) to give ethyl (2R,4S)-4-methyl-5-phenyl-3,4-dihydro-2H-pyrrole-2-carboxylate (400 mg) which was formerly eluted and ethyl (2R,4R)-4-methyl-5-phenyl-3,4-dihydro-2H-pyrrole-2-carboxylate (394 mg) which was latterly eluted of the title compound, respectively.

Reference Example 5-8-D (2R,4S,5S)-4-Methyl-5-phenylpyrrolidine-2-carboxylic acid ethyl To a solution of (2R,4S)-4-methyl-5-phenyl-3,4-dihydro-2H-pyrrole-2-carboxylic acid ethyl (395 mg) in methanol (10 mL) was added platinum on carbon (5%, 40.0 mg) under ice-cooling. The mixture was stirred under a hydrogen atmosphere at room temperature for 12 hours. The reaction mixture was filtered through Celite, and the filtrate was concentrated under reduced pressure. The residue was purified by column chromatography on silica gel (eluent: n-hexane/ethyl acetate=65/35-34/66) to give the title compound (256 mg).

Reference Example 5-8-E (2R,4S,5 S)-1-(tert-Butoxycarbonyl)-4-methyl-5-phenylpyrrolidine-2-carboxylic acid ethyl The title compound was prepared in a similar manner to that described in Reference Example 1-1-C using Reference Example 5-8-D instead of Reference Example 1-1-B.

Reference Example 5-8-F tert-Butyl (2S,3S,5R)-5-(2-hydroxypropan-2-yl)-3-methyl-2-phenylpyrrolidine-1-carboxylate To a solution of Reference Example 5-8-E (340 mg) in THF (5 mL) was added methylmagnesium bromide (3.0 mol/L, diethyl ether) (1.70 mL) under an argon atmosphere under ice-cooling, and the mixture was stirred at room temperature for 40 minutes. To the reaction mixture was added a saturated aqueous solution of ammonium chloride slowly, and then to the reaction mixture was added water. The mixture was extracted with ethyl acetate. The organic layer was washed with brine, dried over anhydrous magnesium sulfate, and concentrated under reduced pressure to give the crude title compound (325 mg).

Reference Example 5-8-G

2-[(2R,4S,5 S)-4-Methyl-5-phenylpyrrolidin-2-yl]propan-2-ol

A mixture of Reference Example 5-8-F (320 mg) and hydrogen chloride in 1,4-dioxane (4 mol/L, 3 mL) was stirred at room temperature for 1 hour. The reaction mixture was concentrated under reduced pressure. To the residue was added a saturated aqueous solution of sodium bicarbonate, and the mixture was extracted with dichloromethane. The organic layer was concentrated under reduced pressure. The residue was purified by column chromatography on aminosilica gel (eluent: n-hexane/ethyl acetate=100/0-60/40) to give the title compound (152 mg). MS (ESI_APCI, m/z): 220 (M+H)$^+$

Reference Example 5-9-A

Ethyl (2R,4R,5S)-4-methyl-5-phenylpyrrolidine-2-carboxylate

The title compound was prepared in a similar manner to that described in Reference Example 5-8-D using ethyl (2R,4R)-4-methyl-5-phenyl-3,4-dihydro-2H-pyrrole-2-carboxylate instead of ethyl (2R,4S)-4-methyl-5-phenyl-3,4-dihydro-2H-pyrrole-2-carboxylate.

Reference Example 5-9-B (2R,4R,5 S)-1-(tert-Butoxycarbonyl)-4-methyl-5-phenylpyrrolidine-2-carboxylic acid ethyl The title compound was prepared in a similar manner to that described in Reference Example 1-1-C using Reference Example 5-9-A instead of Reference Example 1-1-B.

Reference Example 5-9-C tert-Butyl (2S,3R,5R)-5-(2-hydroxypropan-2-yl)-3-methyl-2-phenylpyrrolidine-1-carboxylate The title compound was prepared in a similar manner to that described in Reference Example 5-8-F using Reference Example 5-9-B instead of Reference Example 5-8-E.

Reference Example 5-9-D

2-[(2R,4R,5 S)-4-Methyl-5-phenylpyrrolidin-2-yl]propan-2-ol

The title compound was prepared in a similar manner to that described in Reference Example 5-8-G using Reference Example 5-9-C instead of Reference Example 5-8-F. MS (ESI_APCI, m/z): 220 (M+H)$^+$

Reference Example 5-10-A

Ethyl 2-[(2R,5 S)-5-(3-fluorophenyl)pyrrolidin-2-yl]-2-methylpropanoate

A mixture of Reference Example 1-3-C (418 mg), concentrated sulfuric acid (2.89 mL) and water (9 mL) was refluxed for 24 hours. The reaction mixture was concentrated under reduced pressure. To the residue was added ethanol, and the mixture was concentrated under reduced pressure. This handling was repeated four times. To the residue was added ethanol (15 mL), and the mixture was refluxed for 8 hours. The reaction mixture was concentrated under reduced pressure. The residue was diluted with ethyl acetate and water, and neutralized by the addition of potassium carbonate. The organic layer was separated. The aqueous layer was extracted with ethyl acetate, and then the extract was combined with the above organic layer. The organic layer was washed with brine, dried over anhydrous magnesium sulfate, and concentrated under reduced pressure to give the title compound (486 mg).

Reference Example 5-10-B

2-[(2R,5S)-5-(3-Fluorophenyl)pyrrolidin-2-yl]-2-methylpropan-1-ol

To a solution of Reference Example 5-10-A (23.0 mg) in THF (1 mL) was added LAH (12.5 mg) under ice-cooling, and the mixture was stirred at the same temperature for 40 minutes. To the reaction mixture were added THF (2 mL) and sodium sulfate decahydrate (200 mg) successively under ice-cooling. The mixture was stirred at room temperature for 30 minutes, and then the mixture was filtered. The filtrate was concentrated under reduced pressure to give the title compound (14.6 mg). MS (ESI_APCI, m/z): 238 (M+H)$^+$

Reference Example 5-11-A

Ethyl (2R)-2-{[(tert-butoxy)carbonyl]amino}-5-oxo-5-phenylpentanoate

The title compound was prepared in a similar manner to that described in Reference Example 1-1-A using phenylmagnesium bromide instead of 3-fluorophenylmagnesium bromide.

Reference Example 5-11-B

Ethyl (2R,5 S)-5-phenylpyrrolidine-2-carboxylate

To a solution of Reference Example 5-11-A (33.5 g) in ethyl acetate (180 mL) was added hydrogen chloride in ethyl acetate (4 mol/L, 200 mL) at room temperature, and the mixture was stirred at the same temperature for 1 hour. The reaction mixture was concentrated under reduced pressure. To the residue were added ethyl acetate, a saturated aqueous solution of sodium bicarbonate and water. The organic layer was separated. The organic layer was dried over anhydrous sodium sulfate, and concentrated under reduced pressure to give ethyl (2R)-5-phenyl-3,4-dihydro-2H-pyrrole-2-carboxylate (21.5 g). To a solution of the obtained compound in ethanol (300 mL) was added platinum on carbon (5%, 2.10 g) under ice-cooling. The mixture was stirred under a hydrogen atmosphere at room temperature overnight. The reaction mixture was filtered through Celite, and the filtrate was concentrated under reduced pressure. The residue was purified by column chromatography on silica gel (eluent: n-hexane/ethyl acetate=76/24-55/45) to give the title compound (16.1 g).

Reference Example 5-11-C (2R,5S)-1-(tert-Butoxycarbonyl)-5-phenyl pyrrolidine-2-carboxylic acid ethyl The title compound was prepared in a similar manner to that described in Reference Example 1-1-C using Reference Example 5-11-B instead of Reference Example 1-1-B.

Reference Example 5-11-D tert-Butyl (2R,5S)-2-[methoxy(methyl)carbamoyl]-5-phenylpyrrolidine-1-carboxylate The title compound was prepared in a similar manner to that described in Reference Example 1-2-A using Reference Example 5-11-C instead of Reference Example 1-1-C.

Reference Example 5-11-E tert-Butyl (2R,5 S)-2-acetyl-5-phenylpyrrolidine-1-carboxylate The title compound was prepared in a similar manner to that described in Reference Example 1-2-B using Reference Example 5-11-D instead of Reference Example 1-2-A.

Reference Example 5-11-F tert-Butyl (2S,5R)-2-phenyl-5-(prop-1-en-2-yl)pyrrolidine-1-carboxylate To a suspension of methyltriphenylphosphonium bromide (1.86 g) in THF (25 mL) was added n-butyllithium (1.6 mol/L, n-hexane) (3.10 mL) under ice-cooling. The mixture was stirred under ice-cooling for 40 minutes, and then to the mixture was added a solution of Reference Example 5-11-E (0.756 g) in THF (8 mL). The mixture was stirred at room temperature for 2 hours. The reaction mixture was poured into water, and the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=100/0-80/20) to give the title compound (0.306 g).

Reference Example 5-11-G tert-Butyl (2R,5 S)-2-(1-cyano-1-methylethyl)-5-phenylpyrrolidine-1-carboxylate The title compound was prepared in a similar manner to that described in Reference Example 1-6-C using Reference Example 5-11-F instead of Reference Example 1-6-B.

Reference Example 5-11-H

2-Methyl-2-[(2R,5 S)-5-phenylpyrrolidin-2-yl]propanenitrile

A mixture of Reference Example 5-11-G (161 mg) and hydrogen chloride in 1,4-dioxane (4 mol/L, 1.5 mL) was stirred at room temperature for 1 hour. The reaction mixture was concentrated under reduced pressure. To the residue was added a saturated aqueous solution of sodium bicarbonate, and the mixture was extracted with dichloromethane. The organic layer was concentrated under reduced pressure. The residue was purified by column chromatography on silica gel (eluent: n-hexane/ethyl acetate=100/0-75/25) to give the title compound (64.8 mg). MS (ESI_APCI, m/z): 215 (M+H)$^+$ Reference Example 5-12-A tert-Butyl (2S,5R)-2-(3-fluorophenyl)-5-(2-methoxypropan-2-yl)pyrrolidine-1-carboxylate To a solution of Reference Example 1-3-A (9.1 mg) in methanol (3 mL) were added a solution of Reference Example 1-2-C (152 mg) in methanol (1.8 mL), 1-fluoro-2,4,6-trimethylpyridinium tetrafluoroborate (226 mg) and 1,1,3,3-tetramethyldisiloxane (0.176 mL) successively under an argon atmosphere under ice-cooling. The mixture was stirred under ice-cooling for 1.5 hours. To the reaction mixture was added a saturated aqueous solution of ammonium chloride, and the mixture was extracted with ethyl acetate. The organic layer was dried over anhydrous magnesium sulfate, and concentrated under reduced pressure. The residue was purified by column chromatography on silica gel (eluent: n-hexane/ethyl acetate=100/0-85/15) to give the title compound (23.1 mg).

Reference Example 5-12-B (2S,5R)-2-(3-Fluorophenyl)-5-(2-methoxypropan-2-yl)pyrrolidine A mixture of Reference Example 5-12-A (32.6 mg), hydrogen chloride in ethyl acetate (4 mol/L, 1 mL) and ethyl acetate (1 mL) was stirred at room temperature for 2.5 hours. The reaction mixture was concentrated under reduced pressure. To the residue was added a saturated aqueous solution of sodium bicarbonate, and the mixture was extracted with dichloromethane. The organic layer was concentrated under reduced pressure. The residue was purified by column chromatography on silica gel (eluent: n-hexane/ethyl acetate=50/50-0/100) to give the title compound (17.4 mg). MS (ESI_APCI, m/z): 238 (M+H)$^+$ Reference Example 5-13-A tert-Butyl (2S,5R)-2-(3-fluorophenyl)-5-(1-hydroxy-2-methylpropan-2-yl)pyrrolidine-1-carboxylate To a solution of Reference Example 5-10-A (219 mg) and triethylamine (0.164 mL) in THF (2 mL) was added a solution of di-tert-butyl dicarbonate (222 mg) in THF (2 mL). The mixture was stirred at 50° C. for 13 hours. To the reaction mixture was added water, and the mixture was extracted with dichloromethane. The organic layer was dried over anhydrous sodium sulfate, and concentrated under reduced pressure. The residue was dissolved in THF (1 mL), and then to the mixture was added LAH (89.1 mg) under ice-cooling. The reaction mixture was stirred under ice-cooling for 30 minutes, and to the reaction mixture were added THF (4 mL) and sodium sulfate decahydrate (1.00 g) successively. The mixture was stirred at room temperature for 1 hour, and then the mixture was filtered. The filtrate was concentrated under reduced pressure. The residue was purified by column chromatography on silica gel (eluent: n-hexane/ethyl acetate=90/10-70/30) to give the title compound (231 mg).

Reference Example 5-13-B tert-Butyl (2S,5R)-2-(3-fluorophenyl)-5-(2-methyl-1-oxopropan-2-yl)pyrrolidine-1-carboxylate To a solution of Reference Example 5-13-A (93.6 mg) in dichloromethane (2 mL) was added DMP (152 mg), and the mixture was stirred at room temperature for 1.5 hours. To the reaction mixture were added an aqueous solution of sodium thiosulfate (1 mol/L, 2 mL) and a saturated aqueous solution of sodium bicarbonate (4 mL), and the mixture was stirred at room temperature for 10 minutes. The mixture was extracted twice with dichloromethane. The combined organic layer was dried over anhydrous sodium sulfate, and concentrated under reduced pressure to give the crude title compound (92.3 mg).

Reference Example 5-13-C tert-Butyl (2R,5 S)-2-[(3E)-5-ethoxy-2-methyl-5-oxopent-3-en-2-yl]-5-(3-fluorophenyl)pyrrolidine-1-carboxylate To a suspension of sodium hydride (ca. 60%, 15.0 mg) in THF (3 mL) was added dropwise triethyl phosphonoacetate (0.0830 mL) under ice-cooling, and the mixture was stirred at the same temperature for 20 minutes. To the mixture was added dropwise a solution of Reference Example 5-13-B (93.0 mg) in THF (1 mL) under an argon atmosphere under ice-cooling. The reaction mixture was stirred at room temperature for 2 hours. To the reaction mixture were added a saturated aqueous solution of ammonium chloride and water, and the mixture was extracted with ethyl acetate twice. The combined organic layer was dried over anhydrous magnesium sulfate, and concentrated under reduced pressure. The residue was purified by column chromatography on silica gel (eluent: n-hexane/ethyl acetate=100/0-80/20) to give the title compound (78.7 mg).

Reference Example 5-13-D tert-Butyl (2R,5S)-2-(5-ethoxy-2-methyl-5-oxopentan-2-yl)-5-(3-fluorophenyl)pyrrolidine-1-carboxylate To a solution of Reference Example 5-13-C (76.0 mg) in methanol (0.9 mL) and THF (0.9 mL) was added platinum on carbon (5%, 15.0 mg) under ice-cooling. The mixture was stirred under a hydrogen atmosphere at room temperature for 1 hour. The reaction mixture was filtered through Celite, and the filtrate was concentrated under reduced pressure. The residue was purified by column chromatography on silica gel (eluent: n-hexane/ethyl acetate=100/0-80/20) to give the title compound (59.5 mg).

Reference Example 5-13-E tert-Butyl (2S,5R)-2-(3-fluorophenyl)-5-(5-hydroxy-2-methylpentan-2-yl)pyrrolidine-1-carboxylate To a solution of Reference Example 5-13-D (55.9 mg) in THF (1.4 mL) was added LAH (15.6 mg) under ice-cooling, and the mixture was stirred at the same temperature for 40 minutes. To the reaction mixture were added THF (1.4 mL) and sodium sulfate decahydrate (200 mg) successively under ice-cooling. The mixture was stirred at room temperature for 30 minutes, and then the mixture was filtered. The filtrate was concentrated under reduced pressure to give the crude title compound (50.1 mg).

Reference Example 5-13-F

4-[(2R,5S)-5-(3-Fluorophenyl)pyrrolidin-2-yl]-4-methylpentan-1-ol

A mixture of Reference Example 5-13-E (49.1 mg) and hydrogen chloride in 1,4-dioxane (4 mol/L, 1 mL) was stirred at room temperature for 1 hour. To the reaction mixture was added a saturated aqueous solution of sodium bicarbonate, and the mixture was extracted with dichloromethane. The organic layer was concentrated under reduced pressure to give the crude title compound (35.6 mg). MS (ESI_APCI, m/z): 266 (M+H)$^+$ Reference Example 5-14-A Ethyl (2R,5 S)-5-(3-methylphenyl)pyrrolidine-2-carboxylate To a solution of (R)-1-(tert-butoxycarbonyl)-5-oxopyrrolidine-2-carboxylic acid ethyl (2.00 g) in THF (40 mL) was added m-tolylmagnesium chloride (1.0 mol/L, diethyl ether) (15.6 mL) under an argon atmosphere at −78° C. The mixture was stirred at −40° C. for 1 hour. To the reaction mixture were added a saturated aqueous solution of ammonium chloride (16 mL) and water (8.0 mL). The mixture was stirred at room temperature overnight, and then to the mixture were added ethyl acetate, a saturated aqueous solution of ammonium chloride and water. The organic layer was separated. The organic layer was dried over anhydrous sodium sulfate, and concentrated under reduced pressure to give crude ethyl (2R)-2-{[(tert-butoxy)carbonyl]amino}-5-(3-methylphenyl)-5-oxopentanoate (3.22 g). To a solution of the obtained compound in ethyl acetate (27 mL) was added hydrogen chloride in ethyl acetate (4 mol/L, 27 mL), and the mixture was stirred at room temperature for 1 hour. The reaction mixture was concentrated under reduced pressure. To the residue were added ethyl acetate, a saturated aqueous solution of sodium bicarbonate and water. The organic layer was separated. The organic layer was dried over anhydrous sodium sulfate, and concentrated under reduced pressure to give crude ethyl (2R)-5-(3-methylphenyl)-3,4-dihydro-2H-pyrrole-2-carboxylate (2.18 g). To a solution of the obtained compound in ethanol (27 mL) was added platinum on carbon (5%, 0.180 g) under ice-cooling. The mixture was stirred under a hydrogen atmosphere at room temperature overnight. The reaction mixture was filtered through Celite, and the filtrate was concentrated under reduced pressure. The residue was purified by column chromatography on silica gel (eluent: n-hexane/ethyl acetate=86/14-65/35) to give the title compound (1.45 g).

Reference Example 5-14-B (2R,5S)-1-(tert-Butoxycarbonyl)-5-(3-methyl phenyl)pyrrolidine-2-carboxylic acid ethyl The title compound was prepared in a similar manner to that described in Reference Example 1-1-C using Reference Example 5-14-A instead of Reference Example 1-1-B.

Reference Example 5-14-C tert-Butyl (2R,5S)-2-[methoxy(methyl)carbamoyl]-5-(3-methylphenyl)pyrrolidine-1-carboxylate The title compound was prepared in a similar manner to that described in Reference Example 1-2-A using Reference Example 5-14-B instead of Reference Example 1-1-C.

Reference Example 5-14-D tert-Butyl (2R,5S)-2-acetyl-5-(3-methylphenyl)pyrrolidine-1-carboxylate The title compound was prepared in a similar manner to that described in Reference Example 1-2-B using Reference Example 5-14-C instead of Reference Example 1-2-A.

Reference Example 5-14-E tert-Butyl (2S,5R)-2-(3-methylphenyl)-5-(prop-1-en-2-yl)pyrrolidine-1-carboxylate The title compound was prepared in a similar manner to that described in Reference Example 1-2-C using Reference Example 5-14-D instead of Reference Example 1-2-B.

Reference Example 5-14-F tert-Butyl (2R,5S)-2-(1-cyano-1-methylethyl)-5-(3-methylphenyl)pyrrolidine-1-carboxylate The title compound was prepared in a similar manner to that described in Reference Example 1-6-C using Reference Example 5-14-E instead of Reference Example 1-6-B.

Reference Example 5-14-G

2-Methyl-2-[(2R,5S)-5-(3-methylphenyl)pyrrolidin-2-yl]propanenitrile

The title compound was prepared in a similar manner to that described in Reference Example 5-11-H using Reference Example 5-14-F instead of Reference Example 5-11-G.
MS (ESI_APCI, m/z): 229 (M+H)$^+$

Reference Example 5-15-A tert-Butyl (2S,5R)-2-(3-fluorophenyl)-5-(2-methylbut-3-en-2-yl)pyrrolidine-1-carboxylate To a suspension of methyltriphenylphosphonium bromide (232 mg) in THF (2 mL) was added dropwise potassium bis(trimethylsilyl)amide (1.0 mol/L, THF) (0.626 mL) at room temperature, and the mixture was stirred for 1 hour. To the reaction mixture was added dropwise a solution of Reference Example 5-13-B (87.5 mg) in THF (1 mL) under ice-cooling. The mixture was stirred under ice-cooling for 1 hour and stirred at room temperature for 1.5 hours. To the reaction mixture were added a saturated aqueous solution of ammonium chloride and water, and the mixture was extracted with ethyl acetate twice. The combined organic layer was washed with brine, dried over anhydrous magnesium sulfate, and concentrated under reduced pressure. The residue was purified by column chromatography on silica gel (eluent: n-hexane/ethyl acetate=100/0-85/15) to give the title compound (51.3 mg).

Reference Example 5-15-B (2S,5R)-2-(3-fluorophenyl)-5-(2-methylbut-3-en-2-yl)pyrrolidine The title compound was prepared in a similar manner to that described in Reference Example 5-13-F using Reference Example 5-15-A instead of Reference Example 5-13-E.
MS (ESI_APCI, m/z): 234 (M+H)$^+$

Reference Example 5-16-A tert-Butyl (2R,5S)-2-(1-ethoxy-2-methyl-1-oxopropan-2-yl)-5-(3-fluorophenyl)pyrrolidine-1-carboxylate A mixture of Reference Example 5-10-A (400 mg), di-tert-butyl dicarbonate (375 mg), triethylamine (0.399 mL) and THF (15 mL) was stirred at 50° C. overnight. The reaction mixture was concentrated under reduced pressure. The residue was purified by column chromatography on amino-silica gel (eluent: n-hexane/ethyl acetate=100/0-30/70) to give the title compound (547 mg).

Reference Example 5-16-B

2-[(2R,5S)-1-[(tert-Butoxy)carbonyl]-5-(3-fluorophenyl)pyrrolidin-2-yl]-2-methylpropanoic acid A mixture of Reference Example 5-16-A (547 mg), lithium hydroxide monohydrate (604 mg), THF (4 mL), methanol (4 mL) and water (4 mL) was stirred at 60° C. for 6 hours. To the mixture was added lithium hydroxide monohydrate (604 mg). The mixture was stirred at 50° C. overnight, and then allowed to cool to room temperature. To the reaction mixture was added hydrochloric acid (2 mol/L, 14.5 mL). The mixture was concentrated under reduced pressure. To the residue were added ethyl acetate and water. The organic layer was separated, dried over anhydrous magnesium sulfate, and concentrated under reduced pressure to give the title compound (517 mg).

Reference Example 5-16-C tert-Butyl (2S,5R)-2-(3-fluorophenyl)-5-(1-methoxy-2-methyl-1-oxopropan-2-yl)pyrrolidine-1-carboxylate A mixture of Reference Example 5-16-B (344 mg), iodomethane (0.122 mL), potassium carbonate (202 mg) and DMF (14 mL) was stirred at room temperature for 30 minutes. To the reaction mixture were added water and diethyl ether. The organic layer was separated. The organic layer was washed with water, dried over anhydrous magnesium sulfate, and concentrated under reduced pressure to give the title compound (354 mg).

Reference Example 5-16-D

Methyl 2-[(2R,5S)-5-(3-fluorophenyl)pyrrolidin-2-yl]-2-methylpropanoate

The mixture of Reference Example 5-16-C (354 mg) and hydrogen chloride in 1,4-dioxane (4 mol/L, 5 mL) was stirred at room temperature for 2 hours. The reaction mixture was concentrated under reduced pressure. To the residue were added ethyl acetate and an aqueous solution of sodium bicarbonate. The organic layer was separated. The organic layer was dried over anhydrous sodium sulfate, and concentrated under reduced pressure to give the title compound (246 mg).

Reference Example 5-16-E

Benzyl (2S,5R)-2-(3-fluorophenyl)-5-(1-methoxy-2-methyl-1-oxopropan-2-yl)pyrrolidine-1-carboxylate A mixture of Reference Example 5-16-D (246 mg), benzyl chloroformate (0.143 mL), triethylamine (0.194 mL) and THF (5 mL) was stirred at 50° C. for 1 hour. To the reaction mixture were added ethyl acetate and hydrochloric acid (1 mol/L). The organic layer was separated, and then concentrated under reduced pressure. The residue was purified by column chromatography on silica gel (eluent: n-hexane/ethyl acetate=90/10-20/80) to give the title compound (316 mg).

Reference Example 5-16-F

2-[(2R,5S)-1-[(Benzyloxy)carbonyl]-5-(3-fluorophenyl)pyrrolidin-2-yl]-2-methylpropanoic acid The title compound was prepared in a similar manner to that described in Reference Example 5-16-B using Reference Example 5-16-E instead of Reference Example 5-16-A.

Reference Example 5-16-G

Benzyl (2R,5S)-2-{1-[(2,2-dimethoxyethyl)carbamoyl]-1-methylethyl}-5-(3-fluorophenyl)pyrrolidine-1-carboxylate To a mixture of Reference Example 5-16-F (50.0 mg), aminoacetaldehyde dimethyl acetal (0.0279 mL), HOBT (43.8 mg) and DMF (2 mL) was added EDC·HCl (62.2 mg). The mixture was stirred at room temperature for 1 hour, stirred at 40° C. for 2 hours and stirred at 60° C. overnight. To the reaction mixture were added water and ethyl acetate. The organic layer was separated and was successively washed with water, a saturated aqueous solution of sodium bicarbonate and brine. The organic layer was dried over anhydrous magnesium sulfate, and concentrated under reduced pressure to give the title compound (55.0 mg).

Reference Example 5-16-H

Benzyl (2S,5R)-2-(3-fluorophenyl)-5-{1-methyl-1-[(2-oxoethyl)carbamoyl]ethyl}pyrrolidine-1-carboxylate A mixture of Reference Example 5-16-G (55.0 mg), water (1.5 mL), concentrated hydrochloric acid (1 mL) and THF (3 mL) was stirred at room temperature for 1 hour. To the reaction mixture were added water and ethyl acetate. The organic layer was separated. The organic layer was washed with brine, dried over anhydrous magnesium sulfate, and concentrated under reduced pressure to give the title compound (43.2 mg).

Reference Example 5-16-I

Benzyl (2S,5R)-2-(3-fluorophenyl)-5-[2-(1,3-oxazol-2-yl)propan-2-yl]pyrrolidine-1-carboxylate A mixture of Reference Example 5-16-H (43.2 mg), triphenylphosphine (39.9 mg), iodine (38.6 mg), triethylamine (0.0424 mL) and dichloromethane (3 mL) was stirred at room temperature for 2 hours. To the reaction mixture were added an aqueous solution of sodium sulfite and dichloromethane. The organic layer was separated, and then concentrated under reduced pressure. The residue was purified by column chromatography on silica gel (eluent: n-hexane/ethyl acetate=100/0-50/50) to give the title compound (25.0 mg).

Reference Example 5-16-J

2-{2-[(2R,5S)-5-(3-Fluorophenyl)pyrrolidin-2-yl]propan-2-yl}-1,3-oxazole

A mixture of Reference Example 5-16-I (25.0 mg), platinum on carbon (5%, wet) (30.0 mg) and ethanol (5 mL) was stirred under a hydrogen atmosphere at room temperature for 2 hours. The reaction mixture was filtered through to remove an insoluble material. The filtrate was concentrated under reduced pressure to give the title compound (16.8 mg). MS (ESI_APCI, m/z): 275 (M+H)$^+$

Reference Example 5-17-A

1-[(2R,5S)-5-(3-Fluorophenyl)pyrrolidin-2-yl]cyclopentan-1-ol

To a suspension of magnesium (49.7 mg) in THF (3 mL) were added 1,4-dibromobutane (0.120 mL) and a slight amount of iodine under an argon atmosphere, and the mixture was stirred at room temperature for 1 hour. To the mixture was added dropwise a solution of Reference Example 1-1-C (100 mg) in THF (1.6 mL) under ice-cooling. The mixture was stirred at room temperature for 30 minutes. To the reaction mixture was added a saturated aqueous solution of ammonium chloride slowly. To the mixture were added water and ethyl acetate. The organic layer was separated. The organic layer was dried over anhydrous sodium sulfate, and concentrated under reduced pressure to give crude tert-butyl (2S,5R)-2-(3-fluorophenyl)-5-(1-hydroxycyclopentyl)pyrrolidine-1-carboxylate (134 mg). The mixture of the obtained compound and hydrogen chloride in 1,4-dioxane (4 mol/L, 2 mL) was stirred at room temperature for 1.5 hours. The reaction mixture was concentrated under reduced pressure. To the residue were added ethyl acetate, an aqueous solution of sodium bicarbonate and water. The organic layer was separated, dried over anhydrous sodium sulfate, and concentrated under reduced pressure. The residue was purified by column chromatography on silica gel (eluent: n-hexane/ethyl acetate=90/10-50/50) to give the title compound (46.8 mg). MS (ESI_APCI, m/z): 250 (M+H)$^+$

Reference Example 5-18-A

2-[(2R,5S)-5-Methyl-5-phenylpyrrolidin-2-yl]propan-2-ol

To a solution of (2R)-5-phenyl-3,4-dihydro-2H-pyrrole-2-carboxylic acid ethyl (492 mg) in THF (10 mL) was added methyllithium (1.13 mol/L, diethyl ether) (8.00 mL) under an argon atmosphere at −40° C. The mixture was stirred at −40° C. for 1 hour, and then stirred under ice-cooling for 2 hours. To the reaction mixture were added a saturated aqueous solution of sodium bicarbonate, water and ethyl acetate. The organic layer was separated, dried over anhydrous sodium sulfate, and concentrated under reduced pressure. The residue was purified by column chromatography on silica gel (eluent: n-hexane/ethyl acetate=80/20-10/90) to give the title compound (128 mg). MS (ESI_APCI, m/z): 220 (M+H)$^+$ Reference Example 5-19-A Ethyl (2R,5 S)-5-cyclohexylpyrrolidine-2-carboxylate To a solution of (R)-1-(tert-butoxycarbonyl)-5-oxopyrrolidine-2-carboxylic acid ethyl (6.17 g) in THF (120 mL) was added cyclohexylmagnesium bromide (1.0 mol/L, THF) (48.0 mL) under an argon atmosphere at −78° C. The mixture was stirred at −40° C. for 1.5 hours. To the reaction mixture were added a saturated aqueous solution of ammonium chloride (90 mL) and water (45 mL), and the mixture was stirred at room temperature for 5 hours. To the mixture were added ethyl acetate and water. The organic layer was separated. The organic layer was dried over anhydrous sodium sulfate, and concentrated under reduced pressure to give crude ethyl (2R)-2-{[(tert-butoxy)carbonyl]amino}-5-cyclohexyl-5-oxopentanoate (9.13 g). To a solution of the obtained compound in ethyl acetate (90 mL) was added hydrogen chloride in ethyl acetate (4 mol/L, 90 mL), and the mixture was stirred at room temperature for 2 hours. The reaction mixture was concentrated under reduced pressure. To the residue were added ethyl acetate, a saturated aqueous solution of sodium bicarbonate and water. The organic layer was separated. The organic layer was dried over anhydrous sodium sulfate, and concentrated under reduced pressure to give crude ethyl (2R)-5-cyclohexyl-3,4-dihydro-2H-pyrrole-2-carboxylate (5.29 g). To a solution of the obtained compound in ethanol (90 mL) was added platinum on carbon (5%, 0.530 g) under ice-cooling. The mixture was stirred under a hydrogen atmosphere at room temperature overnight. The reaction mixture was filtered through Celite, and the filtrate was concentrated under reduced pressure. The residue was purified by column chromatography on silica gel (eluent: n-hexane/ethyl acetate=70/30-20/80) to give the title compound (2.04 g).

Reference Example 5-19-B (2R,5S)-1-(tert-Butoxycarbonyl)-5-cyclohexyl pyrrolidine-2-carboxylic acid ethyl The title compound was prepared in a similar manner to that described in Reference Example 1-1-C using Reference Example 5-19-A instead of Reference Example 1-1-B.

Reference Example 5-19-C tert-Butyl (2S,5R)-2-cyclohexyl-5-(hydroxymethyl) pyrrolidine-1-carboxylate To a solution of Reference Example 5-19-B (0.900 g) in THF (18 mL) was added LAH (0.262 g) under an argon atmosphere under ice-cooling, and the mixture was stirred at the same temperature for 50 minutes. To the reaction mixture were added THF (18 mL) and sodium sulfate decahydrate (2.6 g) successively. The mixture was stirred at room temperature for 30 minutes, and then the mixture was filtered. The filtrate was concentrated under reduced pressure to give the title compound (0.958 g).

Reference Example 5-19-D tert-Butyl (2S,5R)-2-cyclohexyl-5-formylpyrrolidine-1-carboxylate To a solution of Reference Example 5-19-C (0.783 g) in dichloromethane (16 mL) was added DMP (1.64 g), and the mixture was stirred at room temperature for 1 hour. To the reaction mixture were added a saturated aqueous solution of sodium thiosulfate (4 mL), a saturated aqueous solution of sodium bicarbonate (4 mL), water (4 mL) and dichloromethane. The mixture was stirred for 10 minutes, and then to the mixture were added water and dichloromethane. The organic layer was separated. The organic layer was dried over anhydrous sodium sulfate, and concentrated under reduced pressure. The residue was purified by column chromatography on silica gel (eluent: n-hexane/ethyl acetate=100/0-80/20) to give the title compound (0.789 g).

Reference Example 5-19-E tert-Butyl (2S,5R)-2-cyclohexyl-5-(1-hydroxyethyl) pyrrolidine-1-carboxylate To a solution of Reference Example 5-19-D (0.789 g) in THF (16 mL) was added methylmagnesium bromide (3.0 mol/L, diethyl ether) (1.90 mL) under an argon atmosphere under ice-cooling, and the mixture was stirred at room temperature for 1 hour. To the reaction mixture was added a saturated aqueous solution of ammonium chloride slowly. To the mixture were added water and ethyl acetate. The organic layer was separated. The organic layer was dried over anhydrous sodium sulfate, and concentrated under reduced pressure to give the title compound (0.782 g).

Reference Example 5-19-F tert-Butyl (2R,5 S)-2-acetyl-5-cyclohexylpyrrolidine-1-carboxylate The title compound was prepared in a similar manner to that described in Reference Example 5-19-D using Reference Example 5-19-E instead of Reference Example 5-19-C.

Reference Example 5-19-G tert-Butyl (2S,5R)-2-cyclohexyl-5-(prop-1-en-2-yl) pyrrolidine-1-carboxylate The title compound was prepared in a similar manner to that described in Reference Example 1-2-C using Reference Example 5-19-F instead of Reference Example 1-2-B.

Reference Example 5-19-H tert-Butyl (2R,5 S)-2-(1-cyano-1-methylethyl)-5-cyclohexylpyrrolidine-1-carboxylate The title compound was prepared in a similar manner to that described in Reference Example 1-6-C using Reference Example 5-19-G instead of Reference Example 1-6-B.

Reference Example 5-19-I

2-[(2R,5 S)-5-Cyclohexylpyrrolidin-2-yl]-2-methylpropanenitrile hydrochloride

The title compound was prepared in a similar manner to that described in Reference Example 5-1-G using Reference Example 5-19-H instead of Reference Example 5-1-F. MS (ESI_APCI, m/z): 221 (M+H)+

Reference Example 5-20-A

Ethyl 2-[(2R,5 S)-5-(3-Fluorophenyl)-1-(prop-2-en-1-yl)pyrrolidin-2-yl]-2-methylpropanoate To a suspension of Reference Example 5-10-A (100 mg) and potassium carbonate (297 mg) in acetonitrile (3.5 mL) was added allyl bromide (0.137 mL), and the mixture was stirred at 50° C. for 20 hours. To the reaction mixture was added water, and the mixture was extracted twice with ethyl acetate. The combined organic layer was dried over anhydrous magnesium sulfate, and concentrated under reduced pressure. The residue was purified by column chromatography on silica gel (eluent: n-hexane/ethyl acetate=100/0-85/15) to give the title compound (103 mg).

Reference Example 5-20-B

2-[(2R,5 S)-5-(3-Fluorophenyl)-1-(prop-2-en-1-yl)pyrrolidin-2-yl]-2-methylpropan-1-ol The title compound was prepared in a similar manner to that described in Reference Example 5-10-B using Reference Example 5-20-A instead of Reference Example 5-10-A.

Reference Example 5-20-C

2-[(2R,5S)-5-(3-Fluorophenyl)-1-(prop-2-en-1-yl)pyrrolidin-2-yl]-2-methylpropanal The title compound was prepared in a similar manner to that described in Reference Example 5-13-B using Reference Example 5-20-B instead of Reference Example 5-13-A.

Reference Example 5-20-D

3-[(2R,5S)-5-(3-Fluorophenyl)pyrrolidin-2-yl]-3-methylbutan-2-ol

To a solution of Reference Example 5-20-C (55.0 mg) in THF (2 mL) was added methylmagnesium bromide (3.0 mol/L, diethyl ether) (0.133 mL) under an argon atmosphere under ice-cooling, and the mixture was stirred at the same temperature for 20 minutes. To the reaction mixture was added a saturated aqueous solution of ammonium chloride slowly. The mixture was extracted twice with ethyl acetate. The combined organic layer was washed with brine, dried over anhydrous magnesium sulfate, and concentrated under reduced pressure. The residue was dissolved in 1,2-dichloroethane (2 mL). To the mixture were successively added 1,3-dimethylbarbituric acid (93.5 mg) and tetrakis(triphenylphosphine)palladium (0) (23.1 mg). The mixture was stirred under an argon atmosphere at 50° C. for 3 hours. To the reaction mixture was added an aqueous solution of potassium carbonate. The mixture was stirred for several minutes, and then the mixture was extracted twice with dichloromethane. The combined organic layer was dried over anhydrous sodium sulfate, and concentrated under reduced pressure to give the crude title compound (83.8 mg). MS (ESI_APCI, m/z): 252 (M+H)+

Reference Example 5-21-A 4-(Benzyloxy)-N-methoxy-N-methylbutanamide

To a solution of 4-benzyloxybutyric acid (3.50 g) in dichloromethane (70 mL) was added CDI (3.79 g). The mixture was stirred at room temperature for 10 minutes, and then to the mixture was added N,O-dimethylhydroxylamine hydrochloride (2.28 g). The mixture was stirred at room temperature for 3 hours. To the reaction mixture were added water and a saturated aqueous solution of sodium bicarbonate, and the mixture was extracted with dichloromethane twice. The combined organic layer was washed with brine, dried over anhydrous sodium sulfate, and concentrated under reduced pressure to give the crude title compound (4.62 g).

Reference Example 5-21-B 4-(Benzyloxy)-1-(3-fluorophenyl)butan-1-one

To a solution of Reference Example 5-21-A (4.27 g) in THF (90 mL) was added dropwise 3-fluorophenylmagnesium bromide (1.0 mol/L, THF) (90 mL) under an argon atmosphere at −10° C., and the mixture was stirred at the same temperature for 70 minutes. To the reaction mixture were added a saturated aqueous solution of ammonium chloride and water at −5° C. The mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=100/0-85/15) to give the title compound (3.90 g).

Reference Example 5-21-C

2-[3-(Benzyloxy)propyl]-2-(3-fluorophenyl)-1,3-dioxolane

A solution of Reference Example 5-21-B (2.60 g), ethylene glycol (2.13 mL) and p-toluenesulfonic acid monohydrate (0.0908 g) in toluene (50 mL) was refluxed using Dean-Stark apparatus for 4 hours. The reaction mixture was allowed to cool to room temperature, and then to the reaction mixture were added a saturated aqueous solution of sodium bicarbonate and water. The mixture was extracted with ethyl acetate. The organic layer was successively washed with water and brine, dried over anhydrous magnesium sulfate, and concentrated under reduced pressure to give the crude title compound (3.32 g).

Reference Example 5-21-D

3-[2-(3-Fluorophenyl)-1,3-dioxolan-2-yl]propan-1-ol

To a solution of Reference Example 5-21-C (3.02 g) in ethanol (20 mL) and THF (20 mL) was added 10% palladium on carbon (wet, 0.600 g) under ice-cooling. The mixture was stirred under a hydrogen atmosphere at room temperature for 1.5 hours. The reaction mixture was filtered through Celite, and the filtrate was concentrated under reduced pressure to give the crude title compound (2.12 g).

Reference Example 5-21-E

3-[2-(3-Fluorophenyl)-1,3-dioxolan-2-yl]propanal

To a solution of Reference Example 5-21-D (1.32 g) in dichloromethane (30 mL) was added DMP (2.72 g) under ice-cooling, and the mixture was stirred at the same temperature for 1.5 hours. To the reaction mixture were added an aqueous solution of sodium thiosulfate (1 mol/L, 20 mL), a saturated aqueous solution of sodium bicarbonate (60 mL) and water, and the mixture was stirred at room temperature for 20 minutes. The mixture was extracted twice with dichloromethane. The combined organic layer was washed with brine, dried over anhydrous sodium sulfate, and concentrated under reduced pressure. The residue was purified by column chromatography on silica gel (eluent: n-hexane/ ethyl acetate=80/20-50/50) to give the title compound (0.869 g).

Reference Example 5-21-F (S)—N-{3-[2-(3-Fluorophenyl)-1,3-dioxolan-2-yl] propylidene}-2-methylpropane-2-sulfinamide To a solution of Reference Example 5-21-E (150 mg) and (S)-(−)-2-methyl-2-propanesulfinamide (97.3 mg) in THF (3.4 mL) was added titanium (IV) ethoxide (0.196 mL), and the mixture was stirred at room temperature for 17 hours. To the reaction mixture were successively added brine (0.196 mL) and ethyl acetate (6.8 mL). The mixture was stirred for several minutes, and then the mixture was filtered through Celite. The filtrate was concentrated under reduced pressure. The residue was purified by column chromatography on silica gel (eluent: n-hexane/ethyl acetate=80/20-50/50) to give the title compound (168 mg).

Reference Example 5-21-G (S)-2-Methyl-N-[(2R)-1,1,1-trifluoro-4-[2-(3-fluorophenyl)-1,3-dioxolan-2-yl]butan-2-yl]propane-2-sulfinamide To a suspension of Reference Example 5-21-F (138 mg) and tetrabutylammonium difluorotriphenylsilicate (250 mg) in THF (4.2 mL) was added (trifluoromethyl)trimethylsilane (0.075 mL) under an argon atmosphere at −10° C. The mixture was stirred for 3 hours while the mixture was allowed to warm to 0° C. slowly. To the reaction mixture were added a saturated aqueous solution of ammonium chloride and water, and the mixture was extracted with ethyl acetate. The organic layer was dried over anhydrous magnesium sulfate, and concentrated under reduced pressure. The residue was purified by column chromatography on silica gel (eluent: n-hexane/ethyl acetate=80/20-50/50) to give the title compound (43.6 mg).

Reference Example 5-21-H (2R)-5-(3-Fluorophenyl)-2-(trifluoromethyl)-3,4-dihydro-2H-pyrrole To a solution of Reference Example 5-21-G (40.0 mg) in THF (2 mL) and methanol (2 mL) was added an hydrochloric acid (2 mol/L, 0.500 mL), and the mixture was stirred at 50° C. for 16 hours. The reaction mixture was concentrated under reduced pressure. To the residue were added a saturated aqueous solution of sodium bicarbonate and water, and the mixture was extracted with dichloromethane twice. The combined organic layer was washed with brine, dried over anhydrous sodium sulfate, and concentrated under reduced pressure. The residue was purified by column chromatography on silica gel (eluent: n-hexane/ethyl acetate=100/0-80/20) to give the title compound (15.7 mg).

Reference Example 5-21-I (2S,5R)-2-(3-Fluorophenyl)-5-(trifluoromethyl)pyrrolidine To a solution of Reference Example 5-21-H (15.0 mg) in ethanol (1 mL) was added platinum on carbon (5%, 6.0 mg) under ice-cooling. The mixture was stirred under a hydrogen atmosphere at room temperature for 4 hours. The reaction mixture was filtered through Celite, and the filtrate was concentrated under reduced pressure to give the title compound (14.2 mg). MS (ESI_APCI, m/z): 234 (M+H)$^+$ Reference Example 5-22-A rac-tert-Butyl (2S,5S)-3,3-difluoro-5-(3-fluorophenyl)-2-(propan-2-yl)pyrrolidine-1-carboxylate To a solution of Reference Example 5-5-D (30.0 mg) in dichloromethane (1 mL) was added bis(2-methoxyethyl) aminosulfur trifluoride (0.038 mL) under ice-cooling, and the mixture was stirred at room temperature overnight. To the mixture was added bis(2-methoxyethyl)aminosulfur trifluoride (0.038 mL) under ice-cooling, and the mixture was stirred at room temperature overnight. To the mixture was added bis(2-methoxyethyl)aminosulfur trifluoride (0.038 mL) under ice-cooling, and the mixture was stirred at room temperature overnight. To the reaction mixture was slowly added water under ice-cooling. To the mixture were added a saturated aqueous solution of sodium bicarbonate and potassium carbonate. The mixture was extracted twice with dichloromethane. The combined organic layer was dried over anhydrous sodium sulfate, and concentrated under reduced pressure. The residue was purified by column chromatography on silica gel (eluent: n-hexane/ethyl acetate=100/0-80/20) to give the title compound (12.8 mg).

Reference Example 5-22-B rac-(2S,5 S)-3,3-Difluoro-5-(3-fluorophenyl)-2-(propan-2-yl)pyrrolidine The title compound was prepared in a similar manner to that described in Reference Example 5-13-F using Reference Example 5-22-A instead of Reference Example 5-13-E. MS (ESI_APCI, m/z): 244 (M+H)$^+$ Reference Example 5-23-A rac-tert-Butyl (2S,3R,5S)-3-(acetyloxy)-5-(3-fluorophenyl)-2-(propan-2-yl)pyrrolidine-1-carboxylate To a solution of Reference Example 5-5-E (92.4 mg) and triphenylphosphine (97.4 mg) in THF (3 mL) was added diisopropyl azodicarboxylate (ca. 1.9 mol/L, toluene) (0.195 mL) under ice-cooling. The mixture was stirred under ice-cooling for 20 minutes, and then to the mixture was added acetic acid (0.021 mL). The reaction mixture was stirred at room temperature for 2 hours, and then concentrated under reduced pressure. The residue was purified by column chromatography on silica gel (eluent: n-hexane/ethyl acetate=50/50-0/100) to give the title compound (29.6 mg).

Reference Example 5-23-B rac-(2S,3R,5 S)-5-(3-Fluorophenyl)-2-(propan-2-yl)
pyrrolidin-3-yl acetate The title compound was prepared in a similar manner to that described in Reference Example 5-13-F using Reference Example 5-23-A instead of Reference Example 5-13-E.
MS (ESI_APCI, m/z): 266 (M+H)$^+$

Reference Example 5-24-A rac-tert-Butyl (2S,3S,5S)-5-(3-fluorophenyl)-3-
methoxy-2-(propan-2-yl)pyrrolidine-1-carboxylate To a solution of Reference Example 5-5-E (50.0 mg) in DMF (1.5 mL) was added sodium hydride (ca. 60%, 9.0 mg) under ice-cooling. The mixture was stirred under ice-cooling for 20 minutes, and then to the mixture was added iodomethane (0.014 mL). The reaction mixture was stirred at room temperature for 2 hours, and then to the reaction mixture were added a saturated aqueous solution of ammonium chloride and water. The mixture was extracted with ethyl acetate. The organic layer was successively washed with water and brine, dried over anhydrous magnesium sulfate, and concentrated under reduced pressure. The residue was purified by column chromatography on silica gel (eluent: n-hexane/ethyl acetate=100/0-80/20) to give the title compound (34.8 mg).

Reference Example 5-24-B rac-(2S,3S,5S)-5-(3-Fluorophenyl)-3-methoxy-2-
(propan-2-yl)pyrrolidine The title compound was prepared in a similar manner to that described in Reference Example 5-13-F using Reference Example 5-24-A instead of Reference Example 5-13-E.
MS (ESI_APCI, m/z): 238 (M+H)$^+$

Reference Example 5-25-A rac-tert-Butyl (2S,3R,5 S)-5-(3-fluorophenyl)-3-
hydroxy-2-(propan-2-yl)pyrrolidine-1-carboxylate To a solution of Reference Example 5-23-A (85.0 mg) in methanol (1 mL) was added an aqueous solution of sodium hydroxide (2 mol/L, 0.345 mL), and the mixture was stirred at 40° C. for 1 hour. To the reaction mixture was added hydrochloric acid (2 mol/L, 0.383 mL). To the mixture were added water and dichloromethane. The organic layer was separated. The aqueous layer was extracted with dichloromethane, and then the extract was combined with the above organic layer. The organic layer was washed with brine, dried over anhydrous sodium sulfate, and concentrated under reduced pressure to give the crude title compound (79.8 mg).

Reference Example 5-25-B rac-tert-Butyl (2S,3R,5S)-5-(3-fluorophenyl)-3-
methoxy-2-(propan-2-yl)pyrrolidine-1-carboxylate The title compound was prepared in a similar manner to that described in Reference Example 5-24-A using Reference Example 5-25-A instead of Reference Example 5-5-E.

Reference Example 5-25-C rac-(2S,3R,5 S)-5-(3-Fluorophenyl)-3-methoxy-2-
(propan-2-yl)pyrrolidine The title compound was prepared in a similar manner to that described in Reference Example 5-13-F using Reference Example 5-25-B instead of Reference Example 5-13-E.
MS (ESI_APCI, m/z): 238 (M+H)$^+$

Reference Example 5-26-A tert-Butyl (2S,5R)-2-(3-fluorophenyl)-5-(hydroxymethyl)pyrrolidine-1-carboxylate The title compound was prepared in a similar manner to that described in Reference Example 5-19-C using Reference Example 1-1-C instead of Reference Example 5-19-B.

Reference Example 5-26-B tert-Butyl (2S,5R)-2-(3-fluorophenyl)-5-formylpyrrolidine-1-carboxylate The title compound was prepared in a similar manner to that described in Reference Example 5-19-D using Reference Example 5-26-A instead of Reference Example 5-19-C.

Reference Example 5-26-C tert-Butyl (2S,5R)-2-(3-fluorophenyl)-5-(2,2,2-trifluoro-1-hydroxyethyl)pyrrolidine-1-carboxylate To a solution of Reference Example 5-26-B (176 mg) and (trifluoromethyl)trimethylsilane (0.107 mL) in THF (2 mL) was added TBAF (ca. 1 mol/L, THF) (0.018 mL), and the mixture was stirred at room temperature for 1 hour. To the mixture was added TBAF (ca. 1 mol/L, THF) (1.20 mL). The reaction mixture was stirred at room temperature overnight, and then to the reaction mixture were added a saturated aqueous solution of sodium bicarbonate, water and dichloromethane. The organic layer was separated, and then concentrated under reduced pressure. The residue was purified by column chromatography on silica gel (eluent: n-hexane/ethyl acetate=85/15-55/45) to give the title compound (164 mg).

Reference Example 5-26-D tert-Butyl (2S,5R)-2-(3-fluorophenyl)-5-(2,2,2-trifluoroethyl)pyrrolidine-1-carboxylate To a solution of Reference Example 5-26-C (164 mg) and DMAP (110 mg) in toluene (3.3 mL) was added phenyl chlorothionoformate (0.086 mL), and the mixture was stirred at room temperature overnight. The reaction mixture was filtered through Celite, and the filtrate was concentrated under reduced pressure. The residue was purified by column chromatography on silica gel (eluent: n-hexane/ethyl acetate=100/0-70/30). The obtained compound (54.0 mg) was dissolved in toluene (2 mL). The mixture was placed under an argon atmosphere, and then allowed to warm to 80° C. To the mixture were added portionwise a suspension of tributyltin hydride (0.115 mL) and 2,2'-azobis(isobutyronitrile) (17.8 mg) in toluene (1 mL). The mixture was stirred at 80° C. for 1 hour. The reaction mixture was allowed to cool to room temperature, and then purified by column chromatography on amino-silica gel (eluent: n-hexane/ethyl acetate=100/0-80/20) to give the title compound (19.2 mg).

Reference Example 5-26-E (2S,5R)-2-(3-Fluorophenyl)-5-(2,2,2-trifluoroethyl)pyrrolidine hydrochloride The title compound was prepared in a similar manner to that described in Reference Example 5-1-G using Reference Example 5-26-D instead of Reference Example 5-1-F. MS (ESI_APCI, m/z): 248 (M+H)$^+$ Reference Example 5-27-A N-[(1 S)-1-[(2R,5 S)-5-(3-Fluorophenyl)-1-(prop-2-en-1-yl)pyrrolidin-2-yl]ethyl]acetamide A mixture of Reference Example 5-2-D (200 mg), hydrogen chloride in ethyl acetate (4 mol/L, 2 mL) and ethyl acetate (6 mL) was stirred at room temperature for 13 hours. To the reaction mixture were added a saturated aqueous solution of sodium bicarbonate and water, and the mixture was extracted with ethyl acetate twice. The combined organic layer was dried over anhydrous magnesium sulfate, and concentrated under reduced pressure. The residue was dissolved in THF (2 mL). To the mixture were successively added DIPEA (0.148 mL) and acetyl chloride (0.052 mL) under ice-cooling. The mixture was stirred at room temperature for 1 hour. To the reaction mixture were added a saturated aqueous solution of sodium bicarbonate and water, and the mixture was extracted with ethyl acetate twice. The combined organic layer was dried over anhydrous magnesium sulfate, and concentrated under reduced pressure. The residue was purified by column chromatography on amino-silica gel (eluent: n-hexane/ethyl acetate=70/30-50/50) to give the title compound (59.0 mg).

Reference Example 5-27-B

N-[(1S)-1-[(2R,5 S)-5-(3-Fluorophenyl)pyrrolidin-2-yl]ethyl]acetamide

A solution of Reference Example 5-27-A (58.0 mg), tetrakis(triphenylphosphine)palladium (0) (23.0 mg) and 1,3-dimethylbarbituric acid (93.6 mg) in 1,2-dichloroethane (2 mL) was stirred under an argon atmosphere at 50° C. for 1 hour. To the reaction mixture were successively added dichloromethane (5 mL) and an aqueous solution (3 mL) of potassium carbonate (275 mg). The mixture was stirred for several minutes. The organic layer was separated, and then concentrated under reduced pressure. The residue was purified by column chromatography on amino-silica gel (eluent: n-hexane/ethyl acetate=50/50-0/100) to give the title compound (50.0 mg). MS (ESI_APCI, m/z): 251 (M+H)$^+$ Reference Example 5-28-A N-[(1 S)-1-[(2R,5S)-5-(3-Fluorophenyl)-1-(prop-2-en-1-yl)pyrrolidin-2-yl]ethyl]-N-methylacetamide To a solution of Reference Example 5-27-A (68.0 mg) in DMF (1.5 mL) was added sodium hydride (ca. 60%, 15.0 mg) under ice-cooling. The mixture was stirred under ice-cooling for 30 minutes, and then to the mixture was added iodomethane (0.029 mL). The mixture was stirred at room temperature for 6 hours, and then to the mixture was added sodium hydride (ca. 60%, 15.0 mg) under ice-cooling. The mixture was stirred under ice-cooling for 30 minutes, and then to the mixture was added iodomethane (0.029 mL). The reaction mixture was stirred at room temperature for 14 hours, and then to the reaction mixture was added a saturated aqueous solution of ammonium chloride. The mixture was extracted twice with ethyl acetate. The combined organic layer was successively washed with water and brine, dried over anhydrous magnesium sulfate, and concentrated under reduced pressure. The residue was purified by column chromatography on amino-silica gel (eluent: n-hexane/ethyl acetate=50/50-0/100) to give the title compound (65.0 mg).

Reference Example 5-28-B

N-[(1S)-1-[(2R,5 S)-5-(3-Fluorophenyl)pyrrolidin-2-yl]ethyl]-N-methylacetamide

The title compound was prepared in a similar manner to that described in Reference Example 5-27-B using Reference Example 5-28-A instead of Reference Example 5-27-A. MS (ESI_APCI, m/z): 265 (M+H)$^+$ Reference Example 5-29-A tert-Butyl (2R,5S)-2-(1,1-difluoroethyl)-5-(3-fluorophenyl)pyrrolidine-1-carboxylate To a solution of Reference Example 1-2-B (445 mg) in dichloromethane (15 mL) was added dropwise bis(2-methoxyethyl)aminosulfur trifluoride (2.67 mL) under ice-cooling, and the mixture was stirred at room temperature for 100 hours. The reaction mixture was poured into ice water. To the mixture was added potassium carbonate (10.0 g). The mixture was stirred for a while, and then extracted twice with dichloromethane. The combined organic layer was dried over anhydrous sodium sulfate, and concentrated under reduced pressure. The residue was purified by column chromatography on silica gel (eluent: n-hexane/ethyl acetate=100/0-80/20) to give the title compound (125 mg).

Reference Example 5-29-B (2R,5S)-2-(1,1-Difluoroethyl)-5-(3-fluorophenyl)pyrrolidine The title compound was prepared in a similar manner to that described in Reference Example 5-13-F using Reference Example 5-29-A instead of Reference Example 5-13-E. MS (ESI_APCI, m/z): 230 (M+H)$^+$ Reference Example 5-30-A (S)—N-[(1R)-3-[2-(3-Chlorophenyl)-1,3-dioxolan-2-yl]-1-(3-cyanooxetan-3-yl)propyl]-2-methylpropane-2-sulfinamide To a solution of LDA (1.13 mol/L, THF) (0.550 mL) in THF (3 mL) was added a solution of oxetane-3-carbonitrile (0.048 mL) in THF (0.6 mL) under an argon atmosphere at −78° C. The mixture was stirred at the same temperature for 30 minutes, and then to the mixture was added a solution of Reference Example 1-8-B (100 mg) in THF (0.6 mL) at −78° C. The reaction mixture was stirred at −78° C. for 2 hours, and then to the reaction mixture were added a saturated aqueous solution of ammonium chloride, water and dichloromethane. The mixture was stirred. The organic layer was separated, and then concentrated under reduced pressure.

The residue was purified by column chromatography on silica gel (eluent: n-hexane/ethyl acetate=60/40-0/100) to give the title compound (29.1 mg).

Reference Example 5-30-B

3-[(2R,5S)-5-(3-Chlorophenyl)pyrrolidin-2-yl]oxetane-3-carbonitrile

A mixture of Reference Example 5-30-A (29.1 mg), THF (1 mL) and concentrated hydrochloric acid (1 mL) was stirred at room temperature for 30 minutes. To the reaction mixture was added an aqueous solution of sodium hydroxide (5 mol/L, 2.5 mL) under ice-cooling, and then the mixture was stirred. To the mixture were added dichloromethane and water. The organic layer was separated, and concentrated under reduced pressure to give crude 3-[(2R)-5-(3-chlorophenyl)-3,4-dihydro-2H-pyrrol-2-yl]oxetane-3-carbonitrile (21.4 mg). To a solution of the obtained compound in ethanol (3 mL) was added platinum on carbon (5%, 40.0 mg) under an argon atmosphere under ice-cooling. The mixture was stirred under a hydrogen atmosphere at room temperature for 3 hours. The reaction mixture was filtered through Celite, and the filtrate was concentrated under reduced pressure. The residue was purified by column chromatography on silica gel (eluent: n-hexane/ethyl acetate=80/20-50/50) to give the title compound (10.0 mg). MS (ESI_APCI, m/z): 263 (M+H)$^+$ Reference Example 5-31-A (2R,5 S)-5-(3-Chlorophenyl)-N-methoxy-N-methylpyrrolidine-2-carboxamide The title compound was prepared in a similar manner to that described in Reference Example 5-16-D using Reference Example 1-6-A instead of Reference Example 5-16-C.

Reference Example 5-31-B (2R,5 S)-5-(3-Chlorophenyl)-N-methoxy-N-methyl-1-(prop-2-en-1-yl)pyrrolidine-2-carboxamide A mixture of Reference Example 5-31-A (200 mg), allyl bromide (0.126 mL), potassium carbonate (257 mg) and acetonitrile (3.0 mL) was stirred at 50° C. for 2 hours. The reaction mixture was allowed to cool to room temperature, and then filtered through to remove an insoluble material. The filtrate was concentrated under reduced pressure. The residue was purified by column chromatography on silica gel (eluent: n-hexane/ethyl acetate=100/0-0/100) to give the title compound (209 mg).

Reference Example 5-31-C

1-[(2R,5 S)-5-(3-Chlorophenyl)-1-(prop-2-en-1-yl)pyrrolidin-2-yl]ethan-1-one

The title compound was prepared in a similar manner to that described in Reference Example 1-10-E using Reference Example 5-31-B instead of Reference Example 1-10-D.

Reference Example 5-31-D (S)—N-[(1S)-1-[(2R,5S)-5-(3-Chlorophenyl)-1-(prop-2-en-1-yl)pyrrolidin-2-yl]ethyl]-2-methylpropane-2-sulfinamide The title compound was prepared in a similar manner to that described in Reference Example 5-2-D using Reference Example 5-31-C instead of Reference Example 5-2-C.

Reference Example 5-31-E (1 S)-1-[(2R,5 S)-5-(3-Chlorophenyl)-1-(prop-2-en-1-yl)pyrrolidin-2-yl]ethan-1-amine The mixture of Reference Example 5-31-D (80.0 mg) and hydrogen chloride in 1,4-dioxane (4 mol/L, 1 mL) was stirred at room temperature for 2 hours. The reaction mixture was concentrated under reduced pressure. To the residue were added dichloromethane and an aqueous solution of sodium bicarbonate. The organic layer was separated, and concentrated under reduced pressure to give the title compound (51.0 mg).

Reference Example 5-31-F

1-[(1 S)-1-[(2R,5S)-5-(3-Chlorophenyl)-1-(prop-2-en-1-yl)pyrrolidin-2-yl]ethyl]pyrrolidin-2-one To the mixture of Reference Example 5-31-E (32.0 mg), triethylamine (0.019 mL) and THF (1 mL) was added 4-chlorobutyryl chloride (0.015 mL) under ice-cooling. The reaction mixture was stirred for 30 minutes, and then filtered through to remove an insoluble material. The filtrate was concentrated under reduced pressure. To a mixture of the residue and THF (1 mL) was added potassium tert-butoxide (67.8 mg) under ice-cooling. The reaction mixture was stirred at room temperature for 1 hour, and then to the reaction mixture were added ethyl acetate and water. The organic layer was separated. The organic layer was washed with brine, and then concentrated under reduced pressure. The residue was purified by column chromatography on silica gel (eluent: n-hexane/ethyl acetate=100/0-0/100) to give the title compound (20.0 mg).

Reference Example 5-31-G

1-[(1 S)-1-[(2R,5 S)-5-(3-Chlorophenyl)pyrrolidin-2-yl]ethyl]pyrrolidin-2-one

The title compound was prepared in a similar manner to that described in Reference Example 5-2-E using Reference Example 5-31-F instead of Reference Example 5-2-D. MS (ESI_APCI, m/z): 293 (M+H)$^+$ Reference Example 5-32-A tert-Butyl (2S,5R)-2-(3,5-difluorophenyl)-5-(2-hydroxypropan-2-yl)pyrrolidine-1-carboxylate The title compound was prepared in a similar manner to that described in Reference Example 5-8-F using Reference Example 1-10-C instead of Reference Example 5-8-E.

Reference Example 5-32-B

2-[(2R,5S)-5-(3,5-Difluorophenyl)pyrrolidin-2-yl]propan-2-ol

A mixture of Reference Example 5-32-A (528 mg) and hydrogen chloride in ethyl acetate (4 mol/L, 5.0 mL) was stirred at room temperature for 1 hour. The reaction mixture was concentrated under reduced pressure. To the residue were added ethyl acetate and a saturated aqueous solution of sodium bicarbonate. The organic layer was separated. The aqueous layer was extracted with ethyl acetate, and then the extract was combined with the above organic layer. The organic layer was dried over anhydrous magnesium sulfate, and concentrated under reduced pressure to give the title compound (315 mg). MS (ESI_APCI, m/z): 242 (M+H)$^+$

Reference Example 5-33-A 4-(Benzyloxy)-1-(3-fluorophenyl)-2-hydroxybutan-1-one A mixture of Reference Example 5-21-B (500 mg), NBS (65.4 mg) and DMSO (3.65 mL) was stirred under an argon atmosphere at 60° C. for 24 hours. The reaction mixture was allowed to cool to room temperature, and then to the reaction mixture were added ethyl acetate, an aqueous solution of sodium thiosulfate (1 mol/L) and water. The organic layer was separated. The organic layer was successively washed with water and brine, dried over anhydrous sodium sulfate, and concentrated under reduced pressure. The residue was purified by column chromatography on silica gel (eluent: n-hexane/ethyl acetate=90/10-70/30) to give the title compound (242 mg).

Reference Example 5-33-B 3-(Benzyloxy)-1-[2-(3-fluorophenyl)-1,3-dioxolan-2-yl]propan-1-ol A solution of Reference Example 5-33-A (0.870 g), ethylene glycol (1.70 mL) and p-toluenesulfonic acid monohydrate (0.0574 g) in toluene (17.4 mL) was refluxed using Dean-Stark apparatus for 2 hours. The reaction mixture was allowed to cool to room temperature, and then to the reaction mixture were added ethyl acetate, a saturated aqueous solution of sodium bicarbonate and water. The organic layer was separated. The organic layer was dried over anhydrous sodium sulfate, and concentrated under reduced pressure. The residue was purified by column chromatography on silica gel (eluent: n-hexane/ethyl acetate=75/25-50/50) to give the title compound (0.985 g).

Reference Example 5-33-C

3-[(tert-Butyldimethylsilyl)oxy]-1-[2-(3-fluorophenyl)-1,3-dioxolan-2-yl]propan-1-ol To a solution of Reference Example 5-33-B (0.984 g) in ethanol (9.8 mL) was added 10% palladium on carbon (wet, 0.246 g) under an argon atmosphere under ice-cooling. The mixture was stirred under a hydrogen atmosphere at room temperature for 1.5 hours. The reaction mixture was filtered through Celite, and the filtrate was concentrated under reduced pressure to give crude 1-[2-(3-fluorophenyl)-1,3-dioxolan-2-yl]propane-1,3-diol (0.882 g). To a solution of the obtained compound and tert-butyldimethylchlorosilane (0.468 g) in DMF (7.2 mL) was added imidazole (0.241 g), and the mixture was stirred at room temperature for 4 hours. To the reaction mixture were added ethyl acetate and water. The organic layer was separated. The organic layer was washed with water, dried over anhydrous sodium sulfate, and concentrated under reduced pressure. The residue was purified by column chromatography on silica gel (eluent: n-hexane/ethyl acetate=80/20-60/40) to give the title compound (1.05 g).

Reference Example 5-33-D

[3-(Benzyloxy)-3-[2-(3-fluorophenyl)-1,3-dioxolan-2-yl]propoxy](tert-butyl)dimethylsilane To a solution of Reference Example 5-33-C (1.05 g), benzyl bromide (0.460 mL) and tetrabutylammonium iodide (1.42 g) in DMF (21 mL) was added sodium hydride (ca. 60%, 155 mg) under an argon atmosphere under ice-cooling. The mixture was allowed to warm to room temperature slowly, and then stirred overnight. To the reaction mixture were added ethyl acetate and water. The organic layer was separated. The organic layer was washed with water, dried over anhydrous sodium sulfate, and concentrated under reduced pressure. The residue was purified by column chromatography on silica gel (eluent: n-hexane/ethyl acetate=92/8-80/20) to give the title compound (1.06 g).

Reference Example 5-33-E 3-(Benzyloxy)-3-[2-(3-fluorophenyl)-1,3-dioxolan-2-yl]propan-1-ol To a solution of Reference Example 5-33-D (1.06 g) in THF (10.5 mL) was added TBAF (ca. 1 mol/L, THF) (3.60 mL) under an argon atmosphere, and the mixture was stirred at room temperature 6 hours. To the reaction mixture were added ethyl acetate and a saturated aqueous solution of ammonium chloride. The organic layer was separated. The aqueous layer was extracted with ethyl acetate, and then the extract was combined with the above organic layer. The organic layer was dried over anhydrous sodium sulfate, and concentrated under reduced pressure. The residue was purified by column chromatography on silica gel (eluent: n-hexane/ethyl acetate=70/30-50/50) to give the title compound (0.790 g).

Reference Example 5-33-F 3-(Benzyloxy)-3-[2-(3-fluorophenyl)-1,3-dioxolan-2-yl]propanal The title compound was prepared in a similar manner to that described in Reference Example 5-21-E using Reference Example 5-33-E instead of Reference Example 5-21-D.

Reference Example 5-33-G (S)—N-[3-(Benzyloxy)-3-[2-(3-fluorophenyl)-1,3-dioxolan-2-yl]propylidene]-2-methylpropane-2-sulfinamide The title compound was prepared in a similar manner to that described in Reference Example 5-21-F using Reference Example 5-33-F instead of Reference Example 5-21-E.

Reference Example 5-33-H (S)—N-[(2R)-4-(Benzyloxy)-1-cyano-4-[2-(3-fluorophenyl)-1,3-dioxolan-2-yl]-1,1-dimethylbutan-2-yl]-2-methylpropane-2-sulfinamide To a solution of isobutyronitrile (0.290 mL) in THF (14 mL) was added dropwise LDA (1.13 mol/L, THF) (3.0 mL) under an argon atmosphere at −78° C. The mixture was stirred at −78° C. for 5 minutes, and then to the mixture was added HMPA (1.10 mL). The mixture was stirred at −78° C. for 15 minutes, and then to the mixture was added a solution of Reference Example 5-33-G (700 mg) in THF (7 mL). The reaction mixture was stirred at −78° C. for 40 minutes, and then to the reaction mixture were added a saturated aqueous solution of ammonium chloride and water. To the mixture were added ethyl acetate and water. The organic layer was separated. The aqueous layer was extracted with ethyl acetate, and then the extract was combined with the above organic layer. The organic layer was dried over anhydrous sodium sulfate, and concentrated under reduced pressure. The residue was purified by column chromatography on silica gel (eluent: n-hexane/ethyl acetate=70/30-40/60) to give the title compound (830 mg).

Reference Example 5-33-I

2-[(2R,4R)-4-(Benzyloxy)-5-(3-fluorophenyl)-3,4-dihydro-2H-pyrrol-2-yl]-2-methylpropanenitrile A mixture of Reference Example 5-33-H (937 mg), THF (4.7 mL) and concentrated hydrochloric acid (4.7 mL) was stirred under an argon atmosphere at 45° C. for 1.5 hours. The mixture was stirred at 60° C. for 4 hours and stirred at 70° C. for 4 hours. To the reaction mixture was added an aqueous solution of sodium hydroxide (5 mol/L, 10 mL) under ice-cooling, and then the mixture was stirred. To the mixture was added ethyl acetate, and the organic layer was separated. The aqueous layer was extracted with ethyl acetate, and then the extract was combined with the above organic layer. The organic layer was dried over anhydrous sodium sulfate, and concentrated under reduced pressure. The residue was purified by column chromatography on silica gel (eluent: n-hexane/ethyl acetate=85/15-65/35) to give 2-[(2R,4S)-4-(benzyloxy)-5-(3-fluorophenyl)-3,4-dihydro-2H-pyrrol-2-yl]-2-methylpropanenitrile (115 mg) which was formerly eluted and the title compound (273 mg) which was latterly eluted, respectively.

Reference Example 5-33-J

2-[(2R,4R,5R)-4-(Benzyloxy)-5-(3-fluorophenyl)pyrrolidin-2-yl]-2-methylpropanenitrile To a solution of Reference Example 5-33-I (29.9 mg) in methanol (1.2 mL) was added decaborane (8.2 mg), and the mixture was stirred at room temperature for 2 hours. To the reaction mixture were added ethyl acetate and a saturated aqueous solution of sodium bicarbonate. The organic layer was separated. The aqueous layer was extracted with ethyl acetate, and then the extract was combined with the above organic layer. The organic layer was dried over anhydrous sodium sulfate, and concentrated under reduced pressure. The residue was purified by column chromatography on amino-silica gel (eluent: n-hexane/ethyl acetate=85/15-60/40) to give the title compound (25.6 mg). MS (ESI_APCI, m/z): 339 (M+H)$^+$

Reference Example 5-34-A

Ethyl (2R)-2-{[(tert-butoxy)carbonyl]amino}-5-(3-chloro-4-fluorophenyl)-5-oxopentanoate To a mixture of magnesium (434 mg) and THF (2 mL) was added a slight amount of iodine under an argon atmosphere. The mixture was allowed to warm to 60° C. To the mixture was added dropwise a solution of 4-bromo-2-chloro-1-fluorobenzene (3.58 g) in THF (6.5 mL) while keeping the temperature at 65° C. The mixture was stirred at 60° C. for 30 minutes, and then allowed to cool to room temperature to give (3-chloro-4-fluorophenyl)magnesium bromide. To a solution of (R)-1-(tert-butoxycarbonyl)-5-oxopyrrolidine-2-carboxylic acid ethyl (2.00 g) in THF (25 mL) was added the obtained (3-chloro-4-fluorophenyl)magnesium bromide under an argon atmosphere at −40° C. The mixture was stirred at −40° C. for 1 hour. To the reaction mixture were added a saturated aqueous solution of ammonium chloride (20 mL) and water (10 mL). The mixture was stirred at room temperature for 2 hours, and then to the mixture were added ethyl acetate and water. The organic layer was separated. The organic layer was dried over anhydrous sodium sulfate, and concentrated under reduced pressure. The residue was purified by column chromatography on silica gel (eluent: n-hexane/ethyl acetate=90/10-60/40) to give the title compound (2.79 g).

Reference Example 5-34-B

Ethyl (2R,5 S)-5-(3-chloro-4-fluorophenyl)pyrrolidine-2-carboxylate

To a solution of Reference Example 5-34-A (2.79 g) in ethyl acetate (16.8 mL) was added hydrogen chloride in ethyl acetate (4 mol/L, 16.8 mL) at room temperature, and the mixture was stirred at the same temperature for 2 hours. The reaction mixture was concentrated under reduced pressure. To the residue were added ethyl acetate, a saturated aqueous solution of sodium bicarbonate and water. The organic layer was separated. The organic layer was dried over anhydrous sodium sulfate, and concentrated under reduced pressure to give ethyl (2R)-5-(3-chloro-4-fluorophenyl)-3,4-dihydro-2H-pyrrole-2-carboxylate (1.81 g). To a suspension of platinum on carbon (10%, wet) (0.360 g) in ethanol (18 mL) was added a solution of the obtained compound in ethanol (9 mL) under ice-cooling. The mixture was stirred under a hydrogen atmosphere at room temperature for 3.5 hours. The reaction mixture was filtered through Celite, and the filtrate was concentrated under reduced pressure. The residue was purified by column chromatography on silica gel (eluent: n-hexane/ethyl acetate=80/20-50/50) to give the title compound (1.20 g).

Reference Example 5-34-C (2R,5 S)-1-(tert-Butoxycarbonyl)-5-(3-chloro-4-fluorophenyl)pyrrolidine-2-carboxylic acid ethyl The title compound was prepared in a similar manner to that described in Reference Example 1-1-C using Reference Example 5-34-B instead of Reference Example 1-1-B.

Reference Example 5-34-D tert-Butyl (2S,5R)-2-(3-chloro-4-fluorophenyl)-5-[methoxy(methyl)carbamoyl]pyrrolidine-1-carboxylate The title compound was prepared in a similar manner to that described in Reference Example 1-2-A using Reference Example 5-34-C instead of Reference Example 1-1-C.

Reference Example 5-34-E tert-Butyl (2R,5 S)-2-acetyl-5-(3-chloro-4-fluorophenyl)pyrrolidine-1-carboxylate To a solution of Reference Example 5-34-D (1.30 g) in THF (13 mL) was added methylmagnesium bromide (3.0 mol/L, diethyl ether) (2.20 mL) under an argon atmosphere under ice-cooling, and the mixture was stirred at the same temperature for 1 hour. To the reaction mixture were added a saturated aqueous solution of ammonium chloride and water. The mixture was extracted with ethyl acetate. The organic layer was dried over anhydrous sodium sulfate, and concentrated under reduced pressure to give the crude title compound (1.22 g).

Reference Example 5-34-F tert-Butyl (2S,5R)-2-(3-chloro-4-fluorophenyl)-5-(prop-1-en-2-yl)pyrrolidine-1-carboxylate The title compound was prepared in a similar manner to that described in Reference Example 1-2-C using Reference Example 5-34-E instead of Reference Example 1-2-B.

Reference Example 5-34-G tert-Butyl (2S,5R)-2-(3-chloro-4-fluorophenyl)-5-(1-cyano-1-methylethyl)pyrrolidine-1-carboxylate The title compound was prepared in a similar manner to that described in Reference Example 1-7-C using Reference Example 5-34-F instead of Reference Example 1-7-B.

Reference Example 5-34-H

2-[(2R,5S)-5-(3-Chloro-4-fluorophenyl)pyrrolidin-2-yl]-2-methylpropanenitrile

The title compound was prepared in a similar manner to that described in Reference Example 5-11-H using Reference Example 5-34-G instead of Reference Example 5-11-G. MS (ESI_APCI, m/z): 267 (M+H)+

Reference Example 5-35-A

Ethyl (2R)-2-{[(tert-butoxy)carbonyl]amino}-5-(5-chloro-2-fluorophenyl)-5-oxopentanoate The title compound was prepared in a similar manner to that described in Reference Example 5-34-A using 2-bromo-4-chloro-1-fluorobenzene instead of 4-bromo-2-chloro-1-fluorobenzene.

Reference Example 5-35-B

Ethyl (2R,5 S)-5-(5-chloro-2-fluorophenyl)pyrrolidine-2-carboxylate

The title compound was prepared in a similar manner to that described in Reference Example 5-34-B using Reference Example 5-35-A instead of Reference Example 5-34-A.

Reference Example 5-35-C (2R,5 S)-1-(tert-Butoxycarbonyl)-5-(5-chloro-2-fluorophenyl)pyrrolidine-2-carboxylic acid ethyl The title compound was prepared in a similar manner to that described in Reference Example 1-1-C using Reference Example 5-35-B instead of Reference Example 1-1-B.

Reference Example 5-35-D tert-Butyl (2S,5R)-2-(5-chloro-2-fluorophenyl)-5-[methoxy(methyl)carbamoyl]pyrrolidine-1-carboxylate The title compound was prepared in a similar manner to that described in Reference Example 1-2-A using Reference Example 5-35-C instead of Reference Example 1-1-C.

Reference Example 5-35-E tert-Butyl (2R,5 S)-2-acetyl-5-(5-chloro-2-fluorophenyl)pyrrolidine-1-carboxylate The title compound was prepared in a similar manner to that described in Reference Example 5-34-E using Reference Example 5-35-D instead of Reference Example 5-34-D.

Reference Example 5-35-F tert-Butyl (2S,5R)-2-(5-chloro-2-fluorophenyl)-5-(prop-1-en-2-yl)pyrrolidine-1-carboxylate The title compound was prepared in a similar manner to that described in Reference Example 1-2-C using Reference Example 5-35-E instead of Reference Example 1-2-B.

Reference Example 5-35-G tert-Butyl (2S,5R)-2-(5-chloro-2-fluorophenyl)-5-(1-cyano-1-methylethyl)pyrrolidine-1-carboxylate To a mixture of Reference Example 5-35-F (203 mg), Reference Example 1-3-A (10.8 mg), p-toluenesulfonyl cyanide (325 mg) and ethanol (3.0 mL) was added phenylsilane (0.095 mL) under an argon atmosphere. The mixture was stirred under an argon atmosphere at room temperature overnight. The reaction mixture was filtered through to remove an insoluble material. The filtrate was concentrated under reduced pressure. The residue was purified by column chromatography on silica gel (eluent: n-hexane/ethyl acetate=100/0-80/20) to give the title compound (159 mg).

Reference Example 5-35-H

2-[(2R,5S)-5-(5-Chloro-2-fluorophenyl)pyrrolidin-2-yl]-2-methylpropanenitrile

The title compound was prepared in a similar manner to that described in Reference Example 1-7-D using Reference Example 5-35-G instead of Reference Example 1-7-C. MS (ESI_APCI, m/z): 267 (M+H)$^+$ Reference Example 5-36-A Ethyl (2R)-2-{[(tert-butoxy)carbonyl]amino}-5-(3-chloro-5-fluorophenyl)-5-oxopentanoate The title compound was prepared in a similar manner to that described in Reference Example 1-1-A using 3-chloro-5-fluorophenylmagnesium bromide instead of 3-fluorophenylmagnesium bromide.

Reference Example 5-36-B

Ethyl (2R)-5-(3-chloro-5-fluorophenyl)-3,4-dihydro-2H-pyrrole-2-carboxylate

To a solution of Reference Example 5-36-A (2.35 g) in ethyl acetate (8 mL) was added hydrogen chloride in ethyl acetate (4 mol/L, 4.8 mL) at room temperature, and the mixture was stirred at the same temperature for 3 hours. To the reaction mixture was added a saturated aqueous solution of sodium bicarbonate, and the mixture was extracted twice with ethyl acetate. The combined organic layer was dried over anhydrous sodium sulfate, and concentrated under reduced pressure. The residue was purified by column chromatography on silica gel (eluent: n-hexane/ethyl acetate=90/10-60/40) to give the title compound (1.44 g).

Reference Example 5-36-C

Ethyl (2R,5 S)-5-(3-chloro-5-fluorophenyl)pyrrolidine-2-carboxylate

A mixture of Reference Example 5-36-B (1.14 g), platinum on carbon (10%, wet) (0.114 g) and ethanol (11.5 mL) was stirred under a hydrogen atmosphere at room temperature for 3 hours. The reaction mixture was filtered through Celite, and the filtrate was concentrated under reduced pressure. The residue was purified by column chromatography on silica gel (eluent: n-hexane/ethyl acetate=95/5-70/30) to give the title compound (0.710 g).

Reference Example 5-36-D (2R,5 S)-1-(tert-Butoxycarbonyl)-5-(3-chloro-5-fluorophenyl)pyrrolidine-2-carboxylic acid ethyl To a solution of Reference Example 5-36-C (0.887 g) in THF (8 mL) was added triethylamine (0.683 mL) and di-tert-butyl dicarbonate (0.783 g) at room temperature, and the mixture was stirred for 1 hour. The reaction mixture was concentrated under reduced pressure. The residue was purified by column chromatography on silica gel (eluent: n-hexane/ethyl acetate=95/5-70/30) to give the title compound (1.24 g).

Reference Example 5-36-E tert-Butyl (2R,5 S)-2-acetyl-5-(3-chloro-5-fluorophenyl)pyrrolidine-1-carboxylate To a solution of Reference Example 5-36-D (1.21 g) in THF (8.4 mL) was added N,O-dimethylhydroxylamine hydrochloride (0.637 g) under an argon atmosphere at −50° C. To the mixture was added dropwise isopropylmagnesium chloride (2.0 mol/L, THF) (6.53 mL) at −50° C. The mixture was stirred in ice salt bath for 1 hour. To the reaction mixture was added a saturated aqueous solution of ammonium chloride, and the mixture was extracted twice with ethyl acetate. The combined organic layer was dried over anhydrous sodium sulfate, and concentrated under reduced pressure to give crude tert-butyl (2S,5R)-2-(3-chloro-5-fluorophenyl)-5-[methoxy(methyl)carbamoyl]pyrrolidine-1-carboxylate (1.42 g). To a solution of the obtained compound in THF (13 mL) was added methylmagnesium bromide (3.0 mol/L, diethyl ether) (2.18 mL) under an argon atmosphere under ice-cooling. The mixture was stirred under ice-cooling for 1 hour, and then to the mixture was added methylmagnesium bromide (3.0 mol/L, diethyl ether) (0.500 mL). The reaction mixture was stirred under ice-cooling for a while, and then to the reaction mixture were added a saturated aqueous solution of ammonium chloride and water. The mixture was stirred at room temperature for 30 minutes, and then extracted with ethyl acetate. The organic layer was washed with brine, dried over anhydrous sodium sulfate, and concentrated under reduced pressure. The residue was purified by column chromatography on silica gel (eluent: n-hexane/ethyl acetate=90/10-40/60) to give the title compound (0.920 g).

Reference Example 5-36-F tert-Butyl (2S,5R)-2-(3-chloro-5-fluorophenyl)-5-(prop-1-en-2-yl)pyrrolidine-1-carboxylate The title compound was prepared in a similar manner to that described in Reference Example 1-2-C using Reference Example 5-36-E instead of Reference Example 1-2-B.

Reference Example 5-36-G tert-Butyl (2S,5R)-2-(3-chloro-5-fluorophenyl)-5-(1-cyano-1-methylethyl)pyrrolidine-1-carboxylate The title compound was prepared in a similar manner to that described in Reference Example 1-7-C using Reference Example 5-36-F instead of Reference Example 1-7-B.

Reference Example 5-36-H

2-[(2R,5S)-5-(3-Chloro-5-fluorophenyl)pyrrolidin-2-yl]-2-methylpropanenitrile

The title compound was prepared in a similar manner to that described in Reference Example 1-7-D using Reference Example 5-36-G instead of Reference Example 1-7-C. MS (ESI_APCI, m/z): 267 (M+H)$^+$ Reference Example 5-37-A

[4-(Benzyloxy)butoxy](tert-butyl)diphenylsilane

To a solution of 4-benzyloxy-1-butanol (1.94 mL) in dichloromethane (50 mL) were added tert-butyldiphenylchlorosilane (3.42 mL), triethylamine (2.31 mL) and DMAP (0.0136 g) under ice-cooling, and the mixture was stirred at room temperature for 3 hours. To the reaction mixture was added water, and the mixture was extracted with dichloromethane. The organic layer was dried over anhydrous magnesium sulfate, and concentrated under reduced pressure. The residue was purified by column chromatography on silica gel (eluent: n-hexane/ethyl acetate=95/5-85/15) to give the title compound (4.20 g).

Reference Example 5-37-B

4-[(tert-Butyldiphenylsilyl)oxy]butan-1-ol

To a solution of Reference Example 5-37-A (4.20 g) in ethanol (42 mL) were added 10% palladium on carbon (wet, 420 mg) and acetic acid (2.41 g) under an argon atmosphere under ice-cooling. The mixture was stirred under a hydrogen atmosphere at room temperature for 4 hours. The reaction mixture was filtered through Celite, and the filtrate was concentrated under reduced pressure. The residue was dissolved in ethanol (42 mL). To the mixture were added 10% palladium on carbon (wet, 420 mg) and acetic acid (2.41 g). The mixture was stirred under a hydrogen atmosphere at room temperature overnight. The reaction mixture was filtered through Celite, and the filtrate was concentrated under reduced pressure. The residue was purified by column chromatography on silica gel (eluent: n-hexane/ethyl acetate=80/20-50/50) to give the title compound (1.39 g).

Reference Example 5-37-C

4-[(tert-Butyldiphenylsilyl)oxy]butanal

To a mixture of Reference Example 5-37-B (1.39 g), TEMPO (0.0133 g), potassium bromide (0.0507 g), dichloromethane (6 mL) and a saturated aqueous solution of sodium bicarbonate (6 mL) was added dropwise a mixture of sodium hypochlorite pentahydrate (0.771 g) in water (4 mL) and a saturated aqueous solution of sodium bicarbonate (1 mL) under an argon atmosphere under ice-cooling. The mixture was stirred under ice-cooling for 30 minutes. To the reaction mixture was added an aqueous solution of sodium thiosulfate (1 mol/L, 5 mL). The mixture was stirred at room temperature for 5 minutes, and then extracted with ethyl acetate. The aqueous layer was extracted with ethyl acetate, and then the extract was combined with the above organic layer. The organic layer was dried over anhydrous magnesium sulfate, and concentrated under reduced pressure to give the title compound (1.30 g).

Reference Example 5-37-D (S)—N-{4-[(tert-Butyldiphenylsilyl)oxy]butylidene}-2-methylpropane-2-sulfinamide To a solution of Reference Example 5-37-C (1.30 g) and (S)-(−)-2-methyl-2-propane sulfinamide (0.483 g) in toluene (13 mL) was added copper (II) sulfate (0.382 g), and the mixture was stirred at 60° C. for 4 hours. The reaction mixture was filtered, and the filtrate was concentrated under reduced pressure to give the title compound (1.69 g).

Reference Example 5-37-E (S)—N-[(2R)-5-[(tert-Butyldiphenylsilyl)oxy]-1-cyano-1,1-dimethylpentan-2-yl]-2-methylpropane-2-sulfinamide To LDA (1.13 mol/L, THF) (12.2 mL) was added isobutyronitrile (1.24 mL) under an argon atmosphere under ice-cooling. The mixture was stirred under ice-cooling for 10 minutes. The mixture was cooled to −78° C., and then to the mixture was added dropwise a solution of Reference Example 5-37-D (1.69 g) in THF (3.5 mL). The mixture was stirred at −78° C. for 1 hour. To the reaction mixture were added a saturated aqueous solution of ammonium chloride and water, and the mixture was extracted with ethyl acetate twice. The combined organic layer was washed with brine, dried over anhydrous magnesium sulfate, and concentrated under reduced pressure. The residue was purified by column chromatography on silica gel to give the title compound (1.35 g).

Reference Example 5-37-F (3R)-3-Amino-6-hydroxy-2,2-dimethylhexanenitrile

To a suspension of Reference Example 5-37-E (1.35 g) in THF (2.7 mL) was slowly added concentrated hydrochloric acid (2.27 mL) under an argon atmosphere under ice-cooling. The mixture was stirred at room temperature for 1 hour. To the reaction mixture was added an aqueous solution of sodium hydroxide (5 mol/L, 5.4 mL) in ice salt bath. To the mixture were added a saturated aqueous solution of sodium bicarbonate and ethyl acetate. The aqueous layer was separated. The aqueous layer was concentrated under reduced pressure. To the residue were added dichloromethane and anhydrous magnesium sulfate. The mixture was stirred for 20 minutes, and then the mixture was filtered. The filtrate was concentrated under reduced pressure to give the title compound (0.414 g).

Reference Example 5-37-G tert-Butyl N-[(2R)-1-cyano-5-hydroxy-1,1-dimethylpentan-2-yl]carbamate To a solution of Reference Example 5-37-F (414 mg) in THF (3 mL) was added a solution of di-tert-butyl dicarbonate (637 mg) in THF (1 mL). The reaction mixture was stirred at room temperature for 1 hour, and then concentrated under reduced pressure. The residue was purified by column chromatography on silica gel (eluent: n-hexane/ethyl acetate=50/50-30/70) to give the title compound (357 mg).

Reference Example 5-37-H tert-Butyl (2R)-2-(1-cyano-1-methylethyl)-5-oxopyrrolidine-1-carboxylate To a solution of Reference Example 5-37-G (250 mg) in dichloromethane (3 mL) were added 2-hydroxy-2-azaadamantane (15.0 mg) and iodobenzene diacetate (691 mg) under ice-cooling, and the mixture was stirred at room temperature for 3 hours. To the reaction mixture was added an aqueous solution of sodium thiosulfate, and the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-50/50) to give the title compound (230 mg).

Reference Example 5-37-I

2-[(2R)-5-(3-Bromophenyl)-3,4-dihydro-2H-pyrrol-2-yl]-2-methylpropanenitrile

To a solution of 1-bromo-3-iodobenzene (0.112 mL) in THF (1.0 mL) was added dropwise isopropylmagnesium chloride (2.0 mol/L, THF) (0.415 mL) under an argon atmosphere at −40° C. The mixture was stirred at −40° C. for 10 minutes, and then to the mixture was slowly added a solution of Reference Example 5-37-H (104 mg) in THF (1.0 mL). The reaction mixture was stirred at the same temperature for 20 minutes, and then to the reaction mixture were added a saturated aqueous solution of ammonium chloride and water at room temperature. The mixture was stirred at room temperature overnight, and then extracted twice with ethyl acetate. The combined organic layer was dried over anhydrous magnesium sulfate, and concentrated under reduced pressure to give crude tert-butyl N-[(2R)-5-(3-bromophenyl)-1-cyano-1,1-dimethyl-5-oxopentan-2-yl]carbamate (213 mg). A mixture of the obtained compound and hydrogen chloride in ethyl acetate (4 mol/L, 2 mL) was stirred at room temperature for 5 hours. The reaction mixture was concentrated under reduced pressure. To the residue were added ethyl acetate and a saturated aqueous solution of sodium bicarbonate. The organic layer was separated. The aqueous layer was extracted with ethyl acetate, and then the extract was combined with the above organic layer. The organic layer was dried over anhydrous magnesium sulfate, and concentrated under reduced pressure. The residue was purified by column chromatography on silica gel (eluent: n-hexane/ethyl acetate=80/20) to give the title compound (100 mg).

Reference Example 5-37-J

2-[(2R,5S)-5-(3-Bromophenyl)pyrrolidin-2-yl]-2-methylpropanenitrile

To a solution of Reference Example 5-37-I (100 mg) in THF (1 mL) and acetic acid (0.197 mL) was added sodium triacetoxyborohydride (109 mg), and the mixture was stirred at 45° C. for 1.5 hours. To the reaction mixture was slowly added an aqueous solution of sodium hydroxide (5 mol/L, 1.0 mL) under ice-cooling. The mixture was extracted twice with ethyl acetate. The combined organic layer was washed with brine, dried over anhydrous magnesium sulfate, and concentrated under reduced pressure to give the crude title compound (110 mg). MS (ESI_APCI, m/z): 293 (M+H)$^+$ Reference Example 5-38-A (S)—N-{[(2R,5 S)-5-(3-Chlorophenyl)-1-(prop-2-en-1-yl]pyrrolidin-2-yl]methylidene}-2-methylpropane-2-sulfinamide To a solution of Reference Example 5-31-B (1.00 g) in THF (10 mL) was added zirconocene chloride hydride (1.50 g) under an argon atmosphere under ice-cooling. The mixture was stirred at room temperature for 1.5 hours, and then to the mixture was added (S)-(−)-2-methyl-2-propane sulfinamide (0.784 g). The reaction mixture was stirred at 60° C. for 3.5 hours, and then diluted with ethyl acetate. The mixture was filtered through Celite. The filtrate was concentrated under reduced pressure. The residue was purified by column chromatography on silica gel (eluent: n-hexane/ethyl acetate=100/0-80/20) to give the title compound (0.652 g).

Reference Example 5-38-B (S)—N-{1-[(2R,5 S)-5-(3-Chlorophenyl)-1-(prop-2-en-1-yl)pyrrolidin-2-yl]-2,2,2-trifluoroethyl}-2-methylpropane-2-sulfinamide To a suspension of Reference Example 5-38-A (534 mg) and tetrabutylammonium difluorotriphenylsilicate (899 mg) in THF (10 mL) was added (trifluoromethyl)trimethylsilane (0.269 mL) under an argon atmosphere under ice-cooling, and the mixture was stirred at room temperature for 3 hours. To the mixture were added tetrabutylammonium difluorotriphenylsilicate (899 mg) and (trifluoromethyl)trimethylsilane (0.269 mL) under ice-cooling, and the mixture was stirred at room temperature for 3 hours. To the reaction mixture were added a saturated aqueous solution of ammonium chloride and water, and the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=100/0-80/20) to give the title compound (425 mg).

Reference Example 5-38-C

N-{1-[(2R,5 S)-5-(3-Chlorophenyl)-1-(prop-2-en-1-yl)pyrrolidin-2-yl]-2,2,2-trifluoroethyl}acetamide A solution of Reference Example 5-38-B (425 mg) in methanol (3 mL) was added hydrogen chloride in 1,4-dioxane (4 mol/L, 3 mL), and the mixture was stirred at room temperature for 2 hours. The reaction mixture was concentrated under reduced pressure. To a solution of the residue, pyridine (0.243 mL) and triethylamine (0.420 mL) in dichloromethane (10 mL) was added acetic anhydride (0.142 mL) under ice-cooling, and the mixture was stirred at room temperature for 5 hours. To the reaction mixture were added a saturated aqueous solution of sodium bicarbonate and water, and the mixture was extracted with dichloromethane twice. The combined organic layer was washed with brine, dried over anhydrous sodium sulfate, and concentrated under reduced pressure. The residue was purified by column chromatography on amino-silica gel (eluent: n-hexane/ethyl acetate=100/0-70/30) to give the title compound (283 mg).

Reference Example 5-38-D

N-{1-[(2R,5 S)-5-(3-Chlorophenyl)-1-(prop-2-en-1-yl)pyrrolidin-2-yl]-2,2,2-trifluoroethyl}-N-methylacetamide To a solution of Reference Example 5-38-C (180 mg) in DMF (2 mL) was added sodium hydride (ca. 60%, 31.0 mg) under ice-cooling. The mixture was stirred at the same temperature for 30 minutes, and then to the mixture was added iodomethane (0.062 mL). The reaction mixture was stirred at room temperature for 1.5 hours, and then to the reaction mixture were added a saturated aqueous solution of ammonium chloride and water. The mixture was extracted with ethyl acetate. The organic layer was successively washed with water and brine, dried over anhydrous magnesium sulfate, and concentrated under reduced pressure. The residue was purified by column chromatography on silica gel (eluent: n-hexane/ethyl acetate=80/20-60/40) to give the title compound (175 mg).

Reference Example 5-38-E

N-{1-[(2R,5 S)-5-(3-Chlorophenyl)pyrrolidin-2-yl]-2,2,2-trifluoroethyl}-N-methylacetamide The title compound was prepared in a similar manner to that described in Reference Example 5-27-B using Reference Example 5-38-D instead of Reference Example 5-27-A. MS (ESI_APCI, m/z): 335 (M+H)$^+$ Reference Example 5-39-A

[(1 S)-1-[(2R,5 S)-5-(3-Chlorophenyl)-1-(prop-2-en-1-yl)pyrrolidin-2-yl]ethyl](2,2,2-trifluoroethyl)amine To a solution of Reference Example 5-31-D (200 mg) in methanol (1 mL) was added hydrogen chloride in 1,4-dioxane (4 mol/L, 1 mL), and the mixture was stirred at room temperature for 2.5 hours. The reaction mixture was concentrated under reduced pressure. To the residue were added THF (2 mL) and DMF (1 mL). To the mixture were added DIPEA (0.579 mL) and trifluoromethane sulfonic acid 2,2,2-trifluoroethyl (0.234 mL) under ice-cooling. The mixture was stirred at room temperature for 19 hours. To the reaction mixture were added a saturated aqueous solution of sodium bicarbonate and water, and the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=100/0-80/20) to give the title compound (125 mg).

Reference Example 5-39-B

N-[(1 S)-1-[(2R,5 S)-5-(3-Chlorophenyl)-1-(prop-2-en-1-yl)pyrrolidin-2-yl]ethyl]-N-(2,2,2-trifluoroethyl)acetamide A mixture of Reference Example 5-39-A (125 mg), acetic anhydride (1 mL) and DMAP (13.2 mg) was stirred at 80° C. for 2 hours. To the reaction mixture were added water and a saturated aqueous solution of sodium bicarbonate, and the mixture was extracted with ethyl acetate. The organic layer was successively washed with water and brine, dried over anhydrous magnesium sulfate, and concentrated under reduced pressure. The residue was purified by column chromatography on silica gel (eluent: n-hexane/ethyl acetate=70/30-50/50) to give the title compound (100 mg).

Reference Example 5-39-C

N-[(1S)-1-[(2R,5S)-5-(3-Chlorophenyl)pyrrolidin-2-yl]ethyl]-N-(2,2,2-trifluoroethyl)acetamide The title compound was prepared in a similar manner to that described in Reference Example 5-27-B using Reference Example 5-39-B instead of Reference Example 5-27-A. MS (ESI_APCI, m/z): 349 (M+H)$^+$ Reference Example 5-40-A N-{1-[(2R,5 S)-5-(3-Chlorophenyl)pyrrolidin-2-yl]-2,2,2-trifluoroethyl}acetamide The title compound was prepared in a similar manner to that described in Reference Example 5-27-B using Reference Example 5-38-C instead of Reference Example 5-27-A. MS (ESI_APCI, m/z): 321 (M+H)$^+$ Reference Example 5-41-A (R)—N-[(2S)-4-[2-(3-Chlorophenyl)-1,3-dioxolan-2-yl]-1-cyano-1,1-dimethylbutan-2-yl]-2-methylpropane-2-sulfinamide To a solution of 3-[2-(3-chlorophenyl)-1,3-dioxolan-2-yl]propanal (7.38 g) in toluene (57 mL) were added (R)-(+)-2-methyl-2-propane sulfinamide (3.72 g) and copper (II) sulfate (2.93 g). The mixture was stirred at room temperature for 1.5 hours, and then stirred at 60° C. for 3 hours. The reaction mixture was filtered through Celite, and the filtrate was concentrated under reduced pressure to give crude (R)—N-{3-[2-(3-chlorophenyl)-1,3-dioxolan-2-yl]propylidene}-2-methylpropane-2-sulfinamide (11.0 g). To a mixture of LDA (1.08 mol/L, THF) (100 mL) and THF (100 mL) was added isobutyronitrile (9.64 mL) under an argon atmosphere in ice salt bath. The mixture was cooled to −78° C., and then to the mixture was added a solution of the obtained (R)—N-{3-[2-(3-chlorophenyl)-1,3-dioxolan-2-yl]propylidene}-2-methylpropane-2-sulfinamide in THF (20 mL). The reaction mixture was stirred at the same temperature for 1 hour, and then to the reaction mixture was added an aqueous solution of ammonium chloride. The mixture was stirred at room temperature for 10 minutes, and then to the mixture was added ethyl acetate. The organic layer was separated. The organic layer was washed with brine, dried over anhydrous magnesium sulfate, and concentrated under reduced pressure. To the residue was added TBME (50 mL), and the mixture was concentrated under reduced pressure. To the residue were added TBME (70 mL) and heptane (35 mL). The mixture was stirred at room temperature for 1 hour, and then stirred under ice-cooling for 1 hour. The precipitated solid was collected by filtration, and dried under reduced pressure at 60° C. to give the title compound (6.63 g).

Reference Example 5-41-B

2-[(2S)-5-(3-Chlorophenyl)-3,4-dihydro-2H-pyrrol-2-yl]-2-methylpropanenitrile

To a suspension of Reference Example 5-41-A (6.60 g) and acetonitrile (16.5 mL) was added hydrochloric acid (6 mol/L, 2.72 mL) at 45° C., and the mixture was stirred at the same temperature for 2 hours. To the reaction mixture were added isopropyl acetate and an aqueous solution of sodium hydroxide (5 mol/L, 6.21 mL) under ice-cooling. The pH of the mixture was adjusted to 10 and/or more by addition of an aqueous solution of potassium bicarbonate. The organic layer was separated. The organic layer was washed with brine twice, dried over anhydrous magnesium sulfate, and concentrated under reduced pressure. To a mixture of the residue and acetonitrile (16.5 mL) was added hydrochloric acid (6 mol/L, 2.72 mL). The mixture was stirred at 45° C. for 2 hours, and then to the mixture was added concentrated hydrochloric acid (1.0 mL). The mixture was stirred at 45° C. for 2 hours. To the reaction mixture was added isopropyl acetate under ice-cooling. The pH of the mixture was adjusted to 10 and/or more by addition of an aqueous solution of sodium hydroxide (2 mol/L). The organic layer was separated. The organic layer was washed with brine, dried over anhydrous magnesium sulfate, and concentrated under reduced pressure to give the crude title compound (3.99 g).

Reference Example 5-41-C

2-[(2S,5S)-5-(3-Chlorophenyl)pyrrolidin-2-yl]-2-methylpropanenitrile

A mixture of Reference Example 5-41-B (1.00 g), borane-2-methylpyridine complex (0.867 g), acetic acid (15 mL) and methanol (15 mL) was stirred at room temperature for 1 hour. To the reaction mixture was added hydrochloric acid (6 mol/L, 20 mL), and the mixture was stirred for 30 minutes. To the mixture was added an aqueous solution of sodium hydroxide (5 mol/L) to basify. The mixture was extracted with ethyl acetate. The organic layer was washed with water, and then concentrated under reduced pressure. The residue was purified by column chromatography on silica gel (eluent: n-hexane/ethyl acetate=85/15-65/35), and then purified by ODS column chromatography (eluent: water/acetonitrile=70/30-20/80) to give the title compound (0.157 g). MS (ESI_APCI, m/z): 249 (M+H)$^+$ Reference Example 6-1-A 6-Oxo-1,4,5,6-tetrahydropyridazine-3-carboxylic acid To a solution of 2-oxoglutaric acid (2.00 g) in ethanol (10 mL) was added hydrazine monohydrate (ca. 80%, 1.20 mL), and the mixture was stirred at 60° C. for 2 hours. The reaction mixture was allowed to cool to room temperature, and then the reaction mixture was cooled with ice. The precipitated solid was collected by filtration. The obtained solid was washed with diethyl ether to give the title compound (2.04 g).

Reference Example 6-1-B 2,3,4,5-Tetrahydropyridazin-3-one

Reference Example 6-1-A (2.00 g) was heated at 220° C. for 25 minutes. The reaction mixture was allowed to cool to room temperature to give the title compound (1.19 g).

Reference Example 6-1-C

4-[(4-Bromo-2-methylphenyl)methyl]-2,3-dihydropyridazin-3-one

A mixture of Reference Example 6-1-B (0.963 g), 4-bromo-2-methylbenzaldehyde (1.95 g) and potassium hydroxide (0.5 mol/L, ethanol) (60 mL) was stirred at 70° C. for 2 hours. The reaction mixture was allowed to cool to room temperature, and then the reaction mixture was concentrated under reduced pressure. To the residue were added dichloromethane and hydrochloric acid (2 mol/L, 30 mL). The organic layer was separated. The organic layer was dried over anhydrous sodium sulfate, and concentrated under reduced pressure. The residue was purified by column chromatography on silica gel (eluent: n-hexane/ethyl acetate=50/50-0/100) to give the title compound (0.514 g).

Reference Example 6-1-D

Ethyl 3-methyl-4-[(3-oxo-2,3-dihydropyridazin-4-yl)methyl]benzoate

A solution of Reference Example 6-1-C (514 mg), [1,1-bis(diphenylphosphino)ferrocene]dichloropalladium (II) dichloromethane complex (150 mg), 1,1'-bis(diphenylphosphino) ferrocene (204 mg), triethylamine (1.10 mL), DMAP (67.3 mg) and ethanol (8 mL) in NMP (8 mL) was stirred at 110° C. under a carbon monoxide atmosphere overnight. The reaction mixture was concentrated under reduced pressure. The residue was purified by column chromatography on silica gel (eluent: n-hexane/ethyl acetate=70/30-30/70) to give the title compound (315 mg).

Reference Example 6-1-E

3-Methyl-4-[(3-oxo-2,3-dihydropyridazin-4-yl)methyl]benzoic acid

To a solution of Reference Example 6-1-D (315 mg) in THF (8 mL), methanol (4 mL) and water (0.25 mL) was added an aqueous solution of sodium hydroxide (2 mol/L, 1.75 mL), and the mixture was stirred at 50° C. for 1.5 hours. The reaction mixture was allowed to cool to room temperature, and then the reaction mixture was concentrated under reduced pressure. To the residue were added hydrochloric acid (2 mol/L, 1.90 mL) and water (8 mL), and the mixture was stirred at room temperature for 30 minutes. The precipitated solid was collected by filtration. The obtained solid was washed with water, and dried under reduced pressure at 40° C. to give the title compound (277 mg). MS (ESI_APCI, m/z): 243 (M–H)$^-$ Reference Example 6-2-A Ethyl 3-methyl-4-[(6-methyl-3-oxo-2,3-dihydropyridazin-4-yl)methyl]benzoate To a suspension of Reference Example 2-1-A (200 mg) in ethanol (4 mL) was added concentrated sulfuric acid (0.100 mL), and the mixture was refluxed for 3 hours. To the reaction mixture were added dichloromethane and water, and the mixture was stirred. The organic layer was separated. The organic layer was dried over anhydrous sodium sulfate, and concentrated under reduced pressure to give the crude title compound (218 mg).

Reference Example 6-2-B

Ethyl 3-methyl-4-(6-methyl-3-oxo-2,3-dihydropyridazine-4-carbonyl)benzoate

A suspension of Reference Example 6-2-A (50.0 mg) and sodium dichromate dihydrate (208 mg) in acetic acid (4 mL) was stirred under an argon atmosphere at 125° C. for 24 hours. To the reaction mixture were added hydrochloric acid (2 mol/L), water and dichloromethane. The organic layer was separated, dried over anhydrous sodium sulfate, and concentrated under reduced pressure. The residue was purified by column chromatography on amino-silica gel (eluent: ethyl acetate/methanol=92/8) to give the title compound (9.8 mg).

Reference Example 6-2-C

3-Methyl-4-(6-methyl-3-oxo-2,3-dihydropyridazine-4-carbonyl)benzoic acid

To a solution of Reference Example 6-2-B (14.0 mg) in THF (1 mL), methanol (0.5 mL) and water (0.4 mL) was added an aqueous solution of sodium hydroxide (2 mol/L, 0.100 mL), and the mixture was stirred at room temperature for 1.5 hours. To the reaction mixture was added hydrochloric acid (2 mol/L, 0.200 mL). The mixture was concentrated under reduced pressure. The residue was dried under reduced pressure at 60° C. for 2 hours, and then dried under reduced pressure at room temperature overnight to give the crude title compound (23.0 mg). MS (ESI_APCI, m/z): 271 (M−H)

Reference Example 6-3-A

Ethyl 3-methyl-4-[1-(6-methyl-3-oxo-2,3-dihydropyridazin-4-yl)ethenyl]benzoate

To a suspension of methyltriphenylphosphonium bromide (107 mg) in THF (2.0 mL) was added potassium bis(trimethylsilyl)amide (1.0 mol/L, THF) (0.270 mL) under an argon atmosphere at room temperature, and the mixture was stirred at the same temperature for 40 minutes. To the reaction mixture was added Reference Example 6-2-B (20.0 mg) under ice-cooling. The mixture was stirred under ice-cooling for 40 minutes, and then stirred at room temperature for 1 hour. To the reaction mixture were added dichloromethane, a saturated aqueous solution of ammonium chloride and water. The organic layer was separated. The organic layer was dried over anhydrous sodium sulfate, and concentrated under reduced pressure. The residue was purified by column chromatography on silica gel (eluent: n-hexane/ethyl acetate=80/20-30/70) to give the title compound (15.0 mg).

Reference Example 6-3-B

Ethyl 3-methyl-4-[1-(6-methyl-3-oxo-2,3-dihydropyridazin-4-yl)ethyl]benzoate

To a suspension of Reference Example 6-3-A (15.0 mg) in ethanol (2 mL) was added 10% palladium on carbon (wet, 30.0 mg). The mixture was stirred under a hydrogen atmosphere at room temperature for 1.5 hours. The reaction mixture was filtered through Celite, and the filtrate was concentrated under reduced pressure to give the title compound (14.0 mg).

Reference Example 6-3-C

3-Methyl-4-[1-(6-methyl-3-oxo-2,3-dihydropyridazin-4-yl)ethyl]benzoic acid

To a solution of Reference Example 6-3-B (14.0 mg) in THF (1 mL), methanol (0.5 mL) and water (0.43 mL) was added an aqueous solution of sodium hydroxide (2 mol/L, 0.070 mL). The mixture was stirred at room temperature overnight, and then to the mixture was added an aqueous solution of sodium hydroxide (2 mol/L, 0.070 mL). The mixture was stirred at 45° C. for 2 hours. The reaction mixture was allowed to cool to room temperature, and then to the reaction mixture was added hydrochloric acid (2 mol/L, 0.200 mL). The mixture was stirred at room temperature for 30 minutes, and then concentrated under reduced pressure. The residue was dried under reduced pressure at 50° C. for 4 hours to give the crude title compound (27.1 mg). MS (ESI_APCI, m/z): 271 (M−H)

Reference Example 6-4-A

Ethyl 4-[hydroxy(6-methyl-3-oxo-2,3-dihydropyridazin-4-yl)methyl]-3-methylbenzoate To a solution of Reference Example 6-2-B (40.0 mg) in ethanol (3 mL) was added sodium borohydride (15.1 mg) under ice-cooling, and the mixture was stirred at room temperature for 1.5 hours. To the reaction mixture were added dichloromethane, water, a saturated aqueous solution of ammonium chloride. The organic layer was separated. The organic layer was dried over anhydrous sodium sulfate, and concentrated under reduced pressure. The residue was purified by column chromatography on amino-silica gel (eluent: ethyl acetate/methanol=95/5) to give the title compound (19.5 mg).

Reference Example 6-4-B

4-[Hydroxy(6-methyl-3-oxo-2,3-dihydropyridazin-4-yl)methyl]-3-methylbenzoic acid The title compound was prepared in a similar manner to that described in Reference Example 6-3-C using Reference Example 6-4-A instead of Reference Example 6-3-B. MS (ESI_APCI, m/z): 273 (M−H)

Reference Example 6-5-A

Methyl 4-({2-[(4-methoxyphenyl)methyl]-6-methyl-3-oxo-2,3-dihydropyridazin-4-yl}oxy)benzoate The title compound was prepared in a similar manner to that described in Reference Example 2-2-B using 4-hydroxybenzoic acid methyl instead of 3-fluoro-4-hydroxybenzoic acid methyl.

Reference Example 6-5-B

Methyl 4-[(6-methyl-3-oxo-2,3-dihydropyridazin-4-yl)oxy]benzoate

A mixture of Reference Example 6-5-A (1.12 g), CAN (4.86 g), acetonitrile (52 mL) and water (11 mL) was stirred at room temperature for 2 hours. The reaction mixture was concentrated under reduced pressure. To the residue were added ethyl acetate and water. The organic layer was separated. The organic layer was washed with brine, dried over anhydrous magnesium sulfate, and concentrated under reduced pressure. To the residue was added diethyl ether, and the mixture was filtered. The filtrate was concentrated under reduced pressure. The residue was purified by column chromatography on silica gel (eluent: n-hexane/ethyl acetate=50/50-0/100) to give the title compound (0.556 g).

Reference Example 6-5-C

4-[(6-Methyl-3-oxo-2,3-dihydropyridazin-4-yl)oxy]benzoic acid

A mixture of Reference Example 6-5-B (551 mg), an aqueous solution of sodium hydroxide (2 mol/L, 3.20 mL) and methanol (7 mL) was stirred at 120° C. under microwave irradiation for 30 minutes. The reaction mixture was concentrated under reduced pressure. To the residue were added water, hydrochloric acid (2 mol/L, 3.20 mL) and dichloromethane. The mixture was concentrated under reduced pressure. The residue was washed with water to give the title compound (439 mg). MS (ESI_APCI, m/z): 247 (M+H)$^+$

Reference Example 6-6-A

5-Fluoro-4-methylpyrimidine-2-carbonitrile

A mixture of 2-chloro-5-fluoro-4-methylpyrimidine (0.532 g), zinc cyanide (1.27 g), tetrakis(triphenylphosphine)palladium (0) (0.419 g) and DMF (10 mL) was stirred under an argon atmosphere at 120° C. for 1.5 hours. To the reaction mixture was added ethyl acetate, and the mixture was filtered through Celite. To the filtrate was added water, and then the mixture was extracted with ethyl acetate. The organic layer was successively washed with water and brine, dried over anhydrous magnesium sulfate, and concentrated under reduced pressure. The residue was purified by column chromatography on silica gel (eluent: n-hexane/ethyl acetate=100/0-70/30) to give the title compound (0.393 g).

Reference Example 6-6-B 5-({2-[(4-Methoxyphenyl)methyl]-6-methyl-3-oxo-2,3-dihydropyridazin-4-yl}oxy)-4-methylpyrimidine-2-carbonitrile A mixture of Reference Example 6-6-A (293 mg), Reference Example 2-7-C (300 mg), potassium carbonate (253 mg) and DMF (4 mL) was stirred at 60° C. for 18 hours. To the reaction mixture was added water, and the mixture was extracted twice with ethyl acetate. The combined organic layer was successively washed with water twice and brine, dried over anhydrous magnesium sulfate, and concentrated under reduced pressure. The residue was purified by column chromatography on silica gel (eluent: n-hexane/ethyl acetate=70/30-0/100) to give the title compound (273 mg).

Reference Example 6-6-C

4-Methyl-5-[(6-methyl-3-oxo-2,3-dihydropyridazin-4-yl)oxy]pyrimidine-2-carbonitrile The title compound was prepared in a similar manner to that described in Reference Example 2-9-D using Reference Example 6-6-B instead of Reference Example 2-9-C.

Reference Example 6-6-D

4-Methyl-5-[(6-methyl-3-oxo-2,3-dihydropyridazin-4-yl)oxy]pyrimidine-2-carboxylic acid A mixture of Reference Example 6-6-C (148 mg) and an aqueous solution of sodium hydroxide (2 mol/L, 1.50 mL) was stirred at 60° C. for 1 hour. To the reaction mixture was added hydrochloric acid (2 mol/L, 1.50 mL). The mixture was acidified with hydrochloric acid (2 mol/L) until pH was adjusted from 2 to 3. The mixture was stirred at 0° C. for 15 minutes, and the precipitated solid was collected by filtration. The obtained solid was washed with water, and dried under reduced pressure to give the title compound (126 mg). MS (ESI_APCI, m/z): 261 (M−H)$^−$

Reference Example 6-7-A

Methyl 5-({2-[(4-methoxyphenyl)methyl]-6-methyl-3-oxo-2,3-dihydropyridazin-4-yl}oxy)-6-methylpyrazine-2-carboxylate The title compound was prepared in a similar manner to that described in Reference Example 2-7-D using 5-chloro-6-methylpyrazine-2-carboxylic acid methyl instead of Reference Example 2-7-A.

Reference Example 6-7-B

Methyl 6-methyl-5-[(6-methyl-3-oxo-2,3-dihydropyridazin-4-yl)oxy]pyrazine-2-carboxylate The title compound was prepared in a similar manner to that described in Reference Example 2-4-B using Reference Example 6-7-A instead of Reference Example 2-4-A.

Reference Example 6-7-C

6-Methyl-5-[(6-methyl-3-oxo-2,3-dihydropyridazin-4-yl)oxy]pyrazine-2-carboxylic acid The title compound was prepared in a similar manner to that described in Reference Example 6-2-C using Reference Example 6-7-B instead of Reference Example 6-2-B. $^1$H-NMR δ ppm (DMSO-d6): 2.38 (3H, s), 2.66 (3H, s), 7.39 (1H, s), 8.61 (1H, s)

Reference Example 6-8-A

2-Benzyl-6-methyl-2,3-dihydropyridazin-3-one

To a suspension of 6-methyl-3(2H)pyridazinone (2.00 g) and cesium carbonate (8.87 g) in DMF (36 mL) was added benzyl bromide (2.97 mL), and the mixture was stirred at room temperature for 3 hours. To the reaction mixture was added water, and the mixture was extracted with ethyl acetate. The organic layer was successively washed with water twice and brine, dried over anhydrous magnesium sulfate, and concentrated under reduced pressure. The residue was purified by column chromatography on silica gel (eluent: n-hexane/ethyl acetate=50/50-0/100) to give the title compound (2.08 g).

Reference Example 6-8-B

4-Amino-2-benzyl-6-methyl-2,3-dihydropyridazin-3-one

A mixture of Reference Example 6-8-A (2.06 g) and hydrazine monohydrate (10 mL) was stirred at 200° C. under microwave irradiation for 12 hours. To the reaction mixture was added brine, and the mixture was extracted thrice with dichloromethane. The combined organic layer was dried over anhydrous sodium sulfate, and concentrated under reduced pressure. The residue was purified by column

Reference Example 6-8-C

Methyl 4-[(2-benzyl-6-methyl-3-oxo-2,3-dihydro-pyridazin-4-yl)amino]-3-methylbenzoate A mixture of Reference Example 6-8-B (667 mg), [4-(methoxycarbonyl)-2-methylphenyl]boronic acid (721 mg), copper (II) acetate (506 mg), triethylamine (0.518 mL), molecular sieves 4A (800 mg) and dichloromethane (18 mL) was stirred at room temperature for 13 hours. To the reaction mixture was added water under ice-cooling. The mixture was filtered through Celite. To the filtrate was added water, and the mixture was extracted with dichloromethane. The organic layer was dried over anhydrous sodium sulfate, and concentrated under reduced pressure. The residue was purified by column chromatography on silica gel (eluent: n-hexane/ethyl acetate=85/15-65/35) to give the title compound (192 mg).

Reference Example 6-8-D

Methyl 3-methyl-4-[(6-methyl-3-oxo-2,3-dihydro-pyridazin-4-yl)amino]benzoate

To a solution of Reference Example 6-8-C (90.0 mg) in toluene (2.5 mL) was added aluminum chloride (264 mg), and the mixture was stirred at 90° C. for 2 hours. The reaction mixture was diluted with dichloromethane, and then to the mixture was added water at 0° C. The mixture was extracted twice with dichloromethane. The combined organic layer was dried over anhydrous sodium sulfate, and concentrated under reduced pressure. To the residue was added diethyl ether (5 mL), and then the precipitated solid was collected by filtration. The obtained solid was washed with diethyl ether, and dried under reduced pressure to give the title compound (57.2 mg).

Reference Example 6-8-E

3-Methyl-4-[(6-methyl-3-oxo-2,3-dihydropyridazin-4-yl)amino]benzoic acid

The title compound was prepared in a similar manner to that described in Reference Example 2-9-E using Reference Example 6-8-D instead of Reference Example 2-9-D. MS (ESI_APCI, m/z): 260 (M+H)$^+$

Reference Example 6-9-A

Methyl 3-(1,3-dioxolan-2-yl)-4-hydroxybenzoate

To a suspension of 3-formyl-4-hydroxybenzoic acid methyl (200 mg), triethyl orthoformate (0.190 mL) in ethylene glycol (1.0 mL) was added tetrabutylammonium tribromide (5.4 mg) under an argon atmosphere, and the mixture was stirred at room temperature overnight. To the reaction mixture were added ethyl acetate and a saturated aqueous solution of ammonium chloride. The organic layer was separated. The organic layer was dried over anhydrous magnesium sulfate, and concentrated under reduced pressure. The residue was purified by column chromatography on silica gel (eluent: n-hexane/ethyl acetate=80/20-50/50) to give the title compound (196 mg).

Reference Example 6-9-B

Methyl 3-(1,3-dioxolan-2-yl)-4-({2-[(4-methoxyphenyl)methyl]-6-methyl-3-oxo-2,3-dihydropyridazin-4-yl}oxy)benzoate The title compound was prepared in a similar manner to that described in Reference Example 2-2-B using Reference Example 6-9-A instead of 3-fluoro-4-hydroxybenzoic acid methyl.

Reference Example 6-9-C

Methyl 3-formyl-4-({2-[(4-methoxyphenyl)methyl]-6-methyl-3-oxo-2,3-dihydropyridazin-4-yl}oxy)benzoate To a solution of Reference Example 6-9-B (20.0 mg) in THF (1 mL) was added hydrochloric acid (2 mol/L, 1 mL), and the mixture was stirred at room temperature for 90 minutes. To the reaction mixture were added dichloromethane and hydrochloric acid (2 mol/L), and the mixture was stirred. The organic layer was separated, and concentrated under reduced pressure to give the title compound (17.1 mg).

Reference Example 6-9-D

Methyl 3-(hydroxymethyl)-4-({2-[(4-methoxyphenyl)methyl]-6-methyl-3-oxo-2,3-dihydropyridazin-4-yl}oxy)benzoate To a suspension of Reference Example 6-9-C (16.6 mg) in methanol (2 mL) was added sodium borohydride (3.4 mg) under an argon atmosphere under ice-cooling, and the mixture was stirred at the same temperature for 30 minutes. To the reaction mixture were added dichloromethane and hydrochloric acid (2 mol/L), and the mixture was stirred. The organic layer was separated, and concentrated under reduced pressure to give the title compound (16.5 mg).

Reference Example 6-9-E

Methyl 3-(fluoromethyl)-4-({2-[(4-methoxyphenyl)methyl]-6-methyl-3-oxo-2,3-dihydropyridazin-4-yl}oxy)benzoate To a solution of Reference Example 6-9-D (15.5 mg) in dichloromethane (1 mL) was added (diethylamino)sulfur trifluoride (0.007 mL) under an argon atmosphere in ice salt bath, and the mixture was stirred at the same temperature for 1 hour. To the reaction mixture were added dichloromethane and a saturated aqueous solution of sodium bicarbonate. The organic layer was separated. The organic layer was dried over anhydrous sodium sulfate, and concentrated under reduced pressure to give the title compound (14.3 mg).

Reference Example 6-9-F

Methyl 3-(fluoromethyl)-4-[(6-methyl-3-oxo-2,3-dihydropyridazin-4-yl)oxy]benzoate To a solution of Reference Example 6-9-E (14.3 mg) in acetonitrile (1 mL) and water (0.2 mL) was added CAN (57.1 mg), and the mixture was stirred at room temperature for 5 hours. To the reaction mixture were added dichloromethane and water, and the mixture was stirred. The organic layer was separated, and then concentrated under reduced pressure. The residue was purified by column chromatography on silica gel (eluent: n-hexane/ethyl acetate=40/60-0/100) to give the title compound (6.5 mg).

Reference Example 6-9-G 3-(Fluoromethyl)-4-[(6-methyl-3-oxo-2,3-dihydropyridazin-4-yl)oxy]benzoic acid The title compound was prepared in a similar manner to that described in Reference Example 6-2-C using Reference Example 6-9-F instead of Reference Example 6-2-B. MS (ESI_APCI, m/z): 279 (M+H)$^+$ Reference Example 6-10-A Methyl 4-({2-[(4-methoxyphenyl)methyl]-6-methyl-3-oxo-2,3-dihydropyridazin-4-yl}oxy)-3,5-dimethylbenzoate The title compound was prepared in a similar manner to that described in Reference Example 2-2-B using 4-hydroxy-3,5-dimethylbenzoic acid methyl instead of 3-fluoro-4-hydroxybenzoic acid methyl.

Reference Example 6-10-B 3,5-Dimethyl-4-[(6-methyl-3-oxo-2,3-dihydropyridazin-4-yl)oxy]benzoic acid A suspension of Reference Example 6-10-A (308 mg) in acetic acid (1.5 mL) was heated to 65° C., and then to the suspension was added concentrated hydrochloric acid (1.5 mL). The mixture was stirred at 110° C. for 2 hours. The reaction mixture was allowed to cool to room temperature, and then to the reaction mixture was added water (7.5 mL). The mixture was stirred under ice-cooling, and then the precipitate was collected by filtration to give the title compound (198 mg). MS (ESI_APCI, m/z): 275 (M+H)$^+$ Reference Example 6-11-A 4-(4-Bromo-3-fluoro-2-methylphenoxy)-2-[(4-methoxyphenyl)methyl]-6-methyl-2,3-dihydropyridazin-3-one The title compound was prepared in a similar manner to that described in Reference Example 2-2-B using 4-bromo-3-fluoro-2-methylphenol instead of 3-fluoro-4-hydroxybenzoic acid methyl.

Reference Example 6-11-B

Ethyl 2-fluoro-4-({2-[(4-methoxyphenyl)methyl]-6-methyl-3-oxo-2,3-dihydropyridazin-4-yl}oxy)-3-methylbenzoate The title compound was prepared in a similar manner to that described in Reference Example 2-8-B using Reference Example 6-11-A instead of Reference Example 2-8-A.

Reference Example 6-11-C

2-Fluoro-3-methyl-4-[(6-methyl-3-oxo-2,3-dihydropyridazin-4-yl)oxy]benzoic acid

The title compound was prepared in a similar manner to that described in Reference Example 6-10-B using Reference Example 6-11-B instead of Reference Example 6-10-A. $^1$H-NMR δ ppm (DMSO-d6): 2.11 (3H, d, J=2.0 Hz), 2.18 (3H, s), 6.73 (1H, s), 6.94 (1H, d, J=8.8 Hz), 7.70-7.78 (1H, m), 13.02 (1H, brs), 13.12-13.32 (1H, br)

Reference Example 6-12-A

Methyl 3-methoxy-4-({2-[(4-methoxyphenyl)methyl]-6-methyl-3-oxo-2,3-dihydropyridazin-4-yl}oxy)benzoate The title compound was prepared in a similar manner to that described in Reference Example 2-2-B using 4-hydroxy-3-methoxybenzoic acid methyl instead of 3-fluoro-4-hydroxybenzoic acid methyl.

Reference Example 6-12-B

3-Methoxy-4-[(6-methyl-3-oxo-2,3-dihydropyridazin-4-yl)oxy]benzoic acid

The title compound was prepared in a similar manner to that described in Reference Example 6-10-B using Reference Example 6-12-A instead of Reference Example 6-10-A. $^1$H-NMR δ ppm (DMSO-d6): 2.13 (3H, s), 3.83 (3H, s), 6.37 (1H, s), 7.24 (1H, d, J=8.3 Hz), 7.61 (1H, dd, J=1.8, 8.3 Hz), 7.67 (1H, d, J=1.8 Hz), 12.91 (1H, brs), 13.00-13.40 (1H, br)

Reference Example 6-13-A 4-(4-Bromo-5-fluoro-2-methylphenoxy)-2-[(4-methoxyphenyl)methyl]-6-methyl-2,3-dihydropyridazin-3-one The title compound was prepared in a similar manner to that described in Reference Example 2-2-B using 4-bromo-5-fluoro-2-methylphenol instead of 3-fluoro-4-hydroxybenzoic acid methyl.

Reference Example 6-13-B

Ethyl 2-fluoro-4-({2-[(4-methoxyphenyl)methyl]-6-methyl-3-oxo-2,3-dihydropyridazin-4-yl}oxy)-5-methylbenzoate The title compound was prepared in a similar manner to that described in Reference Example 2-6-B using Reference Example 6-13-A instead of Reference Example 2-6-A.

Reference Example 6-13-C

2-Fluoro-5-methyl-4-[(6-methyl-3-oxo-2,3-dihydropyridazin-4-yl)oxy]benzoic acid

The title compound was prepared in a similar manner to that described in Reference Example 6-10-B using Reference Example 6-13-B instead of Reference Example 6-10-A. MS (ESI_APCI, m/z): 279 (M+H)$^+$ Reference Example 6-14-A 4-(2,6-Difluoro-4-iodophenoxy)-2-[(4-methoxyphenyl)methyl]-6-methyl-2,3-dihydropyridazin-3-one The title compound was prepared in a similar manner to that described in Reference Example 2-2-B using 2,6-difluoro-4-iodophenol instead of 3-fluoro-4-hydroxybenzoic acid methyl.

Reference Example 6-14-B

Ethyl 3,5-difluoro-4-({2-[(4-methoxyphenyl)
methyl]-6-methyl-3-oxo-2,3-dihydropyridazin-4-
yl}oxy)benzoate The title compound was prepared in a similar manner to that described in Reference Example 2-6-B using Reference Example 6-14-A instead of Reference Example 2-6-A.

Reference Example 6-14-C 3,5-Difluoro-4-[(6-methyl-3-oxo-2,3-dihydro-
pyridazin-4-yl)oxy]benzoic acid The title compound was prepared in a similar manner to that described in Reference Example 6-10-B using Reference Example 6-14-B instead of Reference Example 6-10-A. MS (ESI_APCI, m/z): 281 (M−H)−

Reference Example 7-1-A

N-[(1 S)-1-[(2R,5S)-1-[(2R)-2-(1,3-Dioxo-2,3-di-
hydro-1H-isoindol-2-yl)propanoyl]-5-(3-fluorophe-
nyl)pyrrolidin-2-yl]ethyl]acetamide To a solution of (R)-2-phthalimidopropionic acid (55.5 mg) in dichloromethane (2 mL) were successively added oxalyl chloride (0.028 mL) and DMF (0.0015 mL) under ice-cooling, and the mixture was stirred at room temperature for 40 minutes. The reaction mixture was concentrated under reduced pressure. To a solution of Reference Example 5-27-B (46.7 mg) and DIPEA (0.066 mL) in THF (2 mL) was added a solution of the above obtained compound in dichloromethane (1 mL) under ice-cooling. The mixture was stirred at room temperature for 1 hour. To the reaction mixture were added a saturated aqueous solution of sodium bicarbonate and water, and the mixture was extracted with dichloromethane. The organic layer was concentrated under reduced pressure. The residue was purified by column chromatography on silica gel (eluent: ethyl acetate/methanol=100/0-95/5) to give the title compound (37.6 mg).

Reference Example 7-1-B

N-[(1 S)-1-[(2R,5 S)-1-[(2R)-2-Aminopropanoyl]-5-
(3-fluorophenyl)pyrrolidin-2-yl]ethyl]acetamide To a solution of Reference Example 7-1-A (36.0 mg) in ethanol (1.6 mL) was added hydrazine monohydrate (ca. 80%, 0.050 mL), and the mixture was stirred at 50° C. for 3.5 hours. The reaction mixture was allowed to cool to room temperature, and then to the reaction mixture was added ethyl acetate (5 mL). The mixture was stirred at room temperature for 5 minutes, and then the mixture was filtered. The filtrate was concentrated under reduced pressure to give the crude title compound (26.3 mg). MS (ESI_APCI, m/z): 322 (M+H)+

Reference Example 7-2-A

N-[(1 S)-1-[(2R,5 S)-1-[(2R)-2-(1,3-Dioxo-2,3-di-
hydro-1H-isoindol-2-yl)propanoyl]-5-(3-fluorophe-
nyl)pyrrolidin-2-yl]ethyl]-N-methylacetamide The title compound was prepared in a similar manner to that described in Reference Example 7-1-A using Reference Example 5-28-B instead of Reference Example 5-27-B.

Reference Example 7-2-B

N-[(1 S)-1-[(2R,5 S)-1-[(2R)-2-Aminopropanoyl]-5-
(3-fluorophenyl)pyrrolidin-2-yl]ethyl]-N-methylac-
etamide The title compound was prepared in a similar manner to that described in Reference Example 7-1-B using Reference Example 7-2-A instead of Reference Example 7-1-A. MS (ESI_APCI, m/z): 336 (M+H)+

Reference Example 7-3-A

2-[(2R)-1-[(2R,5 S)-2-(1,1-Difluoroethyl)-5-(3-fluo-
rophenyl)pyrrolidin-1-yl]-1-oxopropan-2-yl]-2,3-
dihydro-1H-isoindole-1,3-dione To a solution of (R)-2-phthalimidopropionic acid (153 mg) in dichloromethane (3.5 mL) were successively added oxalyl chloride (0.078 mL) and DMF (0.005 mL) under ice-cooling, and the mixture was stirred at room temperature for 40 minutes. The reaction mixture was concentrated under reduced pressure. To a solution of Reference Example 5-29-B (80.0 mg) and DIPEA (0.182 mL) in THF (2 mL) was added a solution of the above obtained compound in dichloromethane (1 mL) under ice-cooling. The mixture was stirred at room temperature for 1 hour. To the reaction mixture were added a saturated aqueous solution of sodium bicarbonate and water. The mixture was extracted with dichloromethane. The organic layer was concentrated under reduced pressure. The residue was purified by column chromatography on silica gel (eluent: n-hexane/ethyl acetate=85/15-65/35) to give the title compound (126 mg).

Reference Example 7-3-B (2R)-2-Amino-1-[(2R,5 S)-2-(1,1-difluoroethyl)-5-
(3-fluorophenyl)pyrrolidin-1-yl]propan-1-one The title compound was prepared in a similar manner to that described in Reference Example 7-1-B using Reference Example 7-3-A instead of Reference Example 7-1-A. MS (ESI_APCI, m/z): 301 (M+H)+

Reference Example 7-4-A (2R)-3-(Benzyloxy)-2-(1,3-dioxo-2,3-dihydro-1H-
isoindol-2-yl)propanoic acid To a solution of O-benzyl-N-(tert-butoxycarbonyl)-D-serine (1.00 g) in ethyl acetate (10 mL) was added hydrogen chloride in ethyl acetate (4 mol/L, 20 mL), and the mixture was stirred at room temperature for 2 hours. The reaction mixture was concentrated under reduced pressure. To a suspension of the residue and triethylamine (0.480 mL) in water (9.6 mL) were successively added N-ethoxycarbonylphthalimide (717 mg) and triethylamine (0.480 mL). The mixture was stirred at room temperature overnight. To the reaction mixture were added ethyl acetate, hydrochloric acid (2 mol/L) and water. The organic layer was separated. The organic layer was dried over anhydrous sodium sulfate, and concentrated under reduced pressure to give the crude title compound (1.38 g).

Reference Example 7-4-B

2-[(2R,5S)-1-[(2R)-2-Amino-3-(benzyloxy)propanoyl]-5-(3-chlorophenyl)pyrrolidin-2-yl]-2-methylpropanenitrile To a solution of Reference Example 7-4-A (130 mg) in dichloromethane (3 mL) were successively added oxalyl chloride (0.046 mL) and DMF (0.005 mL) under an argon atmosphere under ice-cooling, and the mixture was stirred at room temperature for 2.5 hours. The reaction mixture was concentrated under reduced pressure. To a suspension of the residue and Reference Example 1-7-D (50.1 mg) in THF (2 mL) was added DIPEA (0.140 mL). The mixture was stirred at room temperature for 3 hours. To the reaction mixture were added dichloromethane and water. The organic layer was separated. The organic layer was dried over anhydrous sodium sulfate, and concentrated under reduced pressure to give crude 2-[(2R,5S)-1-[(2R)-3-(benzyloxy)-2-(1,3-dioxo-2,3-dihydro-1H-isoindol-2-yl)propanoyl]-5-(3-chlorophenyl)pyrrolidin-2-yl]-2-methylpropane nitrile. To a solution of the obtained compound in ethanol (4 mL) was added hydrazine monohydrate (ca. 80%, 0.081 mL), and the mixture was stirred at room temperature overnight. The reaction mixture was filtered, and the filtrate was concentrated under reduced pressure. The residue was purified by column chromatography on amino-silica gel (eluent: ethyl acetate/methanol=100/0-90/10) to give the title compound (19.3 mg). MS (ESI_APCI, m/z): 426 (M+H)$^+$

Reference Example 7-5-A

3-[(2R,5S)-1-[(2R)-2-Aminopropanoyl]-5-(3-chlorophenyl)pyrrolidin-2-yl]oxetane-3-carbonitrile The title compound was prepared in a similar manner to that described in Reference Example 3-10-A using Reference Example 5-30-B instead of Reference Example 1-8-D. MS (ESI_APCI, m/z): 334 (M+H)$^+$

Reference Example 7-6-A

1-[(1S)-1-[(2R,5S)-1-[(2R)-2-Aminopropanoyl]-5-(3-chlorophenyl)pyrrolidin-2-yl]ethyl]pyrrolidin-2-one The title compound was prepared in a similar manner to that described in Reference Example 3-7-A using Reference Example 5-31-G instead of Reference Example 1-5-D. MS (ESI_APCI, m/z): 364 (M+H)$^+$

Reference Example 7-7-A

2-[(2R,5S)-1-[(2R)-3-(Benzyloxy)-2-(1,3-dioxo-2,3-dihydro-1H-isoindol-2-yl)propanoyl]-5-(3-chlorophenyl)pyrrolidin-2-yl]-2-methylpropanenitrile To a solution of Reference Example 7-4-A (392 mg) in dichloromethane (4 mL) were successively added oxalyl chloride (0.155 mL) and DMF (0.004 mL) under an argon atmosphere under ice-cooling, and the mixture was stirred at room temperature for 1.5 hours. The reaction mixture was concentrated under reduced pressure. To a solution of Reference Example 1-7-D (200 mg) and DIPEA (0.315 mL) in THF (2 mL) was added a solution of the above obtained compound in THF (1 mL) under ice-cooling. The mixture was stirred at room temperature for 2 hours. To the reaction mixture were added water and dichloromethane, and the mixture was stirred. The organic layer was separated, and then concentrated under reduced pressure. The residue was purified by column chromatography on silica gel (eluent: n-hexane/ethyl acetate=75/25-40/60) to give the title compound (220 mg).

Reference Example 7-7-B

2-[(2R,5S)-5-(3-Chlorophenyl)-1-[(2R)-2-(1,3-dioxo-2,3-dihydro-1H-isoindol-2-yl)-3-hydroxypropanoyl]pyrrolidin-2-yl]-2-methylpropanenitrile To a solution of Reference Example 7-7-A (220 mg) in dichloromethane (4.4 mL) was added titanium(IV) chloride (0.220 mL) under an argon atmosphere, and the mixture was stirred at room temperature for 3 hours. To the reaction mixture were added hydrochloric acid (2 mol/L), dichloromethane and methanol, and the mixture was stirred. The organic layer was separated, and then concentrated under reduced pressure. The residue was purified by column chromatography on silica gel (eluent: n-hexane/ethyl acetate=60/40-0/100) to give the title compound (126 mg).

Reference Example 7-7-C

2-[(2R,5S)-5-(3-Chlorophenyl)-1-[(2S)-2-(1,3-dioxo-2,3-dihydro-1H-isoindol-2-yl)-3-fluoropropanoyl]pyrrolidin-2-yl]-2-methylpropanenitrile To a solution of Reference Example 7-7-B (96.6 mg) in dichloromethane (5 mL) was added a solution of (diethylamino)sulfur trifluoride (0.054 mL) in dichloromethane (0.5 mL) under an argon atmosphere in ice salt bath, and the mixture was stirred at the same temperature for 80 minutes. To the reaction mixture were added dichloromethane and a saturated aqueous solution of ammonium chloride. The organic layer was separated. The organic layer was dried over anhydrous sodium sulfate, and concentrated under reduced pressure. The residue was purified by column chromatography on silica gel (eluent: n-hexane/ethyl acetate=70/30-30/70) to give the title compound (70.6 mg).

Reference Example 7-7-D

2-[(2R,5S)-1-[(2S)-2-Amino-3-fluoropropanoyl]-5-(3-chlorophenyl)pyrrolidin-2-yl]-2-methylpropanenitrile To a solution of Reference Example 7-7-C (70.6 mg) in ethanol (2 mL) was added hydrazine monohydrate (ca. 80%, 0.094 mL), and the mixture was stirred at 45° C. for 2 hours. To the reaction mixture were added ethyl acetate, water and a saturated aqueous solution of sodium bicarbonate. The organic layer was separated. The organic layer was dried over anhydrous magnesium sulfate, and concentrated under reduced pressure to give the crude title compound (56.2 mg). MS (ESI_APCI, m/z): 338 (M+H)$^+$

Reference Example 7-8-A

2-[(2R)-1-[(2S,5R)-2-(3,5-Difluorophenyl)-5-(2-hydroxypropan-2-yl)pyrrolidin-1-yl]-1-oxopropan-2-yl]-2,3-dihydro-1H-isoindole-1,3-dione The title compound was prepared in a similar manner to that described in Reference Example 3-3-A using Reference Example 5-32-B instead of Reference Example 1-3-C.

Reference Example 7-8-B (2R)-2-Amino-1-[(2S,5R)-2-(3,5-difluorophenyl)-5-(2-hydroxypropan-2-yl)pyrrolidin-1-yl]propan-1-one The title compound was prepared in a similar manner to that described in Reference Example 3-3-B using Reference Example 7-8-A instead of Reference Example 3-3-A. MS (ESI_APCI, m/z): 313 (M+H)$^+$

Reference Example 7-9-A

2-[(2R,4R,5R)-4-(Benzyloxy)-1-[2-(1,3-dioxo-2,3-dihydro-1H-isoindol-2-yl)acetyl]-5-(3-fluorophenyl)pyrrolidin-2-yl]-2-methylpropanenitrile The title compound was prepared in a similar manner to that described in Reference Example 3-3-A using N-phthaloylglycine and Reference Example 5-33-J instead of (R)-2-phthalimidopropionic acid and Reference Example 1-3-C.

Reference Example 7-9-B

2-[(2R,4R,5R)-1-(2-Aminoacetyl)-4-(benzyloxy)-5-(3-fluorophenyl)pyrrolidin-2-yl]-2-methylpropanenitrile To a solution of Reference Example 7-9-A (28.0 mg) in ethanol (2 mL) was added hydrazine monohydrate (0.052 mL), and the mixture was stirred at 45° C. for 2 hours. To the reaction mixture were added ethyl acetate, water and a saturated aqueous solution of sodium bicarbonate. The organic layer was separated. The aqueous layer was extracted with ethyl acetate, and then the extract was combined with the above organic layer. The organic layer was dried over anhydrous sodium sulfate, and concentrated under reduced pressure to give the crude title compound (20.2 mg). MS (ESI_APCI, m/z): 396 (M+H)$^+$

Reference Example 7-10-A

2-[(2R,5S)-5-(3-Chloro-4-fluorophenyl)-1-[(2R)-2-(1,3-dioxo-2,3-dihydro-1H-isoindol-2-yl)propanoyl]pyrrolidin-2-yl]-2-methylpropanenitrile To a solution of (R)-2-phthalimidopropionic acid (246 mg) in dichloromethane (2.5 mL) were successively added oxalyl chloride (0.145 mL) and DMF (0.0025 mL) under ice-cooling, and the mixture was stirred at room temperature for 1.5 hours. The reaction mixture was concentrated under reduced pressure. To a solution of Reference Example 5-34-H (200 mg) and 2,6-lutidine (0.174 mL) in dichloromethane (2 mL) was added a solution of the above obtained compound in dichloromethane (1 mL) under ice-cooling. The mixture was stirred at the same temperature for 1 hour. To the reaction mixture were added hydrochloric acid (2 mol/L) and dichloromethane. The organic layer was separated. The aqueous layer was extracted with dichloromethane, and then the extract was combined with the above organic layer. The organic layer was dried over anhydrous magnesium sulfate, and concentrated under reduced pressure. The residue was purified by column chromatography on silica gel (eluent: n-hexane/ethyl acetate=65/35-25/75) to give the title compound (338 mg).

Reference Example 7-10-B

2-[(2R,5S)-1-[(2R)-2-Aminopropanoyl]-5-(3-chloro-4-fluorophenyl)pyrrolidin-2-yl]-2-methylpropanenitrile To a suspension of Reference Example 7-10-A (338 mg) in ethanol (13.6 mL) was added hydrazine monohydrate (0.355 mL), and the mixture was stirred at 60° C. for 2 hours. To the reaction mixture were added ethyl acetate, water and a saturated aqueous solution of sodium bicarbonate. The organic layer was separated. The aqueous layer was extracted with ethyl acetate, and then the extract was combined with the above organic layer. The organic layer was dried over anhydrous sodium sulfate, and concentrated under reduced pressure to give the crude title compound (248 mg). MS (ESI_APCI, m/z): 338 (M+H)$^+$

Reference Example 7-11-A

2-[(2R,5S)-5-(5-Chloro-2-fluorophenyl)-1-[(2R)-2-(1,3-dioxo-2,3-dihydro-1H-isoindol-2-yl)propanoyl]pyrrolidin-2-yl]-2-methylpropanenitrile The title compound was prepared in a similar manner to that described in Reference Example 7-10-A using Reference Example 5-35-H instead of Reference Example 5-34-H.

Reference Example 7-11-B

2-[(2R,5S)-1-[(2R)-2-Aminopropanoyl]-5-(5-chloro-2-fluorophenyl)pyrrolidin-2-yl]-2-methylpropanenitrile The title compound was prepared in a similar manner to that described in Reference Example 7-1-B using Reference Example 7-11-A instead of Reference Example 7-1-A. MS (ESI_APCI, m/z): 338 (M+H)$^+$

Reference Example 7-12-A

2-[(2R,5S)-5-(3-Chloro-5-fluorophenyl)-1-[(2R)-2-(1,3-dioxo-2,3-dihydro-1H-isoindol-2-yl)propanoyl]pyrrolidin-2-yl]-2-methylpropanenitrile The title compound was prepared in a similar manner to that described in Reference Example 3-3-A using Reference Example 5-36-H instead of Reference Example 1-3-C.

Reference Example 7-12-B

2-[(2R,5S)-1-[(2R)-2-Aminopropanoyl]-5-(3-chloro-5-fluorophenyl)pyrrolidin-2-yl]-2-methylpropanenitrile The title compound was prepared in a similar manner to that described in Reference Example 7-10-B using Reference Example 7-12-A instead of Reference Example 7-10-A. MS (ESI_APCI, m/z): 338 (M+H)+

Reference Example 7-13-A

2-[(2R,5S)-5-(3-Bromophenyl)-1-[(2R)-2-(1,3-dioxo-2,3-dihydro-1H-isoindol-2-yl)propanoyl]pyrrolidin-2-yl]-2-methylpropanenitrile The title compound was prepared in a similar manner to that described in Reference Example 3-3-A using Reference Example 5-37-J instead of Reference Example 1-3-C.

Reference Example 7-13-B

2-[(2R,5S)-1-[(2R)-2-Aminopropanoyl]-5-(3-bromophenyl)pyrrolidin-2-yl]-2-methylpropanenitrile The title compound was prepared in a similar manner to that described in Reference Example 3-3-B using Reference Example 7-13-A instead of Reference Example 3-3-A. MS (ESI_APCI, m/z): 364 (M+H)+

Reference Example 7-14-A

2-[(2R,4R,5R)-4-(Benzyloxy)-1-[(2R)-2-(1,3-dioxo-2,3-dihydro-1H-isoindol-2-yl)propanoyl]-5-(3-fluorophenyl)pyrrolidin-2-yl]-2-methylpropanenitrile The title compound was prepared in a similar manner to that described in Reference Example 7-10-A using Reference Example 5-33-J instead of Reference Example 5-34-H.

Reference Example 7-14-B

2-[(2R,4R,5R)-1-[(2R)-2-Aminopropanoyl]-4-(benzyloxy)-5-(3-fluorophenyl)pyrrolidin-2-yl]-2-methylpropanenitril The title compound was prepared in a similar manner to that described in Reference Example 7-10-B using Reference Example 7-14-A instead of Reference Example 7-10-A. MS (ESI_APCI, m/z): 410 (M+H)+

Reference Example 7-15-A

2-[(2R,4R,5R)-1-[(2R)-2-(1,3-Dioxo-2,3-dihydro-1H-isoindol-2-yl)propanoyl]-5-(3-fluorophenyl)-4-hydroxypyrrolidin-2-yl]-2-methylpropanenitrile To a solution of Reference Example 7-14-A (89.8 mg) in ethanol (3 mL) was added 10% palladium on carbon (wet, 90.0 mg) under ice-cooling. The mixture was stirred under a hydrogen atmosphere at room temperature for 4 hours, and then stirred at 45° C. for 4 hours. The reaction mixture was filtered through Celite, and the filtrate was concentrated under reduced pressure. The residue was purified by column chromatography on silica gel (eluent: n-hexane/ethyl acetate=50/50-0/100) to give the title compound (27.9 mg).

Reference Example 7-15-B

2-[(2R,4S,5R)-1-[(2R)-2-Aminopropanoyl]-4-azido-5-(3-fluorophenyl)pyrrolidin-2-yl]-2-methylpropanenitrile To a solution of Reference Example 7-15-A (14.4 mg) and triphenylphosphine (25.2 mg) in THF (1 mL) were successively added diethyl azodicarboxylate (40% in toluene, 0.044 mL) and diphenylphosphorylazide (0.021 mL) under ice-cooling under an argon atmosphere. The mixture was stirred at room temperature for 2 hours. The reaction mixture was purified by column chromatography on silica gel (eluent: n-hexane/ethyl acetate=70/30-20/80) to give 2-[(2R,4S,5R)-4-azido-1-[(2R)-2-(1,3-dioxo-2,3-dihydro-1H-isoindol-2-yl)propanoyl]-5-(3-fluorophenyl)pyrrolidin-2-yl]-2-methylpropanenitrile. To a solution of the obtained compound in ethanol (2 mL) was added hydrazine monohydrate (0.031 mL), and the mixture was stirred at 45° C. for 2.5 hours. To the reaction mixture were added ethyl acetate, water and a saturated aqueous solution of sodium bicarbonate. The organic layer was separated. The aqueous layer was extracted with ethyl acetate, and then the extract was combined with the above organic layer. The organic layer was dried over anhydrous sodium sulfate, and concentrated under reduced pressure to give the crude title compound (24.7 mg). MS (ESI_APCI, m/z): 345 (M+H)+

Reference Example 7-16-A

2-[(2R,4S,5R)-1-[(2R)-2-Aminopropanoyl]-4-fluoro-5-(3-fluorophenyl)pyrrolidin-2-yl]-2-methylpropanenitrile To a solution of Reference Example 7-15-A (20.0 mg) in dichloromethane (0.4 mL) was added a solution of (diethylamino)sulfur trifluoride (0.018 mL) in dichloromethane (0.2 mL) under an argon atmosphere at −78° C. The mixture was stirred at −78° C. for 10 minutes, and then stirred at room temperature for 1 hour. To the reaction mixture was added methanol (0.2 mL). The mixture was stirred for 10 minutes, and then to the mixture were added ethyl acetate and water. The organic layer was separated. The aqueous layer was extracted with ethyl acetate, and then the extract was combined with the above organic layer. The organic layer was concentrated under reduced pressure. The residue was purified by column chromatography on silica gel (eluent: n-hexane/ethyl acetate=70/30-30/70) to give 2-[(2R,4S,5R)-1-[(2R)-2-(1,3-dioxo-2,3-dihydro-1H-isoindol-2-yl)propanoyl]-4-fluoro-5-(3-fluorophenyl)pyrrolidin-2-yl]-2-methylpropanenitrile. To a suspension of the obtained compound in ethanol (2 mL) was added hydrazine monohydrate (0.025 mL), and the mixture was stirred at 45° C. for 2 hours. To the reaction mixture were added ethyl acetate, water and a saturated aqueous solution of sodium bicarbonate. The organic layer was separated. The aqueous layer was extracted with ethyl acetate, and then the extract was combined with the above organic layer. The organic layer was dried over anhydrous sodium sulfate, and concentrated under reduced pressure to give the crude title compound (16.8 mg). MS (ESI_APCI, m/z): 322 (M+H)+

Reference Example 7-17-A

N-{1-[(2R,5 S)-5-(3-Chlorophenyl)-1-[(2R)-2-(1,3-dioxo-2,3-dihydro-1H-isoindol-2-yl)propanoyl]pyrrolidin-2-yl]-2,2,2-trifluoroethyl}-N-methylacetamide To a solution of (R)-2-phthalimidopropionic acid (108 mg) in dichloromethane (3 mL) were successively added oxalyl chloride (0.085 mL) and DMF (0.003 mL) under ice-cooling, and the mixture was stirred at room temperature for 1.5 hours. The reaction mixture was concentrated under reduced pressure. To a solution of Reference Example 5-38-E (110 mg) and 2,6-lutidine (0.076 mL) in dichloromethane (2 mL) was added a solution of the above obtained compound in dichloromethane (1 mL) at −15° C. The mixture was stirred under ice-cooling for 5 hours. To the reaction mixture were added hydrochloric acid (2 mol/L) and water, and the mixture was extracted twice with dichloromethane. The combined organic layer was successively washed with a saturated aqueous solution of sodium bicarbonate and brine, dried over anhydrous sodium sulfate, and concentrated under reduced pressure. The residue was purified by column chromatography on silica gel (eluent: n-hexane/ethyl acetate=40/60-0/100) to give the title compound (141 mg).

Reference Example 7-17-B

N-{1-[(2R,5 S)-1-[(2R)-2-Aminopropanoyl]-5-(3-chlorophenyl)pyrrolidin-2-yl]-2,2,2-trifluoroethyl}-N-methylacetamide To a solution of Reference Example 7-17-A (140 mg) in ethanol (5 mL) was added hydrazine monohydrate (0.131 mL). The mixture was stirred at 60° C. for 2 hours, and then stirred at room temperature overnight. To the reaction mixture were added water and a saturated aqueous solution of sodium bicarbonate, and the mixture was extracted with ethyl acetate 4 times. The combined organic layer was dried over anhydrous magnesium sulfate, and concentrated under reduced pressure to give the crude title compound (97.3 mg). MS (ESI_APCI, m/z): 406 (M+H)$^+$ Reference Example 7-18-A N-[(1S)-1-[(2R,5S)-5-(3-Chlorophenyl)-1-[(2R)-2-(1,3-dioxo-2,3-dihydro-1H-isoindol-2-yl)propanoyl]pyrrolidin-2-yl]ethyl]-N-(2,2,2-trifluoroethyl)acetamide The title compound was prepared in a similar manner to that described in Reference Example 7-17-A using Reference Example 5-39-C instead of Reference Example 5-38-E.

Reference Example 7-18-B

N-[(1 S)-1-[(2R,5 S)-1-[(2R)-2-Aminopropanoyl]-5-(3-chlorophenyl)pyrrolidin-2-yl]ethyl]-N-(2,2,2-trifluoroethyl)acetamide The title compound was prepared in a similar manner to that described in Reference Example 7-17-B using Reference Example 7-18-A instead of Reference Example 7-17-A. MS (ESI_APCI, m/z): 420 (M+H)$^+$ Reference Example 7-19-A N-{1-[(2R,5 S)-5-(3-Chlorophenyl)-1-[(2R)-2-(1,3-dioxo-2,3-dihydro-1H-isoindol-2-yl)propanoyl]pyrrolidin-2-yl]-2,2,2-trifluoroethyl}acetamide The title compound was prepared in a similar manner to that described in Reference Example 7-17-A using Reference Example 5-40-A instead of Reference Example 5-38-E.

Reference Example 7-19-B

N-{1-[(2R,5 S)-1-[(2R)-2-Aminopropanoyl]-5-(3-chlorophenyl)pyrrolidin-2-yl]-2,2,2-trifluoroethyl}acetamide The title compound was prepared in a similar manner to that described in Reference Example 7-17-B using Reference Example 7-19-A instead of Reference Example 7-17-A. MS (ESI_APCI, m/z): 392 (M+H)$^+$ Reference Example 7-20-A 2-[(2S,5S)-5-(3-Chlorophenyl)-1-[(2R)-2-(1,3-dioxo-2,3-dihydro-1H-isoindol-2-yl)propanoyl]pyrrolidin-2-yl]-2-methylpropanenitrile To a mixture of (R)-2-phthalimidopropionic acid (200 mg), DMF (1 drop) and dichloromethane (3 mL) was added dropwise oxalyl chloride (0.118 mL) under ice-cooling. The reaction mixture was stirred at room temperature for 1 hour, and then concentrated under reduced pressure. To a mixture of Reference Example 5-41-C (50.0 mg), 2,6-lutidine (0.047 mL) and isopropyl acetate (0.5 mL) was added a solution of the above obtained compound (71.6 mg) in isopropyl acetate (1 mL) under ice-cooling. The mixture was stirred under ice-cooling for 30 minutes, and then stirred at room temperature for 1 hour. To the mixture was added triethylamine (0.050 mL). The mixture was stirred for 1 hour, and then to the reaction mixture was added a saturated aqueous solution of sodium bicarbonate. The organic layer was separated, and then concentrated under reduced pressure. The residue was purified by column chromatography on silica gel (eluent: n-hexane/ethyl acetate=85/15-0/100) to give the title compound (15.0 mg).

Reference Example 7-20-B

2-[(2S,5 S)-1-[(2R)-2-Aminopropanoyl]-5-(3-chlorophenyl)pyrrolidin-2-yl]-2-methylpropanenitrile The title compound was prepared in a similar manner to that described in Reference Example 7-10-B using Reference Example 7-20-A instead of Reference Example 7-10-A. MS (ESI_APCI, m/z): 320 (M+H)$^+$ Reference Example 7-21-A 2-{2-[(2S,5R)-5-(2-Hydroxypropan-2-yl)-2-methyl-2-phenylpyrrolidin-1-yl]-2-oxoethyl}-2,3-dihydro-1H-isoindole-1,3-dione To a suspension of Reference Example 5-18-A (99.0 mg) and 2-(1,3-dioxoisoindolin-2-yl)acetylchloride (121 mg) in THF (4 mL) was added DIPEA (0.157 mL), and the mixture was stirred at room temperature for 2 hours. To the reaction mixture were added a saturated aqueous solution of ammonium chloride, water and ethyl acetate. The organic layer was separated. The organic layer was dried over anhydrous sodium sulfate, and concentrated under reduced pressure. The residue was purified by column chromatography on silica gel (eluent: n-hexane/ethyl acetate=60/40-20/80) to give the title compound (87.5 mg).

Reference Example 7-21-B

2-Amino-1-[(2S,5R)-5-(2-hydroxypropan-2-yl)-2-methyl-2-phenylpyrrolidin-1-yl]ethan-1-one To a solution of Reference Example 7-21-A (100 mg) in ethanol (3 mL) was added hydrazine monohydrate (ca. 80%, 0.155 mL). The mixture was stirred at 40° C. for 1 hour, and then stirred at room temperature overnight. The reaction mixture was filtered, and the filtrate was concentrated under reduced pressure to give the crude title compound (93.1 mg). MS (ESI_APCI, m/z): 277 (M+H)$^+$

Reference Example 8-1-A

Methyl (2R)-3-methyl-2-({3-methyl-4-[(6-methyl-3-oxo-2,3-dihydropyridazin-4-yl)methyl]phenyl}formamido)butanoate A solution of Reference Example 2-1-A (75.0 mg), D-valine methyl ester hydrochloride (68.2 mg), EDC-HCl (77.9 mg), HOBT (47.1 mg) and triethylamine (0.245 mL) in DMF (2 mL) was stirred at 40° C. overnight. To the reaction mixture were added a saturated aqueous solution of ammonium chloride, water and dichloromethane, and the mixture was stirred. The organic layer was separated, and then concentrated under reduced pressure. The residue was purified by column chromatography on silica gel (eluent: ethyl acetate/methanol=100/0-95/5) to give the title compound (59.3 mg).

Reference Example 8-1-B

(2R)-3-Methyl-2-({3-methyl-4-[(6-methyl-3-oxo-2,3-dihydropyridazin-4-yl)methyl]phenyl}formamido)butanoic acid To a solution of Reference Example 8-1-A (59.3 mg) in THF (2 mL), methanol (1 mL) and water (0.18 mL) was added an aqueous solution of sodium hydroxide (2 mol/L, 0.320 mL), and the mixture was stirred at 40° C. for 1.5 hours. The reaction mixture was allowed to cool to room temperature, and then to the reaction mixture was added hydrochloric acid (2 mol/L, 0.640 mL). The mixture was stirred for 10 minutes, and then the mixture was concentrated under reduced pressure to give the crude title compound (102 mg). MS (ESI_APCI, m/z): 358 (M+H)$^+$

Reference Example 8-2-A tert-Butyl (2R)-2-({3-methyl-4-[(6-methyl-3-oxo-2,3-dihydropyridazin-4-yl)methyl]phenyl}formamido)butanoate A solution of Reference Example 2-1-A (75.0 mg), (2R)-2-aminobutanoic acid tert-butyl hydrochloride (79.6 mg), EDC-HCl (77.9 mg), HOBT (47.1 mg) and triethylamine (0.245 mL) in DMF (2 mL) was stirred at room temperature overnight. To the reaction mixture were added a saturated aqueous solution of ammonium chloride, water and dichloromethane, and the mixture was stirred. The organic layer was separated, and then concentrated under reduced pressure. The residue was purified by column chromatography on silica gel (eluent: ethyl acetate/methanol=100/0-95/5) to give the title compound (79.3 mg).

Reference Example 8-2-B

(2R)-2-({3-Methyl-4-[(6-methyl-3-oxo-2,3-dihydropyridazin-4-yl)methyl]phenyl}formamido)butanoic acid To a solution of Reference Example 8-2-A (79.3 mg) in dichloromethane (2 mL) was added trifluoroacetic acid (1 mL), and the mixture was stirred at room temperature for 1 hour. The reaction mixture was concentrated under reduced pressure. To the residue was added toluene, and the mixture was concentrated under reduced pressure to give the crude title compound (83.6 mg). MS (ESI_APCI, m/z): 344 (M+H)$^+$

Reference Example 9-1-A

N-{2-[(2R,5 S)-2-Ethenyl-2-(methoxy methyl)-5-phenylpyrrolidin-1-yl]-2-oxoethyl}-3-methyl-4-[(6-methyl-3-oxo-2,3-dihydropyridazin-4-yl)methyl]benzamide A solution of Reference Example 5-1-G (40.0 mg), Reference Example 4-1-B (52.2 mg), T3P (50% in ethyl acetate, ca. 1.7 mol/L) (0.185 mL) and DIPEA (0.124 mL) in 1,2-dichloroethane (1 mL) was stirred at 130° C. under microwave irradiation for 1 hour. To the reaction mixture were added water and dichloromethane. The organic layer was separated. The organic layer was dried over anhydrous sodium sulfate, and concentrated under reduced pressure. The residue was purified by column chromatography on silica gel (eluent: ethyl acetate/methanol=100/0-90/10). To the purified compound was added diethyl ether (4 mL). The precipitated solid was collected by filtration to give the title compound (40.6 mg).

Reference Example 9-2-A

N-{2-[(2S,5R)-2-(3-Fluorophenyl)-5-[(1 S)-1-{[(S)-2-methylpropane-2-sulfinyl]amino}ethyl]pyrrolidin-1-yl]-2-oxoethyl}-3-methyl-4-[(6-methyl-3-oxo-2,3-dihydropyridazin-4-yl)methyl]benzamide A solution of Reference Example 5-2-E (57.7 mg), Reference Example 4-1-B (58.2 mg), T3P (50% in ethyl acetate, ca. 1.7 mol/L) (0.210 mL) and DIPEA (0.257 mL) in 1,2-dichloroethane (5 mL) was stirred at 130° C. under microwave irradiation for 30 minutes. To the reaction mixture were added water and dichloromethane. The organic layer was separated, and then concentrated under reduced pressure. The residue was purified by column chromatography on amino-silica gel (eluent: ethyl acetate/methanol=100/0-30/70) to give the title compound (26.7 mg). MS (ESI_APCI, m/z): 610 (M+H)$^+$

Reference Example 9-3-A

N-{2-[(2R,5 S)-2-[(Benzyloxy)methyl]-2-ethenyl-5-(3-fluorophenyl)pyrrolidin-1-yl]-2-oxoethyl}-3-methyl-4-[(6-methyl-3-oxo-2,3-dihydropyridazin-4-yl)methyl]benzamide A solution of Reference Example 5-3-F (35.2 mg), Reference Example 4-1-B (33.5 mg), T3P (50% in ethyl acetate, ca. 1.7 mol/L) (0.120 mL) and DIPEA (0.079 mL) in 1,2-dichloroethane (2 mL) was stirred under microwave irradiation at 110° C. for 30 minutes and at 140° C. for 1 hour. To the reaction mixture were added water and dichloromethane. The organic layer was separated. The organic layer was dried over anhydrous sodium sulfate, and concentrated under reduced pressure. The residue was purified by column chromatography on amino-silica gel (eluent: ethyl acetate/methanol=100/0-93/7), and then purified by preparative thin-layer chromatography (eluent: ethyl acetate/methanol=95/5) to give the title compound (16.4 mg).

Reference Example 9-4-A tert-Butyl N-[(1 S)-1-[(2R,5S)-5-(3-fluorophenyl)-1-[2-({3-methyl-4-[(6-methyl-3-oxo-2,3-dihydropyridazin-4-yl)methyl]phenyl}formamido)acetyl]pyrrolidin-2-yl]ethyl]-N-methylcarbamate A solution of Reference Example 5-4-D (49.0 mg), Reference Example 4-1-B (57.2 mg), T3P (50% in ethyl acetate, ca. 1.7 mol/L) (0.177 mL) and DIPEA (0.140 mL) in 1,2-dichloroethane (3 mL) was stirred at 60° C. overnight. To the reaction mixture were added water and dichloromethane. The organic layer was separated, and then concentrated under reduced pressure. The residue was purified by column chromatography on amino-silica gel (eluent: ethyl acetate/methanol=100/0-30/70) to give the title compound (22.0 mg).

Reference Example 9-4-B

N-{2-[(2S,5R)-2-(3-Fluorophenyl)-5-[(1 S)-1-(methylamino)ethyl]pyrrolidin-1-yl]-2-oxoethyl}-3-methyl-4-[(6-methyl-3-oxo-2,3-dihydropyridazin-4-yl)methyl]benzamide hydrochloride A mixture of Reference Example 9-4-A (20.0 mg), hydrogen chloride in 1,4-dioxane (4 mol/L, 0.5 mL) and methanol (2 mL) was stirred at room temperature for 1 hour. The reaction mixture was concentrated under reduced pressure to give the crude title compound (24.3 mg). MS (ESI_APCI, m/z): 520 (M+H)$^+$ Reference Example 9-5-A rac-N-{2-[(2S,3 S,5 S)-3-(Benzyloxy)-5-(3-fluorophenyl)-2-(propan-2-yl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Reference Example 9-4-A using Reference Example 5-5-G instead of Reference Example 5-4-D. MS (ESI_APCI, m/z): 611 (M+H)$^+$ Reference Example 9-6-A N-{2-[(2S,5 S)-2-Ethenyl-2-ethyl-5-(3-fluorophenyl)pyrrolidin-1-yl]-2-oxoethyl}-3-methyl-4-[(6-methyl-3-oxo-2,3-dihydropyridazin-4-yl)methyl]benzamide A solution of Reference Example 5-6-D (40.4 mg), Reference Example 4-1-B (48.9 mg), T3P (50% in ethyl acetate, ca. 1.7 mol/L) (0.174 mL) and DIPEA (0.116 mL) in 1,2-dichloroethane (1.5 mL) was stirred under microwave irradiation at 130° C. for 1 hour and at 150° C. for 1 hour. To the reaction mixture were added water and dichloromethane. The organic layer was separated. The organic layer was dried over anhydrous sodium sulfate, and concentrated under reduced pressure. The residue was purified by column chromatography on silica gel (eluent: ethyl acetate/methanol=100/0-92/8), and then purified by preparative thin-layer chromatography (eluent: dichloromethane/methanol=16/1) to give the title compound (8.0 mg).

Reference Example 9-7-A

N-{2-[(2S,5R)-2-(3-Fluorophenyl)-5-(3-hydroxy-2-methylbutan-2-yl)pyrrolidin-1-yl]-2-oxoethyl}-3-methyl-4-[(6-methyl-3-oxo-2,3-dihydropyridazin-4-yl)methyl]benzamide A solution of Reference Example 5-20-D (50.1 mg), Reference Example 4-1-B (69.3 mg), T3P (50% in ethyl acetate, ca. 1.7 mol/L) (0.235 mL) and DIPEA (0.105 mL) in 1,2-dichlorobenzene (1.5 mL) was stirred at 90° C. under microwave irradiation for 2 hours. To the reaction mixture was added water, and the mixture was extracted twice with dichloromethane. The combined organic layer was dried over anhydrous sodium sulfate, and concentrated under reduced pressure. The residue was purified by column chromatography on amino-silica gel (eluent: ethyl acetate/methanol=100/0-95/5) to give the title compound (11.8 mg). MS (ESI_APCI, m/z): 549 (M+H)$^+$ Reference Example 9-8-A rac-(2S,3R,5S)-5-(3-Fluorophenyl)-1-[2-({3-methyl-4-[(6-methyl-3-oxo-2,3-dihydropyridazin-4-yl)methyl]phenyl}formamido)acetyl]-2-(propan-2-yl)pyrrolidin-3-yl acetate The title compound was prepared in a similar manner to that described in Reference Example 9-7-A using Reference Example 5-23-B instead of Reference Example 5-20-D. MS (ESI_APCI, m/z): 563 (M+H)$^+$ Reference Example 9-9-A N-[(2R)-3-(Benzyloxy)-1-[(2S,5R)-2-(3-chlorophenyl)-5-(1-cyano-1-methylethyl)pyrrolidin-1-yl]-1-oxopropan-2-yl]-3-methyl-4-[(6-methyl-3-oxo-2,3-dihydropyridazin-4-yl)oxy]benzamide A solution of Reference Example 7-4-B (19.3 mg), Reference Example 2-3-B (24.3 mg), EDC-HCl (17.9 mg), HOBT (12.7 mg) and triethylamine (0.052 mL) in DMF (1 mL) was stirred at room temperature overnight. To the reaction mixture were added ethyl acetate and water. The organic layer was separated. The organic layer was dried over anhydrous sodium sulfate, and concentrated under reduced pressure. The residue was purified by column chromatography on amino-silica gel (eluent: ethyl acetate/methanol=100/0-90/10) to give the title compound (17.5 mg). MS (ESI_APCI, m/z): 666 (M–H)$^-$ Reference Example 9-10-A N-{2-[(2R,3R,5R)-3-(Benzyloxy)-5-(1-cyano-1-methylethyl)-2-(3-fluorophenyl)pyrrolidin-1-yl]-2-oxoethyl}-3-methyl-4-[(6-methyl-3-oxo-2,3-dihydropyridazin-4-yl)oxy]benzamide The title compound was prepared in a similar manner to that described in Reference Example 9-9-A using Reference Example 7-9-B instead of Reference Example 7-4-B. MS (ESI_APCI, m/z): 636 (M−H)⁻

Reference Example 9-11-A

N-[(2R)-1-[(2R,3R,5R)-3-(Benzyloxy)-5-(1-cyano-1-methylethyl)-2-(3-fluorophenyl)pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Reference Example 9-9-A using Reference Example 7-14-B instead of Reference Example 7-4-B. MS (ESI_APCI, m/z): 650 (M−H)⁻

Reference Example 9-12-A

N-[(2R)-1-[(2R,3S,5R)-3-Azido-5-(1-cyano-1-methylethyl)-2-(3-fluorophenyl)pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Reference Example 9-9-A using Reference Example 7-15-B instead of Reference Example 7-4-B. MS (ESI_APCI, m/z): 587 (M+H)⁺

Chemical structures of typical Reference Example are shown in the following tables.

TABLE 9

| Ref. No. | Str. |
|---|---|
| 5-1-G | |
| 5-2-E | |
| 5-3-F | |
| 5-4-D | |

TABLE 9-continued

| Ref. No. | Str. |
|---|---|
| 5-5-G | 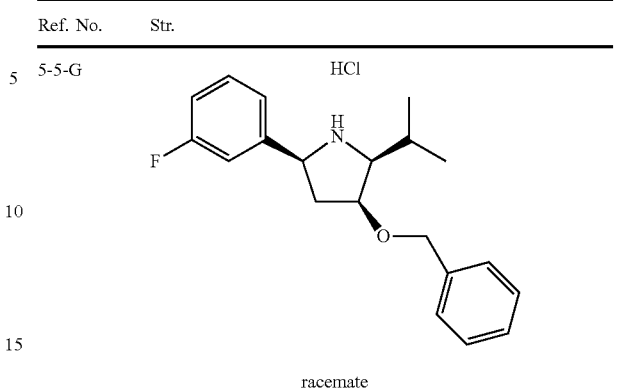 racemate |
| 5-6-D | 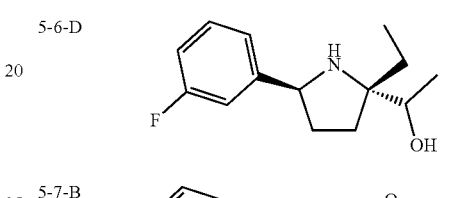 |
| 5-7-B | 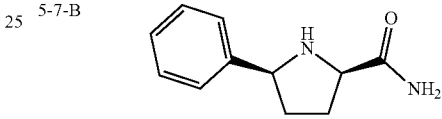 |
| 5-8-G | 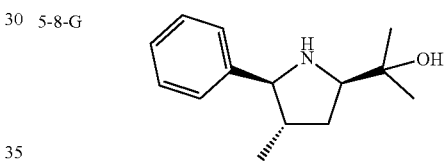 |
| 5-9-D | 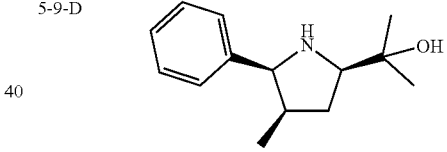 |
| 5-10-B | 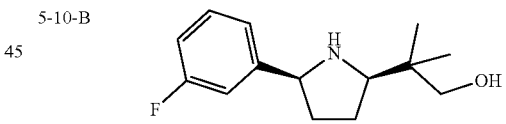 |
| 5-11-H | 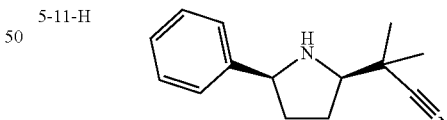 |
| 5-12-B | 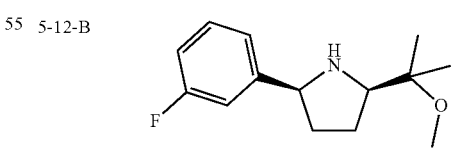 |
| 5-13-F | 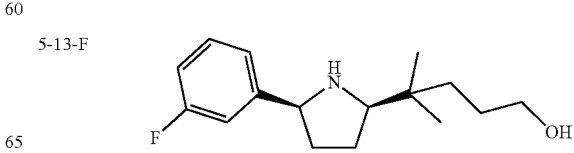 |

TABLE 9-continued
| Ref. No. | Str. |
|---|---|
| 5-14-G | 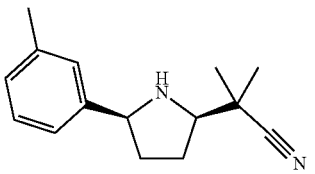 [SMILES: Cc1cccc([C@@H]2CC[C@H](C(C)(C)C#N)N2)c1] |
TABLE 10
| Ref. No. | Str. |
|---|---|
| 5-15-B | |
| 5-16-J | |
| 5-17-A | |
| 5-18-A | |
| 5-19-I | HCl |
| 5-20-D | |
| 5-21-I | |
| 5-22-B | racemate |
TABLE 10-continued
| Ref. No. | Str. |
|---|---|
| 5-23-B | racemate |
| 5-24-B | racemate |
| 5-25-C | racemate |
| 5-26-E | HCl |
| 5-27-B | |
| 5-28-B | |
TABLE 11
| Ref. No. | Str. |
|---|---|
| 5-29-B |  |

TABLE 11-continued
| Ref. No. | Str. |
|---|---|
| 5-30-B | 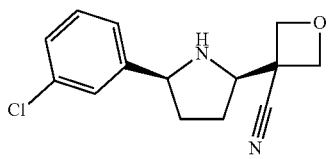 [SMILES: N#CC1([C@H]2CC[C@@H](c3cccc(Cl)c3)N2)COC1] |
| 5-31-G | 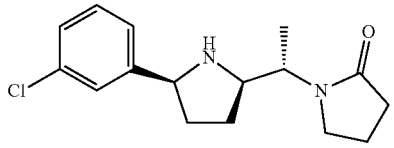 [SMILES: C[C@@H]([C@H]1CC[C@@H](c2cccc(Cl)c2)N1)N1CCCC1=O] |
| 5-32-B | 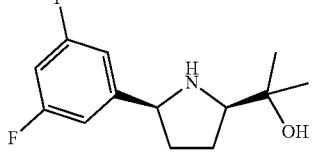 |
| 5-33-J | 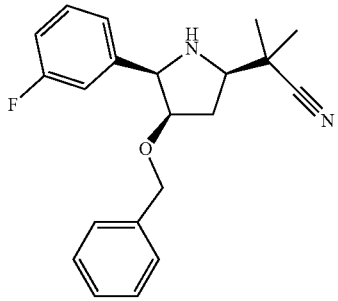 [SMILES: CC(C)(C#N)[C@H]1C[C@@H](OCc2ccccc2)[C@@H](c2cccc(F)c2)N1] |
| 5-34-H | 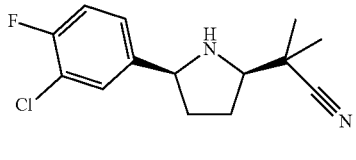 [SMILES: CC(C)(C#N)[C@H]1CC[C@@H](c2ccc(F)c(Cl)c2)N1] |
| 5-35-H | 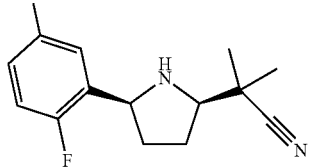 |
| 5-36-H | 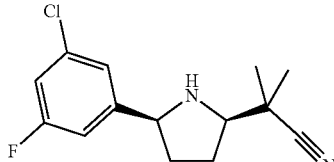 |
| 5-37-J | 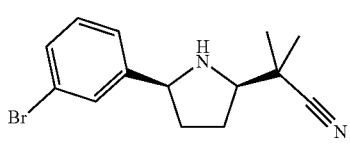 [SMILES: CC(C)(C#N)[C@H]1CC[C@@H](c2cccc(Br)c2)N1] |
TABLE 11-continued
| Ref. No. | Str. |
|---|---|
| 5-38-E | 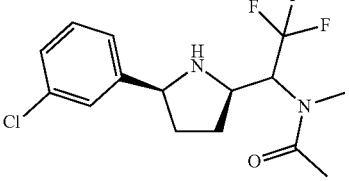 |
| 5-39-C | 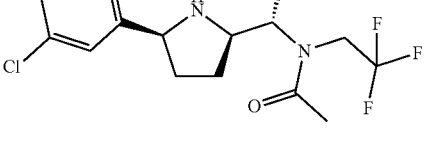 |
| 5-40-A | 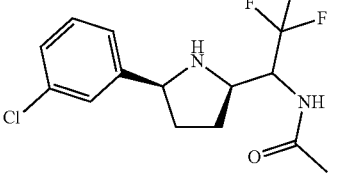 |
| 5-41-C | 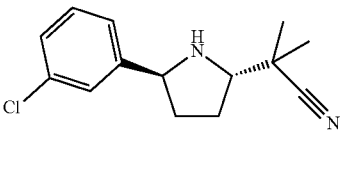 [SMILES: CC(C)(C#N)[C@@H]1CC[C@@H](c2cccc(Cl)c2)N1] |
| 6-1-E | 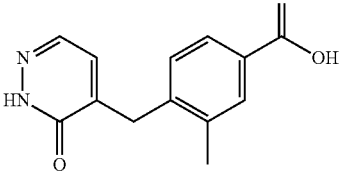 |
TABLE 12
| Ref. No. | Str. |
|---|---|
| 6-2-C | 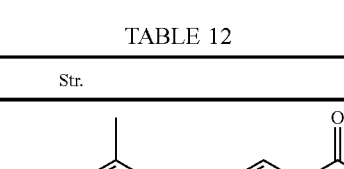 |
| 6-3-C | 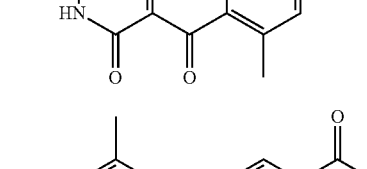 |

TABLE 12-continued
| Ref. No. | Str. |
|---|---|
| 6-4-B | 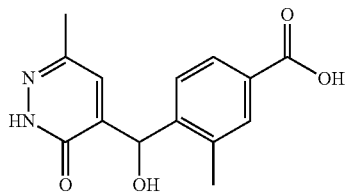 |
| 6-5-C | 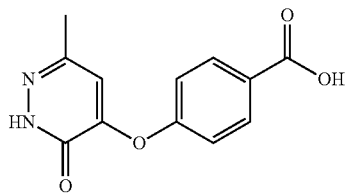 [SMILES: Cc1cc(Oc2ccc(C(=O)O)cc2)c(=O)[nH]n1] |
| 6-6-D | 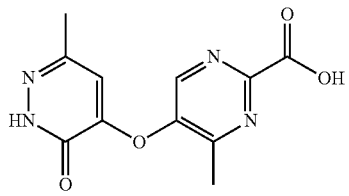 [SMILES: Cc1cc(Oc2cnc(C(=O)O)nc2C)c(=O)[nH]n1] |
| 6-7-C | 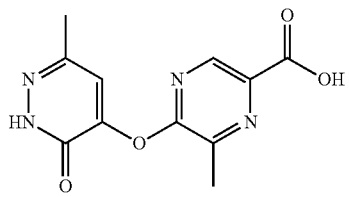 [SMILES: Cc1cc(Oc2ncc(C(=O)O)nc2C)c(=O)[nH]n1] |
| 6-8-E | 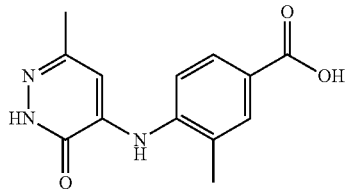 |
| 6-9-G | 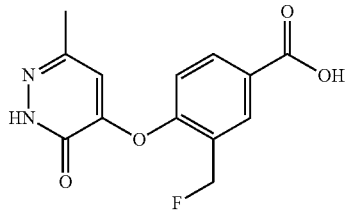 [SMILES: Cc1cc(Oc2ccc(C(=O)O)cc2CF)c(=O)[nH]n1] |
| 6-10-B | 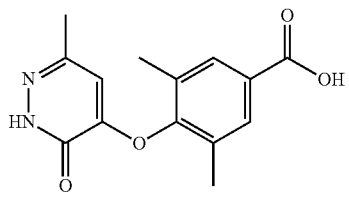 [SMILES: Cc1cc(Oc2c(C)cc(C(=O)O)cc2C)c(=O)[nH]n1] |
TABLE 12-continued
| Ref. No. | Str. |
|---|---|
| 6-11-C | 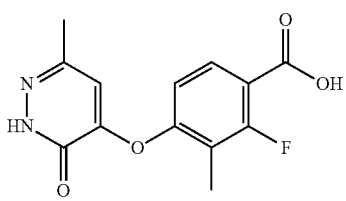 [SMILES: Cc1cc(Oc2ccc(C(=O)O)c(F)c2C)c(=O)[nH]n1] |
| 6-12-B | 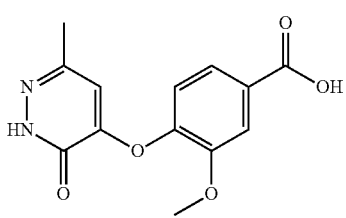 [SMILES: COc1cc(C(=O)O)ccc1Oc1cc(C)n[nH]c1=O] |
| 6-13-C | 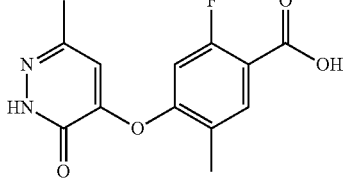 |
TABLE 13
| Ref. No. | Str. |
|---|---|
| 6-14-C | 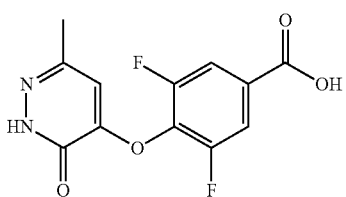 [SMILES: Cc1cc(Oc2c(F)cc(C(=O)O)cc2F)c(=O)[nH]n1] |
| 7-1-B | 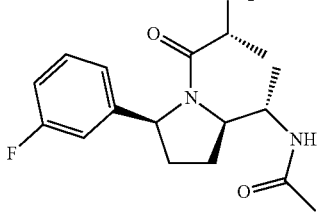 |
| 7-2-B | 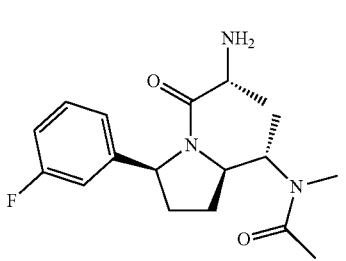 [SMILES: CC(=O)N(C)[C@@H](C)[C@H]1CC[C@@H](c2cccc(F)c2)N1C(=O)[C@@H](C)N] |

TABLE 13-continued
| Ref. No. | Str. |
|---|---|
| 7-3-B | 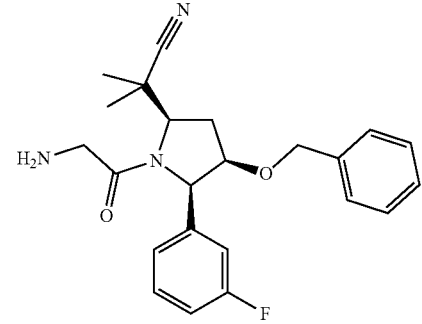 [SMILES: CC(C)(C#N)[C@H]1C[C@@H](OCc2ccccc2)[C@@H](c2cccc(F)c2)N1C(=O)CN] |
| 7-4-B | |
| 7-5-A | |
| 7-6-A | |
| 7-7-D | |
| 7-8-B | |
TABLE 13-continued
| Ref. No. | Str. |
|---|---|
| 7-9-B | 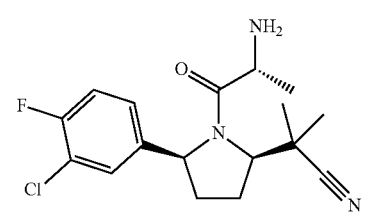 [SMILES: C[C@@H](N)C(=O)N1[C@H](c2ccc(F)c(Cl)c2)CC[C@@H]1C(C)(C)C#N] |
| 7-10-B | |
| 7-11-B | |
TABLE 14
| Ref. No. | Str. |
|---|---|
| 7-12-B | |
| 7-13-B | |

TABLE 14-continued
| Ref. No. | Str. |
|---|---|
| 7-14-B | 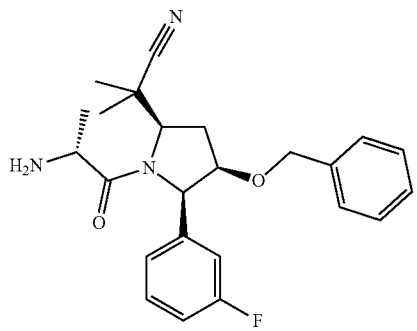 [SMILES: C[C@@H](N)C(=O)N1[C@H](c2cccc(F)c2)[C@H](OCc2ccccc2)C[C@@H]1C(C)(C)C#N] |
| 7-15-B | 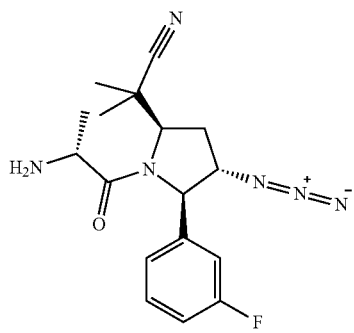 [SMILES: C[C@@H](N)C(=O)N1[C@H](c2cccc(F)c2)[C@@H](N=[N+]=[N-])C[C@@H]1C(C)(C)C#N] |
| 7-16-A | 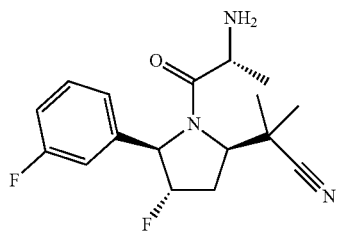 [SMILES: C[C@@H](N)C(=O)N1[C@H](c2cccc(F)c2)[C@@H](F)C[C@@H]1C(C)(C)C#N] |
| 7-17-B | 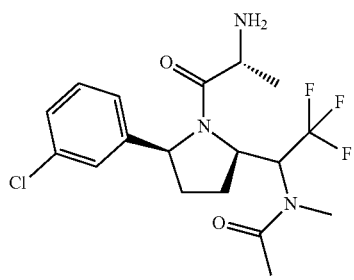 [SMILES: CC(=O)N(C)C([C@H]1CC[C@@H](c2cccc(Cl)c2)N1C(=O)[C@@H](C)N)C(F)(F)F] |
| 7-18-B | 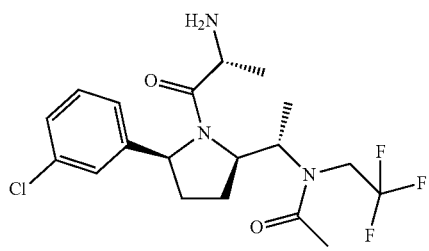 [SMILES: CC(=O)N(CC(F)(F)F)[C@@H](C)[C@H]1CC[C@@H](c2cccc(Cl)c2)N1C(=O)[C@@H](C)N] |
TABLE 14-continued
| Ref. No. | Str. |
|---|---|
| 7-19-B | 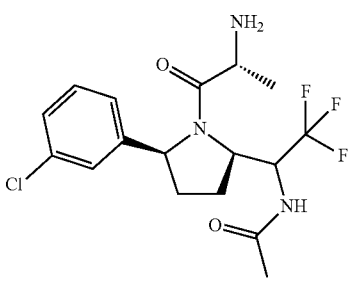 [SMILES: CC(=O)NC([C@H]1CC[C@@H](c2cccc(Cl)c2)N1C(=O)[C@@H](C)N)C(F)(F)F] |
| 7-20-B | 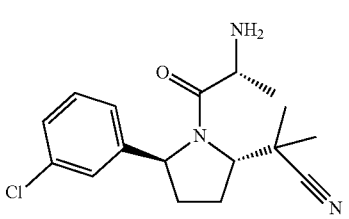 [SMILES: C[C@@H](N)C(=O)N1[C@H](C(C)(C)C#N)CC[C@H]1c1cccc(Cl)c1] |
| 7-21-B | 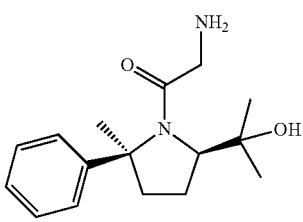 [SMILES: CC(C)(O)[C@H]1CC[C@@](C)(c2ccccc2)N1C(=O)CN] |
| 8-1-B | 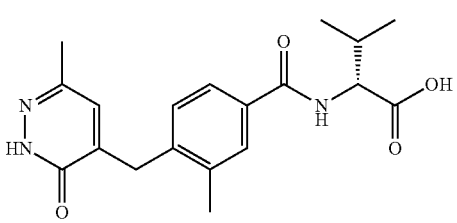 [SMILES: Cc1cc(Cc2ccc(C(=O)N[C@@H](C(=O)O)C(C)C)cc2C)c(=O)[nH]n1] |
| 8-2-B | 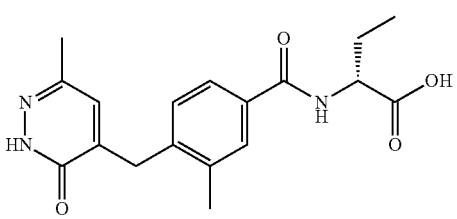 [SMILES: CC[C@@H](NC(=O)c1ccc(Cc2cc(C)n[nH]c2=O)c(C)c1)C(=O)O] |

TABLE 15
| Ref. No. | Str. |
| --- | --- |
| 9-1-A | 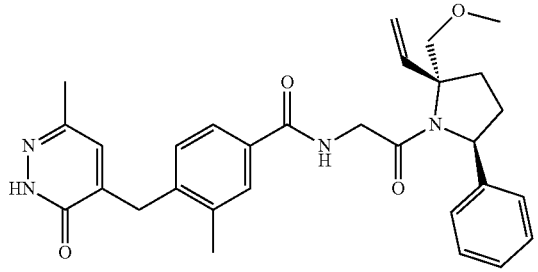 [SMILES: C=C[C@@]1(COC)CC[C@@H](c2ccccc2)N1C(=O)CNC(=O)c1ccc(Cc2cc(C)n[nH]c2=O)c(C)c1] |
| 9-2-A | 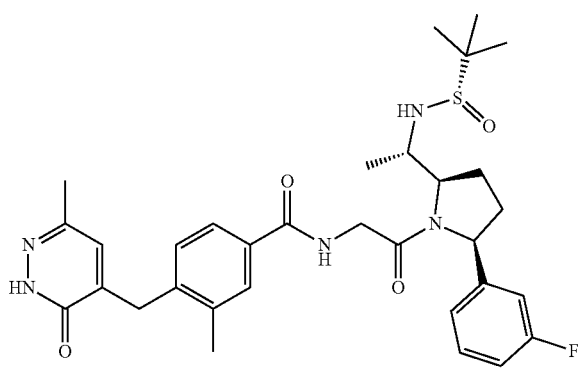 [SMILES: Cc1cc(Cc2ccc(C(=O)NCC(=O)N3[C@@H]([C@H](C)N[S@@](=O)C(C)(C)C)CC[C@H]3c3cccc(F)c3)cc2C)c(=O)[nH]n1] |
| 9-3-A | 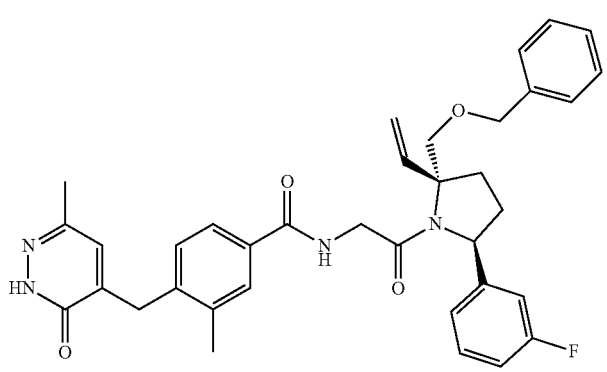 [SMILES: C=C[C@@]1(COCc2ccccc2)CC[C@@H](c2cccc(F)c2)N1C(=O)CNC(=O)c1ccc(Cc2cc(C)n[nH]c2=O)c(C)c1] |
| 9-4-B | 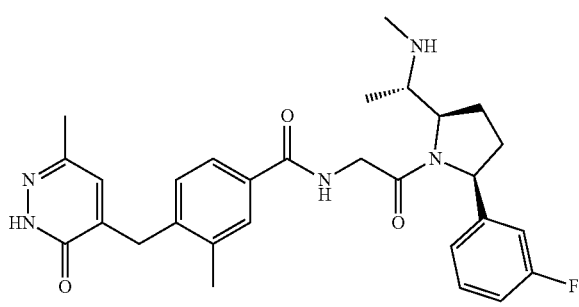 [SMILES: CN[C@@H](C)[C@H]1CC[C@@H](c2cccc(F)c2)N1C(=O)CNC(=O)c1ccc(Cc2cc(C)n[nH]c2=O)c(C)c1] |

TABLE 15-continued
Ref. No. Str.
9-5-A
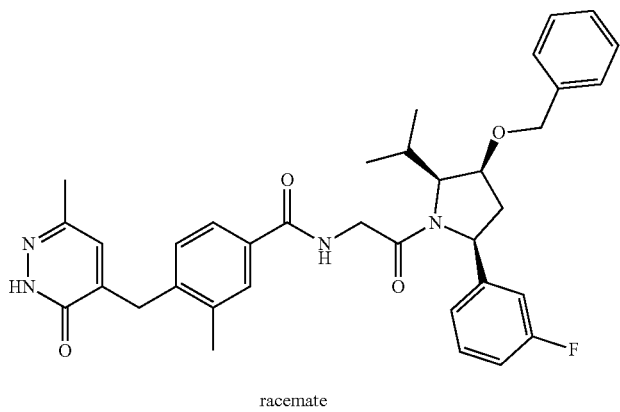 [SMILES: Cc1cc(Cc2ccc(C(=O)NCC(=O)N3[C@H](c4cccc(F)c4)C[C@H](OCc4ccccc4)[C@@H]3C(C)C)cc2C)c(=O)[nH]n1]
racemate
9-6-A
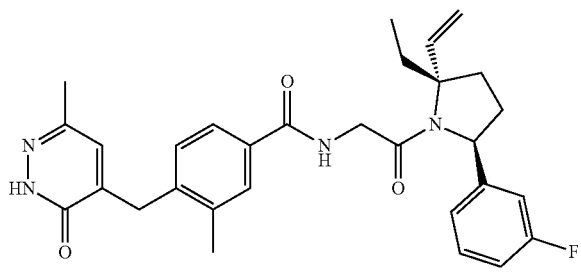 [SMILES: C=C[C@]1(CC)CC[C@@H](c2cccc(F)c2)N1C(=O)CNC(=O)c1ccc(Cc2cc(C)n[nH]c2=O)c(C)c1]
9-7-A
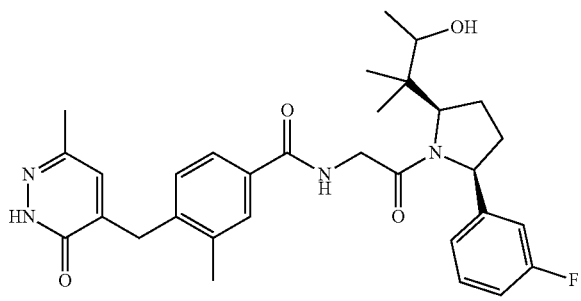 [SMILES: Cc1cc(Cc2ccc(C(=O)NCC(=O)N3[C@H](c4cccc(F)c4)CC[C@@H]3C(C)(C)C(C)O)cc2C)c(=O)[nH]n1]
9-8-A
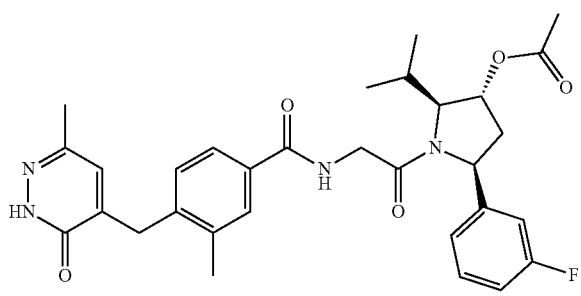
racemate TABLE 15-continued
| Ref. No. | Str. |
|---|---|
| 9-9-A | 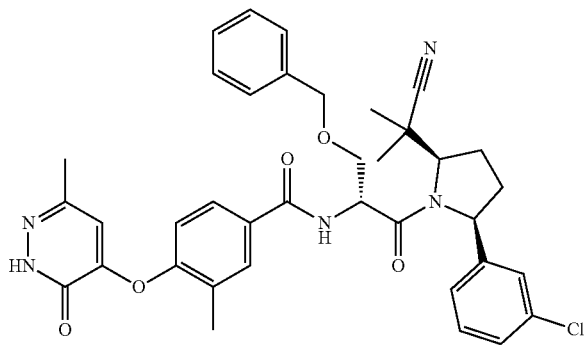 [SMILES: Cc1cc(Oc2ccc(C(=O)N[C@H](COCc3ccccc3)C(=O)N3[C@H](c4cccc(Cl)c4)CC[C@@H]3C(C)(C)C#N)cc2C)c(=O)[nH]n1] |
| 9-10-A | 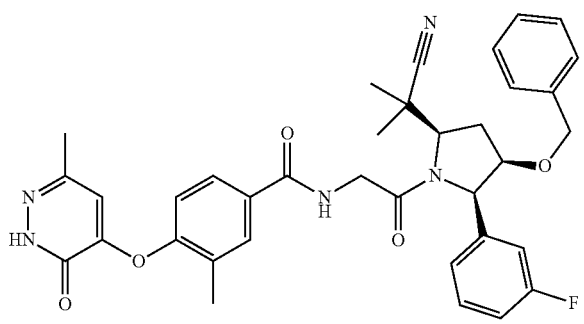 [SMILES: Cc1cc(Oc2ccc(C(=O)NCC(=O)N3[C@H](c4cccc(F)c4)[C@H](OCc4ccccc4)C[C@@H]3C(C)(C)C#N)cc2C)c(=O)[nH]n1] |
TABLE 16
| Ref. No. | Str. |
|---|---|
| 9-11-A | 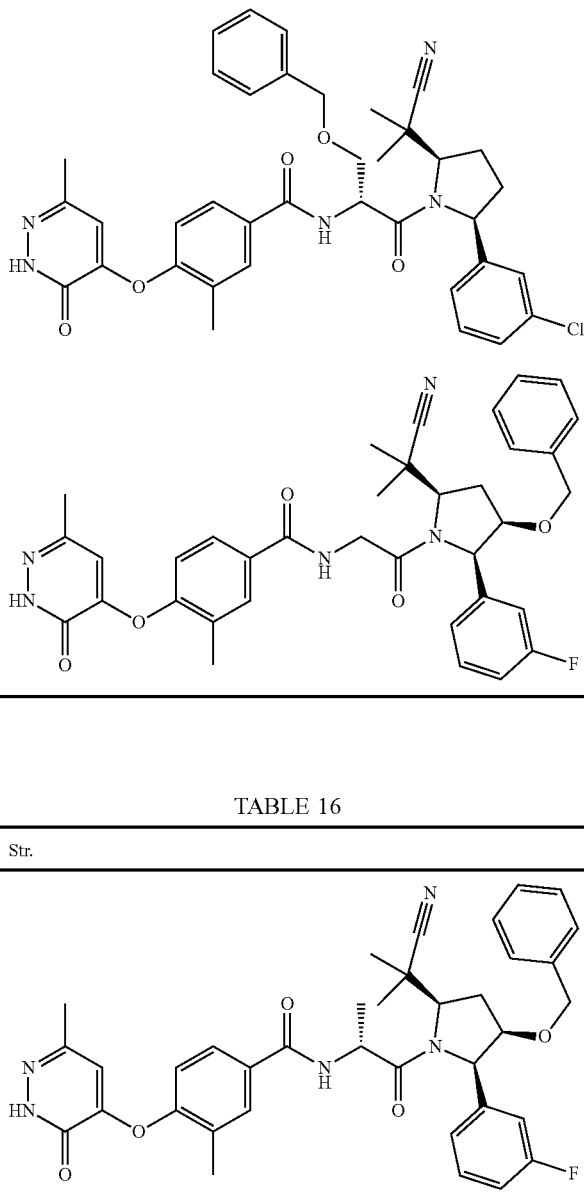 |
| 9-12-A | 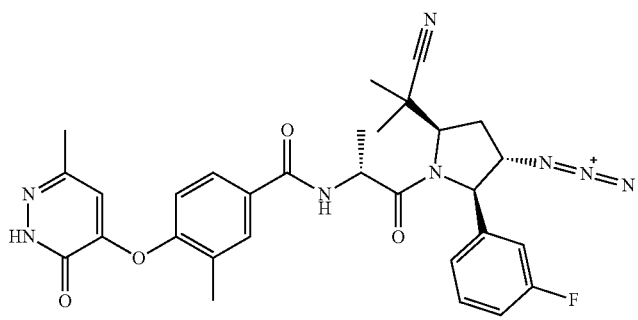 [SMILES: Cc1cc(Oc2ccc(C(=O)N[C@H](C)C(=O)N3[C@H](c4cccc(F)c4)[C@@H](N=[N+]=N)C[C@@H]3C(C)(C)C#N)cc2C)c(=O)[nH]n1] |

Example 3A-1

N-{2-[(2S,3S,5R)-5-(2-Hydroxypropan-2-yl)-3-methyl-2-phenylpyrrolidin-1-yl]-2-oxoethyl}-3-methyl-4-[(6-methyl-3-oxo-2,3-dihydropyridazin-4-yl)methyl]benzamide A solution of Reference Example 5-8-G (65.8 mg), Reference Example 4-1-B (122 mg), T3P (50% in ethyl acetate, ca. 1.7 mol/L) (0.352 mL) and DIPEA (0.157 mL) in 1,2-dichloroethane (3 mL) was stirred at 110° C. under microwave irradiation for 1 hour. To the reaction mixture was added water, and the mixture was extracted with dichloromethane. The organic layer was concentrated under reduced pressure. The residue was purified by column chromatography on amino-silica gel (eluent: ethyl acetate/methanol=100/0-95/5) to give the title compound (115 mg).

Example 3A-2

N-{2-[(2S,3R,5R)-5-(2-Hydroxypropan-2-yl)-3-methyl-2-phenylpyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 3A-1 using Reference Example 5-9-D instead of Reference Example 5-8-G.

Example 3A-3

N-{2-[(2R,5S)-2-Cyano-5-phenylpyrrolidin-1-yl]-2-oxoethyl}-3-methyl-4-[(6-methyl-3-oxo-2,3-dihydropyridazin-4-yl)methyl]benzamide A solution of Reference Example 5-7-B (30.0 mg), Reference Example 4-1-B (45.9 mg), T3P (50% in ethyl acetate, ca. 1.7 mol/L) (0.275 mL) and DIPEA (0.161 mL) in 1,2-dichloroethane (1.5 mL) was stirred at 110° C. under microwave irradiation for 30 minutes. To the reaction mixture was added water, and the mixture was extracted with dichloromethane. The organic layer was dried over anhydrous sodium sulfate, and concentrated under reduced pressure. The residue was purified by column chromatography on silica gel (eluent: dichloromethane/methanol=100/0-92/8) to give the title compound (31.3 mg).

Example 3A-4

N-{2-[(2S,5R)-2-(3-Fluorophenyl)-5-(1-hydroxy-2-methylpropan-2-yl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 3A-1 using Reference Example 5-10-B instead of Reference Example 5-8-G.

Example 3A-5

N-{2-[(2R,5S)-2-(1-Cyano-1-methylethyl)-5-phenylpyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 1A-2 using Reference Example 5-11-H instead of Reference Example 1-3-C.

Example 3A-6

N-{2-[(2S,5R)-2-(3-Fluorophenyl)-5-(2-methoxypropan-2-yl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 3A-1 using Reference Example 5-12-B instead of Reference Example 5-8-G.

Example 3A-7

N-{2-[(2S,5R)-2-(3-Fluorophenyl)-5-(5-hydroxy-2-methylpentan-2-yl)pyrrolidin-1-yl]-2-oxoethyl}-3-methyl-4-[(6-methyl-3-oxo-2,3-dihydropyridazin-4-yl)methyl]benzamide A solution of Reference Example 5-13-F (35.6 mg), Reference Example 4-1-B (55.0 mg), T3P (50% in ethyl acetate, ca. 1.7 mol/L) (0.158 mL) and DIPEA (0.070 mL) in 1,2-dichloroethane (1.5 mL) was stirred at 110° C. under microwave irradiation for 1 hour. To the reaction mixture was added water, and the mixture was extracted with dichloromethane. The organic layer was dried over anhydrous sodium sulfate, and concentrated under reduced pressure. The residue was purified by column chromatography on amino-silica gel (eluent: ethyl acetate/methanol=100/0-90/10) to give 2-({3-methyl-4-[(6-methyl-3-oxo-2,3-dihydropyridazin-4-yl)methyl]phenyl}formamido)acetic acid 4-[(2R,5S)-5-(3-fluorophenyl)-1-[2-({3-methyl-4-[(6-methyl-3-oxo-2,3-dihydropyridazin-4-yl)methyl]phenyl}formamido)acetyl]pyrrolidin-2-yl]-4-methylpentyl (17.5 mg). To a solution of the obtained compound (15.7 mg) in THF (0.5 mL) and methanol (0.5 mL) was added an aqueous solution of sodium hydroxide (2 mol/L, 0.030 mL), and the mixture was stirred at 50° C. for 2.5 hours. The reaction mixture was allowed to cool to room temperature, and then to the reaction mixture was added hydrochloric acid (2 mol/L, 0.060 mL). To the mixture were added ethyl acetate, water and a saturated aqueous solution of sodium bicarbonate. The organic layer was separated. The aqueous layer was extracted with ethyl acetate, and then the extract was combined with the above organic layer. The organic layer was washed with brine, dried over anhydrous magnesium sulfate, and concentrated under reduced pressure. The residue was purified by column chromatography on amino-silica gel (eluent: ethyl acetate/methanol=100/0-85/15) to give the title compound (5.6 mg).

Example 3A-8

N-{2-[(2R,5S)-2-(1-Cyano-1-methylethyl)-5-(3-methylphenyl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 1A-2 using Reference Example 5-14-G instead of Reference Example 1-3-C.

Example 3A-9

N-{2-[(2S,5R)-2-(3-Fluorophenyl)-5-(2-methylbut-3-en-2-yl)pyrrolidin-1-yl]-2-oxoethyl}-3-methyl-4-[(6-methyl-3-oxo-2,3-dihydropyridazin-4-yl)methyl]benzamide A solution of Reference Example 5-15-B (33.0 mg), Reference Example 4-1-B (62.2 mg), T3P (50% in ethyl acetate, ca. 1.7 mol/L) (0.166 mL) and DIPEA (0.074 mL) in 1,2-dichlorobenzene (1 mL) was stirred at 130° C. under microwave irradiation for 3 hours. To the reaction mixture was added water, and the mixture was extracted twice with dichloromethane. The combined organic layer was dried over anhydrous sodium sulfate, and concentrated under reduced pressure. The residue was purified by column chromatography on amino-silica gel (eluent: ethyl acetate/methanol=100/0-95/5) to give the title compound (43.8 mg).

Example 3A-10

N-{2-[(2S,5R)-2-(3-Fluorophenyl)-5-[2-(1,3-oxazol-2-yl)propan-2-yl]pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 3A-9 using Reference Example 5-16-J instead of Reference Example 5-15-B.

Example 3A-11

N-{2-[(2S,5R)-2-(3-Fluorophenyl)-5-(1-hydroxycyclopentyl)pyrrolidin-1-yl]-2-oxoethyl}-3-methyl-4-[(6-methyl-3-oxo-2,3-dihydropyridazin-4-yl)methyl]benzamide A solution of Reference Example 5-17-A (20.0 mg), Reference Example 4-1-B (35.4 mg), T3P (50% in ethyl acetate, ca. 1.7 mol/L) (0.094 mL) and DIPEA (0.042 mL) in 1,2-dichlorobenzene (1 mL) was stirred at 90° C. under microwave irradiation for 1 hour. To the reaction mixture were added a saturated aqueous solution of ammonium chloride and water, and the mixture was extracted with dichloromethane. The organic layer was dried over anhydrous sodium sulfate, and concentrated under reduced pressure. The residue was purified by column chromatography on silica gel (eluent: ethyl acetate/methanol=100/0-94/6) to give the title compound (33.7 mg).

Example 3A-12

N-{2-[(2R,5 S)-2-(1-Cyano-1-methylethyl)-5-cyclohexylpyrrolidin-1-yl]-2-oxoethyl}-3-methyl-4-[(6-methyl-3-oxo-2,3-dihydropyridazin-4-yl)methyl]benzamide A solution of Reference Example 5-19-I (51.7 mg), Reference Example 4-1-B (88.6 mg), T3P (50% in ethyl acetate, ca. 1.7 mol/L) (0.235 mL) and DIPEA (0.140 mL) in 1,2-dichloroethane (1.5 mL) was stirred at 130° C. under microwave irradiation for 1.5 hours. To the reaction mixture were added a saturated aqueous solution of ammonium chloride, water and dichloromethane. The organic layer was separated. The organic layer was dried over anhydrous sodium sulfate, and concentrated under reduced pressure. The residue was purified by column chromatography on silica gel (eluent: ethyl acetate/methanol=100/0-94/6), and then purified by ODS column chromatography (eluent: water/acetonitrile=70/30-10/90) to give the title compound (26.2 mg).

Example 3A-13

N-{2-[(2S,5R)-2-(3-Fluorophenyl)-5-(trifluoromethyl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 3A-9 using Reference Example 5-21-I instead of Reference Example 5-15-B.

Example 3A-14 rac-N-{2-[(2S,5S)-3,3-Difluoro-5-(3-fluorophenyl)-2-(propan-2-yl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 3A-9 using Reference Example 5-22-B instead of Reference Example 5-15-B.

Example 3A-15 rac-N-{2-[(2S,3 S,5S)-5-(3-Fluorophenyl)-3-methoxy-2-(propan-2-yl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 3A-9 using Reference Example 5-24-B instead of Reference Example 5-15-B.

Example 3A-16 rac-N-{2-[(2S,3R,5S)-5-(3-Fluorophenyl)-3-methoxy-2-(propan-2-yl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 3A-9 using Reference Example 5-25-C instead of Reference Example 5-15-B.

Example 3A-17

N-{2-[(2S,5R)-2-(3-Fluorophenyl)-5-(2,2,2-trifluoroethyl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 3A-12 using Reference Example 5-26-E instead of Reference Example 5-19-I.

Example 3B-1

N-[(2R)-1-[(2S,5R)-2-(3-Fluorophenyl)-5-(2-hydroxypropan-2-yl)pyrrolidin-1-yl]-1-oxobutan-2-yl]-3-methyl-4-[(6-methyl-3-oxo-2,3-dihydropyridazin-4-yl)methyl]benzamide A solution of Reference Example 1-1-D (61.9 mg), Reference Example 8-2-B (68.1 mg), T3P (50% in ethyl acetate, ca. 1.7 mol/L) (0.235 mL) and DIPEA (0.345 mL) in 1,2-dichloroethane (1.5 mL) was stirred at 90° C. under microwave irradiation for 1 hour. To the reaction mixture were added a saturated aqueous solution of ammonium chloride, water and dichloromethane, and the mixture was stirred. The organic layer was separated, and then concentrated under reduced pressure. The residue was purified by column chromatography on silica gel (eluent: ethyl acetate/methanol=100/0-90/10), and then purified by ODS column chromatography (eluent: water/acetonitrile=70/30-20/80) to give the title compound (36.0 mg).

Example 3C-1

N-[(2R)-1-[(2S,5R)-2-(3-Fluorophenyl)-5-(2-hydroxypropan-2-yl)pyrrolidin-1-yl]-3-methyl-1-oxobutan-2-yl]-3-methyl-4-[(6-methyl-3-oxo-2,3-dihydropyridazin-4-yl)methyl]benzamide

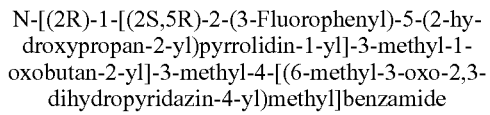

The title compound was prepared in a similar manner to that described in Example 3B-1 using Reference Example 8-1-B instead of Reference Example 8-2-B.

Example 4A-1

N-{2-[(2S,5R)-5-(2-Hydroxypropan-2-yl)-2-methyl-2-phenylpyrrolidin-1-yl]-2-oxoethyl}-3-methyl-4-[(6-methyl-3-oxo-2,3-dihydropyridazin-4-yl)methyl]benzamide

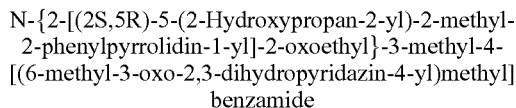

A solution of Reference Example 7-21-B (68.1 mg), Reference Example 2-1-A (88.9 mg), EDC-HCl (75.5 mg), HOBT (49.9 mg) and triethylamine (0.172 mL) in DMF (2 mL) was stirred at 40° C. for 1.5 hours. To the reaction mixture were added a saturated aqueous solution of ammonium chloride and water, and the mixture was extracted with dichloromethane. The organic layer was dried over anhydrous sodium sulfate, and concentrated under reduced pressure. The residue was purified by column chromatography on silica gel (eluent: ethyl acetate/methanol=100/0-94/6), and then purified by ODS column chromatography (eluent: water/acetonitrile=70/30-10/90) to give the title compound (43.0 mg).

Example 4A-2

N-{2-[(2S,5R)-2-(3-Fluorophenyl)-5-(2-hydroxypropan-2-yl)pyrrolidin-1-yl]-2-oxoethyl}-3-methyl-4-(6-methyl-3-oxo-2,3-dihydropyridazine-4-carbonyl)benzamide

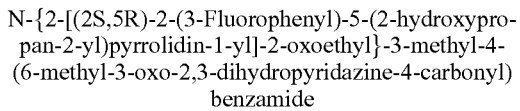

The title compound was prepared in a similar manner to that described in Example 2B-3 using Reference Example 6-2-C and Reference Example 3-1-B instead of Reference Example 2-1-A and Reference Example 3-2-B.

Example 4A-3

N-{2-[(2S,5R)-2-(3-Fluorophenyl)-5-(2-hydroxypropan-2-yl)pyrrolidin-1-yl]-2-oxoethyl}-3-methyl-4-[1-(6-methyl-3-oxo-2,3-dihydropyridazin-4-yl)ethyl]benzamide

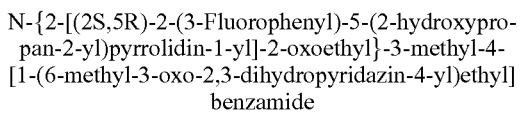

The title compound was prepared in a similar manner to that described in Example 2B-3 using Reference Example 6-3-C and Reference Example 3-1-B instead of Reference Example 2-1-A and Reference Example 3-2-B.

Example 4A-4

N-{2-[(2S,5R)-2-(3-Fluorophenyl)-5-(2-hydroxypropan-2-yl)pyrrolidin-1-yl]-2-oxoethyl}-4-[hydroxy(6-methyl-3-oxo-2,3-dihydropyridazin-4-yl)methyl]-3-methylbenzamide

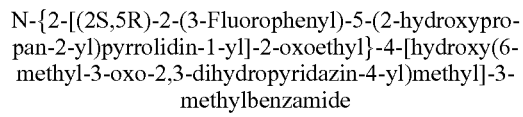

The title compound was prepared in a similar manner to that described in Example 2B-3 using Reference Example 6-4-B and Reference Example 3-1-B instead of Reference Example 2-1-A and Reference Example 3-2-B.

Example 4A-5

N-{2-[(2R,5 S)-2-(1-Cyano-1-methylethyl)-5-(3-fluorophenyl)pyrrolidin-1-yl]-2-oxoethyl}-3-fluoro-4-[(6-methyl-3-oxo-2,3-dihydropyridazin-4-yl)oxy]benzamide

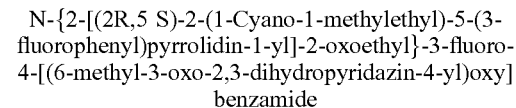

The title compound was prepared in a similar manner to that described in Example 2A-2 using Reference Example 2-2-C instead of Reference Example 2-3-B.

Example 4A-6

N-{2-[(2S,5R)-2-(3-Chlorophenyl)-5-(1-cyano-1-methylethyl)pyrrolidin-1-yl]-2-oxoethyl}-3-fluoro-4-[(6-methyl-3-oxo-2,3-dihydropyridazin-4-yl)oxy]benzamide

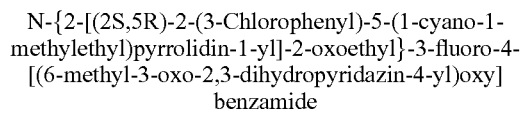

The title compound was prepared in a similar manner to that described in Example 2A-2 using Reference Example 2-2-C and Reference Example 3-9-B instead of Reference Example 2-3-B and Reference Example 3-5-B.

Example 4A-7

N-{2-[(2S,5R)-2-(3-Chlorophenyl)-5-(1-cyano-1-methylethyl)pyrrolidin-1-yl]-2-oxoethyl}-3-methyl-4-[(6-methyl-3-oxo-2,3-dihydropyridazin-4-yl)oxy]benzamide

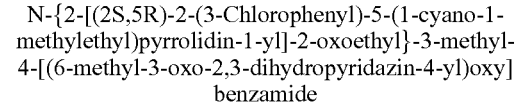

The title compound was prepared in a similar manner to that described in Example 2A-2 using Reference Example 3-9-B instead of Reference Example 3-5-B.

Example 4B-1

N-[(2R)-1-[(2R,5S)-2-(1-Cyano-1-methylethyl)-5-(3-fluorophenyl)pyrrolidin-1-yl]-1-oxopropan-2-yl]-3-methyl-4-[(6-methyl-3-oxo-2,3-dihydropyridazin-4-yl)methyl]benzamide

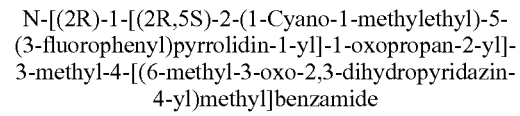

The title compound was prepared in a similar manner to that described in Example 2B-3 using Reference Example 3-3-B instead of Reference Example 3-2-B.

HRMS (ESI) calcd for $C_{31}H_{35}FN_5O_3(M+H)^+$: 544.2718, Found: 544.2719.

Example 4B-2

N-[(2R)-1-[(2R,5S)-2-(1-Cyano-1-methylethyl)-5-(3-fluorophenyl)pyrrolidin-1-yl]-1-oxopropan-2-yl]-3-methyl-4-[(3-oxo-2,3-dihydropyridazin-4-yl)methyl]benzamide

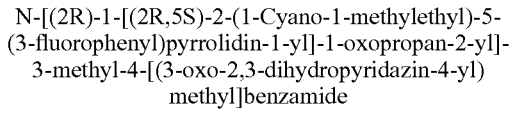

The title compound was prepared in a similar manner to that described in Example 2B-3 using Reference Example 6-1-E and Reference Example 3-3-B instead of Reference Example 2-1-A and Reference Example 3-2-B.

HRMS (ESI) calcd for $C_{30}H_{33}FN_5O_3(M+H)^+$: 530.2562, Found: 530.2565.

Example 4B-3

N-[(2R)-1-[(2S,5R)-2-(3-Fluorophenyl)-5-[(1S)-1-(N-methylacetamido)ethyl]pyrrolidin-1-yl]-1-oxopropan-2-yl]-3-methyl-4-[(6-methyl-3-oxo-2,3-dihydropyridazin-4-yl)methyl]benzamide

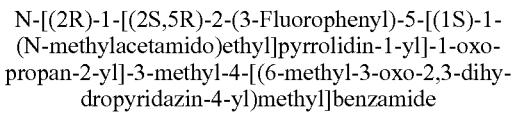

To a suspension of Reference Example 2-1-A (61.7 mg), Reference Example 7-2-B (40.0 mg), HOBT (24.1 mg) and triethylamine (0.050 mL) in acetonitrile (1.5 mL) was added EDC-HCl (45.7 mg), and the mixture was stirred at room temperature for 6 hours. To the reaction mixture were added water and a saturated aqueous solution of sodium bicarbonate. The mixture was extracted twice with ethyl acetate. The combined organic layer was washed with brine, dried over anhydrous magnesium sulfate, and concentrated under reduced pressure. The residue was purified by column chromatography on silica gel (eluent: ethyl acetate/methanol=100/0-80/20) to give the title compound (53.6 mg).

HRMS (ESI) calcd for $C_{32}H_{38}FN_5NaO_4$ $(M+Na)^+$: 598.2800, Found: 598.2800.

Example 4B-4

N-[(2R)-1-[(2S,5R)-2-(3-Chlorophenyl)-5-(1-cyano-1-methylethyl)pyrrolidin-1-yl]-1-oxopropan-2-yl]-4-methyl-5-[(6-methyl-3-oxo-2,3-dihydropyridazin-4-yl)oxy]pyrimidine-2-carboxamide

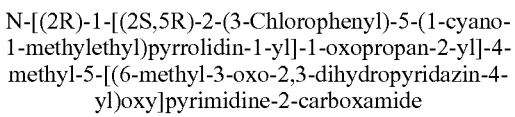

The title compound was prepared in a similar manner to that described in Example 2B-2 using Reference Example 6-6-D instead of Reference Example 2-5-D.

HRMS (ESI) calcd for $C_{28}H_{31}ClN_7O_4(M+H)^+$: 564.2121, Found: 564.2120.

Example 4B-5

N-[(2R)-1-[(2S,5R)-2-(3-Chlorophenyl)-5-(1-cyanocyclobutyl)pyrrolidin-1-yl]-1-oxopropan-2-yl]-3-methyl-4-[(6-methyl-3-oxo-2,3-dihydropyridazin-4-yl)oxy]benzamide

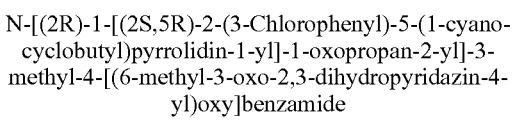

The title compound was prepared in a similar manner to that described in Example 2B-8 using Reference Example 2-3-B and Reference Example 3-11-A instead of Reference Example 2-6-D and Reference Example 3-4-C.

HRMS (ESI) calcd for $C_{31}H_{33}ClN_5O_4(M+H)^+$: 574.2216, Found: 574.2215.

Example 4B-6

N-[(2R)-1-[(2S,5R)-2-(3-Chlorophenyl)-5-(3-cyanooxetan-3-yl)pyrrolidin-1-yl]-1-oxopropan-2-yl]-3-methyl-4-[(6-methyl-3-oxo-2,3-dihydropyridazin-4-yl)oxy]benzamide

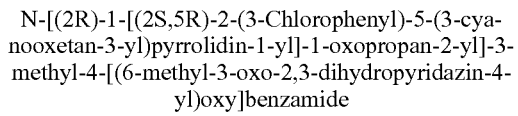

The title compound was prepared in a similar manner to that described in Example 2B-8 using Reference Example 2-3-B and Reference Example 7-5-A instead of Reference Example 2-6-D and Reference Example 3-4-C.

HRMS (ESI) calcd for $C_{30}H_{31}ClN_5O_5(M+H)^+$: 576.2008, Found: 576.2007.

Example 4B-7

N-[(2R)-1-[(2S,5R)-2-(3-Chlorophenyl)-5-[(1 S)-1-(2-oxopyrrolidin-1-yl)ethyl]pyrrolidin-1-yl]-1-oxopropan-2-yl]-3-methyl-4-[(6-methyl-3-oxo-2,3-dihydropyridazin-4-yl)oxy]benzamide

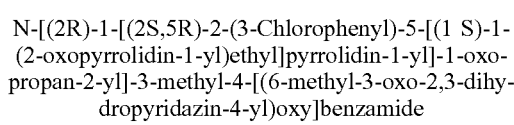

To a mixture of Reference Example 2-3-B (19.5 mg), Reference Example 7-6-A (18.2 mg), HOBT (8.1 mg), triethylamine (0.064 mL) and DMF (2 mL) was added EDC-HCl (14.4 mg). The mixture was stirred at room temperature for 2 hours, stirred at 40° C. for 3 hours and stirred at 50° C. overnight. To the reaction mixture was added water, and the mixture was extracted with ethyl acetate. The organic layer was washed with water, and then concentrated under reduced pressure. The residue was purified by column chromatography on amino-silica gel (eluent: ethyl acetate/methanol=100/0-30/70) to give the title compound (9.5 mg).

HRMS (ESI) calcd for $C_{32}H_{36}ClN_5NaO_5$ $(M+Na)^+$: 628.2297, Found: 628.2297.

Example 4B-8

N-[(2R)-1-[(2S,5R)-2-(3-Chlorophenyl)-5-[(1 S)-1-(2-oxopyrrolidin-1-yl)ethyl]pyrrolidin-1-yl]-1-oxopropan-2-yl]-6-methyl-5-[(6-methyl-3-oxo-2,3-dihydropyridazin-4-yl)oxy]pyridine-2-carboxamide

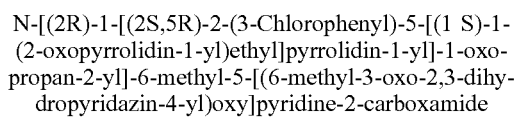

The title compound was prepared in a similar manner to that described in Example 4B-7 using Reference Example 2-5-D instead of Reference Example 2-3-B.

HRMS (ESI) calcd for $C_{31}H_{36}ClN_6O_5(M+H)^+$: 607.2430, Found: 607.2431.

Example 4B-9

N-[(2R)-1-[(2S,5R)-2-(3-Chlorophenyl)-5-(1-cyano-1-methylethyl)pyrrolidin-1-yl]-1-oxopropan-2-yl]-3-methyl-4-[(6-methyl-3-oxo-2,3-dihydropyridazin-4-yl)amino]benzamide

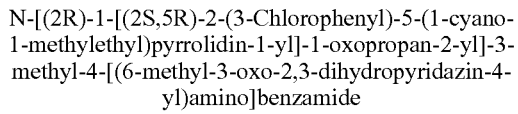

The title compound was prepared in a similar manner to that described in Example 2B-2 using Reference Example 6-8-E instead of Reference Example 2-5-D.

HRMS (ESI) calcd for $C_{30}H_{34}ClN_6O_3(M+H)^+$: 561.2375, Found: 561.2372.

Example 4B-10

N-[(2R)-1-[(2R,5S)-2-(1-Cyano-1-methylethyl)-5-(3-fluorophenyl)pyrrolidin-1-yl]-1-oxopropan-2-yl]-6-methyl-5-[(6-methyl-3-oxo-2,3-dihydropyridazin-4-yl)oxy]pyridine-2-carboxamide The title compound was prepared in a similar manner to that described in Example 2B-2 using Reference Example 3-3-B instead of Reference Example 3-4-C.
HRMS (ESI) calcd for $C_{29}H_{32}FN_6O_4(M+H)^+$: 547.2464, Found: 547.2462.

Example 4B-11

N-[(2R)-1-[(2S,5R)-2-(3-Chlorophenyl)-5-(3-cyanooxetan-3-yl)pyrrolidin-1-yl]-1-oxopropan-2-yl]-3-fluoro-5-methyl-4-[(6-methyl-3-oxo-2,3-dihydropyridazin-4-yl)oxy]benzamide The title compound was prepared in a similar manner to that described in Example 2B-8 using Reference Example 2-8-D and Reference Example 7-5-A instead of Reference Example 2-6-D and Reference Example 3-4-C.
HRMS (ESI) calcd for $C_{30}H_{30}ClFN_5O_5(M+H)^+$: 594.1914, Found: 594.1912.

Example 4B-12

N-[(2R)-1-[(2S,5R)-2-(3-Chlorophenyl)-5-(2-hydroxypropan-2-yl)pyrrolidin-1-yl]-1-oxopropan-2-yl]-3-(fluoromethyl)-4-[(6-methyl-3-oxo-2,3-dihydropyridazin-4-yl)oxy]benzamide The title compound was prepared in a similar manner to that described in Example 2B-19 using Reference Example 6-9-G and Reference Example 3-7-A instead of Reference Example 2-8-D and Reference Example 3-4-C.
HRMS (ESI) calcd for $C_{29}H_{33}ClFN_4O_5(M+H)^+$: 571.2118, Found: 571.2119,

Example 4B-13

N-[(2R)-1-[(2S,5R)-2-(3-Chlorophenyl)-5-(2-hydroxypropan-2-yl)pyrrolidin-1-yl]-1-oxopropan-2-yl]-3,5-dimethyl-4-[(6-methyl-3-oxo-2,3-dihydropyridazin-4-yl)oxy]benzamide The title compound was prepared in a similar manner to that described in Example 2B-2 using Reference Example 6-10-B and Reference Example 3-7-A instead of Reference Example 2-5-D and Reference Example 3-4-C.
HRMS (ESI) calcd for $C_{30}H_{36}ClN_4O_5(M+H)^+$: 567.2369, Found: 567.2366.

Example 4B-14

N-[(2R)-1-[(2S,5R)-2-(3-Chlorophenyl)-5-(1-cyano-1-methylethyl)pyrrolidin-1-yl]-1-oxopropan-2-yl]-2-fluoro-3-methyl-4-[(6-methyl-3-oxo-2,3-dihydropyridazin-4-yl)oxy]benzamide The title compound was prepared in a similar manner to that described in Example 2B-8 using Reference Example 6-11-C instead of Reference Example 2-6-D.
HRMS (ESI) calcd for $C_{30}H_{32}ClFN_5O_4(M+H)^+$: 580.2121, Found: 580.2122.

Example 4B-15

N-[(2R)-1-[(2S,5R)-2-(3-Chlorophenyl)-5-(1-cyano-1-methylethyl)pyrrolidin-1-yl]-1-oxopropan-2-yl]-3-methoxy-4-[(6-methyl-3-oxo-2,3-dihydropyridazin-4-yl)oxy]benzamide The title compound was prepared in a similar manner to that described in Example 2B-8 using Reference Example 6-12-B instead of Reference Example 2-6-D.
HRMS (ESI) calcd for $C_{30}H_{33}ClN_5O_5(M+H)^+$: 578.2165, Found: 578.2164.

Example 4B-16

N-[(2R)-1-[(2S,5R)-2-(3-Chlorophenyl)-5-(1-cyano-1-methylethyl)pyrrolidin-1-yl]-1-oxopropan-2-yl]-2-fluoro-5-methyl-4-[(6-methyl-3-oxo-2,3-dihydropyridazin-4-yl)oxy]benzamide The title compound was prepared in a similar manner to that described in Example 2B-8 using Reference Example 6-13-C instead of Reference Example 2-6-D.
HRMS (ESI) calcd for $C_{30}H_{32}ClFN_5O_4(M+H)^+$: 580.2121, Found: 580.2121.

Example 4B-17

N-[(2R)-1-[(2S,5R)-2-(3-Chlorophenyl)-5-(1-cyano-1-methylethyl)pyrrolidin-1-yl]-1-oxopropan-2-yl]-3,5-difluoro-4-[(6-methyl-3-oxo-2,3-dihydropyridazin-4-yl)oxy]benzamide The title compound was prepared in a similar manner to that described in Example 2B-8 using Reference Example 6-14-C instead of Reference Example 2-6-D.
HRMS (ESI) calcd for $C_{29}H_{29}ClF_2N_5O_4$ $(M+H)^+$: 584.1871, Found: 584.1871.

Example 4B-18

N-[(2R)-1-[(2S,5R)-2-(3-Fluorophenyl)-5-(2-hydroxypropan-2-yl)pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Example 2B-8 using Reference Example 2-3-B and Reference Example 3-2-B instead of Reference Example 2-6-D and Reference Example 3-4-C.
HRMS (ESI) calcd for $C_{29}H_{34}FN_4O_5(M+H)^+$: 537.2508, Found: 537.2507.

Example 4B-19

N-[(2R)-1-[(2S,5R)-2-(3-Chloro-4-fluorophenyl)-5-(1-cyano-1-methylethyl)pyrrolidin-1-yl]-1-oxopropan-2-yl]-6-methyl-5-[(6-methyl-3-oxo-2,3-dihydropyridazin-4-yl)oxy]pyridine-2-carboxamide To a solution of Reference Example 2-5-D (23.2 mg), Reference Example 7-10-B (25.0 mg), HOBT (13.0 mg), triethylamine (0.052 mL) in acetonitrile (2 mL) was added EDC·HCl (18.4 mg), and the mixture was stirred at room temperature for 6 hours. To the reaction mixture was added water, and the mixture was extracted twice with dichloromethane. The combined organic layer was dried over anhydrous magnesium sulfate, and concentrated under reduced pressure. The residue was purified by column chromatography on silica gel (eluent: ethyl acetate/methanol=95/5-90/10) to give the title compound (17.7 mg).

HRMS (ESI) calcd for $C_{29}H_{31}ClFN_6O_4(M+H)^+$: 581.2074, Found: 581.2071.

Example 4B-20

N-[(2R)-1-[(2S,5R)-2-(3-Chloro-4-fluorophenyl)-5-(1-cyano-1-methylethyl)pyrrolidin-1-yl]-1-oxopropan-2-yl]-3-fluoro-5-methyl-4-[(6-methyl-3-oxo-2,3-dihydropyridazin-4-yl)oxy]benzamide The title compound was prepared in a similar manner to that described in Example 4B-19 using Reference Example 2-8-D instead of Reference Example 2-5-D.

HRMS (ESI) calcd for $C_{30}H_{31}ClF_2N_5O_4$ $(M+H)^+$: 598.2027, Found: 598.2028.

Example 4B-21

N-[(2R)-1-[(2S,5R)-2-(5-Chloro-2-fluorophenyl)-5-(1-cyano-1-methylethyl)pyrrolidin-1-yl]-1-oxopropan-2-yl]-6-methyl-5-[(6-methyl-3-oxo-2,3-dihydropyridazin-4-yl)oxy]pyridine-2-carboxamide The title compound was prepared in a similar manner to that described in Example 4B-7 using Reference Example 2-5-D and Reference Example 7-11-B instead of Reference Example 2-3-B and Reference Example 7-6-A.

HRMS (ESI) calcd for $C_{29}H_{31}ClFN_6O_4(M+H)^+$: 581.2074, Found: 581.2072.

Example 4B-22

N-[(2R)-1-[(2S,5R)-2-(5-Chloro-2-fluorophenyl)-5-(1-cyano-1-methylethyl)pyrrolidin-1-yl]-1-oxopropan-2-yl]-3-fluoro-5-methyl-4-[(6-methyl-3-oxo-2,3-dihydropyridazin-4-yl)oxy]benzamide The title compound was prepared in a similar manner to that described in Example 4B-7 using Reference Example 2-8-D and Reference Example 7-11-B instead of Reference Example 2-3-B and Reference Example 7-6-A.

HRMS (ESI) calcd for $C_{30}H_{31}ClF_2N_5O_4$ $(M+H)^+$: 598.2027, Found: 598.2028.

Example 4B-23

N-[(2R)-1-[(2S,5R)-2-(5-Chloro-2-fluorophenyl)-5-(1-cyano-1-methylethyl)pyrrolidin-1-yl]-1-oxopropan-2-yl]-3,5-difluoro-4-[(6-methyl-3-oxo-2,3-dihydropyridazin-4-yl)oxy]benzamide The title compound was prepared in a similar manner to that described in Example 4B-7 using Reference Example 6-14-C and Reference Example 7-11-B instead of Reference Example 2-3-B and Reference Example 7-6-A.

HRMS (ESI) calcd for $C_{29}H_{28}ClF_3N_5O_4$ $(M+H)^+$: 602.1776, Found: 602.1777.

Example 4B-24

N-[(2R)-1-[(2S,5R)-2-(3-Chloro-5-fluorophenyl)-5-(1-cyano-1-methylethyl)pyrrolidin-1-yl]-1-oxopropan-2-yl]-3-methyl-4-[(6-methyl-3-oxo-2,3-dihydropyridazin-4-yl)oxy]benzamide To a solution of Reference Example 7-12-B (23.2 mg) in DMF (1 mL) were successively added Reference Example 2-3-B (19.7 mg), HOBT (12.1 mg) and triethylamine (0.014 mL) at room temperature. To the mixture was added EDC-HCl (17.1 mg). The reaction mixture was stirred at room temperature for 4 hours, and then to the reaction mixture were added water and ethyl acetate. The mixture was stirred for a while. The organic layer was separated. The organic layer was washed with water thrice, dried over anhydrous sodium sulfate, and concentrated under reduced pressure. The residue was purified by column chromatography on silica gel (eluent: ethyl acetate/methanol=100/0-80/20) to give the title compound (29.2 mg).

HRMS (ESI) calcd for $C_{30}H_{32}ClFN_5O_4(M+H)^+$: 580.2121, Found: 580.2122.

Example 4B-25

N-[(2R)-1-[(2S,5R)-2-(3-Chloro-5-fluorophenyl)-5-(1-cyano-1-methylethyl)pyrrolidin-1-yl]-1-oxopropan-2-yl]-6-methyl-5-[(6-methyl-3-oxo-2,3-dihydropyridazin-4-yl)oxy]pyridine-2-carboxamide The title compound was prepared in a similar manner to that described in Example 4B-24 using Reference Example 2-5-D instead of Reference Example 2-3-B.

HRMS (ESI) calcd for $C_{29}H_{31}ClFN_6O_4(M+H)^+$: 581.2074, Found: 581.2071.

Example 4B-26

N-[(2R)-1-[(2S,5R)-2-(3-Chloro-5-fluorophenyl)-5-(1-cyano-1-methylethyl)pyrrolidin-1-yl]-1-oxopropan-2-yl]-3-fluoro-5-methyl-4-[(6-methyl-3-oxo-2,3-dihydropyridazin-4-yl)oxy]benzamide The title compound was prepared in a similar manner to that described in Example 4B-24 using Reference Example 2-8-D instead of Reference Example 2-3-B.

HRMS (ESI) calcd for $C_{30}H_{31}ClF_2N_5O_4$ $(M+H)^+$: 598.2027, Found: 598.2026.

Example 4B-27

N-[(2R)-1-[(2S,5R)-2-(3-Chloro-5-fluorophenyl)-5-(1-cyano-1-methylethyl)pyrrolidin-1-yl]-1-oxopropan-2-yl]-3,5-difluoro-4-[(6-methyl-3-oxo-2,3-dihydropyridazin-4-yl)oxy]benzamide The title compound was prepared in a similar manner to that described in Example 4B-24 using Reference Example 6-14-C instead of Reference Example 2-3-B.

HRMS (ESI) calcd for $C_{29}H_{28}ClF_3N_5O_4$ (M+H)$^+$: 602.1776, Found: 602.1774.

Example 4B-28

N-[(2R)-1-[(2S,5R)-2-(3-Chloro-4-fluorophenyl)-5-(1-cyano-1-methylethyl)pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Example 4B-19 using Reference Example 2-3-B instead of Reference Example 2-5-D.
HRMS (ESI) calcd for $C_{30}H_{32}ClFN_5O_4$(M+H)$^+$: 580.2121, Found: 580.2121.

Example 4B-29

N-[(2R)-1-[(2S,5R)-2-(3-Chloro-4-fluorophenyl)-5-(1-cyano-1-methylethyl)pyrrolidin-1-yl]-1-oxopropan-2-yl]-3,5-difluoro-4-[(6-methyl-3-oxo-2,3-dihydropyridazin-4-yl)oxy]benzamide The title compound was prepared in a similar manner to that described in Example 4B-19 using Reference Example 6-14-C instead of Reference Example 2-5-D.
HRMS (ESI) calcd for $C_{29}H_{28}ClF_3N_5O_4$ (M+H)$^+$: 602.1776, Found: 602.1775.

Example 4B-30

N-[(2R)-1-[(2S,5R)-2-(3-Bromophenyl)-5-(1-cyano-1-methylethyl)pyrrolidin-1-yl]-1-oxopropan-2-yl]-3-fluoro-5-methyl-4-[(6-methyl-3-oxo-2,3-dihydropyridazin-4-yl)oxy]benzamide The title compound was prepared in a similar manner to that described in Example 2B-8 using Reference Example 2-8-D and Reference Example 7-13-B instead of Reference Example 2-6-D and Reference Example 3-4-C.
HRMS (ESI) calcd for $C_{30}H_{32}BrFN_5O_4$ (M+H)$^+$: 626.1601, Found: 626.1601.

Example 4B-31

N-[(2R)-1-[(2S,5R)-2-(3-Chlorophenyl)-5-[2,2,2-trifluoro-1-(N-methylacetamido)ethyl]pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Example 2B-8 using Reference Example 2-3-B and Reference Example 7-17-B instead of Reference Example 2-6-D and Reference Example 3-4-C.
HRMS (ESI) calcd for $C_{31}H_{34}ClF_3N_5O_5$ (M+H)$^+$: 648.2195, Found: 648.2194.

Example 4B-32

N-[(2R)-1-[(2S,5R)-2-(3-Chlorophenyl)-5-[2,2,2-trifluoro-1-(N-methylacetamido)ethyl]pyrrolidin-1-yl]-1-oxopropan-2-yl]-6-methyl-5-[(6-methyl-3-oxo-2,3-dihydropyridazin-4-yl)oxy]pyridine-2-carboxamide The title compound was prepared in a similar manner to that described in Example 2B-8 using Reference Example 2-5-D and Reference Example 7-17-B instead of Reference Example 2-6-D and Reference Example 3-4-C.
HRMS (ESI) calcd for $C_{30}H_{33}ClF_3N_6O_5$ (M+H)$^+$: 649.2148, Found: 649.2146.

Example 4B-33

N-[(2R)-1-[(2S,5R)-2-(3-Chlorophenyl)-5-[(1 S)-1-[N-(2,2,2-trifluoroethyl)acetamido]ethyl]pyrrolidin-1-yl]-1-oxopropan-2-yl]-6-methyl-5-[(6-methyl-3-oxo-2,3-dihydropyridazin-4-yl)oxy]pyridine-2-carboxamide The title compound was prepared in a similar manner to that described in Example 2B-8 using Reference Example 2-5-D and Reference Example 7-18-B instead of Reference Example 2-6-D and Reference Example 3-4-C.
HRMS (ESI) calcd for $C_{31}H_{35}ClF_3N_6O_5$ (M+H)$^+$: 663.2304, Found: 663.2301.

Example 4B-34

N-[(2R)-1-[(2R,5S)-2-[(1 S)-1-Acetamidoethyl]-5-(3-fluorophenyl)pyrrolidin-1-yl]-1-oxopropan-2-yl]-3-methyl-4-[(6-methyl-3-oxo-2,3-dihydropyridazin-4-yl)methyl]benzamide The title compound was prepared in a similar manner to that described in Example 4B-3 using Reference Example 7-1-B instead of Reference Example 7-2-B.

Example 4B-35

N-[(2R)-1-[(2R,5S)-2-(1-Cyano-1-methylethyl)-5-(3-fluorophenyl)pyrrolidin-1-yl]-1-oxopropan-2-yl]-4-[(6-methyl-3-oxo-2,3-dihydropyridazin-4-yl)oxy]benzamide The title compound was prepared in a similar manner to that described in Example 2B-3 using Reference Example 6-5-C and Reference Example 3-3-B instead of Reference Example 2-1-A and Reference Example 3-2-B.

Example 4B-36

N-[(2R)-1-[(2R,5 S)-2-(1,1-Difluoroethyl)-5-(3-fluorophenyl)pyrrolidin-1-yl]-1-oxopropan-2-yl]-3-fluoro-4-[(6-methyl-3-oxo-2,3-dihydropyridazin-4-yl)oxy]benzamide The title compound was prepared in a similar manner to that described in Example 2B-2 using Reference Example 2-2-C and Reference Example 7-3-B instead of Reference Example 2-5-D and Reference Example 3-4-C.

Example 4B-37

N-[(2R)-1-[(2R,5 S)-2-(1,1-Difluoroethyl)-5-(3-fluorophenyl)pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Example 2B-2 using Reference Example 2-3-B and Reference Example 7-3-B instead of Reference Example 2-5-D and Reference Example 3-4-C.

Example 4B-38

N-[(2R)-1-[(2S,5R)-2-(3-Chlorophenyl)-5-(1-cyano-1-methylethyl)pyrrolidin-1-yl]-1-oxopropan-2-yl]-6-methyl-5-[(6-methyl-3-oxo-2,3-dihydropyridazin-4-yl)oxy]pyrazine-2-carboxamide The title compound was prepared in a similar manner to that described in Example 2B-8 using Reference Example 6-7-C instead of Reference Example 2-6-D.

Example 4B-39

N-[(2R)-1-[(2S,5R)-2-(3,5-Difluorophenyl)-5-(2-hydroxypropan-2-yl)pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Example 2B-8 using Reference Example 2-3-B and Reference Example 7-8-B instead of Reference Example 2-6-D and Reference Example 3-4-C.

Example 4B-40

N-[(2R)-1-[(2R,3S,5R)-5-(1-Cyano-1-methylethyl)-3-fluoro-2-(3-fluorophenyl)pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Example 2B-19 using Reference Example 2-3-B and Reference Example 7-16-A instead of Reference Example 2-8-D and Reference Example 3-4-C.

Example 4B-41

N-[(2R)-1-[(2S,5R)-2-(3-Chlorophenyl)-5-[(1 S)-1-[N-(2,2,2-trifluoroethyl)acetamido]ethyl]pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Example 2B-8 using Reference Example 2-3-B and Reference Example 7-18-B instead of Reference Example 2-6-D and Reference Example 3-4-C.

Example 4B-42

N-[(2R)-1-[(2S,5R)-2-(3-Chlorophenyl)-5-(1-acetamido-2,2,2-trifluoroethyl)pyrrolidin-1-yl]-1-oxopropan-2-yl]-6-methyl-5-[(6-methyl-3-oxo-2,3-dihydropyridazin-4-yl)oxy]pyridine-2-carboxamide The title compound was prepared in a similar manner to that described in Example 2B-1 using Reference Example 2-5-D and Reference Example 7-19-B instead of Reference Example 2-3-B and Reference Example 3-4-C.

Example 4B-43

N-[(2R)-1-[(2S,5S)-2-(3-Chlorophenyl)-5-(1-cyano-1-methylethyl)pyrrolidin-1-yl]-1-oxopropan-2-yl]-3-methyl-4-[(6-methyl-3-oxo-2,3-dihydropyridazin-4-yl)oxy]benzamide A mixture of Reference Example 2-3-B (6.3 mg), Reference Example 7-20-B (7.0 mg), EDC-HCl (5.0 mg), HOBT monohydrate (3.7 mg) and DMF (1 mL) was stirred at 50° C. for 2 hours. To the reaction mixture was added water, and the mixture was extracted with ethyl acetate. The organic layer was washed with water, and then concentrated under reduced pressure. The residue was purified by column chromatography on amino-silica gel (eluent: ethyl acetate/methanol=100/0-30/70) to give the title compound (11.3 mg).

Example 4C-1

N-[(2S)-1-[(2S,5R)-2-(3-Chlorophenyl)-5-(1-cyano-1-methylethyl)pyrrolidin-1-yl]-3-fluoro-1-oxopropan-2-yl]-6-methyl-5-[(6-methyl-3-oxo-2,3-dihydropyridazin-4-yl)oxy]pyridine-2-carboxamide The title compound was prepared in a similar manner to that described in Example 2B-8 using Reference Example 2-5-D and Reference Example 7-7-D instead of Reference Example 2-6-D and Reference Example 3-4-C.

Example 5A-1

N-{2-[(2R,5 S)-2-[(1 S)-1-Aminoethyl]-5-(3-fluorophenyl)pyrrolidin-1-yl]-2-oxoethyl}-3-methyl-4-[(6-methyl-3-oxo-2,3-dihydropyridazin-4-yl)methyl]benzamide hydrochloride A mixture of Reference Example 9-2-A (25.0 mg), hydrogen chloride in 1,4-dioxane (4 mol/L, 0.030 mL) and methanol (1 mL) was stirred at room temperature for 1 hour. The reaction mixture was concentrated under reduced pressure to give the title compound (25.1 mg).

Example 5A-2

N-{2-[(2R,5 S)-2-[(1 S)-1-(Dimethylamino)ethyl]-5-(3-fluorophenyl)pyrrolidin-1-yl]-2-oxoethyl}-3-methyl-4-[(6-methyl-3-oxo-2,3-dihydropyridazin-4-yl)methyl]benzamide To a mixture of Example 5A-1 (14.5 mg), formalin (37%, 0.012 mL), triethylamine (0.004 mL), acetic acid (0.009 mL) and THF (2 mL) was added sodium triacetoxyborohydride (22.7 mg). The reaction mixture was stirred at room temperature for 30 minutes, and then to the reaction mixture was added an aqueous solution of sodium bicarbonate. The mixture was stirred for 10 minutes, and then to the mixture was added dichloromethane. The organic layer was separated, and then concentrated under reduced pressure. The residue was purified by column chromatography on amino-silica gel (eluent: ethyl acetate/methanol=100/0-70/30) to give the title compound (6.9 mg).

Example 5A-3

N-{2-[(2R,5 S)-2-[(1 S)-1-Acetamidoethyl]-5-(3-fluorophenyl)pyrrolidin-1-yl]-2-oxoethyl}-3-methyl-4-[(6-methyl-3-oxo-2,3-dihydropyridazin-4-yl)methyl]benzamide To a mixture of Reference Example 5A-1 (14.5 mg), triethylamine (0.013 mL) and THF (2 mL) was added acetyl chloride (0.006 mL) under ice-cooling. The reaction mixture was stirred at room temperature for 30 minutes, and then to the reaction mixture were added an aqueous solution of sodium bicarbonate and ethyl acetate. The organic layer was separated, and then concentrated under reduced pressure. The residue was purified by column chromatography on amino-silica gel (eluent: ethyl acetate/methanol=100/0-30/70) to give the title compound (8.3 mg).

Example 5A-4

N-{2-[(2S,5R)-2-(3-Fluorophenyl)-5-[(1 S)-1-(phenylformamido)ethyl]pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 5A-3 using benzoyl chloride instead of acetyl chloride.

Example 5A-5

N-{2-[(2S,5R)-2-(3-Fluorophenyl)-5-[(1S)-1-(N-methylacetamido)ethyl]pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 5A-3 using Reference Example 9-4-B instead of Example 5A-1.

Example 5A-6

N-{2-[(2S,5R)-2-(3-Fluorophenyl)-5-(2-methanesulfonylpropan-2-yl)pyrrolidin-1-yl]-2-oxoethyl}-3-methyl-4-[(6-methyl-3-oxo-2,3-dihydropyridazin-4-yl)methyl]benzamide To a solution of Example 1A-3 (9.7 mg) in dichloromethane (0.6 mL) was added 3-chloroperoxybenzoic acid (ca. 70%, 11.0 mg) under ice-cooling, and the mixture was stirred at the same temperature for 1 hour. To the reaction mixture were added a saturated aqueous solution of sodium bicarbonate and water, and the mixture was extracted with dichloromethane. The organic layer was concentrated under reduced pressure. The residue was purified by column chromatography on amino-silica gel (eluent: ethyl acetate/methanol=100/0-95/5) to give the title compound (6.1 mg).

Example 5A-7

N-{2-[(2S,5R)-2-(3-Fluorophenyl)-5-(2-methylbutan-2-yl)pyrrolidin-1-yl]-2-oxoethyl}-3-methyl-4-[(6-methyl-3-oxo-2,3-dihydropyridazin-4-yl)methyl]benzamide To a solution of Example 3A-9 (33.0 mg) in THF (0.6 mL) and methanol (0.6 mL) was added platinum on carbon (5%, 7.0 mg) under ice-cooling. The mixture was stirred under a hydrogen atmosphere at room temperature for 1.5 hours. The reaction mixture was filtered through Celite. The filtrate was concentrated under reduced pressure to give the title compound (28.1 mg).

Example 5A-8

N-{2-[(2S,5 S)-2-ethyl-5-(3-Fluorophenyl)-2-(hydroxymethyl)pyrrolidin-1-yl]-2-oxoethyl}-3-methyl-4-[(6-methyl-3-oxo-2,3-dihydropyridazin-4-yl)methyl]benzamide To a solution of Reference Example 9-3-A (14.0 mg) in ethanol (2 mL) was added 10% palladium on carbon (wet, 4.9 mg). The mixture was stirred under a hydrogen atmosphere at room temperature for 1 hour. The reaction mixture was filtered through Celite, and the filtrate was concentrated under reduced pressure. The residue was purified by column chromatography on silica gel (eluent: ethyl acetate/methanol=100/0-85/15) to give the title compound (6.7 mg).

Example 5A-9

N-{2-[(2S,5 S)-2-Ethyl-2-(methoxymethyl)-5-phenylpyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 5A-8 using Reference Example 9-1-A instead of Reference Example 9-3-A.

Example 5A-10

N-{2-[(5 S)-2,2-Diethyl-5-(3-fluorophenyl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 5A-8 using Reference Example 9-6-A instead of Reference Example 9-3-A.

Example 5A-11 rac-N-{2-[(2S,3S,5S)-5-(3-Fluorophenyl)-3-hydroxy-2-(propan-2-yl)pyrrolidin-1-yl]-2-oxoethyl}-3-methyl-4-[(6-methyl-3-oxo-2,3-dihydropyridazin-4-yl)methyl]benzamide The title compound was prepared in a similar manner to that described in Example 5A-8 using Reference Example 9-5-A instead of Reference Example 9-3-A.

Example 5A-12 rac-N-{2-[(2S,3R,5S)-5-(3-Fluorophenyl)-3-hydroxy-2-(propan-2-yl)pyrrolidin-1-yl]-2-oxoethyl}-3-methyl-4-[(6-methyl-3-oxo-2,3-dihydropyridazin-4-yl)methyl]benzamide To a solution of Reference Example 9-8-A (19.0 mg) in methanol (1 mL) was added an aqueous solution of sodium hydroxide (2 mol/L, 0.050 mL). The reaction mixture was stirred at 40° C. for 2 hours, and then to the reaction mixture was added hydrochloric acid (2 mol/L, 0.060 mL). The mixture was concentrated under reduced pressure. To the residue was added water, and the mixture was extracted twice with dichloromethane. The combined organic layer was washed with brine, dried over anhydrous sodium sulfate, and concentrated under reduced pressure. The residue was purified by column chromatography on amino-silica gel (eluent: ethyl acetate/methanol=100/0-85/15) to give the title compound (15.1 mg).

Example 5A-13

N-{2-[(2R,3R,5R)-5-(1-Cyano-1-methylethyl)-2-(3-fluorophenyl)-3-hydroxypyrrolidin-1-yl]-2-oxoethyl}-3-methyl-4-[(6-methyl-3-oxo-2,3-dihydropyridazin-4-yl)oxy]benzamide To a solution of Reference Example 9-10-A (17.0 mg) in ethanol (2 mL) was added 10% palladium on carbon (wet, 20.0 mg) under ice-cooling. The mixture was stirred under a hydrogen atmosphere at room temperature for 4 hours. The reaction mixture was filtered through Celite, and the filtrate was concentrated under reduced pressure. The residue was purified by ODS column chromatography (eluent: water/acetonitrile=70/30-20/80) to give the title compound (7.1 mg).

Example 5A-14

N-{2-[(2S,5R)-2-(3-Fluorophenyl)-5-(2-methyl-3-oxobutan-2-yl)pyrrolidin-1-yl]-2-oxoethyl}-3-methyl-4-[(6-methyl-3-oxo-2,3-dihydropyridazin-4-yl)methyl]benzamide To a solution of Reference Example 9-7-A (12.0 mg) in dichloromethane (0.6 mL) was added DMP (13.0 mg) under ice-cooling. The mixture was stirred at room temperature for 1.5 hours, and then to the mixture was added DMP (2.8 mg). The mixture was stirred at room temperature for 1.5 hours. To the reaction mixture were added an aqueous solution of sodium thiosulfate (1 mol/L, 0.5 mL), a saturated aqueous solution of sodium bicarbonate (1.5 mL) and water, and the mixture was stirred at room temperature for 10 minutes. The mixture was extracted with dichloromethane. The organic layer was concentrated under reduced pressure. The residue was purified by ODS column chromatography (eluent: water/acetonitrile=90/10-10/90) to give the title compound (5.4 mg).

Example 5B-1

N-[(2R)-1-[(2R,3R,5R)-5-(1-Cyano-1-methylethyl)-2-(3-fluorophenyl)-3-hydroxypyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Example 5A-13 using Reference Example 9-11-A instead of Reference Example 9-10-A.

HRMS (ESI) calcd for $C_{30}H_{33}FN_5O_5(M+H)^+$: 562.2460, Found: 562.2463.

Example 5B-2

N-[(2R)-1-[(2R,3S,5R)-3-Amino-5-(1-cyano-1-methylethyl)-2-(3-fluorophenyl)pyrrolidin-1-yl]-1-oxopropan-2-yl]-3-methyl-4-[(6-methyl-3-oxo-2,3-dihydropyridazin-4-yl)oxy]benzamide The title compound was prepared in a similar manner to that described in Example 5A-13 using Reference Example 9-12-A instead of Reference Example 9-10-A.

Example 5C-1

N-[(2R)-1-[(2S,5R)-2-(3-Chlorophenyl)-5-(1-cyano-1-methylethyl)pyrrolidin-1-yl]-3-hydroxy-1-oxopropan-2-yl]-3-methyl-4-[(6-methyl-3-oxo-2,3-dihydropyridazin-4-yl)oxy]benzamide To a solution of Reference Example 9-9-A (17.5 mg) in dichloromethane (2 mL) was added titanium(IV) chloride (0.029 mL) under an argon atmosphere under ice-cooling. The mixture was stirred under ice-cooling for 100 minutes, and then stirred at room temperature for 3 hours. To the reaction mixture were added dichloromethane and hydrochloric acid (2 mol/L), and the mixture was stirred. The organic layer was separated, and then concentrated under reduced pressure. The residue was purified by ODS column chromatography (eluent: water/acetonitrile=70/30-20/80) to give the title compound (5.2 mg).

The following tables show chemical structure, physical property and Ki (see, Test Example 1) of Example.

[Table 17]

TABLE 17

| Ex. No. | Str. | Physical data | Ki (nM) |
|---|---|---|---|
| 3A-1 | | HRMS (ESI) calcd for $C_{30}H_{37}N_4O_4$ $(M + H)^+$: 517.2809, Found: 517.2810 | 1.8 |
| 3A-2 | | HRMS (ESI) calcd for $C_{30}H_{37}N_4O_4$ $(M + H)^+$: 517.2809, Found: 517.2809 | 2.4 |

TABLE 17-continued

| Ex. No. | Str. | Physical data | Ki (nM) |
| --- | --- | --- | --- |
| 3A-3 | | HRMS (ESI) calcd for $C_{27}H_{26}N_5O_3$ (M + H)$^+$: 470.2187, Found: 470.2188 | 5.4 |
| 3A-4 | | HRMS (ESI) calcd for $C_{30}H_{36}FN_4O_4$ (M + H)$^+$: 535.2715, Found: 535.2715 | 0.16 |
| 3A-5 | | HRMS (ESI) calcd for $C_{30}H_{34}N_5O_3$ (M + H)$^+$: 512.2656, Found: 512.2656 | 0.35 |
| 3A-6 | | HRMS (ESI) calcd for $C_{30}H_{36}FN_4O_4$ (M + H)$^+$: 535.2715, Found: 535.2713 | 0.24 |
| 3A-7 | | HRMS (ESI) calcd for $C_{32}H_{40}FN_4O_4$ (M + H)$^+$: 563.3028, Found: 563.3027 | 0.08 |

TABLE 18

| Ex. No. | Str. | Physical data | Ki (nM) |
|---|---|---|---|
| 3A-8 | | HRMS (ESI) calcd for $C_{31}H_{36}N_5O_3$ (M + H)$^+$: 526.2813, Found: 526.2813 | 0.02 |
| 3A-9 | | HRMS (ESI) calcd for $C_{31}H_{36}FN_4O_3$ (M + H)$^+$: 531.2766, Found: 531.2766 | 0.05 |
| 3A-10 | | HRMS (ESI) calcd for $C_{32}H_{35}FN_5O_4$ (M + H)$^+$: 572.2668, Found: 572.2664 | 0.76 |
| 3A-11 | | HRMS (ESI) calcd for $C_{31}H_{36}FN_4O_4$ (M + H)$^+$: 547.2715, Found: 547.2715 | 0.19 |
| 3A-12 | | HRMS (ESI) calcd for $C_{30}H_{40}N_5O_3$ (M + H)$^+$: 518.3126, Found: 518.3126 | 0.11 |

TABLE 18-continued
| Ex. No. | Str. | Physical data | Ki (nM) |
|---|---|---|---|
| 3A-13 | 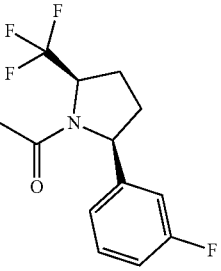 | HRMS (ESI) calcd for $C_{27}H_{27}F_4N_4O_3$ (M + H)+: 531.2014, Found: 531.2015 | 0.46 |
TABLE 19
| Ex. No. | Str. | Physical data | Ki (nM) |
|---|---|---|---|
| 3A-14 | 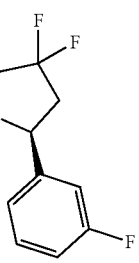racemate | HRMS (ESI) calcd for $C_{29}H_{32}F_3N_4O_3$ (M + H)+: 541.2421, Found: 541.2421 | 1.4 |
| 3A-15 | 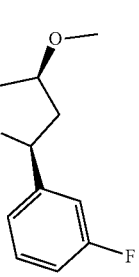racemate | HRMS (ESI) calcd for $C_{30}H_{36}FN_4O_4$ (M + H)+: 535.2715, Found: 535.2714 | 0.49 |
| 3A-16 | 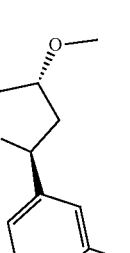racemate | HRMS (ESI) calcd for $C_{30}H_{36}FN_4O_4$ (M + H)+: 535.2714, Found: 535.2714 | 5.2 |

TABLE 19-continued

| Ex. No. | Str. | Physical data | Ki (nM) |
|---|---|---|---|
| 3A-17 | | HRMS (ESI) calcd for $C_{23}H_{29}F_4N_4O_3$ (M + H)$^+$: 545.2170, Found: 545.2169 | 0.79 |
| 3B-1 | | HRMS (ESI) calcd for $C_{31}H_{38}FN_4O_4$ (M + H)$^+$: 549.2872, Found: 549.2871 | 0.22 |
| 3C-1 | | HRMS (ESI) calcd for $C_{32}H_{39}FN_4Na_4O_4$ (M + H)$^+$: 585.2848, Found: 585.2847 | 1.5 |

TABLE 20

| Ex. No. | Str. | Physical data | Ki (nM) |
|---|---|---|---|
| 4A-1 | | HRMS (ESI) calcd for $C_{30}H_{37}N_4O_4$ (M + H)$^+$: 517.2809, Found: 517.2810 | 22 |
| 4A-2 | | HRMS (ESI) calcd for $C_{29}H_{32}FN_4O_5$ (M + H)$^+$: 535.2351, Found: 535.2351 | 0.33 |

TABLE 20-continued

| Ex. No. | Str. | Physical data | Ki (nM) |
| --- | --- | --- | --- |
| 4A-3 | | HRMS (ESI) calcd for C$_{30}$H$_{36}$FN$_4$O$_4$ (M + H)$^+$: 535.2715, Found: 535.2718 | 0.28 |
| 4A-4 | | HRMS (ESI) calcd for C$_{29}$H$_{34}$FN$_4$O$_6$ (M + H)$^+$: 537.2508, Found: 537.2509 | 0.63 |
| 4A-5 | | HRMS (ESI) calcd for C$_{28}$H$_{28}$F$_2$N$_5$O$_4$ (M + H)$^+$: 536.2104, Found: 536.2104 | 0.11 |
| 4A-6 | | HRMS (ESI) calcd for C$_{28}$H$_{28}$ClFN$_5$O$_4$ (M + H)$^+$: 552.1808, Found: 552.1809 | 0.07 |
| 4A-7 | | HRMS (ESI) calcd for C$_{29}$H$_{31}$ClN$_5$O$_4$ (M + H)$^+$: 548.2059, Found: 548.2059 | 0.06 |

TABLE 21

| Ex. No. | Str. | Physical data | Ki (nM) |
|---|---|---|---|
| 4B-1 | | ¹H-NMR δ ppm (DMSO-d6): 0.95 (3H, d, J = 6.9 Hz), 1.43 (6H, s), 1.95-2.35 (9H, m), 3.78 (2H, s), 4.20-4.40 (2H, m), 5.57-5.68 (1H, m), 6.65 (1H, s), 7.10-7.40 (4H, m), 7.43-7.55 (1H, m), 7.62-7.82 (2H, m), 8.60 (1H, d, J = 5.4 Hz), 12.75 (1H, brs) | 0.18 |
| 4B-2 | | ¹H-NMR δ ppm (DMSO-d6): 0.95 (3H, d, J = 7.0 Hz), 1.43 (6H, s), 1.95-2.35 (6H, m), 3.81 (2H, s), 4.20-4.40 (2H, m), 5.56-5.68 (1H, m), 6.74 (1H, d, J = 4.1 Hz), 7.10-7.40 (4H, m), 7.44-7.55 (1H, m), 7.61-7.84 (3H, m), 8.60 (1H, d, J = 5.7 Hz), 13.07 (1H, brs) | 0.31 |
| 4B-3 | | ¹H-NMR δ ppm (DMSO-d6): 0.80-1.40 (6H, m), 1.43-2.17 (10H, m), 2.24 (3H, s), 2.68-2.93 (3H, m), 3.79 (2H, s), 4.10-5.10 (3H, m), 5.46-5.63 (1H, m), 6.61-6.68 (1H, m), 6.93-7.89 (7H, m), 8.40-8.64 (1H, m), 12.75 (1H, brs) | 0.16 |
| 4B-4 | | ¹H-NMR δ ppm (DMSO-d6): 0.96 (3H, d, J = 6.8 Hz), 1.44 (6H, s), 2.00-2.31 (6H, m), 2.46 (3H, s), 4.21-4.46 (2H, m), 5.40-5.56 (1H, m), 6.96 (1H, s), 7.12-7.60 (4H, m), 8.63 (1H, s), 8.71 (1H, d, J = 6.5 Hz), 13.07 (1H, brs) | 0.08 |
| 4B-5 | | ¹H-NMR δ ppm (DMSO-d6): 0.98 (3H, d, J = 6.9 Hz), 1.66-2.45 (15H, m), 2.58-2.72 (1H, m), 4.15-4.27 (1H, m), 4.37-4.49 (1H, m), 5.58-5.68 (1H, m), 6.40 (1H, s), 7.10 (1H, d, J = 8.5 Hz), 7.27-7.54 (3H, m), 7.58-7.64 (1H, m), 7.80 (1H, dd, J = 1.8, 8.5 Hz), 7.93 (1H, d, J = 1.8 Hz), 8.70 (1H, d, J = 5.7 Hz), 12.95 (1H, brs) | 0.06 |

TABLE 21-continued

| Ex. No. | Str. | Physical data | Ki (nM) |
|---|---|---|---|
| 4B-6 | | ¹H-NMR δ ppm (DMSO-d6): 0.98 (3H, d, J = 6.8 Hz), 1.51-1.69 (1H, m), 1.82-1.94 (1H, m), 2.04-2.24 (8H, m), 4.16-4.42 (2H, m), 4.66-4.82 (3H, m), 5.03 (1H, d, J = 7.2 Hz), 5.62-5.71 (1H, m), 6.41 (1H, s), 7.11 (1H, d, J = 8.5 Hz), 7.35-7.47 (2H, m), 7.51-7.58 (1H, m), 7.69-7.74 (1H, m), 7.80 (1H, dd, J = 1.8, 8.5 Hz), 7.94 (1H, d, J = 1.8 Hz), 8.72 (1H, d, J = 5.9 Hz), 12.95 (1H, brs) | 0.04 |

TABLE 22

| Ex. No. | Str. | Physical data | Ki (nM) |
|---|---|---|---|
| 4B-7 | | ¹H-NMR δ ppm (CDCl₃): 0.94 (3H, d, J = 6.9 Hz), 1.33 (3H, d, J = 6.8 Hz), 1.75-1.95 (2H, m), 1.95-2.30 (9H, m), 2.35-2.55 (3H, m), 3.30-3.58 (2H, m), 4.35-4.77 (3H, m), 5.32-5.41 (1H, m), 6.02 (1H, s), 6.87 (1H, d, J = 7.7 Hz), 7.06 (1H, d, J = 8.5 Hz), 7.28-7.41 (3H, m), 7.65-7.81 (2H, m), 10.71 (1H, brs) | 0.05 |
| 4B-8 | | ¹H-NMR δ ppm (CDCl₃): 0.99 (3H, d, J = 6.5 Hz), 1.34 (3H, d, J = 6.9 Hz), 1.74-1.86 (2H, m), 1.95-2.21 (3H, m), 2.24 (3H, s), 2.37-2.47 (3H, m), 2.48 (3H, s), 3.32-3.56 (2H, m), 4.35-4.48 (1H, m), 4.55-4.77 (2H, m), 5.29-5.38 (1H, m), 6.14 (1H, s), 7.28-7.46 (5H, m), 8.03-8.12 (1H, m), 8.30 (1H, d, J = 8.0 Hz) | 0.05 |
| 4B-9 | | ¹H-NMR δ ppm (DMSO-d6): 0.97 (3H, d, J = 6.9 Hz), 1.43 (6H, s), 2.00-2.31 (9H, m), 4.19-4.40 (2H, m), 5.57-5.68 (1H, m), 6.16 (1H, s), 7.33-7.60 (5H, m), 7.71-7.89 (2H, m), 8.17 (1H, s), 8.64 (1H, d, J = 5.4 Hz), 12.64 (1H, brs) | 0.10 |

TABLE 22-continued

| Ex. No. | Str. | Physical data | Ki (nM) |
|---|---|---|---|
| 4B-10 | | ¹H-NMR δ ppm (DMSO-d6): 0.95 (3H, d, J = 6.8 Hz), 1.44 (6H, s), 2.00-2.31 (6H, m), 2.44 (3H, s), 4.23-4.60 (2H, m), 5.36-5.50 (1H, m), 6.79 (1H, s), 6.90-7.70 (5H, m), 7.88 (1H, d, J = 8.3 Hz), 8.46 (1H, d, J = 7.1 Hz), 13.02 (1H, brs) | 0.13 |
| 4B-11 | | ¹H-NMR δ ppm (DMSO-d6): 0.98 (3H, d, J = 6.9 Hz), 1.51-1.79 (1H, m), 1.81-1.95 (1H, m), 2.06-2.17 (4H, m), 2.20 (3H, s), 4.17-4.28 (1H, m), 4.32-4.42 (1H, m), 4.65-4.83 (3H, m), 5.02 (1H, d, J = 7.2 Hz), 5.60-5.68 (1H, m), 6.39 (1H, s), 7.35-7.59 (3H, m), 7.68-7.90 (3H, m), 8.83 (1H, d, J = 5.6 Hz), 13.00 (1H, brs) | 0.07 |

TABLE 23

| Ex. No. | Str. | Physical data | Ki (nM) |
|---|---|---|---|
| 4B-12 | | ¹H-NMR δ ppm (CDCl₃): 1.14 (3H, d, J = 6.9 Hz), 1.23-1.37 (6H, m), 1.78-1.93 (1H, m), 2.00-2.16 (2H, m), 2.23 (3H, s), 2.35-2.50 (1H, m), 4.22-4.34 (1H, m), 4.66-4.79 (1H, m), 5.37 (1H, s), 5.49 (1H, s), 5.65-5.75 (1H, m), 6.26 (1H, s), 7.07 (1H, d, J = 8.7 Hz), 7.21-7.45 (4H, m), 7.51-7.58 (1H, m), 7.85-8.10 (2H, m) | 0.14 |
| 4B-13 | | ¹H-NMR δ ppm (DMSO-d6): 0.82 (3H, d, J = 6.8 Hz), 1.06-1.27 (6H, m), 1.68-1.84 (1H, m), 2.01-2.26 (12H, m), 4.10-4.24 (1H, m), 4.33-4.47 (1H, m), 4.77 (1H, s), 5.35-5.48 (1H, m), 5.96 (1H, s), 7.25-7.48 (2H, m), 7.55-7.63 (1H, m), 7.73-7.87 (3H, m), 8.56-8.64 (1H, m), 12.92 (1H brs) | 0.15 |

TABLE 23-continued

| Ex. No. | Str. | Physical data | Ki (nM) |
|---|---|---|---|
| 4B-14 | | ¹H-NMR δ ppm (DMSO-d6): 0.92 (3H, d, J = 6.9 Hz), 1.38-1.50 (6H, m), 2.00-2.30 (10H, m), 4.20-4.42 (2H, m), 5.46-5.56 (1H, m), 6.60 (1H, s), 6.95 (1H, d, J = 8.4 Hz), 7.36-7.60 (5H, m), 8.51-8.60 (1H, m), 13.00 (1H, brs) | 0.13 |
| 4B-15 | | ¹H-NMR δ ppm (DMSO-d6): 0.99 (3H, d, J = 6.8 Hz), 1.43 (6H, s), 1.97-2.31 (6H, m), 3.83 (3H, s), 4.23-4.40 (2H, m), 5.55-5.68 (1H, m), 6.27 (1H, s), 7.23 (1H, d, J = 8.2 Hz), 7.35-7.72 (6H, m), 8.76-8.84 (1H, m), 12.90 (1H, brs) | 0.09 |
| 4B-16 | | ¹H-NMR δ ppm (DMSO-d6): 0.92 (3H, d, J = 6.9 Hz), 1.38-1.48 (6H, m), 2.00-2.31 (10H, m), 4.16-4.41 (2H, m), 5.43-5.57 (1H, m), 6.60 (1H, s), 7.07 (1H, d, J = 10.9 Hz), 7.35-7.65 (5H, m), 8.49-8.56 (1H, m), 12.99 (1H, brs) | 0.08 |
| 4B-17 | | ¹H-NMR δ ppm (DMSO-d6): 0.98 (3H, d, J = 6.9 Hz), 1.43 (6H, s), 1.95-2.31 (7H, m), 4.20-4.40 (2H, m), 5.48-5.61 (1H, m), 6.85 (1H, s), 7.35-7.60 (4H, m), 7.85 (2H, d, J = 9.0 Hz), 8.92 (1H, d, J = 5.7 Hz), 13.09 (1H, brs) | 0.07 |

TABLE 24

| Ex. No. | Str. | Physical data | Ki (nM) |
|---|---|---|---|
| 4B-18 | | ¹H-NMR δ ppm (DMSO-d6): 0.81 (3H, d, J = 6.7 Hz), 1.06-1.37 (6H, m), 1.68-1.84 (1H, m), 1.94-2.41 (9H, m), 4.18 (1H, d, J = 8.7 Hz), 4.37-4.51 (1H, m), 4.78 (1H, s), 5.34-5.50 (1H, m), 6.39 (1H, s), 7.01-7.22 (2H, m), 7.34-7.53 (2H, m), 7.57-8.00 (3H, m), 8.61 (1H, d, J = 6.3 Hz), 12.95 (1H, s) | 0.09 |
| 4B-19 | | ¹H-NMR δ ppm (DMSO-d6): 0.94-1.61 (9H, m), 1.97-2.31 (6H, m), 2.45 (3H, s), 4.20-4.52 (2H, m), 5.02-5.54 (1H, m), 6.79 (1H, s), 7.10-8.02 (5H, m), 8.41-8.57 (1H, m), 13.04 (1H, brs) | 0.07 |
| 4B-20 | | ¹H-NMR δ ppm (DMSO-d6): 1.00 (3H, d, J = 6.9 Hz), 1.43 (6H, s), 1.95-2.31 (9H, m), 4.20-4.39 (2H, m), 5.52-5.66 (1H, m), 6.38 (1H, s), 7.52 (2H, d, J = 7.0 Hz), 7.65-7.83 (3H, m), 8.81 (1H, d, J = 5.6 Hz), 12.99 (1H, brs) | 0.10 |
| 4B-21 | | ¹H-NMR δ ppm (CDCl₃): 1.18 (3H, d, J = 6.9 Hz), 1.50 (3H, s), 1.56 (3H, s), 2.11-2.21 (2H, m), 2.24 (3H, s), 2.43-2.70 (5H, m), 4.40-4.50 (1H, m), 4.54-4.65 (1H, m), 5.75-5.84 (1H, m), 6.14 (1H, s), 7.05-7.14 (1H, m), 7.42 (1H, d, J = 8.4 Hz), 7.62 (1H, dd, J = 2.6, 6.3 Hz), 8.06 (1H, d, J = 8.3 Hz), 8.27 (1H, d, J = 7.5 Hz), 10.60 (1H, brs) | 0.11 |

TABLE 24-continued
| Ex. No. | Str. | Physical data | Ki (nM) |
|---|---|---|---|
| 4B-22 | 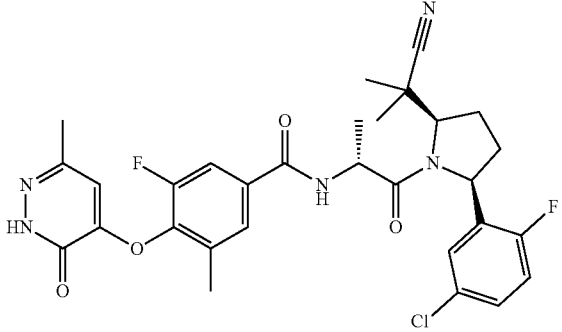 [SMILES: Cc1cc(Oc2c(C)cc(C(=O)N[C@H](C)C(=O)N3[C@H](c4cc(Cl)ccc4F)CC[C@@H]3C(C)(C)C#N)cc2F)c(=O)[nH]n1] | ¹H-NMR δ ppm (CDCl₃): 1.15 (3H, d, J = 6.8 Hz), 1.51 (3H, s), 1.56 (3H, s), 2.11-2.37 (8H, m), 2.41-2.71 (2H, m), 4.40-4.50 (1H, m), 4.51-4.63 (1H, m), 5.77-5.88 (1H, m), 6.04 (1H, d, J = 1.4 Hz), 7.04-7.14 (2H, m), 7.48-7.57 (2H, m), 7.62 (1H, dd, J = 2.5, 6.4 Hz), 10.80 (1H, brs) | 0.11 |
TABLE 25
| Ex. No. | Str. | Physical data | Ki (nM) |
|---|---|---|---|
| 4B-23 | 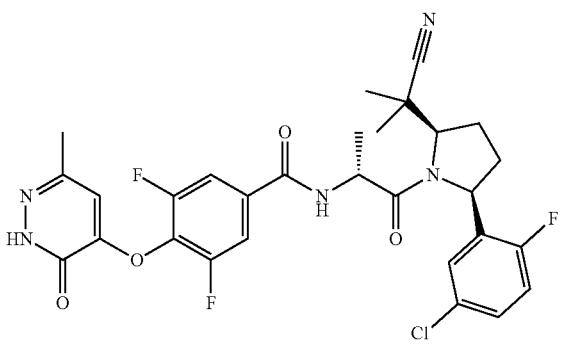 [SMILES: Cc1cc(Oc2c(F)cc(C(=O)N[C@H](C)C(=O)N3[C@H](c4cc(Cl)ccc4F)CC[C@@H]3C(C)(C)C#N)cc2F)c(=O)[nH]n1] | ¹H-NMR δ ppm (CDCl₃): 1.12 (3H, d, J = 6.8 Hz), 1.52 (3H, s), 1.58 (3H, s), 2.11-2.23 (2H, m), 2.29 (3H, s), 2.43-2.70 (2H, m), 4.41-4.60 (2H, m), 5.79-5.89 (1H, m), 6.41 (1H, s), 7.04-7.14 (1H m), 7.43-7.54 (2H, m), 7.59 (1H, dd, J = 2.5, 6.4 Hz), 7.71-7.82 (1H, m), 11.29 (1H, brs) | 0.08 |
| 4B-24 | 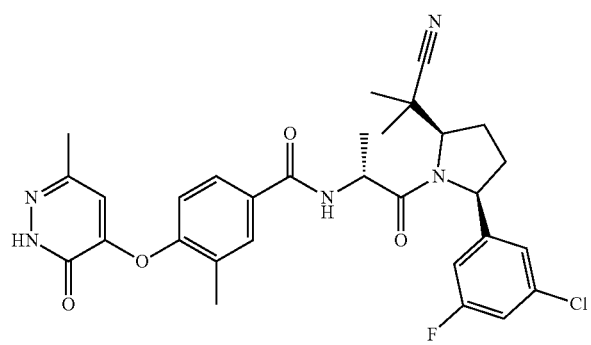 | ¹H-NMR δ ppm (DMSO-d6): 1.04 (3H, d, J = 6.9 Hz), 1.42 (6H, s), 1.95-2.31 (10H, m), 4.17-4.40 (2H, m), 5.60-5.74 (1H, m), 6.41 (1H, s), 7.10 (1H, d, J = 8.5 Hz), 7.20-7.52 (3H, m), 7.71-8.00 (2H, m), 8.73 (1H, d, J = 5.5 Hz), 12.95 (1H, brs) | 0.08 |
| 4B-25 | 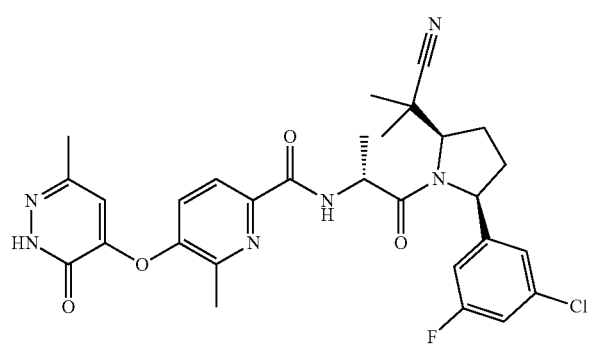 [SMILES: Cc1cc(Oc2ccc(C(=O)N[C@H](C)C(=O)N3[C@H](c4cc(F)cc(Cl)c4)CC[C@@H]3C(C)(C)C#N)cc2C)c(=O)[nH]n1] | ¹H-NMR δ ppm (DMSO-d6): 1.04 (3H, d, J = 6.7 Hz), 1.43 (6H, s), 2.00-2.30 (7H, m), 2.45 (3H, s), 4.30-4.49 (2H, m), 5.41-5.83 (1H, m), 6.80 (1H, s), 7.20-7.70 (4H, m), 7.88 (1H, d, J = 8.7 Hz), 8.51 (1H, d, J = 6.9 Hz), 13.04 (1H, brs) | 0.06 |

TABLE 25-continued

| Ex. No. | Str. | Physical data | Ki (nM) |
|---|---|---|---|
| 4B-26 | | ¹H-NMR δ ppm (DMSO-d6): 1.05 (3H, d, J = 6.5 Hz), 1.42 (6H, s), 1.95-2.30 (10H, m), 4.17-4.40 (2H, m), 5.57-5.70 (1H, m), 6.38 (1H, s), 7.14-7.55 (3H, m), 7.70-7.90 (2H, m), 8.84 (1H, d, J = 5.2 Hz), 13.00 (1H, brs) | 0.07 |
| 4B-27 | | ¹H-NMR δ ppm (DMSO-d6): 1.05 (3H, d, J = 6.9 Hz), 1.42 (6H, s), 1.95-2.30 (7H, m), 4.20-4.38 (2H, m), 5.55-5.66 (1H, m), 6.85 (1H, s), 7.25-7.51 (3H, m), 7.80-7.95 (2H, m), 8.95 (1H, d, J = 5.7 Hz), 13.09 (1H, brs) | 0.09 |
| 4B-28 | | ¹H-NMR δ ppm (DMSO-d6): 0.99 (3H, d, J = 6.4 Hz), 1.42 (6H, s), 1.95-2.31 (9H, m), 4.20-4.40 (2H, m), 5.56-5.68 (1H, m), 6.41 (1H, s), 7.10 (1H, d, J = 8.5 Hz), 7.46-7.58 (2H, m), 7.63-7.83 (2H, m), 7.88-7.97 (1H, m), 8.71 (1H, d, J = 5.2 Hz), 12.95 (1H, brs) | 0.08 |

TABLE 26

| Ex. No. | Str. | Physical data | Ki (nM) |
|---|---|---|---|
| 4B-29 | | ¹H-NMR δ ppm (DMSO-d6): 1.00 (3H, d, J = 6.7 Hz), 1.43 (6H, s), 1.93-2.30 (6H, m), 4.20-4.38 (2H, m), 5.50-5.60 (1H, m), 6.85 (1H, s), 7.52 (2H, d, J = 7.3 Hz), 7.69 (1H, d, J = 7.3 Hz), 7.79-7.89 (2H, m), 8.93 (1H, d, J = 5.5 Hz), 13.09 (1H, brs) | 0.07 |

TABLE 26-continued

| Ex. No. | Str. | Physical data | Ki (nM) |
|---|---|---|---|
| 4B-30 | | ¹H-NMR δ ppm (DMSO-d6): 0.98 (3H, d, J = 6.9 Hz), 1.43 (6H, s), 1.94-2.31 (9H, m), 4.20-4.40 (2H, m), 5.53-5.62 (1H, m), 6.38 (1H, s), 7.37-7.58 (3H, m), 7.65-7.88 (3H, m), 8.81 (1H, d, J = 5.7 Hz), 13.00 (1H, s) | 0.06 |
| 4B-31 | | ¹H-NMR δ ppm (DMSO-d6): 0.95 (3H, d, J = 6.8 Hz), 1.65-1.95 (3H, m), 2.08-2.16 (6H, m), 2.18 (3H, s), 2.98 (3H, s), 4.15-4.25 (1H, m), 4.97-5.07 (1H, m), 5.35-5.50 (1H, m), 5.60-5.73 (1H, m), 6.41 (1H, s), 7.10 (1H, d, J = 8.5 Hz), 7.31-7.56 (4H, m), 7.79 (1H, dd, J = 1.9, 8.5 Hz), 7.92 (1H, d, J = 1.9 Hz), 8.69 (1H, d, J = 5.9 Hz), 12.95 (1H, brs) | 0.06 |
| 4B-32 | | ¹H-NMR δ ppm (DMSO-d6): 0.84-1.43 (3H, m), 1.60-2.25 (9H, m), 2.40-2.48 (3H, m), 2.95-3.10 (3H, m), 4.34-4.53 (1H, m), 4.90-5.58 (3H, m), 6.74-6.82 (1H, m), 7.10-7.70 (5H, m), 7.84-8.00 (1H, m), 8.44-8.59 (1H, m), 13.03 (1H, brs) | 0.06 |
| 4B-33 | | ¹H-NMR δ ppm (DMSO-d6): 0.80-2.22 (17H, m), 2.40-2.47 (3H, m), 3.89-5.44 (5H, m), 6.70-6.81 (1H, m), 7.04-7.70 (5H, m), 7.84-8.00 (1H, m), 8.40-8.56 (1H, m), 13.03 (1H, brs) | 0.05 |

TABLE 27

| Ex. No. | Str. | Physical data | Ki (nM) |
|---|---|---|---|
| 4B-34 | | HRMS (ESI) calcd for $C_{31}H_{36}FN_5NaO_4$ (M + Na)$^+$: 584.2644, Found: 584.2643 | 0.12 |
| 4b-35 | | HRMS (ESI) calcd for $C_{29}H_{31}FN_5O_4$ (M + H)$^+$: 532.2355, Found: 532.2355 | 0.14 |
| 4B-36 | | HRMS (ESI) calcd for $C_{27}H_{27}F_4N_4O_4$ (M + H)$^+$: 547.1963, Found: 547.1965 | 0.12 |
| 4B-37 | | HRMS (ESI) calcd for $C_{28}H_{30}F_3N_4O_4$ (M + H)$^+$: 543.2214, Found: 543.2217 | 0.13 |
| 4B-38 | | HRMS (ESI) calcd for $C_{28}H_{31}ClN_7O_4$ (M + H)$^+$: 564.2121, Found: 564.2122 | 0.26 |

TABLE 27-continued

| Ex. No. | Str. | Physical data | Ki (nM) |
|---|---|---|---|
| 4B-39 | | HRMS (ESI) calcd for $C_{29}H_{33}F_2N_4O_5$ (M + H)$^+$: 555.2414, Found: 555.2412 | 0.26 |
| 4B-40 | | HRMS (ESI) calcd for $C_{30}H_{32}F_2N_5O_4$ (M + H)$^+$: 564.2417, Found: 564.2417 | 0.31 |

TABLE 28

| Ex. No. | Str. | Physical data | Ki (nM) |
|---|---|---|---|
| 4B-41 | | HRMS (ESI) calcd for $C_{32}H_{35}ClF_3N_5NaO_5$ (M + Na)$^+$: 684.2171, Found: 684.2168 | 0.05 |
| 4B-42 | | HRMS (ESI) calcd for $C_{29}H_{31}ClF_3N_8O_5$ (M + H)$^+$: 635.1991, Found: 635.1988 | 0.08 |

TABLE 28-continued

| Ex. No. | Str. | Physical data | Ki (nM) |
|---|---|---|---|
| 4B-43 | | HRMS (ESI) calcd for C$_{30}$H$_{33}$ClN$_5$O$_4$ (M + H)$^+$: 562.2216, Found: 562.2215 | 0.31 |
| 4C-1 | | HRMS (ESI) calcd for C$_{29}$H$_{31}$ClFN$_6$O$_4$ (M + H)$^+$: 581.2074, Found: 581.2071 | 0.12 |
| 5A-1 | | HRMS (ESI) calcd for C$_{28}$H$_{33}$FN$_5$O$_3$ (M + H)$^+$: 506.2562, Found: 506.2561 | 6.9 |
| 5A-2 | | HRMS (ESI) calcd for C$_{30}$H$_{37}$FN$_5$O$_3$ (M + H)$^+$: 534.2875, Found: 534.2874 | 6.3 |
| 5A-3 | | HRMS (ESI) calcd for C$_{30}$H$_{35}$FN$_5$O$_4$ (M + H)$^+$: 548.2668, Found: 548.2669 | 0.18 |

TABLE 29
| Ex. No. | Str. | Physical data | Ki (nM) |
|---|---|---|---|
| 5A-4 | 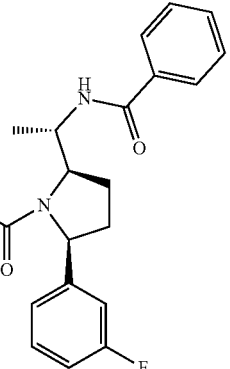 | HRMS (ESI) calcd for $C_{35}H_{37}FN_5O_4$ (M + H)$^+$: 610.2824, Found: 610.2825 | 0.31 |
| 5A-5 | 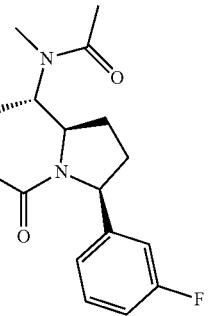 | HRMS (ESI) calcd for $C_{31}H_{37}FN_5O_4$ (M + H)$^+$: 562.2824, Found: 562.2825 | 0.09 |
| 5A-6 | 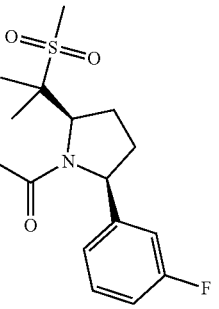 | HRMS (ESI) calcd for $C_{30}H_{36}FN_4O_5S$ (M + H)$^+$: 583.2385, Found: 583.2384 | 0.24 |
| 5A-7 | 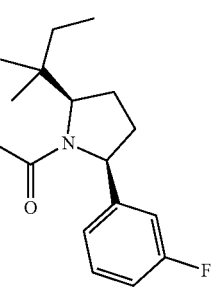 | HRMS (ESI) calcd for $C_{31}H_{38}FN_4O_3$ (M + H)$^+$: 533.2922, Found: 533.2921 | 0.05 |
| 5A-8 | 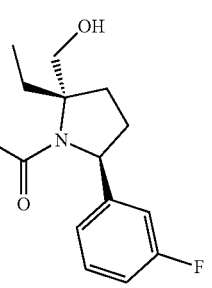 | HRMS (ESI) calcd for $C_{29}H_{34}FN_4O_4$ (M + H)$^+$: 521.2559, Found: 521.2558 | 0.22 |

TABLE 29-continued

| Ex. No. | Str. | Physical data | Ki (nM) |
|---|---|---|---|
| 5A-9 | | HRMS (ESI) calcd for $C_{30}H_{37}N_4O_4$ $(M + H)^+$: 517.2809, Found: 517.2810 | 2.3 |
| 5A-10 | | HRMS (ESI) calcd for $C_{30}H_{36}FN_4O_3$ $(M + H)^+$: 519.2766, Found: 519.2765 | 0.41 |

TABLE 30

| Ex. No, | Str. | Physical data | Ki (nM) |
|---|---|---|---|
| 5A-11 | racemate | HRMS (ESI) calcd for $C_{29}H_{34}FN_4O_4$ $(M + H)^+$: 521.2559, Found: 521.2561 | 1.2 |
| 5A-12 | racemate | HRMS (ESI) calcd for $C_{29}H_{34}FN_4O_4$ $(M + H)^+$: 521.2559, Found: 521.2559 | 2.9 |

TABLE 30-continued

| Ex. No, | Str. | Physical data | Ki (nM) |
|---|---|---|---|
| 5A-13 | | HRMS (ESI) calcd for $C_{29}H_{31}FN_5O_5$ (M + H)$^+$: 548.2304, Found: 548.2304 | 0.16 |
| 5A-14 | | HRMS (ESI) calcd for $C_{31}H_{36}FN_4O_4$ (M + H)$^+$: 547.2715, Found: 547.2713 | 0.27 |
| 5B-1 | | $^1$H-NMR δ ppm (DMSO-d$_6$): 1.14 (3H, d, J = 6.7 Hz), 1.41 (3H, s), 1.47 (3H, s), 1.79-1.92 (1H, m), 2.14 (3H, s), 2.18 (3H, s), 2.27-2.39 (1H, m), 4.15-4.32 (2H, m), 4.36-4.50 (1H, m), 5.39 (1H, brs), 5.74 (1H, d, J = 7.6 Hz), 6.41 (1H, s), 7.06-7.15 (2H, m), 7.28-7.48 (3H, m), 7.78 (1H, dd, J = 2.0, 8.6 Hz), 7.91 (1H, d, J = 2.0 Hz), 8.72 (1H, d, J = 5.6 Hz), 12.96 (1H, brs) | 0.06 |

TABLE 31

| Ex. No. | Str. | Physical data | Ki (nM) |
|---|---|---|---|
| 5B-2 | | HRMS (ESI) calcd for $C_{30}H_{34}FN_6O_4$ (M + H)$^+$: 561.2620, Found: 561.2617 | 0.11 |

TABLE 31-continued

| Ex. No. | Str. | Physical data | Ki (nM) |
|---|---|---|---|
| 5C-1 | (structure) | HRMS (ESI) calcd for $C_{30}H_{33}ClN_5O_5$ (M + H)$^+$: 578.2165, Found: 578.2165 | 0.04 |

Test Example 1

Determination of Binding Affinity for CGRP Receptor by Radioligand Binding Assay in SK-N-MC Cell Membranes The binding affinity assay of compounds for human CGRP receptor was carried out by inhibition of radiolabeled ligand [$^{125}$I]-CGRP binding in human neuroblastoma cell line SK-N-MC cell membranes.

Cell membranes prepared from SK-N-MC cells expressing CGRP receptors endogenously (Muff et al., Ann N Y Acad Sci. 1992; 657: 106-116) were used for radioligand binding assay. Radioligand binding assay was performed using 96-well microplate in a total volume of 200 μL in each well. A 2.5 μL of serial dilution of compound dissolved in dimethylsulfoxide (DMSO) was mixed with SK-N-MC cell membranes (40 μg membrane protein per well) and [$^{125}$I]-CGRP (PerkinElmer NEX354, final concentration of 150 pM) in an assay buffer consisting of 50 mM Tris-HCl, 5 mM MgCl2 and 0.1% bovine serum albumin (pH 7.4). The assay plate was incubated with shaking on a plate shaker at room temperature for 90 minutes. The incubation was terminated by filtration through a GF/C glass fiber filter plate (Merck Millipore) pre-soaked with 0.3% polyethyleneimine (PEI). Filters were washed 4 times with 300 μL of ice-cold assay buffer. After drying the filter plate, 100 μL of scintillation fluid (PerkinElmer, MicroScint-20) was added to each well and the radioactivity was counted using a TopCount NXT (PerkinElmer). Non-specific binding was determined in the presence of 1.25 μM unlabelled human α-CGRP (Bachem). The radioactivity was converted to the percent of specific binding using the equation below.

$$\% \text{ of specific binding} = \frac{(Y - Y\text{min})}{(Y\text{max} - Y\text{min})} \times 100 \quad [\text{Number 1}]$$

In the formulae, Y is observed radioactivity, Ymax is total bound activity, and Ymin is non-specific bound activity.

From these data, the concentration of compound required for 50% inhibition of radioligand binding (IC$_{50}$) was determined using Prism (GraphPad Inc.). The IC$_{50}$ value is then converted to the equilibrium dissociation constant (Ki) using the Cheng-Prusoff equation below (Cheng & Prusoff (1973) Biochem. Pharmacol. 22, 3099-3108).

$$Ki = \frac{IC_{50}}{1 + \frac{[L]}{Kd}} \quad [\text{Number 2}]$$

In the formulae, [L] is the concentration of radioligand, Kd is the apparent dissociation constant of the radioligand for the receptor as determined by saturation binding assay with [$^{125}$I]-CGRP.

As shown in Table 4 to Table 8, and Table 17 to Table 31, it was demonstrated that the compounds of the present invention exhibit a high binding affinity for human CGRP receptor.

Test Example 2

Determination of Functional Receptor Antagonism by Inhibition of CGRP-Induced cAMP Production in SK-N-MC Cells Human neuroblastoma cell line SK-N-MC cells expressing CGRP receptors endogenously (Muff et al., Ann NY Acad Sci. 1992; 657: 106-116) were cultured in MEM containing 10% FBS, 1 mM sodium pyruvate, non-essential amino acid, 0.5 U Penicillin and 0.5 μg Streptomycin. These cells were harvested by treatment with trypsin-EDTA, and cell suspension was obtained in an assay buffer (DMEM without Phenol-red containing 0.1% Bovine serum albumin, 30 μM Rolipram, L-alanyl-L-glutamine and 25 mM HEPES).

The cAMP production assay was performed using 96-well microplate (NUNC) in a total volume of 100 μL in each well, and the amount of cAMP production was determined using HTRF cAMP HiRange Kit (Cisbio). In brief, after adding of SK-N-MC cell suspension (50 μL) into each well (15,000 cells/well), a 25 μL of test compound solution was added to the suspension and the plate was incubated at 37° C. for 30 minutes. To the suspension was added 25 μL of human α-CGRP (Bachem, final concentration of 3 nM), and then the plate was further incubated at 37° C. for 15 minutes. The reaction was stopped by incubating with cell lysis buffer (Cisbio) at 37° C. for 30 minutes. The obtained cell lysate was treated in 384-well white plate (CORNING) according to the manufacturer's instructions, and then the fluorescence was measured using a microplate reader (Infinity M1000, Tecan). The raw data were converted to cAMP content of each sample using a standard curve. Data were plotted as the percent of control value against the concentrations of test compound using Prism (GraphPad Inc.) and the IC$_{50}$ values shown below were obtained.

TABLE 32

| Ex. No. | IC$_{50}$ (nM) |
|---|---|
| 1 A-2 | 0.12 |
| 1A-4 | 0.04 |
| 2A-1 | 0.86 |
| 2A-2 | 0.04 |
| 2A-3 | 0.05 |
| 2A-4 | 0.09 |
| 2B-1 | 0.02 |
| 2B-2 | 0.02 |
| 2B-4 | 0.06 |
| 2B-5 | 0.03 |
| 2B-6 | 0.02 |
| 2B-7 | 0.02 |
| 2B-8 | 0.04 |
| 2B-9 | 0.03 |
| 2B-10 isomerA | 0.11 |
| 2B-10 isomerB | 0.07 |
| 2B-11 | 0.03 |
| 2B-12 | 0.02 |
| 2B-13 | 0.03 |
| 2B-14 | 0.03 |
| 2B-15 | 0.07 |
| 2B-16 | 0.04 |
| 2B-17 | 0.03 |
| 2B-18 | 0.02 |
| 2B-19 | 0.01 |
| 2C-1 | 0.09 |
| 2C-2 | 0.04 |

TABLE 33

| Ex. No. | IC$_{50}$ (nM) |
|---|---|
| 3A-5 | 0.68 |
| 3A-8 | 0.36 |
| 3B-1 | 0.31 |
| 4A-5 | 0.13 |
| 4A-7 | 0.02 |
| 4B-1 | 0.14 |
| 4B-2 | 0.16 |
| 4B-3 | 0.10 |
| 4B-4 | 0.03 |
| 4B-5 | 0.02 |
| 4B-6 | 0.03 |
| 4B-7 | 0.03 |
| 4B-8 | 0.04 |
| 4B-9 | 0.09 |
| 4B-10 | 0.08 |
| 4B-11 | 0.02 |
| 4B-12 | 0.16 |
| 4B-13 | 0.02 |
| 4B-14 | 0.19 |
| 4B-15 | 0.17 |
| 4B-16 | 0.03 |
| 4B-17 | 0.02 |
| 4B-18 | 0.13 |
| 4B-19 | 0.04 |
| 4B-20 | 0.03 |
| 4B-21 | 0.13 |
| 4B-22 | 0.04 |
| 4B-23 | 0.02 |
| 4B-24 | 0.01 |
| 4B-25 | 0.05 |
| 4B-26 | 0.02 |
| 4B-27 | 0.03 |
| 4B-28 | 0.01 |
| 4B-29 | 0.04 |
| 4B-30 | 0.02 |
| 4B-31 | 0.01 |
| 4B-32 | 0.01 |
| 4B-33 | 0.03 |
| 4B-35 | 0.27 |
| 4B-36 | 0.69 |
| 4B-37 | 0.20 |
| 4B-38 | 0.36 |

TABLE 33-continued

| Ex. No. | IC$_{50}$ (nM) |
|---|---|
| 4B-39 | 0.21 |
| 4B-43 | 0.35 |

TABLE 34

| Ex. No. | IC$_{50}$ (nM) |
|---|---|
| 4C-1 | 0.11 |
| 5A-7 | 1.1 |
| 5B-1 | 0.06 |
| 5B-2 | 0.10 |
| 5C-1 | 0.04 |

As shown in above tables, it was demonstrated that the compounds of the present invention exhibit a human CGRP receptor antagonist activity.

INDUSTRIAL APPLICABILITY

The compounds of the present invention or a pharmaceutically acceptable salt thereof have an excellent CGRP receptor antagonist activity, and thus are useful as agents for the treatment of various diseases mediated by CGRP receptors.

The invention claimed is:
1. A compound represented by the formula (I):

[Chem.1]

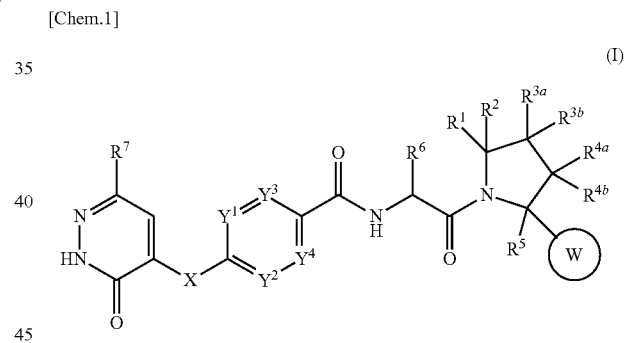

(I)

wherein
ring W is a group selected from the group consisting of following (a) to (d):
(a) $C_{3-6}$ cycloalkyl,
(b) phenyl which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{1-6}$ alkylsulfanyl, $C_{1-6}$ alkylsulfinyl, $C_{1-6}$ alkylsulfonyl, $C_{3-6}$ cycloalkyl, hydroxy, cyano, —NR$^a$R$^b$, —CONR$^a$R$^b$ and —CO$_2$R$^c$,
(c) 6-membered aromatic heterocycle which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{1-6}$ alkylsulfanyl, $C_{1-6}$ alkylsulfinyl, $C_{1-6}$ alkylsulfonyl, $C_{3-6}$ cycloalkyl, hydroxy, cyano, —NR$^a$R$^b$, —CONR$^a$R$^b$ and —CO$_2$R$^c$, and
(d) 5-membered aromatic heterocycle which may have a substituent selected from group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{1-6}$ alkylsulfanyl, $C_{1-6}$ alkylsulfinyl, $C_{1-6}$ alkylsulfonyl, $C_{3-6}$ cycloalkyl, hydroxy, cyano, —$NR^aR^b$, —$CONR^aR^b$ and —$CO_2R^c$, X is a group selected from the group consisting of following (a) to (g):

(a) a carbon atom which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl and hydroxy, (b) a nitrogen atom which may have a substituent selected from the group consisting of $C_{1-6}$ alkyl, halo-$C_{1-6}$ alkyl and $C_{3-6}$ cycloalkyl, (c) an oxygen atom, (d) —(C=O)—, (e) a sulfur atom, (f) —SO—, and (g) —$SO_2$—;

$Y^1$, $Y^2$, $Y^3$ and $Y^4$ are each independently =CH—, =$CR^8$— or a nitrogen atom;

$R^8$ is a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{1-6}$ alkylsulfanyl, $C_{1-6}$ alkylsulfinyl, $C_{1-6}$ alkylsulfony, $C_{3-6}$ cycloalkyl, hydroxy, cyano, —$NR^aR^b$, —$CONR^aR^b$ or —$CO_2R^c$;

$R^a$ and $R^b$ are each independently a hydrogen atom, $C_{1-6}$ alkyl, halo-$C_{1-6}$ alkyl or hydroxy $C_{1-6}$ alkyl;

$R^c$ is a hydrogen atom or $C_{1-6}$ alkyl;

$R^1$ is a group selected from the group consisting of following (a) to (j):

[Chem.2]

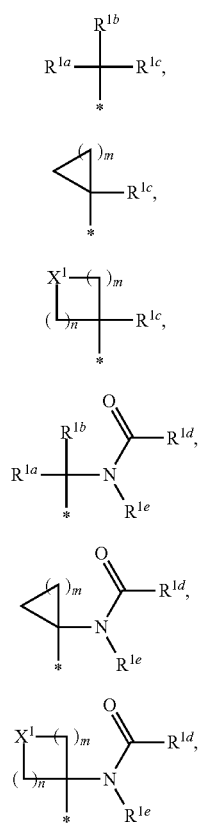

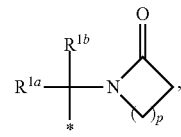

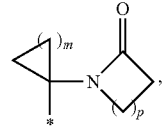

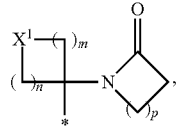

and (j) cyano;

wherein bonds with * are bonding sites to pyrrolidine ring of the formula (I);

$X^1$ is a group selected from the group consisting of following (a) to (e):

(a) a nitrogen atom which may have a substituent selected from the group consisting of $C_{1-6}$ alkyl, halo-$C_{1-6}$ alkyl and $C_{3-6}$ cycloalkyl, (b) an oxygen atom, (c) a sulfur atom, (d) —SO—, and (e) —$SO_2$—, $R^{1a}$ and $R^{1b}$ are each independently a hydrogen atom, a halogen atom, $C_{1-6}$ alkyl, halo-$C_{1-6}$ alkyl, hydroxy $C_{1-6}$ alkyl, $C_{1-6}$ alkoxy or halo-$C_{1-6}$ alkoxy;

$R^{1c}$ is a group selected from the group consisting of following (a) to (r):

(a) $C_{1-6}$ alkyl which may have a substituent selected from the group consisting of a halogen atom, $C_{1-6}$ alkoxy, halo-$C_{1-6}$ alkoxy, $C_{1-6}$ alkylsulfanyl, $C_{1-6}$ alkylsulfinyl, $C_{1-6}$ alkylsulfonyl, $C_{3-6}$ cycloalkyl, hydroxy, cyano and —$NR^aR^b$, (b) phenyl which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy and cyano, (c) 6-membered aromatic heterocycle which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy and cyano, (d) 5-membered aromatic heterocycle which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy and cyano, (e) a hydrogen atom, (f) a halogen atom, (g) $C_{1-6}$ alkoxy, (h) halo-$C_{1-6}$ alkoxy, (i) $C_{1-6}$ alkylsulfanyl, (j) $C_{1-6}$ alkylsulfinyl, (k) $C_{1-6}$ alkylsulfonyl, (l) $C_{3-6}$ cycloalkyl, (m) hydroxy, (n) cyano, (o) $C_{2-7}$ acyl,
(p) $C_{2-6}$ alkenyl,
(q) $C_{2-6}$ alkynyl, and
(r) $-NR^aR^b$;
$R^{1d}$ is $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, $-NR^aR^b$ or phenyl which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy and cyano;
$R^{1e}$ is a hydrogen atom, $C_{1-6}$ alkyl or halo-$C_{1-6}$ alkyl;
m is an integer number 1 to 4;
n and p are each independently an integer number 1 to 3;
$R^2$, $R^{3a}$, $R^{3b}$, $R^{4a}$, $R^{4b}$ and $R^5$ are each independently a hydrogen atom, a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy, cyano or $-NR^aR^b$;
$R^6$ is a hydrogen atom, $C_{1-6}$ alkyl, $C_{3-6}$ cycloalkyl, halo-$C_{1-6}$ alkyl or hydroxy $C_{1-6}$ alkyl; and
$R^7$ is a hydrogen atom, $C_{1-6}$ alkyl, $C_{3-6}$ cycloalkyl or halo-$C_{1-6}$ alkyl;
or a pharmaceutically acceptable salt thereof.

2. The compound according to claim 1 or a pharmaceutically acceptable salt thereof, wherein $R^5$ is a hydrogen atom.

3. The compound according to claim 2 or a pharmaceutically acceptable salt thereof, wherein $R^{3a}$, $R^{3b}$, $R^{4a}$ and $R^{4b}$ are hydrogen atoms.

4. The compound according to claim 3:
wherein ring W is $C_{3-6}$ cycloalkyl or phenyl which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{1-6}$ alkylsulfanyl, $C_{1-6}$ alkylsulfinyl, $C_{1-6}$ alkylsulfonyl, $C_{3-6}$ cycloalkyl, hydroxy, cyano, $-NR^aR^b$, $-CONR^aR^b$ and $-CO_2R^c$; or a pharmaceutically acceptable salt thereof.

5. The compound according to claim 4, wherein X is a group selected from the group consisting of following (a) to (c):
(a) a carbon atom which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl and hydroxy,
(b) a nitrogen atom which may have a substituent selected from the group consisting of $C_{1-6}$ alkyl, halo-$C_{1-6}$ alkyl and $C_{3-6}$ cycloalkyl, and
(c) an oxygen atom;
or a pharmaceutically acceptable salt thereof.

6. The compound according to claim 5 or a pharmaceutically acceptable salt thereof, wherein $R^2$ is a hydrogen atom.

7. The compound according to claim 1, wherein $R^1$ is a group selected from the group consisting of following (a) to (d) and (g):

[Chem. 3]

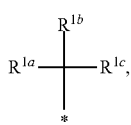
(a)

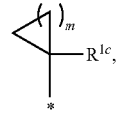
(b)

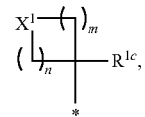
(c)

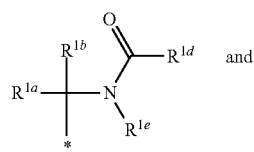
(d)

[Chem. 4]

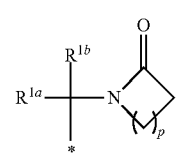
(g)

wherein
bonds with * are bonding sites to pyrrolidine ring of the formula (I)
$X^1$ is a group selected from the group consisting of following (a) to (e):
(a) a nitrogen atom which may have a substituent selected from the group consisting of $C_{1-6}$ alkyl, halo-$C_{1-6}$ alkyl and $C_{3-6}$ cycloalkyl,
(b) an oxygen atom,
(c) a sulfur atom,
(d) $-SO-$, and
(e) $-SO_2-$;
$R^{1a}$ and $R^{1b}$ are each independently a hydrogen atom, a halogen atom, $C_{1-6}$ alkyl, halo-$C_{1-6}$ alkyl, hydroxy $C_{1-6}$ alkyl, $C_{1-6}$ alkoxy or halo-$C_{1-6}$ alkoxy;
$R^{1c}$ is a group selected from the group consisting of following (a) to (r):
(a) $C_{1-6}$ alkyl which may have a substituent selected from the group consisting of a halogen atom, $C_{1-6}$ alkoxy, halo-$C_{1-6}$ alkoxy, $C_{1-6}$ alkylsulfanyl, $C_{1-6}$ alkylsulfinyl, $C_{1-6}$ alkylsulfonyl, $C_{3-6}$ cycloalkyl, hydroxy, cyano and $-NR^aR^b$,
(b) phenyl which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy and cyano,
(c) 6-membered aromatic heterocycle which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy and cyano,
(d) 5-membered aromatic heterocycle which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy and cyano,
(e) a hydrogen atom,
(f) a halogen atom, (g) $C_{1-6}$ alkoxy,
(h) halo-$C_{1-6}$ alkoxy,
(i) $C_{1-6}$ alkylsulfanyl,
(j) $C_{1-6}$ alkylsulfinyl,
(k) $C_{1-6}$ alkylsulfonyl,
(l) $C_{3-6}$ cycloalkyl,
(m) hydroxy,
(n) cyano,
(o) $C_{2-7}$ acyl,
(p) $C_{2-6}$ alkenyl,
(q) $C_{2-6}$ alkynyl, and
(r) —$NR^a R^b$;

$R^{1d}$ is $C_{1-6}$ alkyl, halo-$C_{1-6}$ alkoxy, hydroxy $C_{1-6}$ alkyl, $C_{1-6}$ alkoxy, halo-$C_{1-6}$ alkoxy, $C_{3-6}$ cycloalkyl, —$NR^a R^b$ or phenyl which may have a substituent selected from the group consisting of a halogen atom, $C_{1-6}$ alkyl, halo-$C_{1-6}$ alkyl, hydroxy $C_{1-6}$ alkyl, $C_{1-6}$ alkoxy, halo-$C_{1-6}$ alkoxy, $C_{3-6}$ cycloalkyl, hydroxy and cyano, $R^{1e}$ is a hydrogen atom, $C_{1-6}$ alkyl or halo-$C_{1-6}$ alkyl;
m is an integer number 1 to 4; and
n and p are each independently an integer number 1 to 3;
or a pharmaceutically acceptable salt thereof.

8. The compound according to claim 1:

[Chem.5]

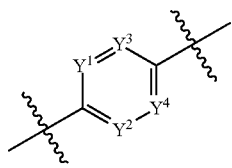

wherein the group represented by the above formula is a group selected from the group consisting of following (a) to (f):

[Chem.6]

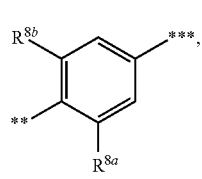
(a)

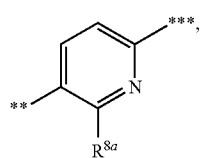
(b)

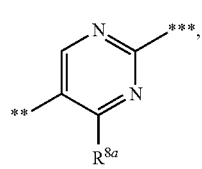
(c)

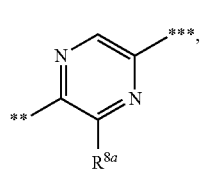
(d)

[Chem.7]

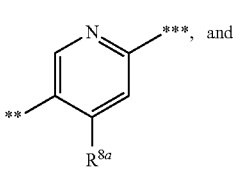
(e), and

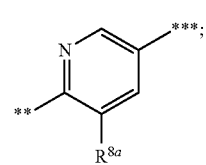
(f);

wherein $R^{8a}$ is a hydrogen atom, a halogen atom, $C_{1-6}$ alkyl or halo-$C_{1-6}$ alkyl;

$R^{8b}$ is a hydrogen atom, a halogen atom, $C_{1-6}$ alkyl or halo-$C_{1-6}$ alkoxy; and bonds with  are bonding sites to X and bonds with * are bonding sites to the carbonyl of the formula (I);

or a pharmaceutically acceptable salt thereof.

9. The compound according to claim 1:
wherein $X^1$ is an oxygen atom;
$R^{1a}$ and $R^{1b}$ are each independently a hydrogen atom, a halogen atom, $C_{1-6}$ alkyl or halo-$C_{1-6}$ alkyl;
$R^{1c}$ is a group selected from the group consisting of following (a) to (l):
(a) $C_{1-6}$ alkyl which may have a substituent selected from the group consisting of a halogen atom and hydroxy,
(b) oxazolyl,
(c) a hydrogen atom,
(d) a halogen atom,
(e) $C_{1-6}$ alkoxy,
(f) $C_{1-6}$ alkylsulfanyl,
(g) $C_{1-6}$ alkylsulfonyl,
(h) hydroxy,
(i) cyano,
(j) $C_{2-7}$ acyl,
(k) $C_{2-6}$ alkenyl, and
(l) —$NR^{aa}R^{bb}$;

$R^{1d}$ is $C_{1-6}$ alkyl or phenyl;
$R^{1e}$ is a hydrogen atom or $C_{1-6}$ alkyl;
and
$R^{aa}$ and $R^{bb}$ are each independently a hydrogen atom or $C_{1-6}$ alkyl;
or a pharmaceutically acceptable salt thereof.

10. The compound according to claim 1 or a pharmaceutically acceptable salt thereof, wherein $R^6$ is a hydrogen atom, methyl, ethyl, isopropyl, hydroxymethyl or monofluoromethyl.

11. The compound according to claim 1 or a pharmaceutically acceptable salt thereof, wherein $R^7$ is a hydrogen atom or methyl.

12. The compound according to claim 1 which is represented by the formula (IA)

[Chem. 8]

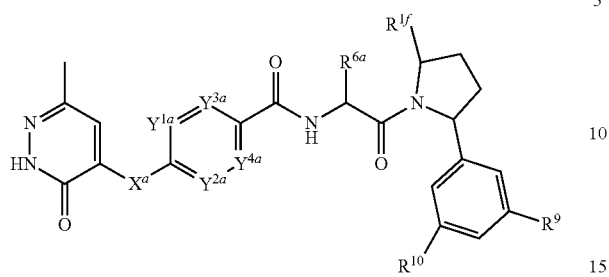
(IA)

wherein

R⁹ and R¹⁰ are each independently a hydrogen atom, a fluorine atom or a chlorine atom;

$X^a$ is —CH$_2$— or —O—;

[Chem.9]

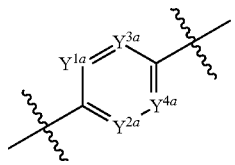

the group represented by the above formula is a group selected from the group consisting of following (a) to (h):

[Chem. 10]

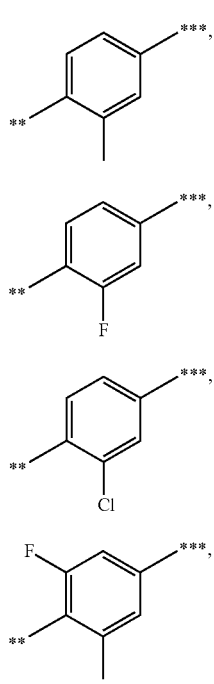

(a)

(b)

(c)

(d)

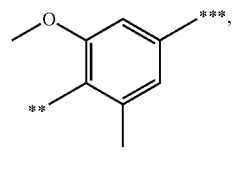
(e)

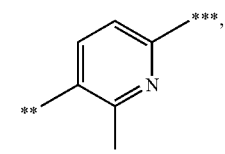
(f)

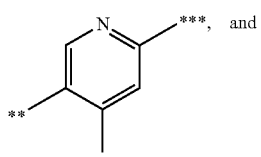
(g)

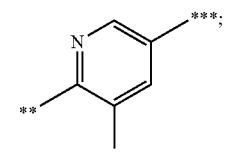
(h)

[Chem. 11]

bonds with  are bonding sites to $X^a$, and bonds with * are bonding sites to the carbonyl of the formula (IA);

$R^{1f}$ is a group selected from the group consisting of following (a) to (g):

[Chem.12]

(a)

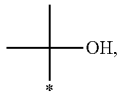
(b)

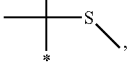
(c)

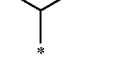
(d)

(e)

(f)

-continued

[Chem.13]

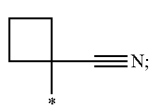

(g)

bonds with * are bonding sites to the pyrrolidine ring of the formula (IA);
R$^{6a}$ is a hydrogen atom, methyl or ethyl;
or a pharmaceutically acceptable salt thereof.

13. A pharmaceutical composition comprising the compound according to claim 1 or a pharmaceutically acceptable salt thereof, and pharmaceutical additive.

14. A method of treating migraine, comprising:
administering an effective amount of the pharmaceutical composition according to claim 13 to a subject in need thereof.

15. A compound represented by the following formula:

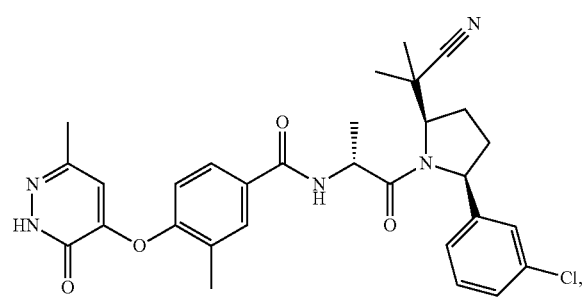 [SMILES: Cc1cc(Oc2ccc(C(=O)N[C@H](C)C(=O)N3[C@H](c4cccc(Cl)c4)CC[C@@H]3C(C)(C)C#N)cc2C)c(=O)[nH]n1]

or a pharmaceutically acceptable salt thereof.

16. A compound represented by the following formula:

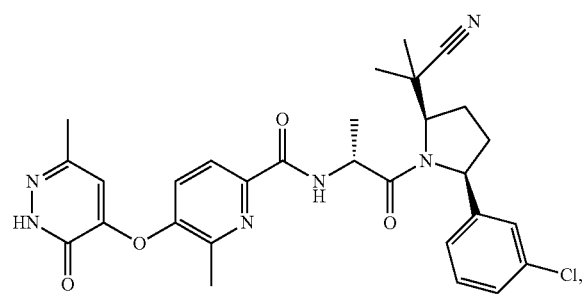 [SMILES: Cc1cc(Oc2ccc(C(=O)N[C@H](C)C(=O)N3[C@H](c4cccc(Cl)c4)CC[C@@H]3C(C)(C)C#N)nc2C)c(=O)[nH]n1]

or a pharmaceutically acceptable salt thereof.

17. A compound represented by the following formula:

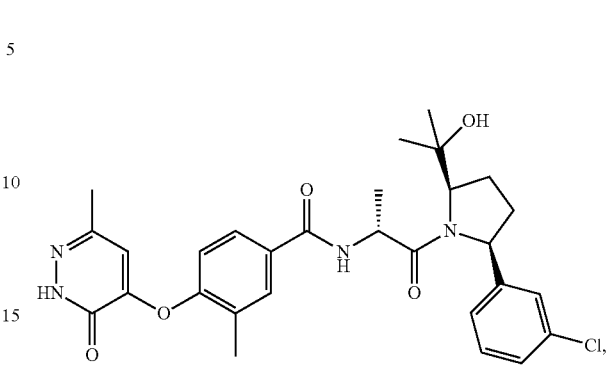

or a pharmaceutically acceptable salt thereof.

18. A compound represented by the following formula:

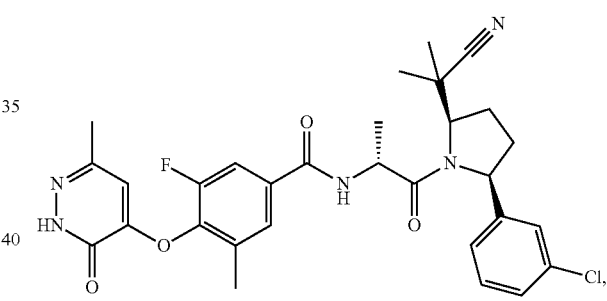

or a pharmaceutically acceptable salt thereof.

* * * * *